US010081647B2

(12) United States Patent
Yu et al.

(10) Patent No.: US 10,081,647 B2
(45) Date of Patent: Sep. 25, 2018

(54) PHOSPHATE SUBSTITUTED QUINOLIZINE DERIVATIVES USEFUL AS HIV INTEGRASE INHIBITORS

(71) Applicant: Merck Sharp & Dohme Corp., Rahway, NJ (US)

(72) Inventors: Tao Yu, Edison, NJ (US); Sherman T. Waddell, Westfield, NJ (US); John A. McCauley, Maple Glen, PA (US); Thomas H. Graham, Quincy, MA (US); Hong Li, Edison, NJ (US); Izzat Raheem, Doylestown, PA (US); Jay A. Grobler, North Wales, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/560,896

(22) PCT Filed: Mar. 25, 2016

(86) PCT No.: PCT/US2016/024193
§ 371 (c)(1),
(2) Date: Sep. 22, 2017

(87) PCT Pub. No.: WO2016/154527
PCT Pub. Date: Sep. 29, 2016

(65) Prior Publication Data
US 2018/0051043 A1 Feb. 22, 2018

Related U.S. Application Data

(60) Provisional application No. 62/138,716, filed on Mar. 26, 2015.

(51) Int. Cl.
*A61K 31/675* (2006.01)
*C07F 9/6561* (2006.01)
*A61K 31/683* (2006.01)

(52) U.S. Cl.
CPC .......... *C07F 9/6561* (2013.01); *A61K 31/675* (2013.01); *A61K 31/683* (2013.01)

(58) Field of Classification Search
CPC .... C07F 9/6561; A61K 31/675; A61K 31/683
See application file for complete search history.

(56) References Cited

U.S. PATENT DOCUMENTS 9,822,138 B2 * 11/2017 Vachal ................ C07F 9/65616
9,861,620 B2 * 1/2018 Yu ............................ A61K 31/52

2007/0179196 A1 8/2007 Han et al.
2014/0200209 A1 * 7/2014 Johns ..................... C07D 471/04 514/214.02
2015/0218164 A1 * 8/2015 Coleman ............... C07D 471/14 514/81
2015/0315221 A1 * 11/2015 Butora ................. C07D 339/08 514/86
2015/0329539 A1 * 11/2015 Embrey ............... C07D 471/04 514/80
2016/0228419 A1 * 8/2016 Yu ........................ C07D 519/00
2016/0317543 A1 * 11/2016 Graham ................ A61K 31/513
2017/0190701 A1 * 7/2017 Yu ........................ A61K 31/427
2017/0334924 A1 * 11/2017 Embrey ............... C07D 491/20
2018/0065999 A1 * 3/2018 Vachal ................ A61K 31/675

FOREIGN PATENT DOCUMENTS

| WO | 2006066414 A1 | 6/2006 | |
| WO | 2007023242 A1 | 3/2007 | |
| WO | WO-2007023242 A1 * | 3/2007 | .......... C07D 215/20 |
| WO | 2015048363 A1 | 4/2015 | |
| WO | WO-2015048363 A1 * | 4/2015 | .......... A61K 31/52 |
| WO | WO-2016187788 A1 * | 12/2016 | .......... A61K 31/427 |
| WO | WO-2016191239 A1 * | 12/2016 | .......... A61K 31/427 |
| WO | WO-2017106071 A1 * | 6/2017 | ........ A61K 31/4375 |
| WO | WO-2018057408 A1 * | 3/2018 | |

OTHER PUBLICATIONS

International Search Report and Written Opinion of the ISA for PCT/US16/024193 dated Jun. 10, 2016, 10 pages.

* cited by examiner

*Primary Examiner* — Alexander R Pagano
(74) *Attorney, Agent, or Firm* — Nicole M. Beeler; John C. Todaro

(57) ABSTRACT

The present invention relates to Phosphate Substituted Quinolizine Derivatives of Formula (I): and pharmaceutically acceptable salts or prodrug thereof, wherein X, Y, $R^1$, $R^2$, $R^3$, $R^4$, $R^5$, $R^9$ and $R^{10}$ are as defined herein. The present invention also relates to compositions comprising at least one Phosphate Substituted Quinolizine Derivative, and methods of using the Phosphate Substituted Quinolizine Derivatives for treating or preventing HIV infection in a subject.

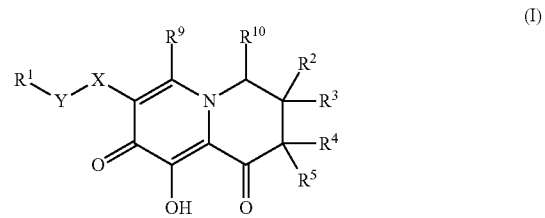

(I)

21 Claims, No Drawings

PHOSPHATE SUBSTITUTED QUINOLIZINE DERIVATIVES USEFUL AS HIV INTEGRASE INHIBITORS

CROSS REFERENCE TO RELATED APPLICATIONS

This application is a U.S. National Phase application under 35 U.S.C. § 371 of PCT Application No. PCT/US2016/024193 filed Mar. 25, 2016, which claims priority from U.S. Provisional Application Ser. No. 62/138,716 filed Mar. 26, 2015.

FIELD OF THE INVENTION

The present invention relates to Phosphate-Substituted Quinolizine Derivatives, compositions comprising at least one Phosphate-Substituted Quinolizine Derivative, and methods of using the Phosphate-Substituted Quinolizine Derivatives for treating or preventing HIV infection in a subject.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. A common feature of retrovirus replication is the insertion by virally-encoded integrase of proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA and covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Tohours, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication.

The following references may be of interest as background:

International Publication Nos. WO 11/045330 and WO 11/121105 disclose macrocyclic compounds having HIV integrase inhibitory activity.

Kinzel et al., Tet. Letters 2007, 48(37): pp. 6552-6555 discloses the synthesis of tetrahydropyridopyrimidones as a scaffold for HIV-1 integrase inhibitors.

Ferrara et al., Tet. Letters 2007, 48(37), pp. 8379-8382 discloses the synthesis of a hexahydropyrimido[1,2-a] azepine-2-carboxamide derivative useful as an HIV integrase inhibitor.

Muraglia et al., J. Med. Chem. 2008, 51: 861-874 discloses the design and synthesis of bicyclic pyrimidinones as potent and orally bioavailable HIV-1 integrase inhibitors.

US2004/229909 discloses certain compounds having integrase inhibitory activity.

U.S. Pat. No. 7,232,819 and US 2007/0083045 disclose certain 5,6-dihydroxypyrimidine-4-carboxamides as HIV integrase inhibitors.

U.S. Pat. No. 7,169,780, U.S. Pat. No. 7,217,713, and US 2007/0123524 disclose certain N-substituted 5-hydroxy-6-oxo-1,6-dihydropyrimidine-4-carboxamides as HIV integrase inhibitors.

U.S. Pat. No. 7,279,487 discloses certain hydroxynaphthyridinone carboxamides that may be useful as HIV integrase inhibitors.

U.S. Pat. No. 7,135,467 and U.S. Pat. No. 7,037,908 disclose certain pyrimidine carboxamides that may be useful as HIV integrase inhibitors.

U.S. Pat. No. 7,211,572 discloses certain nitrogenous condensed ring compounds that are HIV integrase inhibitors.

U.S. Pat. No. 7,414,045 discloses certain tetrahydro-4H-pyrido[1,2-a]pyrimidine carboxamides, hexahydropyrimido[1,2-a]azepine carboxamides, and related compounds that may be useful as HIV integrase inhibitors.

U.S. Pat. No. 8,129,385 discloses certain hexahydro-2H-pyrido[1',2':4,5]pyrazino[2,1-b][1,3]oxazine-9-carboxamides, and related compounds that may be useful as HIV integrase inhibitors.

WO 2006/103399 discloses certain tetrahydro-4H-pyrimidooxazepine carboaxmides, tetrahydropyrazinopyrimidine carboxamides, hexahydropyrimidodiazepine carboxamides, and related compounds that may be useful as HIV integrase inhibitors.

US 2007/0142635 discloses processes for preparing hexahydropyrimido[1,2-a]azepine-2-carboxylates and related compounds.

US 2007/0149556 discloses certain hydroxypyrimidinone derivatives having HIV integrase inhibitory activity.

Various pyrimidinone compounds useful as HIV integrase inhibitors are also disclosed in U.S. Pat. No. 7,115,601, U.S. Pat. No. 7,157,447, U.S. Pat. No. 7,173,022, U.S. Pat. No. 7,176,196, U.S. Pat. No. 7,192,948, U.S. Pat. No. 7,273,859, and U.S. Pat. No. 7,419,969.

US 2007/0111984 discloses a series of bicyclic pyrimidinone compounds useful as HIV integrase inhibitors.

US 2006/0276466, US 2007/0049606, US 2007/0111985, US 2007/0112190, US 2007/0281917, US 2008/0004265 each disclose a series of bicyclic pyrimidinone compounds useful as HIV integrase inhibitors.

U.S. Pat. No. 7,462,608 and U.S. Pat. No. 7,649,015 each disclose phosphate and phosphonate substituted heterocycles useful as HIV nNRTI inhibitors and HIV protease inhibitors, respectively.

SUMMARY OF THE INVENTION

In one aspect, the present invention provides Compounds of Formula (I):

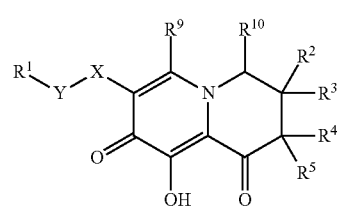

or a pharmaceutically acceptable salt thereof, wherein:

$R^1$ is selected from $C_6$-$C_{10}$ aryl, 5 or 6-membered monocyclic heteroaryl and 9 or 10-membered bicyclic heteroaryl, wherein said $C_6$-$C_{10}$ aryl group, said 5 or 6-membered monocyclic heteroaryl group and said 9 or 10-membered bicyclic heteroaryl group can each be optionally substituted with up to three $R^8$ groups;

$R^2$ is selected from H, $C_1$-$C_6$ alkyl, —N($R^{11}$)$_2$, —($C_1$-$C_6$ alkylene)$_m$-Z—($C_1$-$C_6$ alkylene)$_m$-$R^{13}$, —($C_1$-$C_6$ alkylene)$_m$-Z—($C_1$-$C_6$ alkylene)$_m$-N($R^{22}$)$_2$ and —OR$^7$, or $R^2$ and $R^4$, together with the carbon atoms to which they are attached, can join to form a 5 to 8-membered monocyclic cycloalkyl group, 5 to 8-membered monocyclic heterocycloalkyl group, 5 to 8-membered monocyclic heterocycloalkenyl group or a 8 to 11-membered bicyclic heterocycloalkyl, wherein said 5 to 8-membered monocyclic cycloalkyl group, said 5 to 8-membered monocyclic heterocycloalkyl group, said 5 to 8-membered monocyclic heterocycloalkenyl group and said 8 to 11-membered bicyclic heterocycloalkyl group can be optionally substituted with up to three $R^8$ groups, which can be the same or different;

$R^3$ is H, $C_1$-$C_6$ alkyl, —N($R^{11}$)$_2$ or —OR$^7$;

$R^4$ is selected from H, $C_1$-$C_6$ alkyl, —($C_1$-$C_6$ alkylene)-O—($C_1$-$C_6$ alkyl), —($C_1$-$C_6$ alkylene)$_m$-Z—($C_1$-$C_6$ alkylene)$_m$-$R^{13}$, —($C_1$-$C_6$ alkylene)$_m$-Z—($C_1$-$C_6$ alkylene)$_m$-N($R^{22}$)$_2$, —N($R^{11}$)$_2$ and —OR$^7$, such that when $R^2$ and/or $R^3$ are —N($R^{11}$)$_2$, then $R^4$ is other than H;

$R^5$ is selected from H, $C_1$-$C_6$ alkyl, —($C_1$-$C_6$ alkylene)-O—($C_1$-$C_6$ alkyl), —N($R^{11}$)$_2$ and —OR$^7$, such that when $R^2$ and/or $R^3$ are —N($R^{11}$)$_2$, then $R^5$ is other than H;

each occurrence of $R^6$ is independently H or $C_1$-$C_6$ alkyl;

each occurrence of $R^7$ is independently selected from H, $C_1$-$C_6$ alkyl, —($C_1$-$C_6$ alkylene)-O—($C_1$-$C_6$ alkyl) and $C_3$-$C_7$ cycloalkyl;

each occurrence of $R^8$ is independently selected from $C_1$-$C_6$ alkyl, halo, —OR$^6$, —SR$^6$, $C_1$-$C_6$ haloalkyl, $C_1$-$C_6$ hydroxyalkyl, —($C_1$-$C_6$ alkylene)$_m$-Z—$R^{13}$, —N($R^{22}$)$_2$, —O—($C_1$-$C_6$ haloalkyl), —CN, —NO$_2$, —N($R^6$)$_2$, —C(O)OR$^7$, —C(O)N($R^7$)$_2$ and —NHC(O)R$^7$;

$R^9$ is selected from H, $C_1$-$C_6$ alkyl, —$C_1$-$C_6$ alkyl-O—$C_1$-$C_6$ alkyl, —$C_1$-$C_6$ alkyl-NR$^6$—$C_1$-$C_6$ alkyl, —$C_1$-$C_6$ haloalkyl and —$C_1$-$C_6$ hydroxyalkyl;

$R^{10}$ is selected from H, $C_1$-$C_6$ alkyl, —($C_1$-$C_6$ alkylene)$_m$-Z—($C_1$-$C_6$ alkylene)$_m$-$R^{13}$, —($C_1$-$C_6$ alkylene)$_m$-Z—($C_1$-$C_6$ alkylene)$_m$-N($R^{22}$)$_2$, —($C_1$-$C_6$ alkylene)-O—$C_1$-$C_6$ alkyl, —($C_1$-$C_6$ alkylene)-N($R^6$)—$C_1$-$C_6$ alkyl, —$C_1$-$C_6$ haloalkyl and —$C_1$-$C_6$ hydroxyalkyl;

each occurrence of $R^{11}$ is independently selected from H, $C_1$-$C_6$ alkyl, —S(O)$_2$R$^{12}$ and —C(O)R$^{12}$; and each occurrence of $R^{12}$ is independently selected from $C_1$-$C_6$ alkyl, $C_3$-$C_7$ cycloalkyl, $C_6$-$C_{10}$ aryl, 4 to 7-membered monocyclic heterocycloalkyl, 8 to 11-membered bicyclic heterocycloalkyl, 5 or 6-membered monocyclic heteroaryl and 9 or 10-membered bicyclic heteroaryl, wherein said $C_3$-$C_7$ cycloalkyl group, said $C_6$-$C_{10}$ aryl group, said 4 to 7-membered monocyclic heterocycloalkyl, said 8 to 11-membered bicyclic heterocycloalkyl group, said 5 or 6-membered monocyclic heteroaryl group and said 9 or 10-membered bicyclic heteroaryl group can each be optionally substituted with up to three $R^8$ groups;

each occurrence of $R^{13}$ is independently selected from —P(O)(—OR$^{21}$)$_2$,

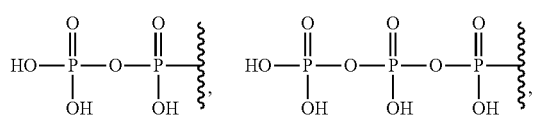

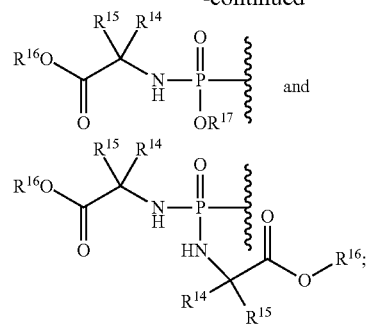
and each occurrence of $R^{14}$ is independently selected from H, $C_1$-$C_6$ alkyl, $C_3$-$C_7$ cycloalkyl, phenyl and benzyl, wherein said $C_1$-$C_6$ alkyl can be optionally substituted with a group selected from halo, —OR$^{18}$, —SR$^{18}$, guanidino, —N($R^{18}$)$_2$, —C(O)OR$^{18}$, —C(O)N($R^{18}$)$_2$, —NHC(O)R$^{18}$, 5- or 6-membered monocyclic heteroaryl and 9- or 10-membered bicyclic heteroaryl, and wherein said phenyl group and said benzyl group can be optionally substituted with up to 2 groups, each independently selected from $C_1$-$C_6$ alkyl, halo and —OR$^6$;

each occurrence of $R^{15}$ is independently selected from H, $C_1$-$C_6$ alkyl, $C_3$-$C_7$ cycloalkyl, phenyl and benzyl, wherein said $C_1$-$C_6$ alkyl can be optionally substituted with a group selected from halo, —OR$^{18}$, —SR$^{18}$, guanidino, —N($R^{18}$)$_2$, —C(O)OR$^{18}$, —C(O)N($R^{18}$)$_2$, —NHC(O)R$^{18}$, 5- or 6-membered monocyclic heteroaryl and 9- or 10-membered bicyclic heteroaryl, and wherein said phenyl group and said benzyl group can be optionally substituted with up to 2 groups, each independently selected from $C_1$-$C_6$ alkyl, halo and —OR$^{18}$;

each occurrence of $R^{16}$ is independently selected from H, $C_1$-$C_{20}$ alkyl, $C_2$-$C_{20}$ alkenyl, —($C_1$-$C_3$ alkylene)$_m$-($C_3$-$C_7$ cycloalkyl), —($C_1$-$C_3$ alkylene)$_m$-($C_6$-$C_{10}$ aryl) and —($C_1$-$C_3$ alkylene)$_m$-adamantyl, wherein said $C_1$-$C_{20}$ alkyl group, said $C_2$-$C_{20}$ alkenyl group, said $C_6$-$C_{10}$ aryl group and said adamantyl group can be optionally substituted with up to three groups, each independently selected from halo, —OR$^{18}$, —C(O)OR$^{18}$, —CN, —NO$_2$, $C_1$-$C_6$ haloalkyl, $C_1$-$C_6$ hydroxyalkyl, $C_3$-$C_7$ cycloalkyl, $C_6$-$C_{10}$ aryl, 5- or 6-membered monocyclic heteroaryl, 9- or 10-membered bicyclic heteroaryl, —N($R^{18}$)$_2$, —C(O)N($R^{18}$)$_2$, —SR$^{18}$, —S(O)R$^{18}$, —S(O)$_2$R$^{18}$, —S(O)$_2$N($R^{18}$)$_2$, —NHC(O)R$^{18}$, —NHC(O)OR$^{18}$ and —NHC(O)N($R^{18}$)$_2$;

each occurrence of $R^{17}$ is independently selected from H, $C_6$-$C_{10}$ aryl, 5- or 6-membered monocyclic heteroaryl and 9- or 10-membered bicyclic heteroaryl, wherein said $C_6$-$C_{10}$ aryl group, said 5- or 6-membered monocyclic heteroaryl group and said 9- or 10-membered bicyclic heteroaryl group can be optionally substituted with up to five $R^{19}$ groups;

each occurrence of $R^{18}$ is independently H, $C_1$-$C_{10}$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl), wherein said $C_3$-$C_7$ cycloalkyl group, said $C_6$-$C_{10}$ aryl group, said 4 to 7-membered heterocycloalkyl group, said -5- or 6-membered monocyclic heteroaryl group or said 9- or 10-membered bicyclic heteroaryl group can be optionally substituted with up to five $R^{19}$ groups;

each occurrence of $R^{19}$ is independently selected from $C_1$-$C_6$ alkyl, halo, —OR$^{23}$, —SR$^{23}$, $C_1$-$C_6$ haloalkyl, $C_1$-$C_6$ hydroxyalkyl, —O—($C_1$-$C_6$ haloalkyl), —CN, —$NO_2$, —N($R^{18}$)$_2$, —C(O)O$R^{23}$, —C(O)N($R^{23}$)$_2$ and —NHC(O)$R^{23}$, or any two $R^{19}$ groups on adjacent ring carbon atoms can combine to form —O—$R^{20}$—O—;

$R^{20}$ is [C($R^6$)$_2$]$_n$—;

each occurrence of $R^{21}$ is independently selected from H, $C_1$-$C_6$ alkyl, $C_6$-$C_{10}$ aryl, —($C_1$-$C_6$ alkylene)-O—($C_1$-$C_{20}$ alkyl), —($C_1$-$C_6$ alkylene)-O—C(O)—$R^{18}$, and —($C_1$-$C_6$ alkylene)-O—C(O)—O—$R^{18}$;

each occurrence of $R^{22}$ is independently selected from H, $C_1$-$C_6$ alkyl and —($C_1$-$C_6$ alkylene)-Z—$R^{13}$;

each occurrence of $R^{23}$ is independently selected from H, $C_1$-$C_{10}$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) and —($C_1$-$C_3$ alkylene)$_m$-(9- or 10-membered bicyclic heteroaryl);

X is selected from a single bond, 5 or 6-membered monocyclic heteroaryl and —N($R^6$)C(O)—;

Y is a single bond or $C_1$-$C_3$ alkylene;

each occurrence of Z is independently O or a bond;

each occurrence of m is independently 0 or 1; and n is 1 or 2, such that at least one —($C_1$-$C_6$ alkylene)$_m$-Z—($C_1$-$C_6$ alkylene)$_m$-$R^{13}$ group or at least one —($C_1$-$C_6$ alkylene)$_m$-Z—($C_1$-$C_6$ alkylene)$_m$-N($R^{22}$)$_2$ group is present in the compound of formula (I).

The Compounds of Formula (I) (also referred to herein as the "Phosphate-Substituted Quinolizine Derivatives") and pharmaceutically acceptable salts or prodrugs thereof may be useful, for example, for inhibiting HIV viral replication or replicon activity, or for treating or preventing HIV infection in a subject. Without being bound by any specific theory, it is believed that the Phosphate-Substituted Quinolizine Derivatives inhibit HIV viral replication by inhibiting HIV Integrase.

Accordingly, the present invention provides methods for treating or preventing HIV infection in a subject, comprising administering to the subject an effective amount of at least one Phosphate-Substituted Quinolizine Derivative.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention includes Phosphate-Substituted Quinolizine Derivatives, compositions comprising at least one Phosphate-Substituted Quinolizine Derivative, and methods of using the Phosphate-Substituted Quinolizine Derivatives for treating or preventing HIV infection in a subject.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . . .

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of a Phosphate-Substituted Quinolizine Derivative and/or an additional therapeutic agent, or a composition thereof that is effective in inhibiting HIV replication and in producing the desired therapeutic, ameliorative, inhibitory or preventative effect when administered to a subject suffering from HIV infection or AIDS. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH₂, —NH(alkyl), —N(alkyl)₂, —NH(cycloalkyl), —O—C(O)-alkyl, —O—C(O)-aryl, —O—C(O)-cycloalkyl, —C(O)OH and —C(O)O-alkyl. The term "C₂-C₆ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH₂, —NH(alkyl), —N(alkyl)₂, —NH(cycloalkyl), —O—C(O)— alkyl, —O—C(O)-aryl, —O—C(O)-cycloalkyl, —C(O)OH and —C(O)O-alkyl. The term "C₂-C₆ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH₂—, —CH₂CH₂—, —CH₂CH₂CH₂—, —CH₂CH₂CH₂CH₂—, —CH(CH₃)CH₂CH₂—, —CH(CH₃)— and —CH₂CH(CH₃)CH₂—. In one embodiment, an alkylene group has from 1 to about 6 carbon atoms. In another embodiment, an alkylene group has from about 3 to about 5 carbon atoms. In another embodiment, an alkylene group is branched. In another embodiment, an alkylene group is linear. In one embodiment, an alkylene group is —CH₂—. The term "C₁-C₆ alkylene" refers to an alkylene group having from 1 to 6 carbon atoms. The term "C₁-C₃ alkylene" refers to an alkylene group having from 1 to 3 carbon atoms.

The term "alkenylene," as used herein, refers to an alkenyl group, as defined above, wherein one of the alkenyl group's hydrogen atoms has been replaced with a bond. Non-limiting examples of alkenylene groups include —CH=CH—, —CH=CHCH₂—, —CH₂CH=CH—, —CH₂CH=CHCH₂—, —CH=CHCH₂CH₂—, —CH₂CH₂CH=CH— and —CH(CH₃)CH=CH—. In one embodiment, an alkenylene group has from 2 to about 6 carbon atoms. In another embodiment, an alkenylene group has from about 3 to about 5 carbon atoms. In another embodiment, an alkenylene group is branched. In another embodiment, an alkenylene group is linear. The term "C₂-C₆ alkenylene" refers to an alkenylene group having from 2 to 6 carbon atoms. The term "C₃-C₅ alkenylene" refers to an alkenylene group having from 3 to 5 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

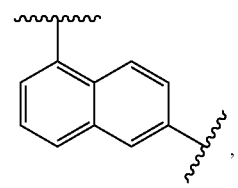 [SMILES: *c1ccc2c(*)cccc2c1]

is understood to represent both:

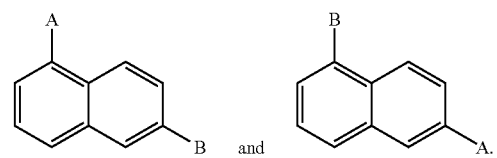

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

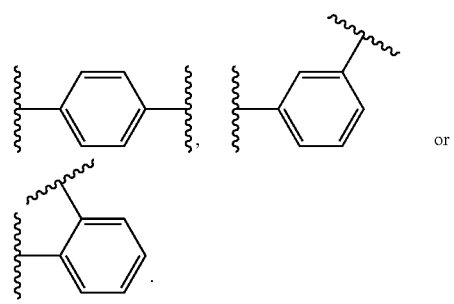

Unless otherwise indicated, an arylene group is unsubstituted.

The term "cycloalkyl," as used herein, refers to a non-aromatic mono- or multicyclic saturated ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 7-membered cycloalkyl" refers to a cycloalkyl group having from 3 to 7 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

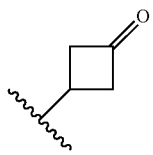

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$. The term "C$_1$-C$_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. In another embodiment, a heteroaryl group is bicyclic and has 9 or 10 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered monocyclic heteroaryl. In another embodiment, a heteroaryl group comprises a 5- to 6-membered monocyclic heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 5 to about 8 ring atoms. In another embodiment, a heterocycloalkyl group is bicyclic and has from about 8 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

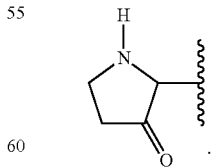

In one embodiment, a heterocycloalkyl group is a 5-membered monocyclic heterocycloalkyl. In another embodiment, a heterocycloalkyl group is a 6-membered monocyclic heterocycloalkyl. The term "4 to 7-membered monocyclic heterocycloalkyl" refers to a monocyclic heterocycloalkyl group having from 4 to 7 ring atoms. The term "5 to 8-membered monocyclic heterocycloalkyl" refers to a monocyclic heterocycloalkyl group having from 5 to 8 ring atoms. The term "8 to 11-membered bicyclic heterocycloalkyl" refers to a bicyclic heterocycloalkyl group having from 8 to 11 ring atoms. Unless otherwise indicated, a heterocycloalkyl group is unsubstituted.

The term "heterocycloalkenyl," as used herein, refers to an heterocycloalkyl group, as defined above, which is non-aromatic and contains at least one endocyclic double bond between two adjacent ring atoms. A heterocycloalkenyl group can be joined via a ring carbon, ring silicon atom or ring nitrogen atom. In one embodiment, a heterocycloalkenyl group is monocyclic and has from about 3 to about 7 ring atoms. In another embodiment, a heterocycloalkenyl group is monocyclic has from about 5 to about 8 ring atoms. In another embodiment, a heterocycloalkenyl group is bicyclic and has from about 8 to about 11 ring atoms. In still another embodiment, a heterocycloalkenyl group is monocyclic and has 5 or 6 ring atoms. In one embodiment, a heterocycloalkenyl group is monocyclic. In another embodiment, a heterocycloalkenyl group is bicyclic. There are no adjacent oxygen and/or sulfur atoms present in the ring system. Any —NH group in a heterocycloalkenyl ring may be substituted or may exist protected such as, for example, as an —N(BOC), —N(Cbz), —N(Tos) group and the like; such protected heterocycloalkenyl groups are considered part of this invention. The term "heterocycloalkenyl" also encompasses a heterocycloalkenyl group, as defined above, which is fused to an aryl (e.g., benzene) or heteroaryl ring. A heterocycloalkenyl group can be optionally substituted by one or more "ring system substituents" which may be the same or different, and are as defined herein below. The nitrogen or sulfur atom of the heterocycloalkenyl can be optionally oxidized to the corresponding N-oxide, S-oxide or S,S-dioxide.

A ring carbon atom of a heterocycloalkenyl group may be functionalized as a carbonyl group. An illustrative example of such a heterocycloalkenyl group is:

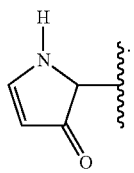 [SMILES: *C1NC=CC1=O]

In one embodiment, a heterocycloalkenyl group is a 5-membered monocyclic heterocycloalkenyl. In another embodiment, a heterocycloalkenyl group is a 6-membered monocyclic heterocycloalkenyl. The term "4 to 7-membered monocyclic heterocycloalkenyl" refers to a monocyclic heterocycloalkenyl group having from 4 to 7 ring atoms. The term "5 to 8-membered monocyclic heterocycloalkenyl" refers to a monocyclic heterocycloalkenyl group having from 5 to 8 ring atoms. The term "8 to 11-membered bicyclic heterocycloalkenyl" refers to a bicyclic heterocycloalkenyl group having from 8 to 11 ring atoms. Unless otherwise indicated, a heterocycloalkenyl group is unsubstituted.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O— alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si(alkyl)$_2$, —Si(aryl)$_2$, —Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

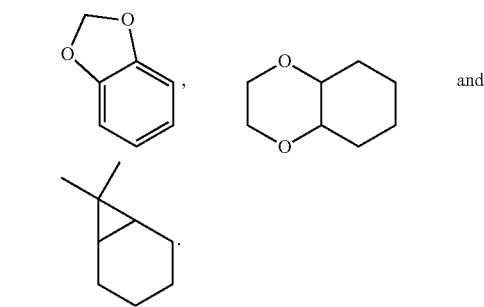

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., m, $C_1$-$C_6$ alkyl, $R^7$, $R^{11}$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Phosphate-Substituted Quinolizine Derivative or a pharmaceutically acceptable salt of the compound. The transformation may occur by various mechanisms (e.g., by metabolic or chemical processes), such as, for example, through hydrolysis in blood. For example, if a Phosphate-Substituted Quinolizine Derivative or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$) alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$)alkyl, and the like.

Similarly, if a Phosphate-Substituted Quinolizine Derivative contains an alcohol functional group, a prodrug can be formed by the replacement of one or more of the hydrogen atoms of the alcohol groups with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$) alkoxycarbonyloxymethyl, N—($C_1$-$C_6$)alkoxycarbonylaminomethyl, succinoyl, ($C_1$-$C_6$)alkanoyl, α-amino($C_1$-$C_4$) alkyl, α-amino($C_1$-$C_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a Phosphate-Substituted Quinolizine Derivative incorporates an amine functional group, a prodrug can be formed by the replacement of a hydrogen atom in the amine group with a group such as, for example, R-carbonyl-, RO-carbonyl-, NRR'-carbonyl- wherein R and R' are each independently ($C_1$-$C_{10}$)alkyl, ($C_3$-$C_7$) cycloalkyl, benzyl, a natural α-aminoacyl, —C(OH)C(O)OY$^1$ wherein Y$^1$ is H, ($C_1$-$C_6$) alkyl or benzyl, —C(OY$^2$)Y$^3$ wherein Y$^2$ is ($C_1$-$C_4$) alkyl and Y$^3$ is ($C_1$-$C_6$)alkyl; carboxy ($C_1$-$C_6$)alkyl; amino($C_1$-$C_4$)alkyl or mono-N— or di-N,N—($C_1$-$C_6$)alkylaminoalkyl; —C(Y$^4$)Y$^5$ wherein Y$^4$ is H or methyl and Y$^5$ is mono-N— or di-N,N—($C_1$-$C_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters, including those corresponding to both natural and non-natural amino acids (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvates, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Phosphate-Substituted Quinolizine Derivatives can form salts which are also within the scope of this invention. Reference to a Phosphate-Substituted Quinolizine Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Phosphate-Substituted Quinolizine Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Phosphate-Substituted Quinolizine Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), arylalkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Phosphate-Substituted Quinolizine Derivatives may be atropisomers (e.g., substituted biaryls) and are considered as part of this invention. Enantiomers can also be directly separated using chiral chromatographic techniques.

It is also possible that the Phosphate-Substituted Quinolizine Derivatives may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Phosphate-Substituted Quinolizine Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

The Phosphate-Substituted Quinolizine Derivatives may be useful in human and veterinary medicine for treating or preventing HIV infection in a subject. In one embodiment, the Phosphate-Substituted Quinolizine Derivatives can be inhibitors of HIV viral replication. In a specific embodiment, the Phosphate-Substituted Quinolizine Derivatives are inhibitors of HIV-1. Accordingly, the Phosphate-Substituted Quinolizine Derivatives may be useful for treating HIV infections and AIDS. In accordance with the invention, the Phosphate-Substituted Quinolizine Derivatives can be administered to a subject in need of treatment or prevention of HIV infection.

Accordingly, in one embodiment, the invention provides methods for treating HIV infection in a subject comprising administering to the subject an effective amount of at least one Phosphate-Substituted Quinolizine Derivative or a pharmaceutically acceptable salt thereof In a specific embodiment, the present invention provides methods for treating AIDS in a subject comprising administering to the subject an effective amount of at least one Phosphate-Substituted Quinolizine Derivative or a pharmaceutically acceptable salt thereof.

LIST OF ABBREVIATIONS

ACN=acetonitrile
AcOH=acetic acid
BnBr=benzyl bromide
$Boc_2O$=t-butyloxycarbonate anhydride
$Bu_3SnH$=tributyltin hydride
DCM=dichloromethane
Dess-Martin reagent=1,1,1-Triacetoxy-1,1-dihydro-1,2-benziodoxol-3(1H)-one
DIBAL=diisobutylaluminum hydride
DIPEA or DIEA=N,N-diisopropylethylamine
DMAP=dimethylamino pyridine
DMF=dimethylformamide
DMSO=dimethyl sulfoxide
$Et_2O$=diethylether
$NEt_3$ or $Et_3N$=triethylamine
Et=ethyl
EtOAc=ethyl acetate
EtOH=ethanol
HCl=hydrochloric acid
HPLC=high-pressure liquid chromatography
i-$Pr_2$Net=diisopropylethyl amine
LCMS=liquid chromatography-mass spectrometry
LDA=lithium diisopropylamide
MeCN=acetonitrile
MeOH=methyl alcohol
MS=mass spectroscopy
MeI=iodomethane
MOMCl=methyl chloromethyl ether
MSCl=methanesulfonyl chloride
NBS=N-bromosuccinimide
NHS=normal human serum
NMO=N-methylmorpholine-N-oxide
NMR=nuclear magnetic resonance spectroscopy
Pd/C=palladium on carbon
$Pd(PPh_3)_4$=tetrakis (triphenylphoshpine) palladium(0)
RPMI=Roswell Park Memorial Institute medium
rt=room temperature
$SiO_2$=silical gel
TBAF=tetra-n-butylammonium fluoride
TBDPSCl=tert-butyldiphenylsilyl chloride
TFA=trifluoroacetic acid
THF=tetrahydrofuran
TLC=thin-layer chromatography
TMSBr=trimethylsilyl bromide
$TMSN_3$=trimethylsilyl azide
TsCl=para-toluene sulfonyl chloride The Compounds of Formula (I)

The present invention provides Phosphate-Substituted Quinolizine Derivatives of Formula (I):

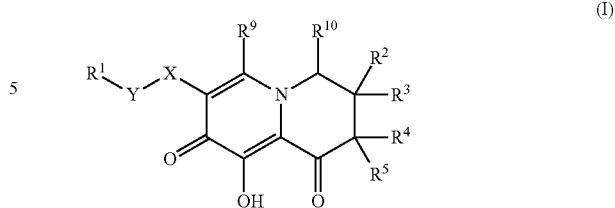

and pharmaceutically acceptable salts thereof, wherein X, Y, $R^1$, $R^2$, $R^3$, $R^4$, $R^5$, $R^9$ and $R^{10}$ are defined above for the Compounds of Formula (I).

In one embodiment, X is a single bond.

In another embodiment, X is —NHC(O)—.

In another embodiment, X is 5 or 6-membered heteroaryl.

In still another embodiment, X is 5-membered heteroaryl.

In another embodiment, X is 1,3,4-thiadiazole.

In one embodiment, Y is a single bond.

In another embodiment, Y is $C_1$-$C_3$ alkylene.

In another embodiment, Y is $CH_2$.

In one embodiment, X is —NHC(O)— and Y is $CH_2$.

In another embodiment, X is 5-membered heteroaryl and Y is $CH_2$.

In one embodiment, $R^1$ is optionally substituted $C_6$-$C_{10}$ aryl or optionally substituted 9 or 10-membered bicyclic heteroaryl.

In another embodiment, $R^1$ is optionally substituted $C_6$-$C_{10}$ aryl.

In another embodiment, $R^1$ is optionally substituted phenyl.

In one embodiment, $R^1$ is selected from:

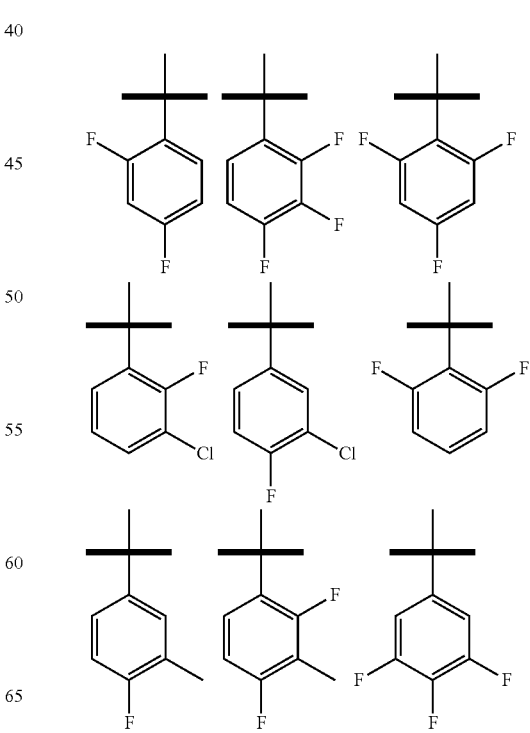

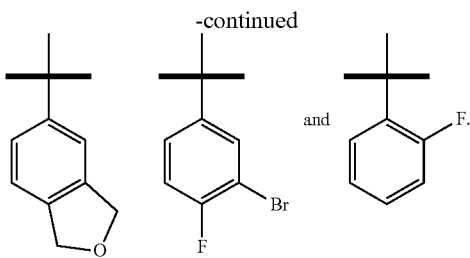

In another embodiment, $R^1$ is phenyl which is substituted with one or more halo groups.

In another embodiment, $R^1$ is phenyl which is substituted with 1-3 halo groups.

In still another embodiment, $R^1$ is phenyl which is substituted with one or two F groups.

In another embodiment, $R^1$ is 4-fluorophenyl.

In yet another embodiment, $R^1$ is 2,4-difluorophenyl.

In another embodiment, $R^1$ is 3-chloro-2-fluorophenyl.

In one embodiment, the group $R^1$—Y— is phenyl-$CH_2$—, wherein said phenyl group is substituted with 1-3 groups, independently selected from F and Cl.

In another embodiment, the group $R^1$—Y— is phenyl-$CH_2$—, wherein said phenyl group is substituted with one or two F groups.

In one embodiment, $R^2$ is H.

In another embodiment, $R^2$ is —O—($C_1$-$C_6$ alkylene)-O—($C_1$-$C_6$ alkyl).

In another embodiment, $R^2$ is —O—($C_1$-$C_6$ alkylene)$_m$-O—($C_1$-$C_6$ alkylene)$_m$-$R^{13}$.

In another embodiment, $R^2$ is —O—($C_1$-$C_6$ alkylene)$_m$-O—($C_1$-$C_6$ alkylene)$_m$-N($R^{22}$)$_2$.

In still another embodiment, $R^2$ is —O—($C_1$-$C_6$ alkylene)-O—($C_1$-$C_6$ alkylene)-$R^{13}$.

In another embodiment, $R^2$ is —O—($C_1$-$C_6$ alkylene)-O—($C_1$-$C_6$ alkylene)-N($R^{22}$)$_2$.

In one embodiment, $R^3$ is H.

In another embodiment, $R^3$ is —OH.

In one embodiment, $R^3$ is —O—($C_1$-$C_6$ alkyl).

In another embodiment, $R^3$ is methoxy.

In one embodiment, $R^2$ and $R^3$ are each independently H, —OH or —O—($C_1$-$C_6$ alkyl).

In another embodiment, $R^2$ is H and $R^3$ is —OH or —O—($C_1$-$C_6$ alkyl).

In another embodiment, $R^2$ is H and $R^3$ is methoxy.

In another embodiment, $R^4$ is H.

In another embodiment, $R^4$ is $C_1$-$C_6$ alkyl.

In another embodiment, $R^4$ is —($C_1$-$C_6$ alkylene)-O—($C_1$-$C_6$ alkyl).

In still another embodiment, $R^4$ is —O—($C_1$-$C_6$ alkylene)$_m$-O—($C_1$-$C_6$ alkylene)$_m$-$R^{13}$.

In another embodiment, $R^4$ is —O—($C_1$-$C_6$ alkylene)$_m$-O—($C_1$-$C_6$ alkylene)$_m$-N($R^{22}$)$_2$.

In another embodiment, $R^4$ is —O—($C_1$-$C_6$ alkylene)-O—($C_1$-$C_6$ alkylene)-$R^{13}$.

In yet another embodiment, $R^4$ is —O—($C_1$-$C_6$ alkylene)-O—($C_1$-$C_6$ alkylene)-N($R^{22}$)$_2$.

In still another embodiment, $R^4$ is methyl.

In another embodiment, $R^4$ is —$CH_2CH_2OCH_3$.

In one embodiment, $R^5$ is H.

In another embodiment, $R^5$ is $C_1$-$C_6$ alkyl.

In another embodiment, $R^5$ is —($C_1$-$C_6$ alkylene)-O—($C_1$-$C_6$ alkyl).

In another embodiment, $R^5$ is methyl.

In still another embodiment, $R^5$ is —$CH_2CH_2OCH_3$.

In one embodiment, $R^4$ and $R^5$ are each independently H, $C_1$-$C_6$ alkyl or —($C_1$-$C_6$ alkylene)-O—($C_1$-$C_6$ alkyl).

In another embodiment, $R^4$ and $R^5$ are each $C_1$-$C_6$ alkyl.

In still another embodiment, $R^4$ and $R^5$ are each methyl.

In one embodiment, $R^2$ and $R^4$, together with the carbon atoms to which they are attached, join to form a 5 to 8-membered monocyclic heterocycloalkyl group.

In one embodiment, $R^3$ is —O—($C_1$-$C_6$ alkyl) and $R^4$ is —($C_1$-$C_6$ alkylene)-O—($C_1$-$C_6$ alkyl).

In another embodiment, $R^{10}$ is H.

In another embodiment, $R^9$ and $R^{10}$ are each H.

In one embodiment, the compounds of formula (I) have the formula (Ia):

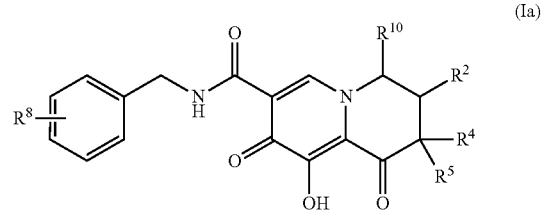

(Ia)

or a pharmaceutically acceptable salt thereof,
wherein
$R^2$, $R^4$, $R^5$ and $R^{10}$ are as defined above for the compounds of formula (I); and
$R^8$ represents from 1 to 3 phenyl group substituents, each independently selected from halo,
such that at least one —($C_1$-$C_6$ alkylene)$_m$-Z—$R^{13}$ group or at least one —N($R^{22}$)$_2$ group is present in the compound of formula (Ia), wherein m, Z, $R^{13}$ and $R^{22}$ are as defined above for the compounds of formula (I).

In one embodiment, for the compounds of formulas (I) or (Ia), $R^2$ and $R^4$, together with the carbon atoms to which they are attached, can join to form a 5 to 8-membered monocyclic heterocycloalkyl group, 5 to 8-membered monocyclic heterocycloalkenyl group or a 8 to 11-membered bicyclic heterocycloalkyl, wherein said 5 to 8-membered monocyclic heterocycloalkyl group, said 5 to 8-membered monocyclic heterocycloalkenyl group and said 8 to 11-membered bicyclic heterocycloalkyl group can be optionally substituted with up to three $R^8$ groups, which can be the same or different;

In one embodiment, for the compounds of formulas (I) or (Ia), $R^2$ and $R^4$, together with the carbon atoms to which they are attached, join to form a 5 to 8-membered monocyclic heterocycloalkyl group, and $R^5$ is H.

In another embodiment, for the compounds of formulas (I) or (Ia), $R^2$ and $R^4$, together with the carbon atoms to which they are attached, join to form a 5 to 8-membered monocyclic heterocycloalkyl group, and $R^5$ is methyl.

In another embodiment, for the compounds of formulas (I) or (Ia), $R^2$ and $R^4$, together with the carbon atoms to which they are attached, join to form a 6-membered monocyclic heterocycloalkyl group.

In still another embodiment, for the compounds of formulas (I) or (Ia), $R^2$ and $R^4$, together with the carbon atoms to which they are attached, join to form a 5-membered monocyclic heterocycloalkyl group.

In another embodiment, for the compounds of formulas (I) or (Ia), $R^2$ and $R^4$, together with the carbon atoms to which they are attached, join to form a 1,3-dioxane group or a 1,4-dioxane group.

In one embodiment, for the compounds of formulas (I) or (Ia), $R^2$ and $R^4$, together with the carbon atoms to which they are attached, join to form a group selected from:

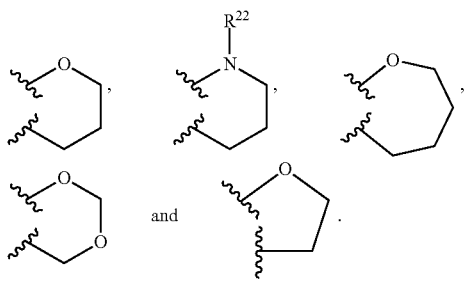

In another embodiment, for the compounds of formulas (I) or (Ia), $R^2$ and $R^4$, together with the carbon atoms to which they are attached, join to form a group selected from:

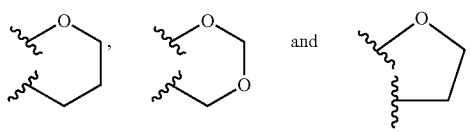

In another embodiment, for the compounds of formulas (I) or (Ia), $R^2$ and $R^4$, together with the carbon atoms to which they are attached, join to form the following group:

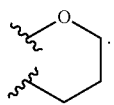

In one embodiment, for the compounds of formulas (I) or (Ia), $R^5$ is H or methyl; and $R^2$ and $R^4$, together with the carbon atoms to which they are attached, join to form a group selected from:

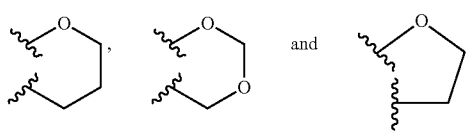

In another embodiment, for the compounds of formulas (I) or (Ia), $R^5$ is methyl; and $R^2$ and $R^4$, together with the carbon atoms to which they are attached, join to form a group having the structure:

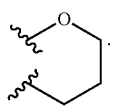

In one embodiment, for the compounds of formula (I) or (Ia), $R^2$ is $-(C_1-C_6 \text{ alkylene})_m-Z-(C_1-C_6 \text{ alkylene})_m-R^{13}$ or $-N(R^{22})_2$.

In another embodiment, for the compounds of formula (I) or (Ia), $R^4$ is $-(C_1-C_6 \text{ alkylene})_m-Z-(C_1-C_6 \text{ alkylene})_m-R^{13}$ or $-N(R^{22})_2$.

In another embodiment, for the compounds of formula (I) or (Ia), $R^{10}$ is $-(C_1-C_6 \text{ alkylene})_m-Z-(C_1-C_6 \text{ alkylene})_m-R^{13}$ or $-N(R^{22})_2$.

In one embodiment, for the compounds of formula (I) or (Ia), $R^2$ and $R^4$, together with the carbon atoms to which they are attached, join to form a 5 to 8-membered monocyclic heterocycloalkyl group, which is substituted with at least one $-(C_1-C_6 \text{ alkylene})_m-Z-R^{13}$ group or at least one $-N(R^{22})_2$ group.

In another embodiment, for the compounds of formula (I) or (Ia), $R^2$ and $R^4$, together with the carbon atoms to which they are attached, join to form:

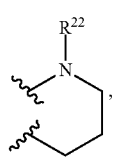

which is substituted on the nitrogen ring atom with $-(C_1-C_6 \text{ alkylene})_m-Z-(C_1-C_6 \text{ alkylene})_m-R^{13}$ or on a carbon ring atom with $-N(R^{22})_2$.

In one embodiment, for the compounds of formula (I) or (Ia), the $R^{13}$ moiety of a $-(C_1-C_6 \text{ alkylene})_m-Z-R^{13}$ group and/or an $-N(R^{22})_2$ group present in a compound of formula (I) or (Ia) is selected from: $-P(O)(-OH)_2$, $-P(O)(-OCH_3)_2$, $-P(O)(-OCH_2CH_3)_2$, $-P(O)(-CH_2OC(O)O-CH(CH_3)_2)_2$, $-P(O)(-CH_2OC(O)O-CH_2CH_3)_2$ and

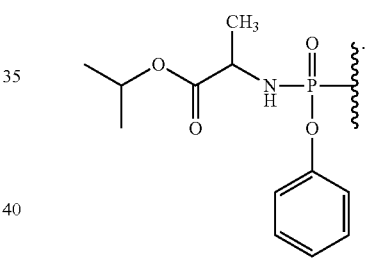

In one embodiment, variables X, Y, $R^1$, $R^2$, $R^3$, $R^4$, $R^5$, $R^9$ and $R^{10}$ for the Compounds of Formula (I) are selected independently of each other.

It is to be understood that any of the aforementioned embodiments can be combined with one or more separate embodiments.

In another embodiment, the Compounds of Formula (I) are in substantially purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of HIV antiviral agents, immunomodulators, and anti-infective agents.

(c) The pharmaceutical composition of (b), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(d) A pharmaceutical combination that is (i) a Compound of Formula (I) and (ii) a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.

(e) The combination of (d), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(f) A method of inhibiting HIV replication in a subject in need thereof which comprises administering to the subject an effective amount of a Compound of Formula (I).

(g) A method of treating HIV infection and/or reducing the likelihood or severity of symptoms of HIV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HIV antiviral agents, immunomodulators, and anti-infective agents.

(i) The method of (h), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine, (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (k) above are understood to include all embodiments of the compounds, including such embodiments as result from combinations of embodiments.

The Compounds of Formula (I) may be referred to herein by chemical structure and/or by chemical name. In the instance that both the structure and the name of a Compound of Formula (I) are provided and a discrepancy is found to exist between the chemical structure and the corresponding chemical name, it is understood that the chemical structure will predominate.

Non-limiting examples of the Compounds of Formula (I) include compounds 1-31 as set forth immediately below, and pharmaceutically acceptable salts thereof. Additional Non-limiting examples of the Compounds of Formula (I) include compounds 32-110 as set forth in the Examples below, and pharmaceutically acceptable salts thereof.

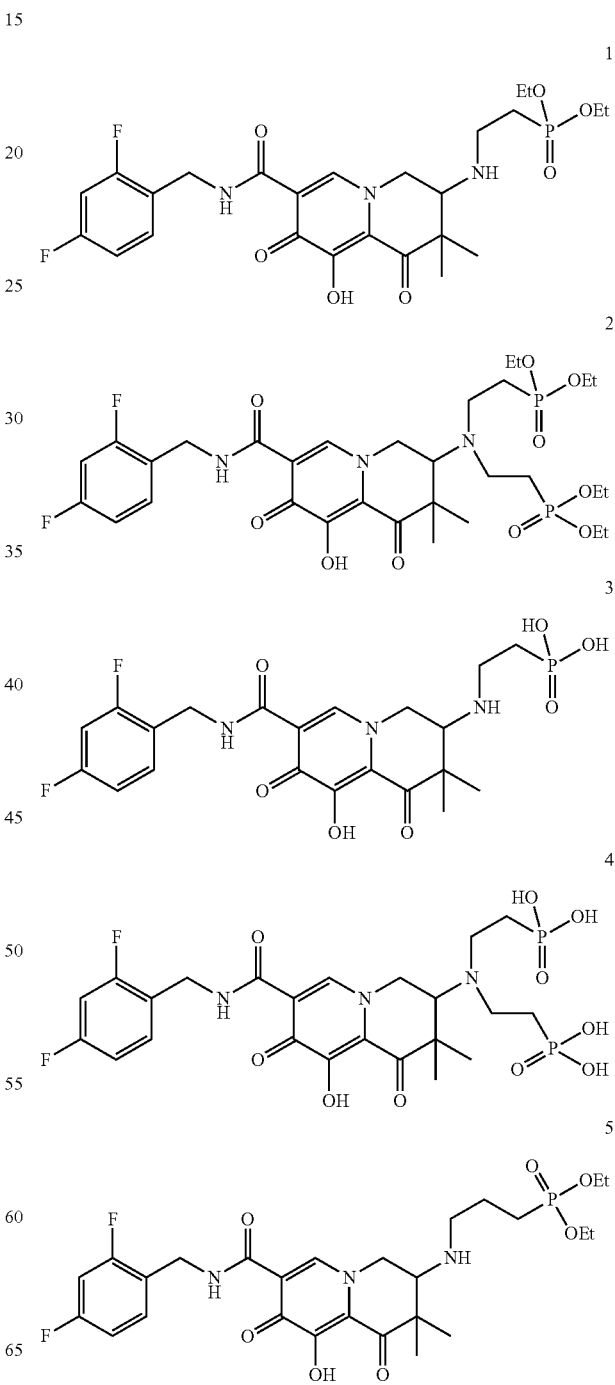

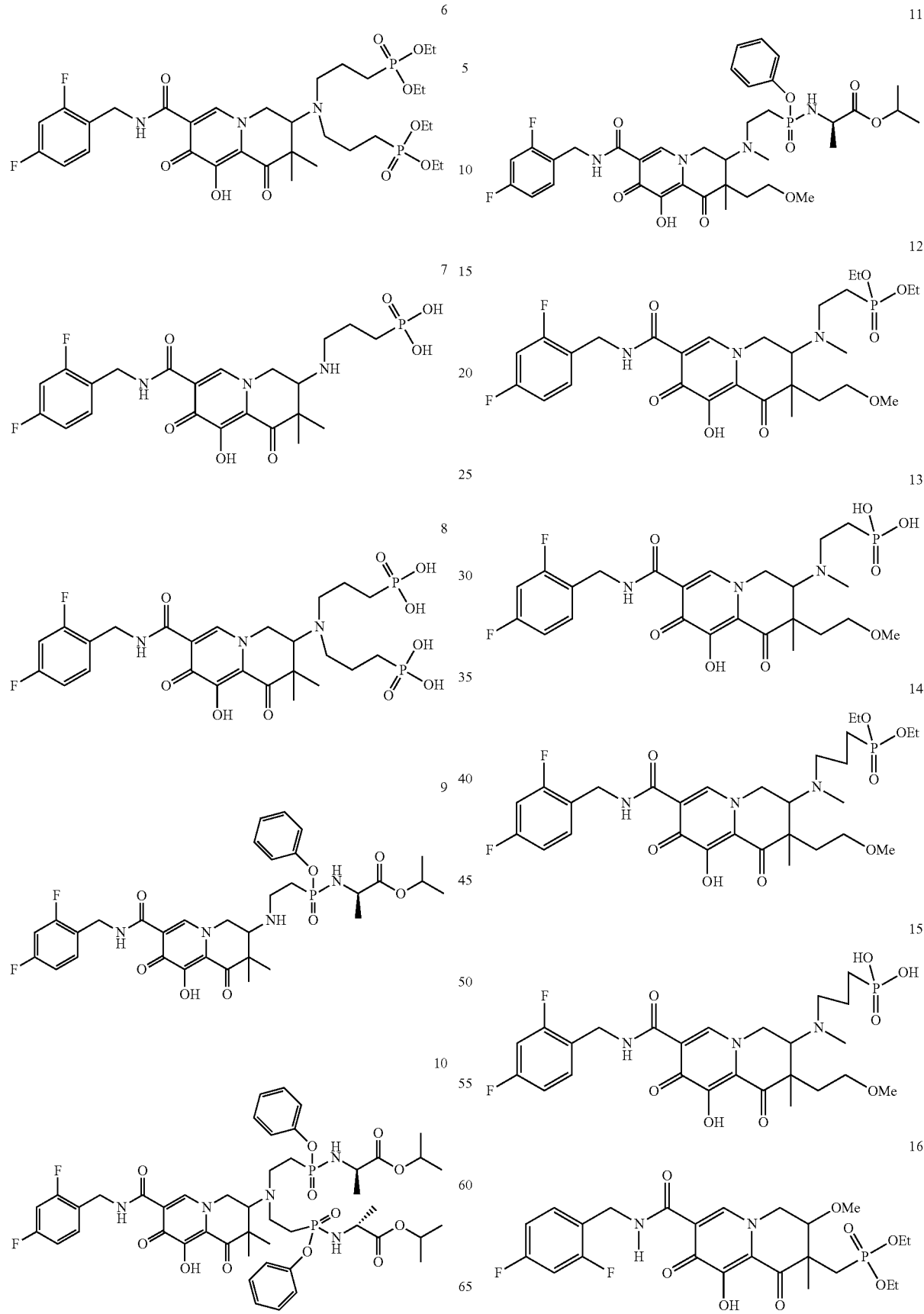

17
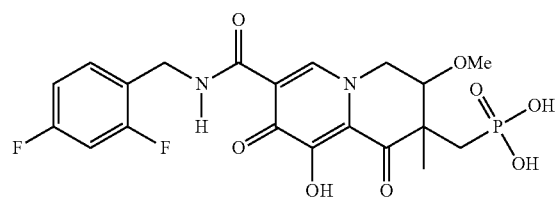
18
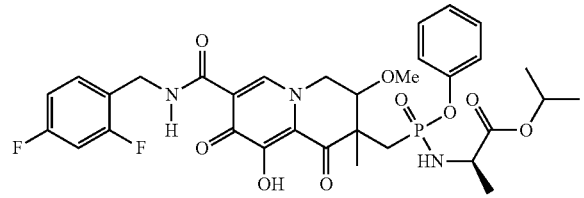
19
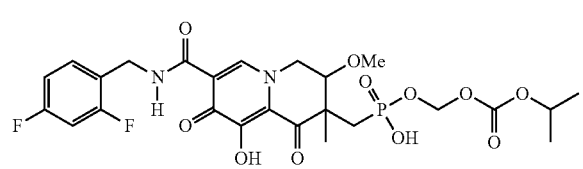
20
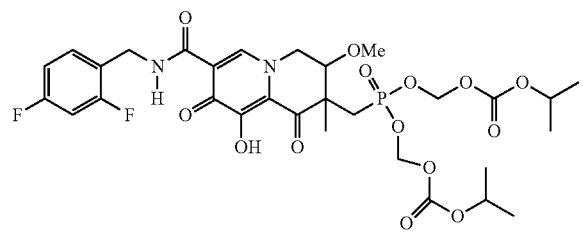
21
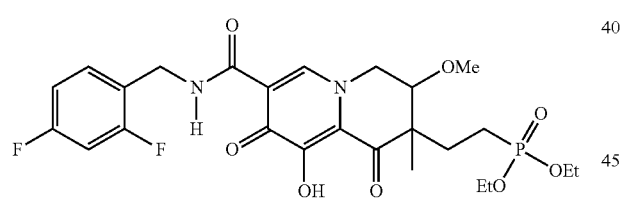
22
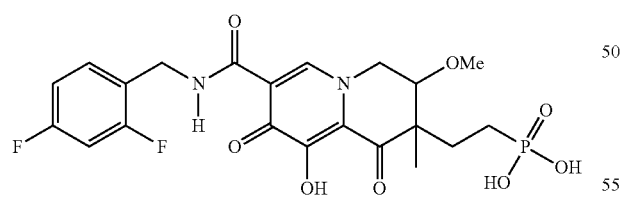
23
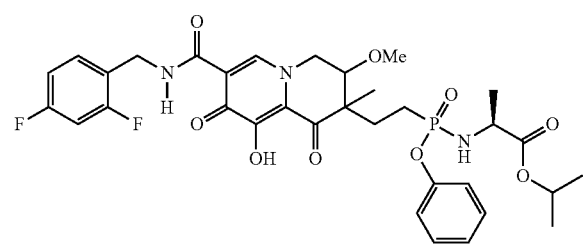
24
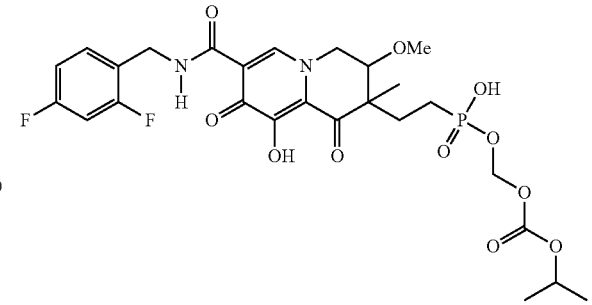
25
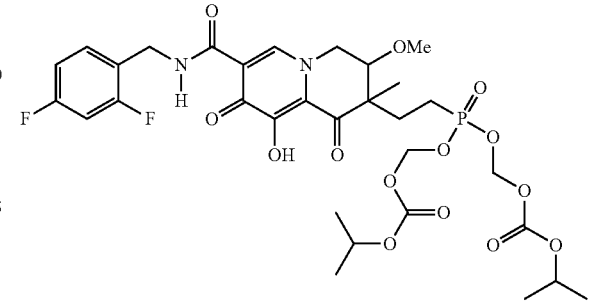
26
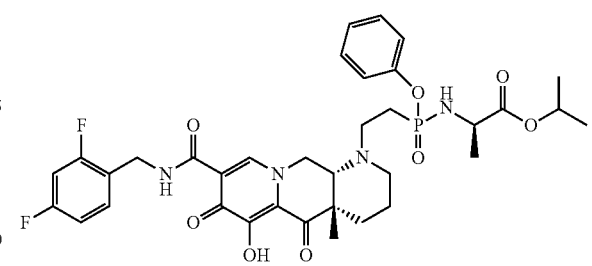
27
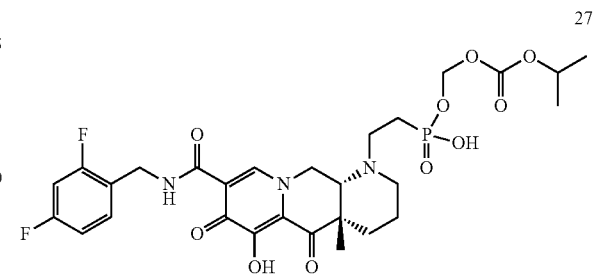
28
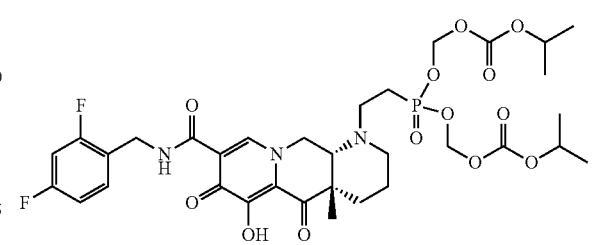

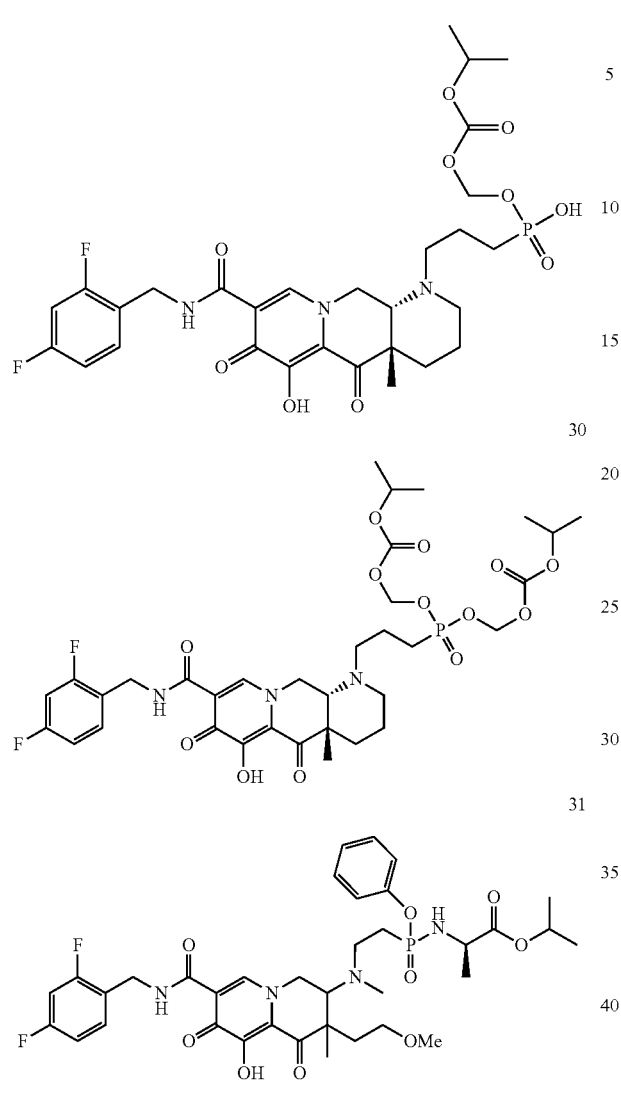

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in Schemes 1-15 below and in the Examples below. Illustrative compounds 1-31 of the present invention may be made using the methods set forth in Schemes 1-15 below. Alternative synthetic pathways and analogous structures will be apparent to those skilled in the art of organic synthesis.

Scheme 1

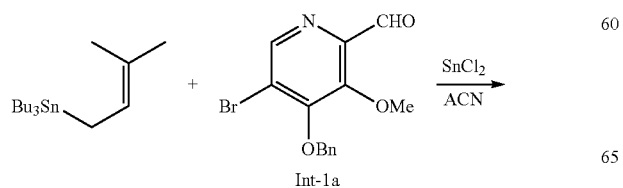

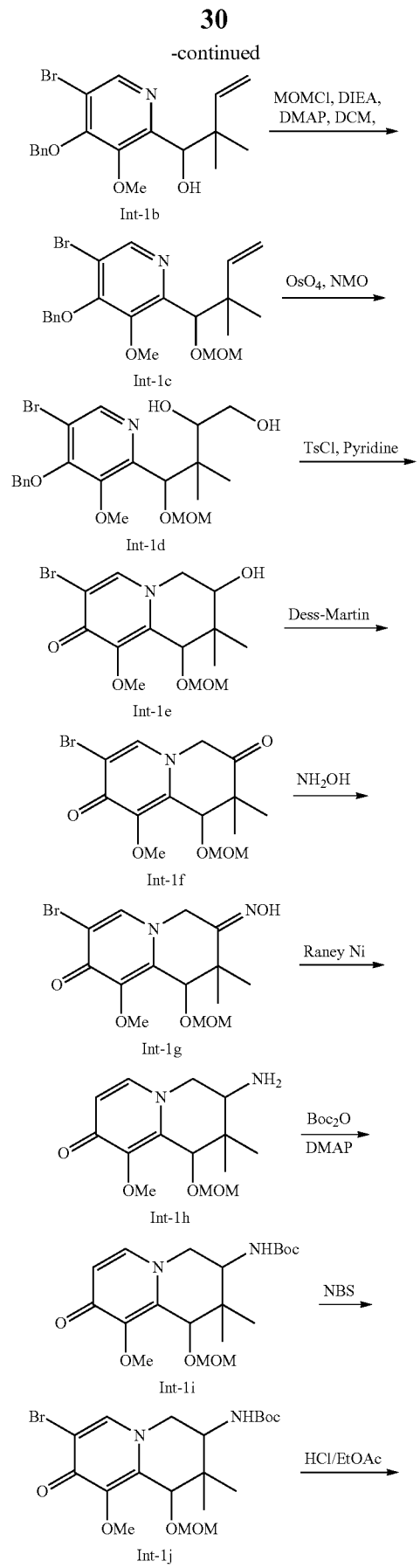

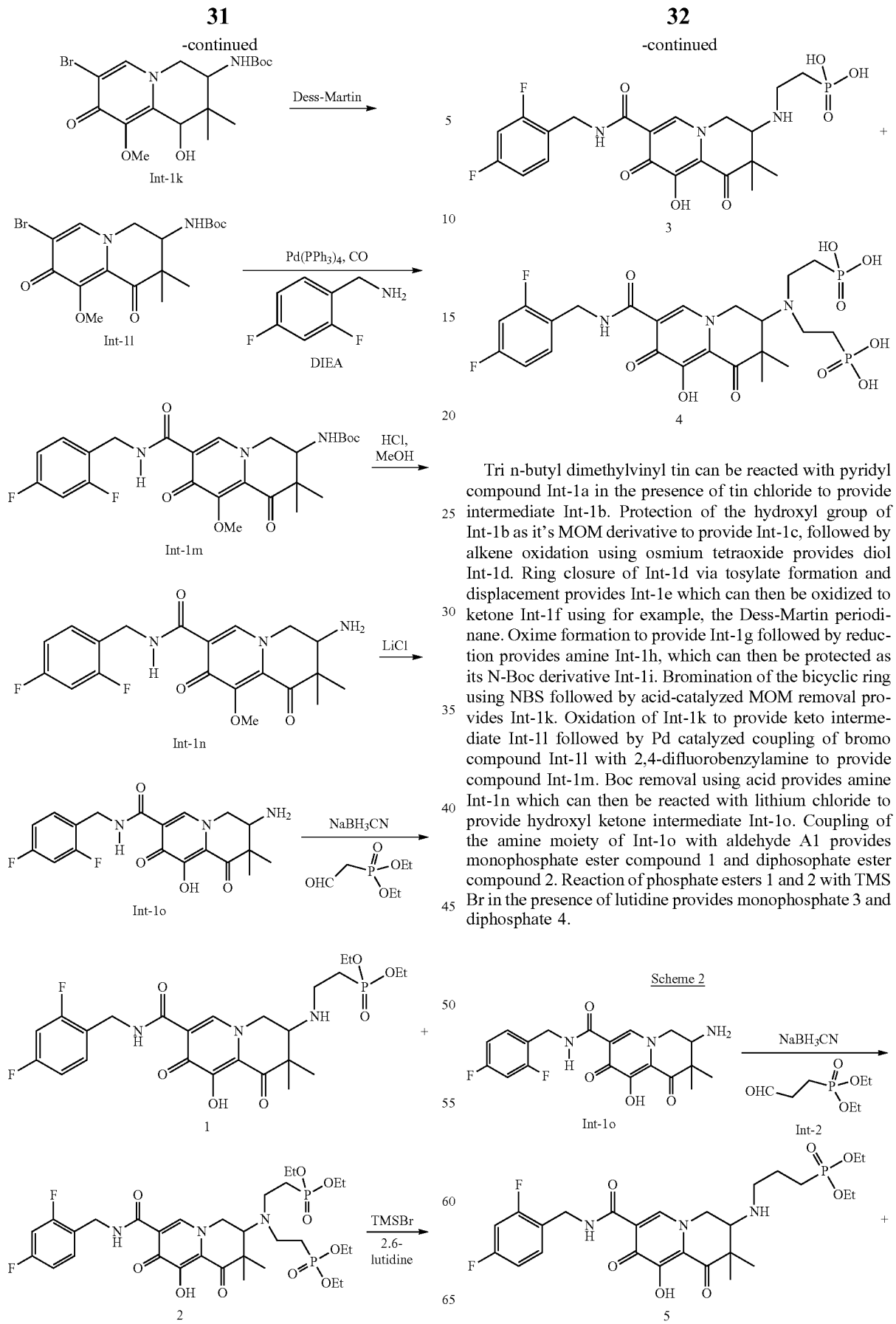

Tri n-butyl dimethylvinyl tin can be reacted with pyridyl compound Int-1a in the presence of tin chloride to provide intermediate Int-1b. Protection of the hydroxyl group of Int-1b as it's MOM derivative to provide Int-1c, followed by alkene oxidation using osmium tetraoxide provides diol Int-1d. Ring closure of Int-1d via tosylate formation and displacement provides Int-1e which can then be oxidized to ketone Int-1f using for example, the Dess-Martin periodinane. Oxime formation to provide Int-1g followed by reduction provides amine Int-1h, which can then be protected as its N-Boc derivative Int-1i. Bromination of the bicyclic ring using NBS followed by acid-catalyzed MOM removal provides Int-1k. Oxidation of Int-1k to provide keto intermediate Int-1l followed by Pd catalyzed coupling of bromo compound Int-1l with 2,4-difluorobenzylamine to provide compound Int-1m. Boc removal using acid provides amine Int-1n which can then be reacted with lithium chloride to provide hydroxyl ketone intermediate Int-1o. Coupling of the amine moiety of Int-1o with aldehyde A1 provides monophosphate ester compound 1 and diphosophate ester compound 2. Reaction of phosphate esters 1 and 2 with TMS Br in the presence of lutidine provides monophosphate 3 and diphosphate 4.

-continued
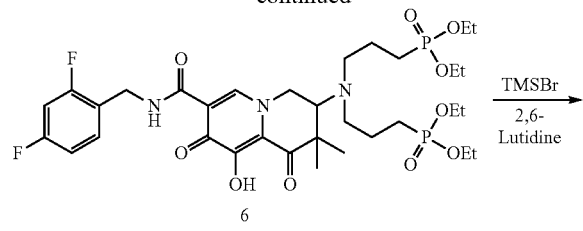
6
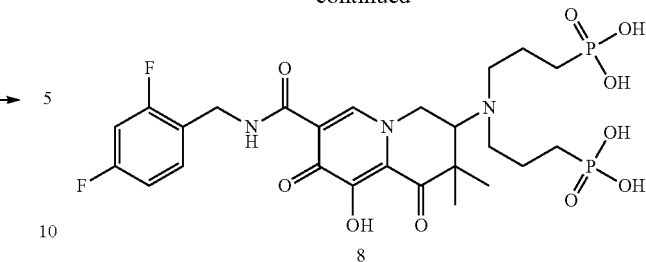
8
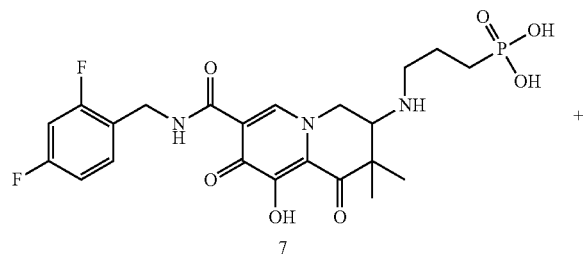
7
Coupling of the amine moiety of Int-1o with aldehyde A2, using methods described in Scheme 1 above, provides monophosphate ester compound 5 and diphosophate ester compound 6. Reaction of phosphate esters 5 and 6 with TMSBr in the presence of lutidine provides monophosphate 7 and diphosphate 8.
Scheme 3
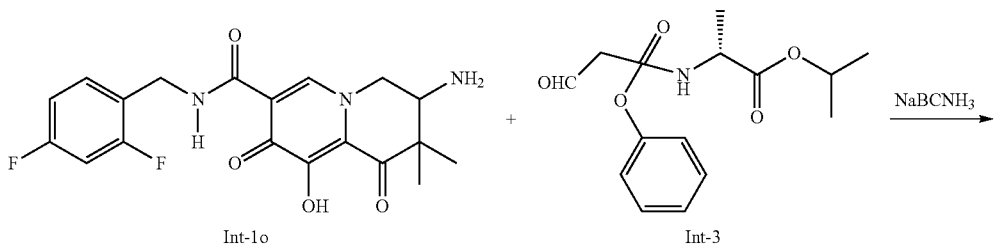
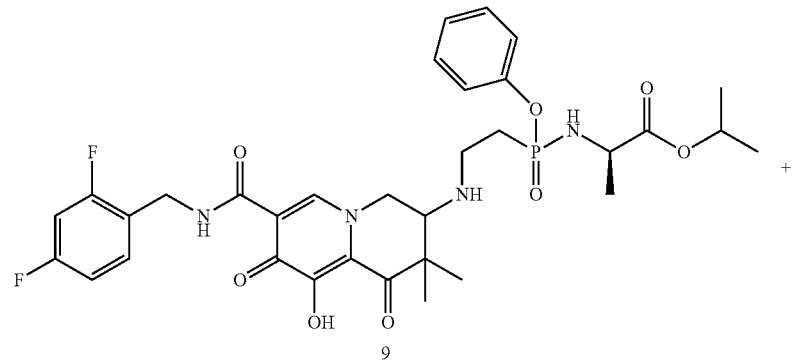
9
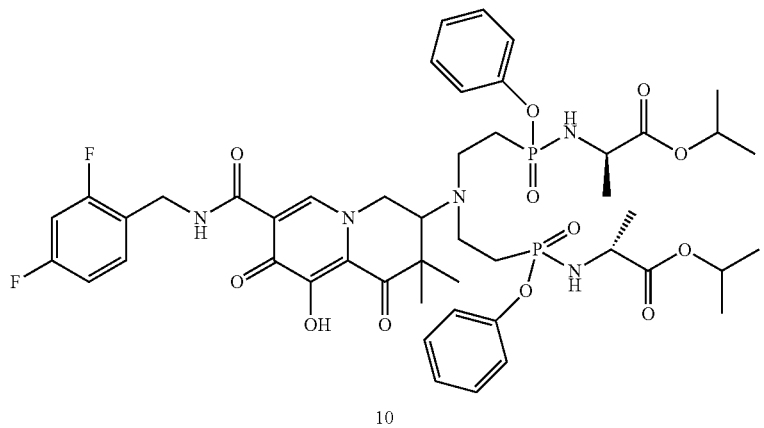
10

Coupling of the amine moiety of Int-1o with Int-3 (made using the methods described in International Publication No. WO 04/096237), using methods described in Scheme 1 above, provides monophosphoramidate compound 9 and diphosphoramidate compound 10.
Scheme 4
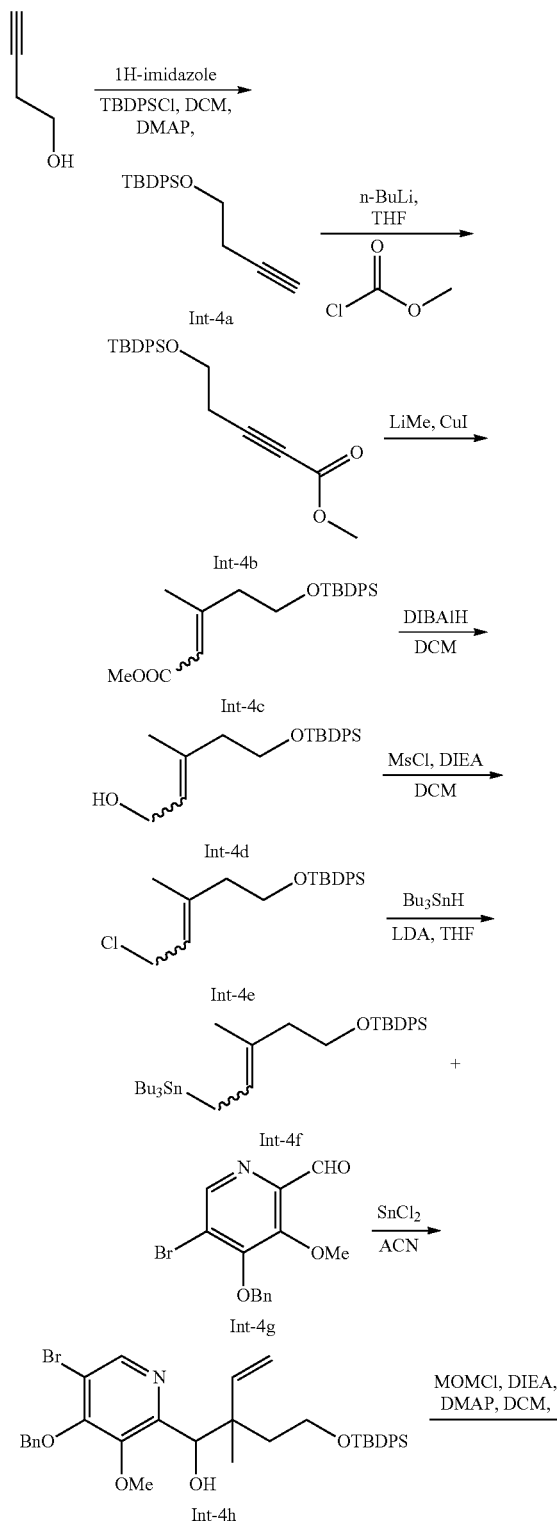
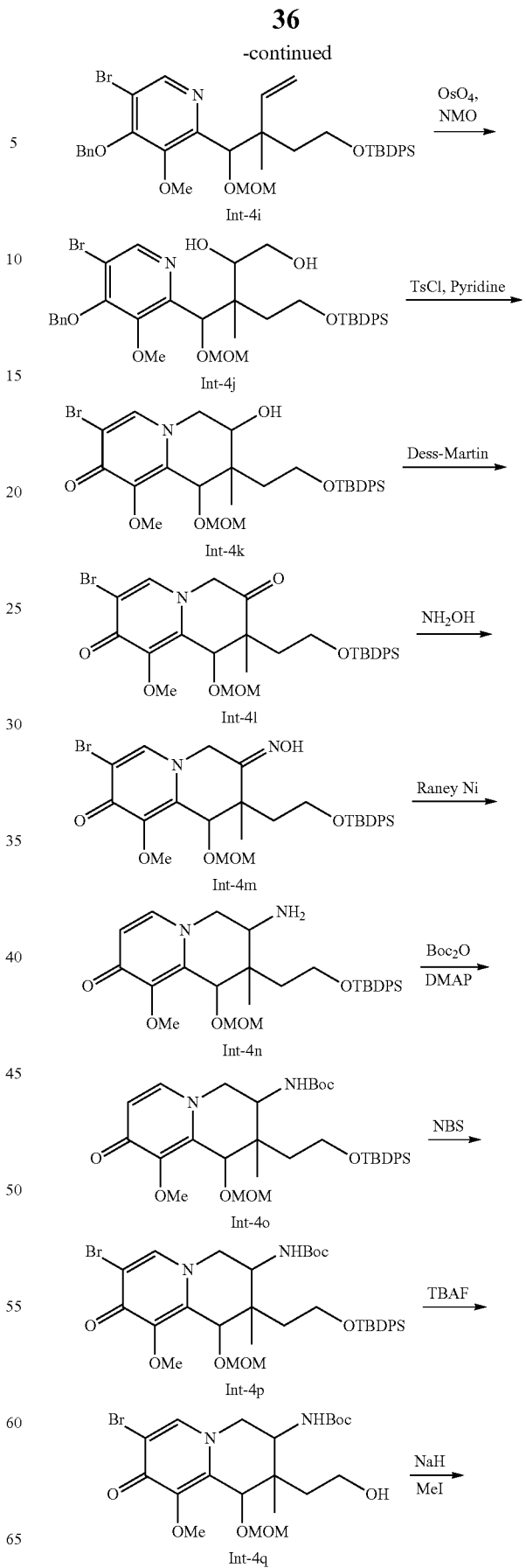

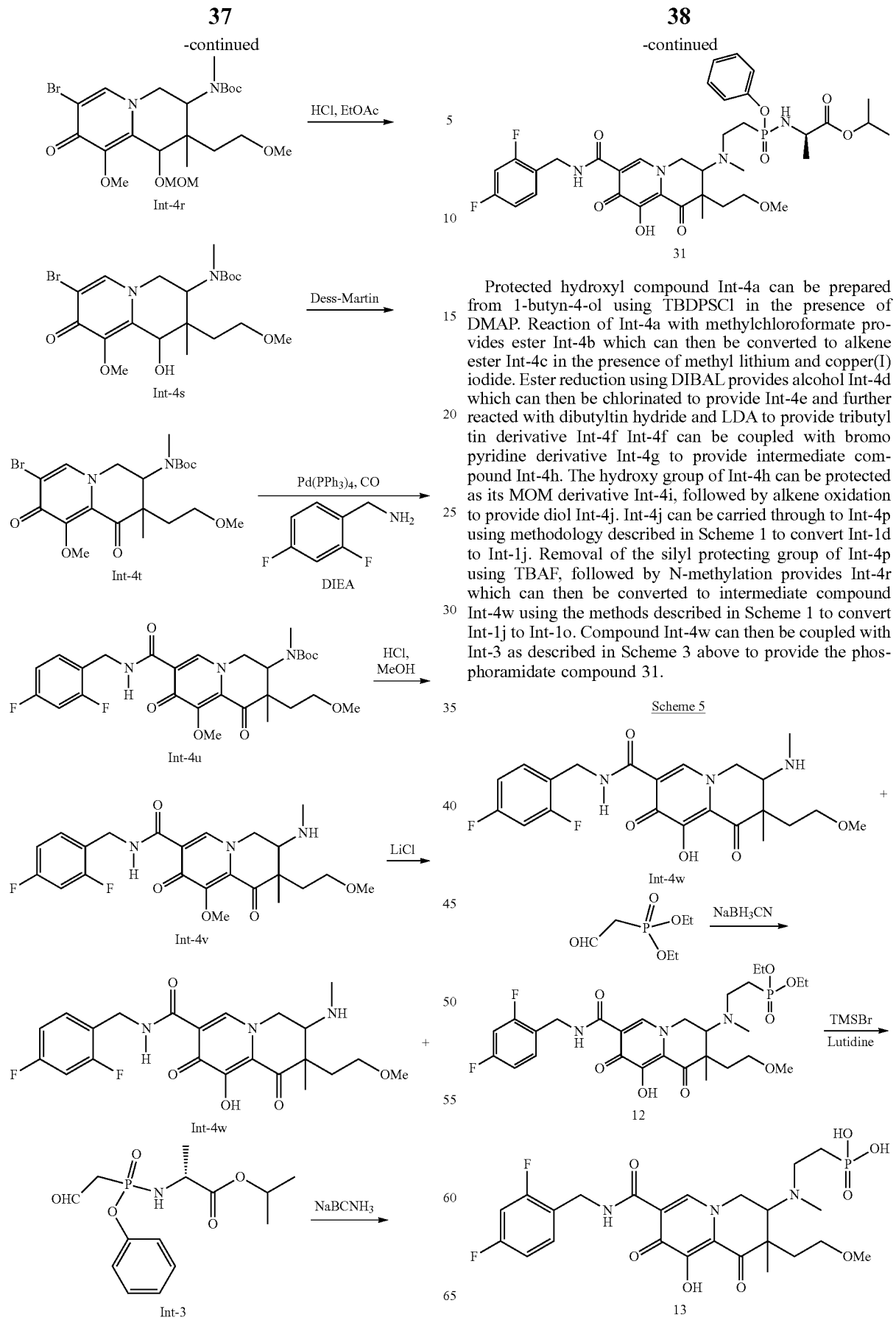

Protected hydroxyl compound Int-4a can be prepared from 1-butyn-4-ol using TBDPSCl in the presence of DMAP. Reaction of Int-4a with methylchloroformate provides ester Int-4b which can then be converted to alkene ester Int-4c in the presence of methyl lithium and copper(I) iodide. Ester reduction using DIBAL provides alcohol Int-4d which can then be chlorinated to provide Int-4e and further reacted with dibutyltin hydride and LDA to provide tributyl tin derivative Int-4f Int-4f can be coupled with bromo pyridine derivative Int-4g to provide intermediate compound Int-4h. The hydroxy group of Int-4h can be protected as its MOM derivative Int-4i, followed by alkene oxidation to provide diol Int-4j. Int-4j can be carried through to Int-4p using methodology described in Scheme 1 to convert Int-1d to Int-1j. Removal of the silyl protecting group of Int-4p using TBAF, followed by N-methylation provides Int-4r which can then be converted to intermediate compound Int-4w using the methods described in Scheme 1 to convert Int-1j to Int-1o. Compound Int-4w can then be coupled with Int-3 as described in Scheme 3 above to provide the phosphoramidate compound 31.

Scheme 5

Coupling of the amine moiety of Int-4w with aldehyde A1, using methods described in Scheme 1 above, provides phosphate ester compound 12 which can then be converted to phosphate compound 13 using TMSBr in the presence of lutidine.

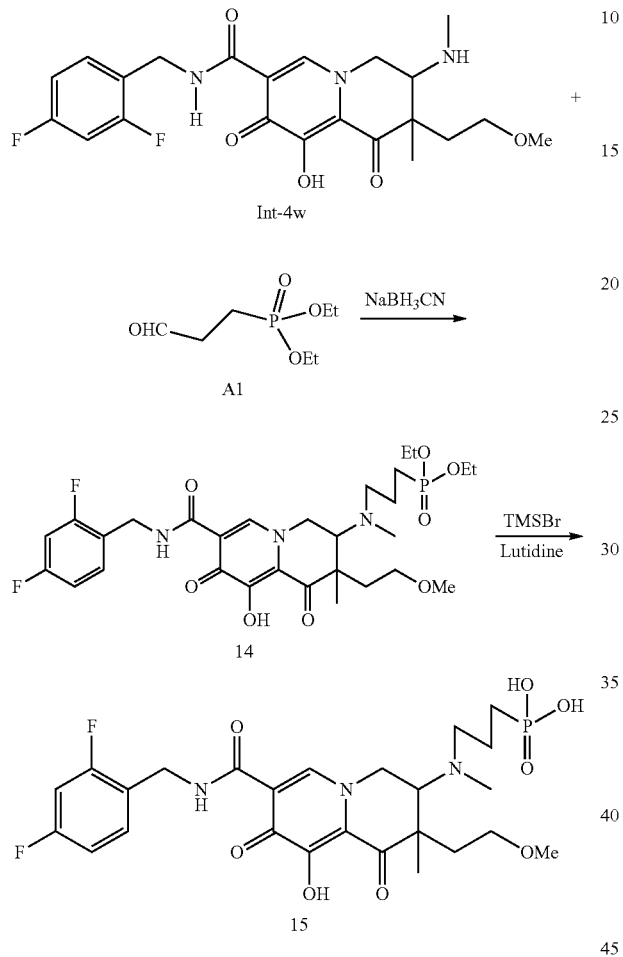

Coupling of the amine moiety of Int-4w with aldehyde A2, using methods described in Scheme 2 above, provides phosphate ester compound 14 which can then be converted to phosphate compound 15 using TMSBr in the presence of lutidine.

Scheme 7

Ref: Zhao, Yu-jun and Loh, Teck-Peng
Tetrahedron, 64(22), 4972-4978; 2008

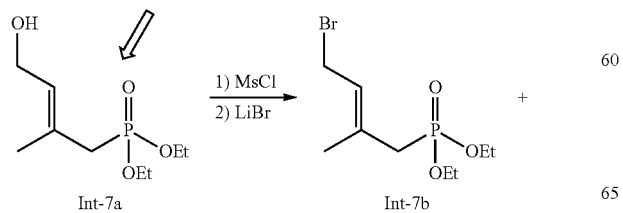

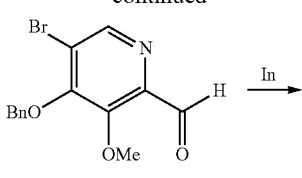

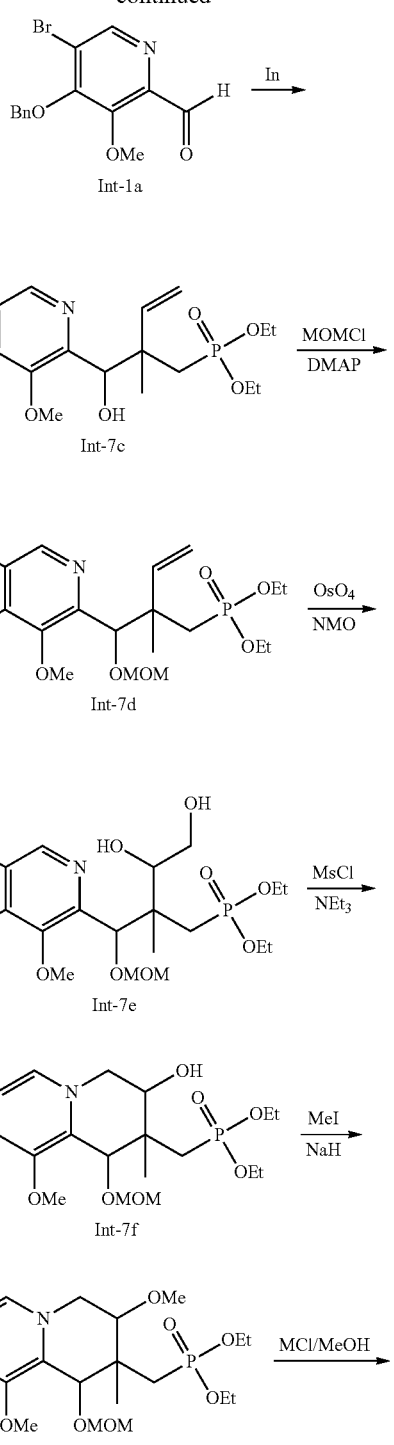

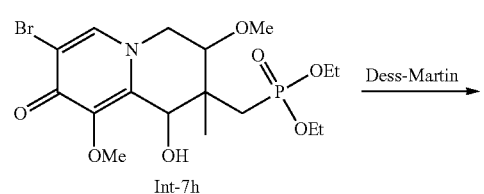

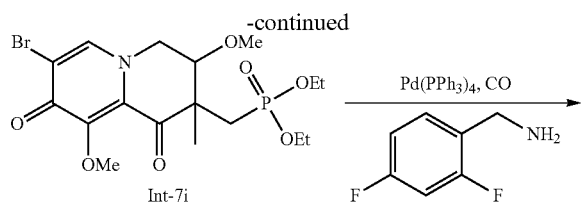

Int-7i

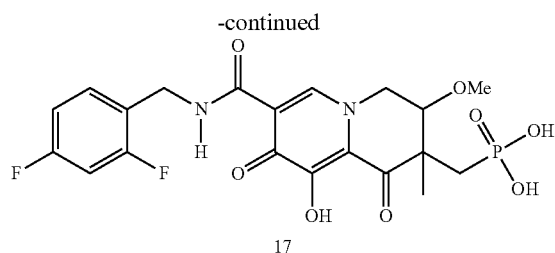

17

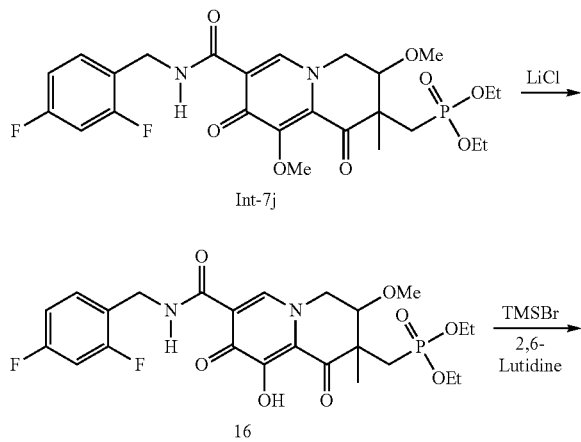

Int-7j

16

Int-7a (made using the methods described in Zhao, et al., *Tetrahedron* 64(22), 4972-4978 (2008)) can be converted to its bromo derivative Int-7b which is then coupled with Int-1a to provide alkene Int-7c. Protection of the hydroxyl group of Int-7c as its MOM derivative to provide Int-7d, followed by alkene oxidation using osmium tetraoxide provides diol Int-7e. Ring closure of Int-7e via mesylate formation and displacement provides Int-7f which can then be methylated to methoxy intermediate Int-7, which can then be oxidized to ketone Int-7h using for example, the Dess-Martin periodinane. Oxidation of Int-7g to provide keto intermediate Int-7h followed by Pd catalyzed coupling of bromo compound Int-7i with 2,4-difluorobenzylamine provides compound Int-7j. Int-7j can then be reacted with lithium chloride to provide hydroxyl ketone compound 16. Reaction of the phosphate ester of 16 with TMS Br in the presence of lutidine provides monophosphate 17.

Scheme 8

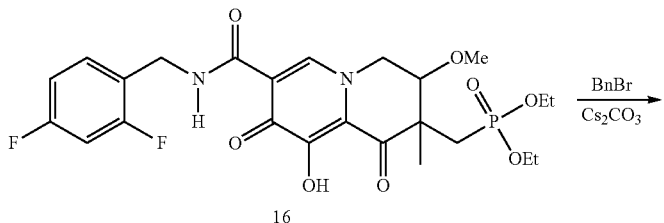

16

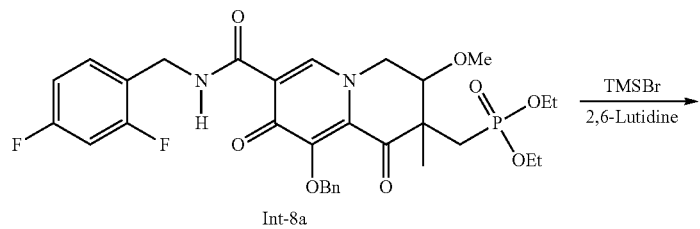

Int-8a

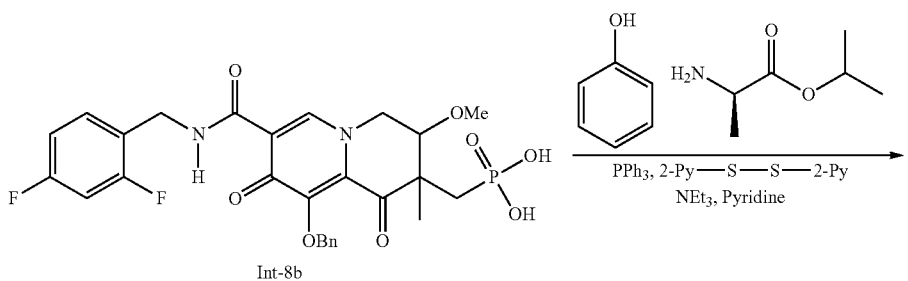

Int-8b

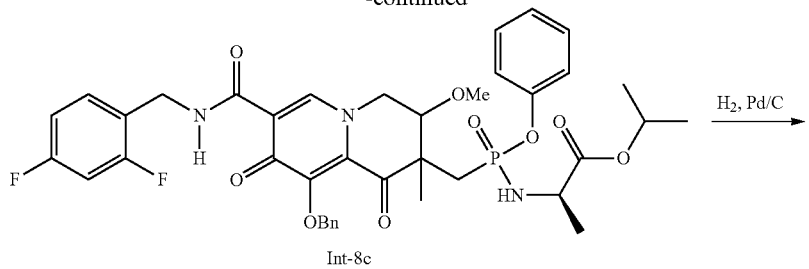
Int-8c
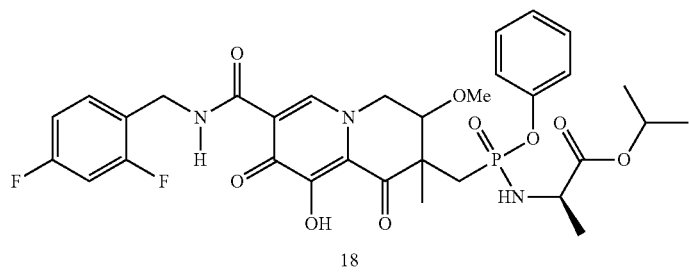
18
The hydroxy group of compound 16 can be protected as its benzyl derivative (Int-8a), followed by reduction of phosphate ester to provide the phosphate intermediate Int-8b. Reaction of Int-11B with alanine and phenol provides phosphoramidate compound Int-8c which is then deprotected using catalytic hydrogenation to provide compound 18.
Scheme 9
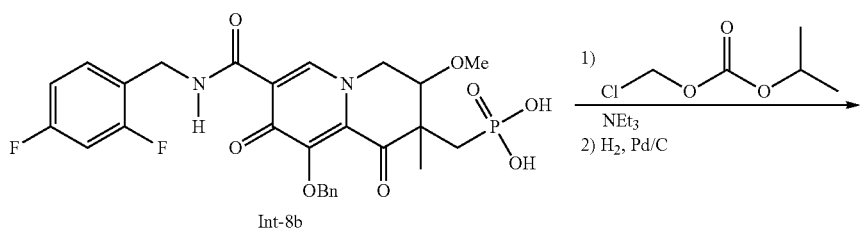
Int-8b
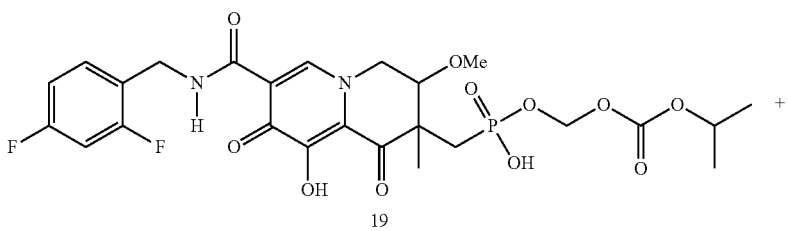
19
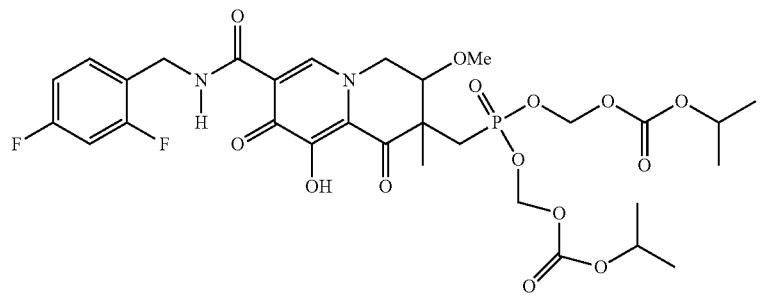
20

Reaction of the phosphate group of O-benzyl intermediate compound Int-8b with chloromethyl isopropyl carbonate, followed by benzyl group removal using catalytic hydrogenation can provide monocarbonate ester 19 and dicarbonate ester 20.

Scheme 10

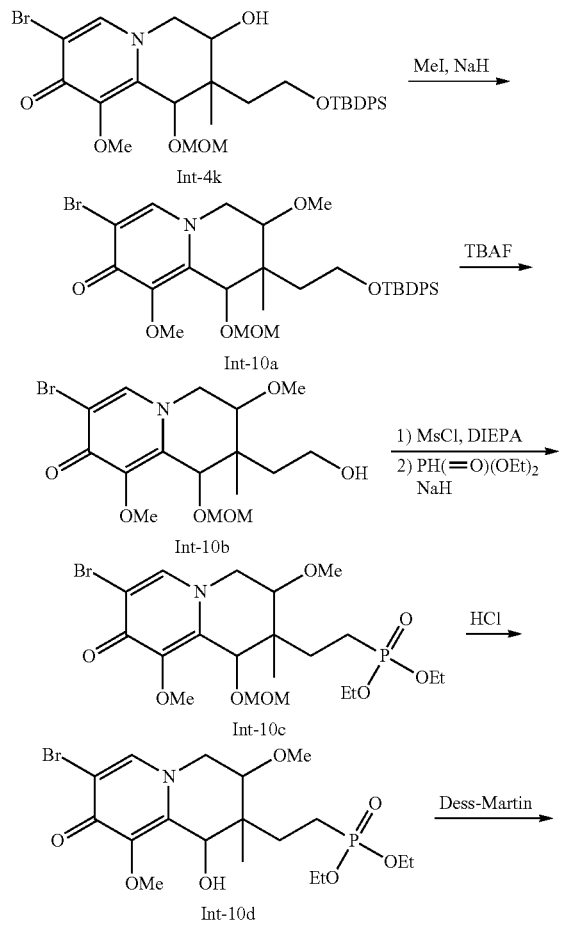

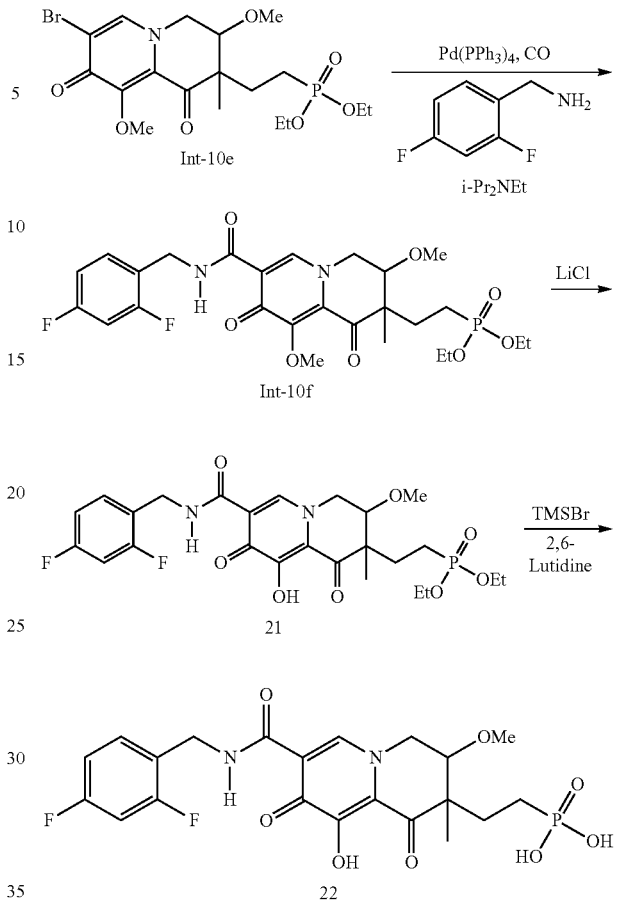

Methylation of the hydroxy group of Int-4k provides methoxy compound Int-10a which can then be treated with TBAF to provide primary alcohol Int-10b. Conversion of the hydroxyl group of Int-10b to its mesyl derivative followed by reaction with diethyl phosphonate provides phosphate ester Int-10c. Conversion of Int-10c to compound 22 can be achieved using the methods described in Scheme 10.

Scheme 11

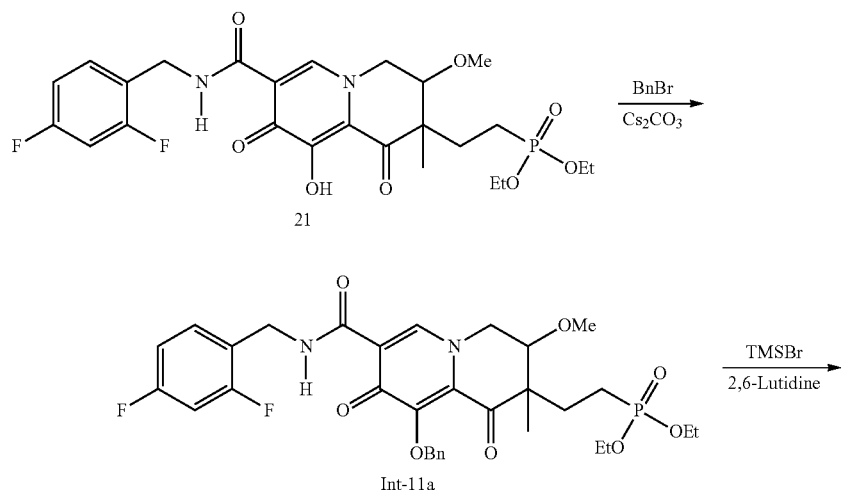

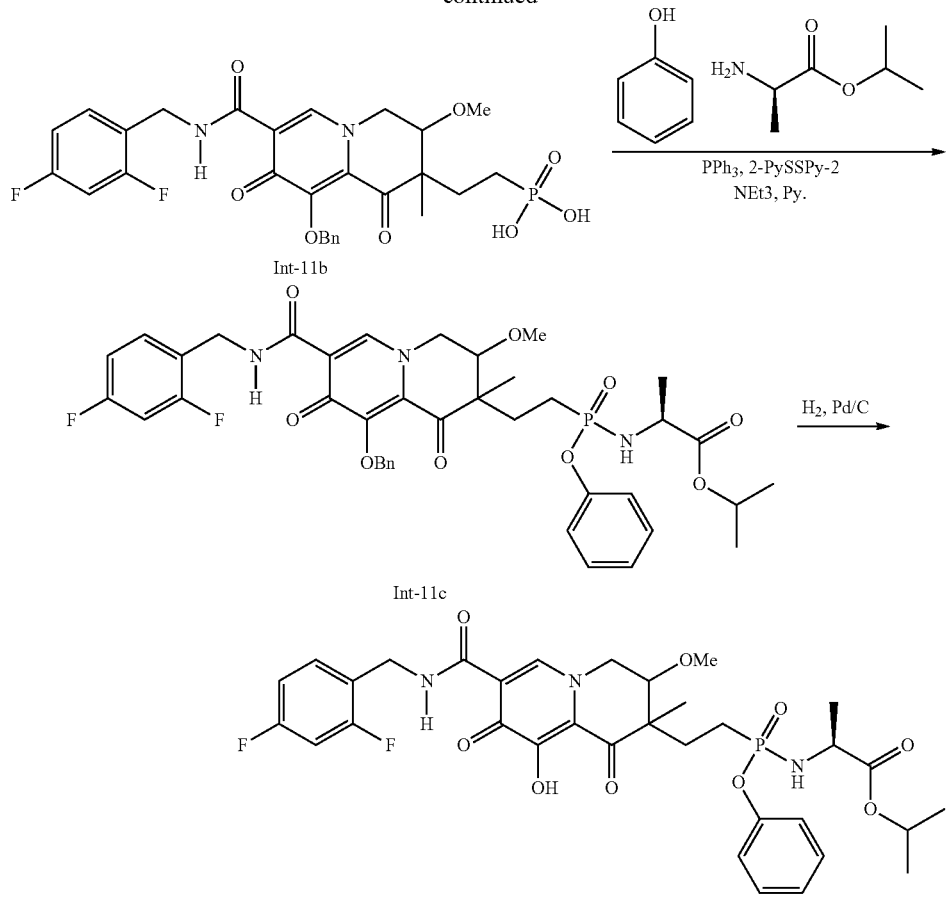
Protection of the hydroxy group of compound 21 as its benzyl derivative (Int-11a), followed by reduction of phosphate ester provides phosphate intermediate Int-11b. Int-11B can then be reacted with alanine and phenol to provide phosphoramidate compound Int-11c which can then be deprotected using catalytic hydrogenation to provide compound 23.
Scheme 12
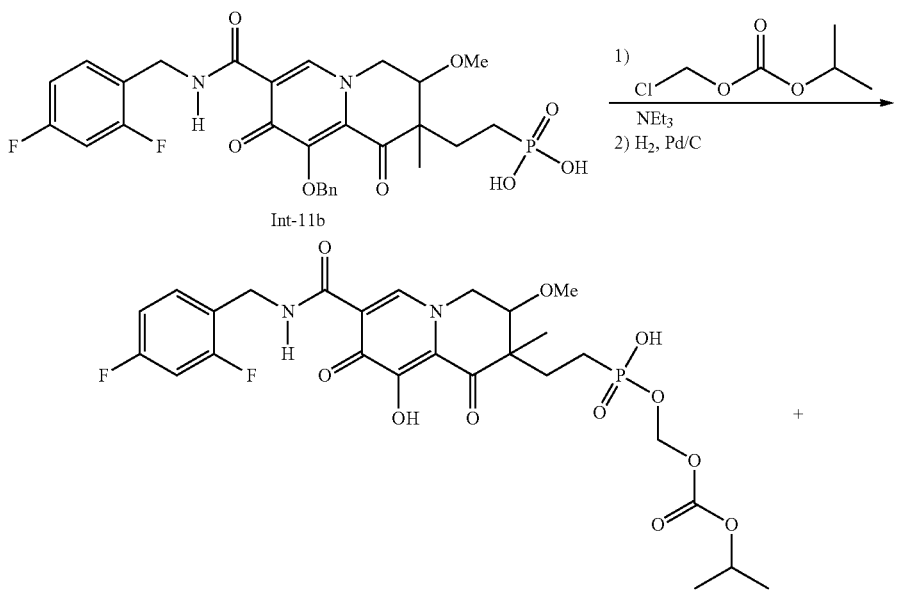

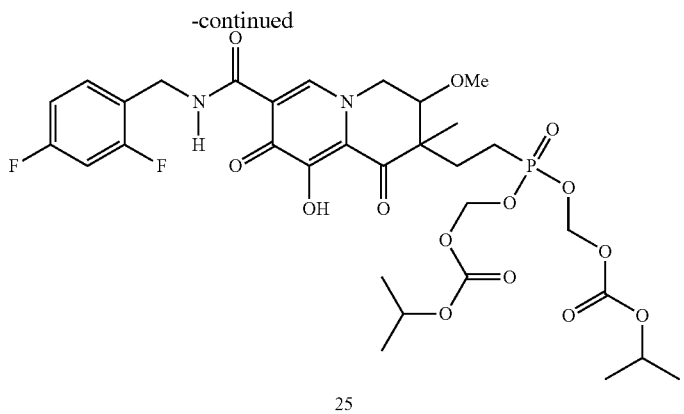
25
Int-11 can be converted to compounds 24 and 25 using the methods described above in Scheme 9.
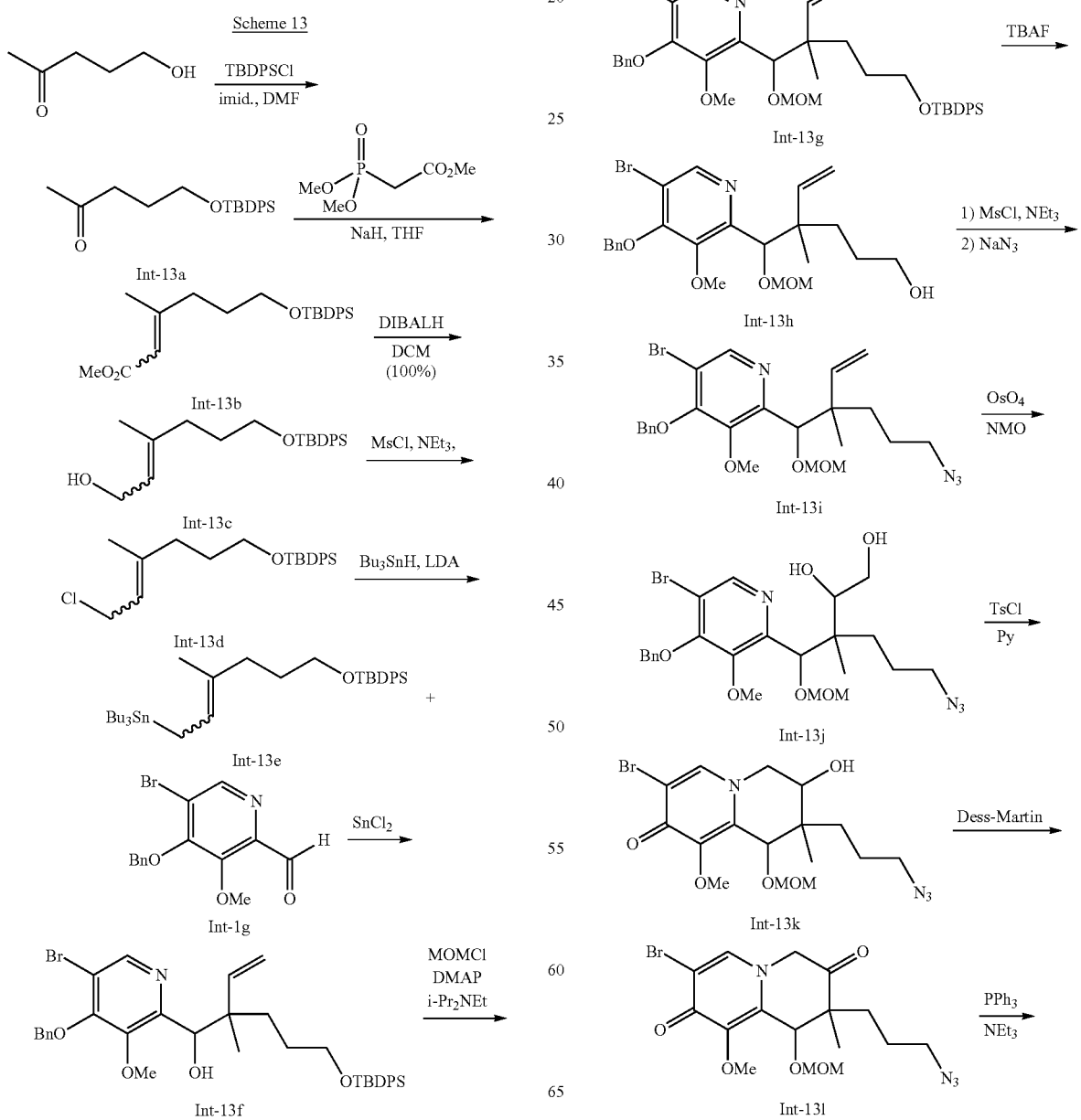

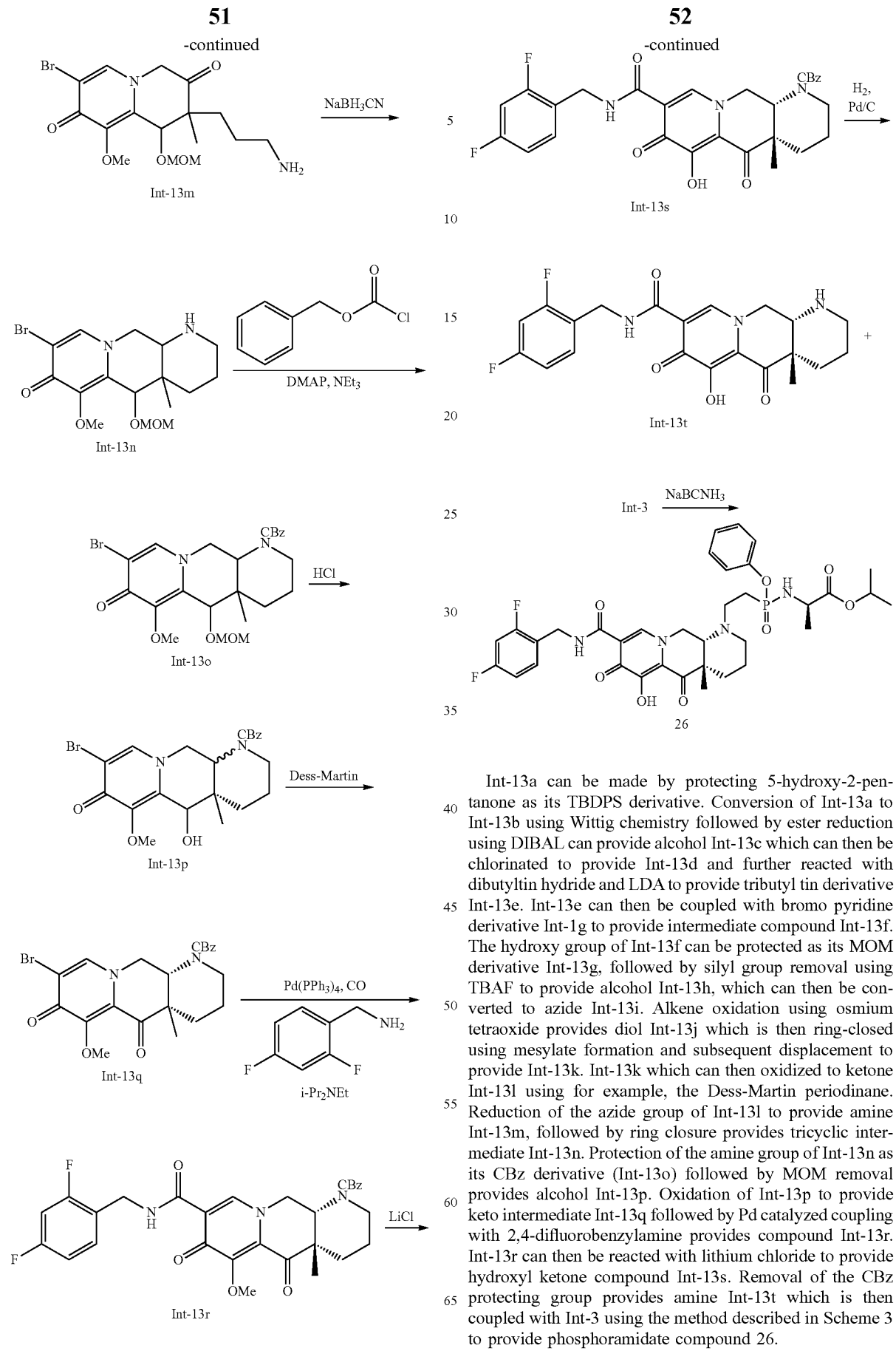

Int-13a can be made by protecting 5-hydroxy-2-pentanone as its TBDPS derivative. Conversion of Int-13a to Int-13b using Wittig chemistry followed by ester reduction using DIBAL can provide alcohol Int-13c which can then be chlorinated to provide Int-13d and further reacted with dibutyltin hydride and LDA to provide tributyl tin derivative Int-13e. Int-13e can then be coupled with bromo pyridine derivative Int-1g to provide intermediate compound Int-13f. The hydroxy group of Int-13f can be protected as its MOM derivative Int-13g, followed by silyl group removal using TBAF to provide alcohol Int-13h, which can then be converted to azide Int-13i. Alkene oxidation using osmium tetraoxide provides diol Int-13j which is then ring-closed using mesylate formation and subsequent displacement to provide Int-13k. Int-13k which can then oxidized to ketone Int-13l using for example, the Dess-Martin periodinane. Reduction of the azide group of Int-13l to provide amine Int-13m, followed by ring closure provides tricyclic intermediate Int-13n. Protection of the amine group of Int-13n as its CBz derivative (Int-13o) followed by MOM removal provides alcohol Int-13p. Oxidation of Int-13p to provide keto intermediate Int-13q followed by Pd catalyzed coupling with 2,4-difluorobenzylamine provides compound Int-13r. Int-13r can then be reacted with lithium chloride to provide hydroxyl ketone compound Int-13s. Removal of the CBz protecting group provides amine Int-13t which is then coupled with Int-3 using the method described in Scheme 3 to provide phosphoramidate compound 26.

Scheme 14
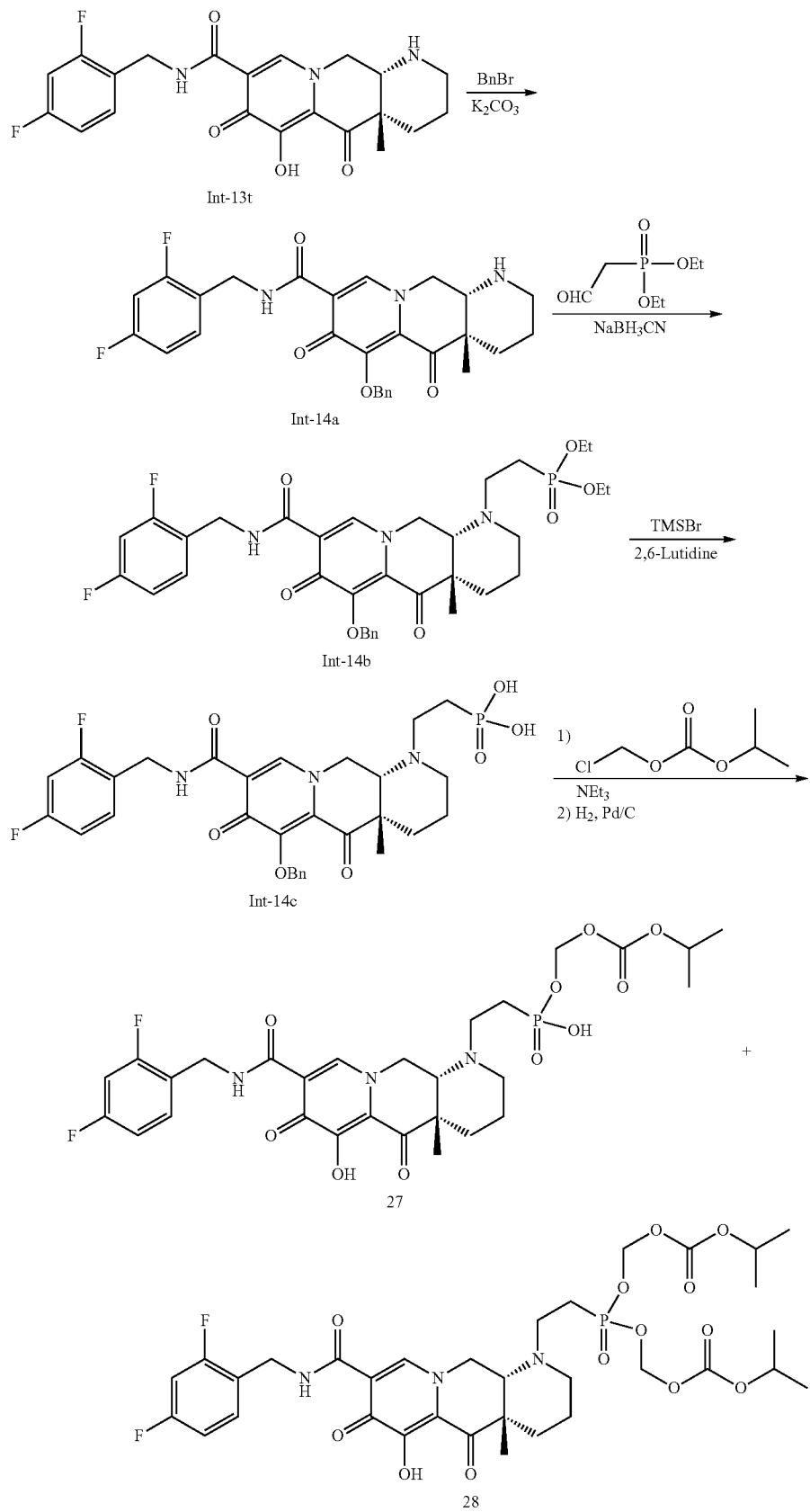

Protection of the hydroxy group of compound Int-13t as its benzyl derivative (Int-14a), followed by coupling of the amine moiety of Int-14a with aldehyde A1, using methods described in Scheme 1 above, can provide the phosphate ester compound Int-14b which can then be converted to phosphate compound Int-14c using TMSBr in the presence of lutidine. Phosphate Int-14c can then be converted to compounds 27 and 28 using the methods described above in Scheme 9.

Scheme 15

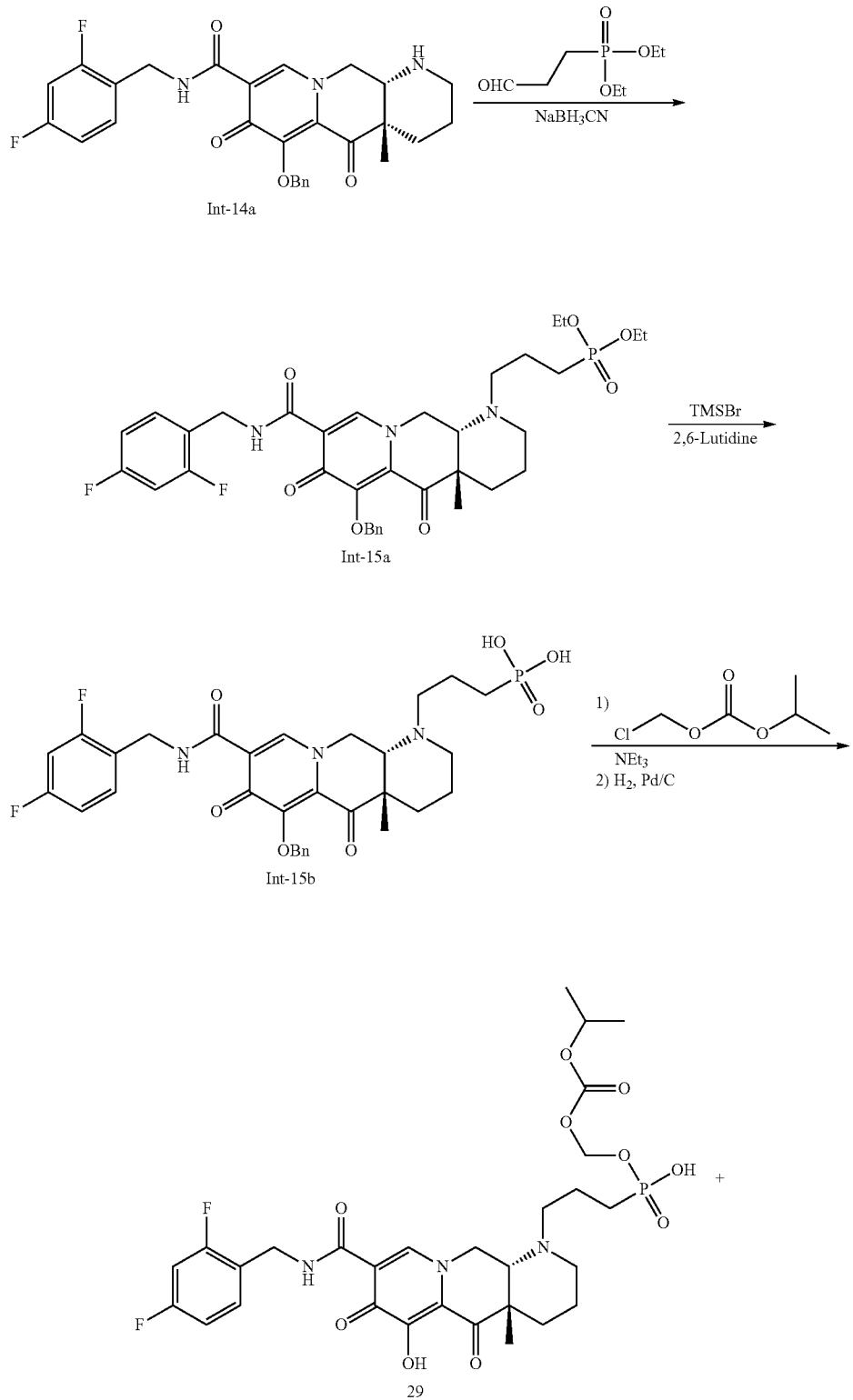

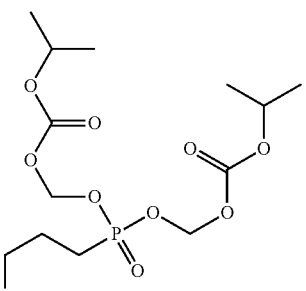
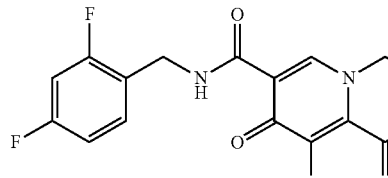

30

Coupling of the amine moiety of Int-14a with aldehyde A2, using methods described in Scheme 2 above, provides phosphate ester compound Int-15a which can then be converted to phosphate compound Int-15b using TMSBr in the presence of lutidine. Int-15b can be converted to compounds 29 and 30 using the methods described above in Scheme 9.

In the methods for preparing compounds of the present invention set forth in the foregoing schemes, functional groups in various moieties and substituents (in addition to those already explicitly noted in the foregoing schemes) may be sensitive or reactive under the reaction conditions employed and/or in the presence of the reagents employed. Such sensitivity/reactivity can interfere with the progress of the desired reaction to reduce the yield of the desired product, or possibly even preclude its formation. Accordingly, it may be necessary or desirable to protect sensitive or reactive groups on any of the molecules concerned. Protection can be achieved by means of conventional protecting groups, such as those described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, 3' edition, 1999, and $2^{nd}$ edition, 1991. The protecting groups may be removed at a convenient subsequent stage using methods known in the art. Alternatively the interfering group can be introduced into the molecule subsequent to the reaction step of concern.

One skilled in the art of organic synthesis will recognize that the synthesis of compounds with multiple reactive functional groups, such as —OH and $NH_2$, may require protection of certain functional groups (i.e., derivatization for the purpose of chemical compatibility with a particular reaction condition). Suitable protecting groups for the various functional groups of these compounds and methods for their installation and removal are well-known in the art of organic chemistry. A summary of many of these methods can be found in Greene & Wuts, *Protecting Groups in Organic Synthesis*, John Wiley & Sons, $3^{rd}$ edition (1999).

One skilled in the art of organic synthesis will also recognize that one route for the synthesis of the Compounds of Formula (I) may be more desirable depending on the choice of appendage substituents. Additionally, one skilled in the relevant art will recognize that in some cases the order of reactions may differ from that presented herein to avoid functional group incompatibilities and thus adjust the synthetic route accordingly.

The starting materials used and the intermediates prepared using the methods set forth in Schemes 1-15 above and in the Examples below may be isolated and purified if desired using conventional techniques, including but not limited to filtration, distillation, crystallization, chromatography and alike. Such materials can be characterized using conventional means, including physical constants and spectral data.

EXAMPLES

General Methods

The following examples serve only to illustrate the invention and its practice. The examples are not to be construed as limitations on the scope or spirit of the invention. In these examples, all temperatures are degrees Celsius unless otherwise noted, and "room temperature" refers to a temperature in a range of from about 20° C. to about 25° C. Reactions sensitive to moisture or air were performed under nitrogen using anhydrous solvents and reagents. The progress of reactions was determined by either analytical thin layer chromatography (TLC) performed with E. Merck precoated TLC plates, silica gel 60E-254, layer thickness 0.25 mm or liquid chromatography-mass spectrum (LC-MS). For HPLC/MS data, two HPLC conditions used were as follows: 1) LC1 (SHIMADZU C18 Xtimate 3 um 2.1×30 mm column with gradient 10:90-80:20 v/v CH3CN/H20+v 0.0375% TFA over 0.9 min then hold at 80:20 v/v CH3CN/H20+v 0.0375% TFA for 0.6 min; flow rate 1.2 mL/min, UV wavelength 220 & 254 nm); 2) LC2 (Agilent C18 Xtimate 3 um 2.1×30 mm column with gradient 10:90-80:20 v/v CH3CN/H20+v 0.0375% TFA over 3.0 min then hold at 80:20 v/v CH3CN/H20+v 0.0375% TFA for 0.5 min; flow rate 0.8 mL/min, UV wavelength 220 & 254 nm). Mass analysis was performed with electrospray ionization in positive ion detection mode. $^1$H NMR spectra were recorded on Varian or Bruker instruments at 400-500 MHz. Concentration of solutions was carried out on a rotary evaporator under reduced pressure or by lyophilization. Flash chromatography was performed on pre-packed silica gel columns using a commercial MPLC system. Compound Int-1 and compound Int-18a were prepared using the method described in Patent Publication No. WO2015048363(A1).

Example 1

Preparation of Compounds 32-35

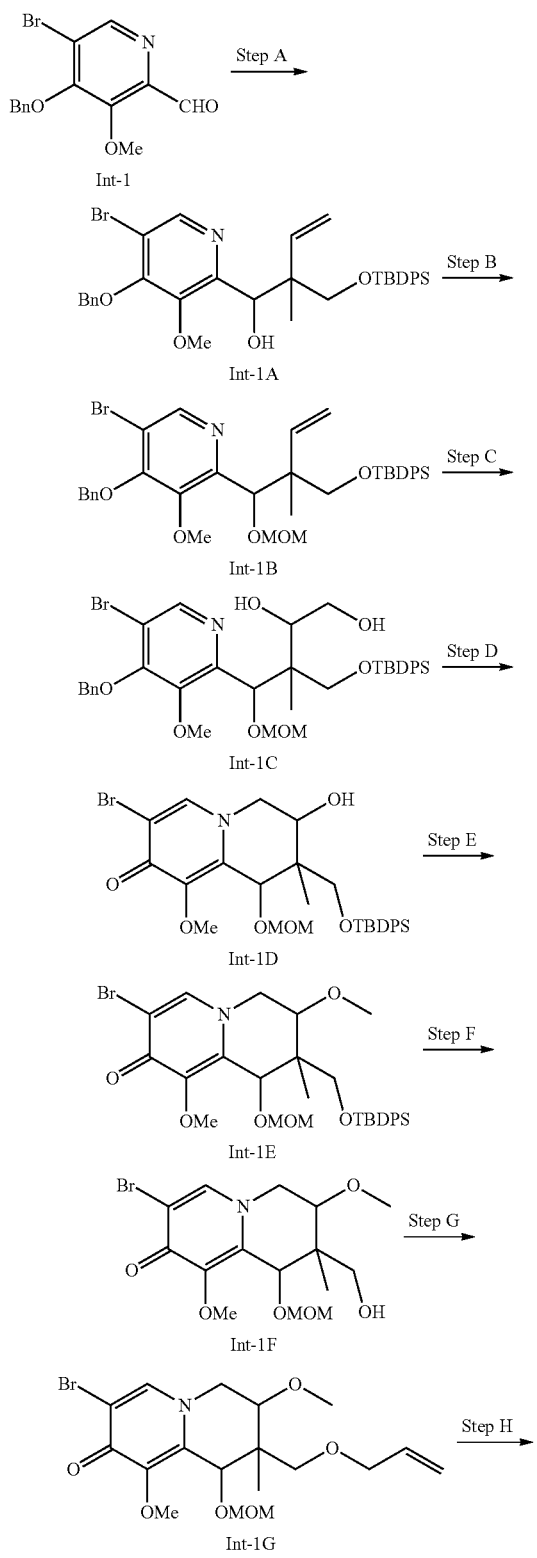

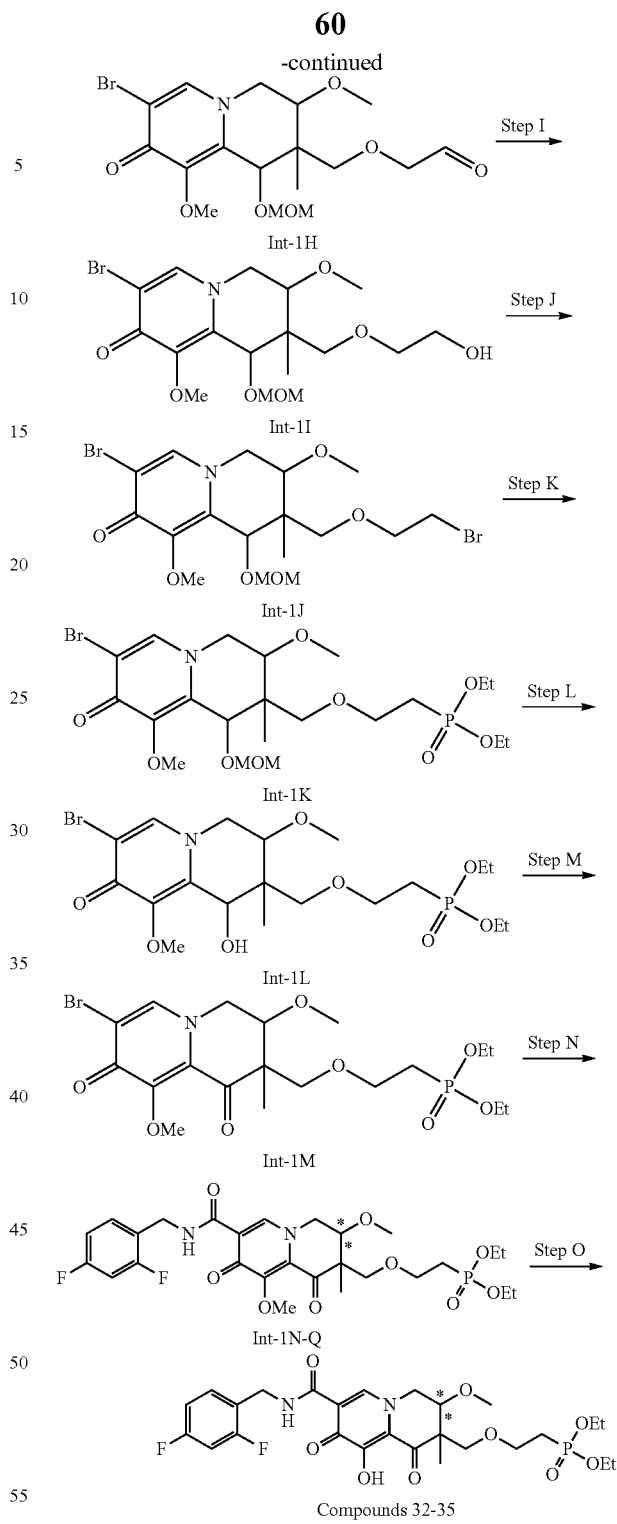

Compounds 32-35

Step A—Synthesis of Compound Int-1A

To a stirred solution of compound Int-1 (19.05 g, 31.0 mmol) and 4-(benzyloxy)-5-bromo-3-methoxypicolinaldehyde (5 g, 15.52 mmol) in acetonitrile (150 mL) was added tin(II) chloride (4.41 g, 23.28 mmol) at 0° C. The reaction solution was warmed to 20° C. and stirred at this temperature for 1 hour. The mixture was diluted with 50 mL EtOAc and then treated with saturated KF (300 mL). The resulting mixture was allowed to stir at room temperature for 1 hour. After the solid was filtered off, the filtrate was separated and the aqueous layer was extracted with EtOAc (50 mL×3). The combined organic layer was dried over sodium sulfate, filtered and concentrated. The residue was purified using a silica gel column eluting with 9% EtOAc/petroleum ether to provide compound Int-1A as a solid. $^1$H NMR (400 MHz, CHLOROFORM-d): δ 8.35 (d, J=5.1 Hz, 1H), 7.68-7.77 (m, 4H), 7.34-7.48 (m, 11H), 6.30 (dd, J=17.6, 11.0 Hz, 1H), 5.80 (dd, J=17.8, 11.2 Hz, 1H), 4.91-5.34 (m, 6H), 4.78 (d, J=17.6 Hz, 1H), 4.10 (d, J=9.4 Hz, 1H), 3.74-3.96 (m, 3H), 3.35-3.51 (m, 2H), 1.10 (d, J=5.5 Hz, 9H). MS: m/z=648.1 (M+1).

Step B—Synthesis of Compound Int-1B

To a stirred solution of diisopropylethylamine (27.0 mL, 155 mmol), DMAP (1.889 g, 15.46 mmol) and compound Int-1A (10 g, 15.46 mmol) in DMF (120 mL) was added chloro(methoxy)methane (12.45 g, 155 mmol) via syringe at 0° C., and the mixture was allowed to stir at 38° C. for 15 hours. The mixture was poured into water (100 mL) and the aqueous layer was extracted with EtOAc (100 mL×3). The combined organic layers were dried over sodium sulfate and filtered. The filtrate was concentrated in vacuo to provide a crude residue, which was purified using a silica gel column eluting with 9~17% EtOAc/petroleum ether to provide compound Int-1B as an oil. $^1$H NMR (400 MHz, CHLOROFORM-d): δ 8.41 (s, 1H), 7.63-7.73 (m, 4H), 7.28-7.52 (m, 11H), 6.09-6.32 (m, 2H), 5.42-5.51 (m, 1H), 4.98-5.33 (m, 4H), 4.65-4.93 (m, 4H), 4.46 (d, J=6.6 Hz, 1H), 3.86-3.95 (m, 4H), 3.07 (s, 3H), 1.15 (d, J=4.6 Hz, 6H), 1.02-1.09 (m, 3H). MS: m/z=692.2 (M+1).

Step C—Synthesis of Compound Int-1C

To a stirred solution of compound Int-1B (6.5 g, 9.41 mmol) in THF (70 mL) and water (10 mL) was added osmium(VIII) oxide (0.239 g, 0.941 mmol) and 4-methylmorpholine 4-oxide (2.205 g, 18.82 mmol) at 0° C. The mixture was allowed to stir at 25° C. for 5 hours. The mixture was quenched with aqueous solution of Na$_2$SO$_3$, and the aqueous layer was extracted with EtOAc (300 mL×3). The combined organic layers were dried over sodium sulfate and filtered. The filtrate was concentrated in vacuo to provide a crude residue, which was purified using a silica gel column eluting with 0~50% EtOAc/petroleum ether to provide compound Int-1C as an oil. $^1$H NMR (400 MHz, CHLOROFORM-d): δ 8.17-8.37 (m, 1H), 7.45-7.71 (m, 4H), 7.21-7.40 (m, 10H), 4.90-5.25 (m, 3H), 4.29-4.60 (m, 2H), 3.78-3.93 (m, 2H), 3.54-3.76 (m, 6H), 2.90-3.03 (m, 3H), 1.59 (s, 3H), 0.93-1.10 (m, 10H) MS: m/z=726.1 (M+1).

Step D—Synthesis of Compound Int-1D

To a stirred solution of compound Int-1C (6.0 g, 8.28 mmol) in pyridine (100 mL) was added 4-methylbenzene-1-sulfonyl chloride (3.16 g, 16.56 mmol) at 0° C., and the mixture was allowed to stir at 38° C. for 12 hours. The mixture was poured into a solution of water (50 mL) and NH$_3$.H$_2$O (10 mL, 37% w/w). The aqueous layer was extracted with EtOAc (50 mL×3), and the combined organic layers were dried over sodium sulfate and filtered. The filtrate was concentrated in vacuo to provide a crude residue, which was purified using a silica gel column eluting with 17~100% EtOAc/petroleum ether to provide compound Int-1D as an oil. MS: m/z=616.2 (M+1).

Step E—Synthesis of Compound Int-1E

To a stirred solution of compound Int-1D (4.2 g, 6.81 mmol) in DMF (60 mL) was added NaH (0.545 g, 13.62 mmol) at 0° C., followed by addition of iodomethane (1.934 g, 13.62 mmol). The mixture was allowed to stir at 0° C. for 30 min. The mixture was poured into water (50 mL), and the aqueous was extracted with EtOAc (50 mL×3). The combined organic layers were dried over sodium sulfate and filtered. The filtrate was concentrated in vacuo to provide a crude residue, which was purified using a silica gel column eluting with 17~50% EtOAc/petroleum ether to provide compound Int-1E as a solid. $^1$H NMR (400 MHz, CHLOROFORM-d): δ 7.49-7.73 (m, 5H), 7.30-7.46 (m, 6H), 5.00-5.13 (m, 1H), 4.44-4.67 (m, 2H), 4.04-4.14 (m, 1H), 3.97-4.02 (m, 2H), 3.88-3.92 (m, 1H), 3.70-3.78 (m, 1H), 3.16-3.38 (m, 6H), 3.08-3.14 (m, 2H), 1.66 (s, 3H), 1.22-1.30 (m, 1H), 1.00-1.14 (m, 9H). MS: m/z=632.2 (M+1).

Step F—Synthesis of Compound Int-1F

A solution of compound Int-1E (2.7 g, 4.28 mmol) and TBAF (12.84 mL, 12.84 mmol, 1M in THF) in THF (40 mL) was allowed to stir at 25° C. for 24 hours. The color turned to dark yellow from light yellow. The mixture was concentrated under reduced pressure and the residue was purified using a silica gel column eluting with 25~100% EtOAc/petroleum ether to provide compound Int-1F as a solid. $^1$H NMR (400 MHz, CHLOROFORM-d): δ 7.69 (s, 1H), 4.92-4.99 (m, 1H), 4.70-4.79 (m, 1H), 4.58-4.65 (m, 1H), 4.49-4.56 (m, 1H), 4.30-4.43 (m, 1H), 4.09-4.24 (m, 1H), 3.74-3.83 (m, 2H), 3.45-3.50 (m, 3H), 3.39-3.43 (m, 2H), 3.31-3.36 (m, 3H), 3.04-3.25 (m, 2H), 1.18-1.28 (m, 2H). MS: m/z=394.0 (M+1).

Step G—Synthesis of Compound Int-1G

To a stirred solution of compound Int-1F (7 g, 17.85 mmol) in DMF (100 mL) was added NaH (2.141 g, 53.5 mmol, 60% w/w) at 0° C., followed by addition of 3-bromoprop-1-ene (4.32 g, 35.7 mmol). The mixture was allowed to stir at 25° C. for 15 hours. The mixture was poured into water (100 mL) and the aqueous layer was extracted with EtOAc (100 mL×3). The combined organic layers were dried over sodium sulfate and filtered. The filtrate was concentrated in vacuo to provide a crude residue, which was purified using a silica gel column eluting with 50~100% EtOAc/petroleum ether to provide compound Int-1G as an oil. $^1$H NMR (400 MHz, CHLOROFORM-d): δ 7.57-7.67 (m, 1H), 5.68-5.96 (m, 1H), 4.92-5.32 (m, 3H), 4.57-4.76 (m, 2H), 4.29-4.53 (m, 2H), 3.88-4.20 (m, 5H), 3.66-3.85 (m, 2H), 3.22-3.47 (m, 5H), 2.97-3.05 (m, 1H), 1.62 (s, 2H), 1.15-1.29 (m, 1H), 0.80-0.91 (m, 1H).

Step H—Synthesis of Compound Int-1H

To a stirred solution of compound Int-1G (6 g, 13.88 mmol) in THF (60 mL) and water (40 mL) was added osmium tetroxide (0.436 mL, 1.388 mmol) and sodium periodate (8.91 g, 41.6 mmol) at 0° C., and the mixture was allowed to stir at 25° C. for 2 hours. The mixture was poured into water (50 mL) and the aqueous layer was extracted with EtOAc (50 mL×3). The combined organic layers were dried over sodium sulfate and filtered. The filtrate was concentrated in vacuo to provide a crude residue, which was purified using a silica gel column eluting with 100% EtOAc to provide compound Int-1H as yellow oil. $^1$H NMR (400 MHz, CHLOROFORM-d): δ 7.57-7.73 (m, 1H), 4.93-5.16 (m, 1H), 4.27-4.77 (m, 4H), 3.90-4.05 (m, 4H), 3.24-3.46 (m, 8H), 3.09-3.21 (m, 1H), 2.74-2.99 (m, 1H), 1.68 (s, 1H), 1.23-1.33 (m, 1H), 1.18-1.28 (m, 1H), 0.77-0.96 (m, 1H). MS: m/z=452.0 (M+18+1).

Step I—Synthesis of Compound Int-1I

To a stirred solution of compound Int-1H (4.8 g, 11.05 mmol) in MeOH (50 mL) was added NaBH$_4$ (0.627 g, 16.58 mmol) at 0° C., and the mixture was allowed to stir at 0° C. for 30 min. The mixture was poured into aqueous solution of NH$_4$Cl (50 mL) and the aqueous layer was extracted with EtOAc (50 mL×3). The combined organic layers were dried over sodium sulfate and filtered. The filtrate was concentrated in vacuo to provide a crude residue, which was purified purified using a silica gel column eluting with 2~5% MeOH/dichloromethane to provide compound Int-1I as an oil. $^1$H NMR (400 MHz, CHLOROFORM-d): δ 7.57-7.69 (m, 1H), 4.96-5.17 (m, 1H), 4.09-4.85 (m, 5H), 3.84-4.03 (m, 3H), 3.51-3.81 (m, 4H), 3.25-3.49 (m, 7H), 2.94-3.18 (m, 1H), 1.08-1.30 (m, 2H), 0.80-0.88 (m, 1H). MS: m/z=436.1 (M+1).

Step J—Synthesis of Compound Int-1J

To a mixture of compound Int-1I (3.4 g, 7.79 mmol) and Et$_3$N (3.26 mL, 23.38 mmol) in CH$_2$Cl$_2$ (40 mL) was added MsCl (0.789 mL, 10.13 mmol) at 0° C., and the mixture was allowed to stir at 0° C. for 30 min. The reaction mixture was poured into water (40 mL) and extracted with dichloromethane (40 mL×3). The combined organic layers were dried over sodium sulfate, filtered and concentrated in vacuo. The mixture was purified using a silica gel column eluting with 100% EtOAc to provide 2-((7-bromo-3,9-dimethoxy-1-(methoxymethyl)-2-methyl-8-oxo-2,3,4,8-tetrahydro-1H-quinolizin-2-yl)methoxy)ethyl methanesulfonate as an oil. MS: m/z=514.1 (M+1). This material was dissolved in DMF (40 mL) and sodium bromide (3.50 g, 34.0 mmol) was then added. The resulting mixture was allowed to stir at 50° C. for 2 hours. The mixture was concentrated in vacuo and the residue was purified using a silica gel column eluting with 2~10% MeOH/dichloromethane to provide compound Int-1J as an oil. $^1$H NMR (400 MHz, CHLOROFORM-d): δ 7.52-7.70 (m, 1H), 4.84-5.10 (m, 1H), 4.23-4.79 (m, 3H), 4.05-4.17 (m, 1H), 3.68-3.97 (m, 4H), 3.17-3.59 (m, 8H), 2.97-3.13 (m, 2H), 1.54-1.68 (m, 1H), 1.07-1.28 (m, 2H), 0.69-0.88 (m, 2H). MS: m/z=499.9 (M+1).

Step K—Synthesis of Compound Int-1K

A solution of compound Int-1J (3 g, 6.01 mmol) in triethyl phosphite (30 mL, 6.01 mmol) was allowed to stir at 150° C. for 2 hours. The mixture was concentrated in vacuo and the residue was purified using a silica gel column eluting with 2~10% MeOH/dichloromethane to provide compound Int-1K as an oil. $^1$H NMR (400 MHz, CHLOROFORM-d): δ 7.60-7.67 (m, 1H), 4.86-5.06 (m, 1H), 4.55-4.78 (m, 2H), 4.29-4.54 (m, 2H), 3.88-4.14 (m, 8H), 3.62-3.79 (m, 2H), 3.23-3.53 (m, 8H), 2.93-3.09 (m, 1H), 2.08-2.18 (m, 1H), 2.02 (s, 1H), 1.92 (dt, J=11.2, 7.7 Hz, 1H), 1.74-1.77 (m, 1H), 1.18-1.34 (m, 6H). MS: m/z=558.2 (M+1).

Step L—Synthesis of Compound Int-1l

A solution of compound Int-1K (3 g, 5.39 mmol) in HCl/MeOH (30 mL, 60.0 mmol, 2 M) was allowed to stir at 25° C. for 1 hour. The mixture was concentrated under reduced pressure and the residue was purified using a silica gel column eluting with 2~10% MeOH/dichloromethane to provide compound Int-1L as an oil. $^1$H NMR (400 MHz, CHLOROFORM-d): δ 7.47-7.58 (m, 1H), 4.58-4.82 (m, 1H), 3.78-4.33 (m, 9H), 3.50-3.73 (m, 4H), 3.32-3.46 (m, 4H), 3.09-3.25 (m, 1H), 1.84-2.05 (m, 2H), 1.11-1.30 (m, 8H). MS: m/z=514.1 (M+1).

Step M—Synthesis of Compound Int-1M

To a solution of compound Int-1L (3 g, 5.86 mmol) in CH$_2$Cl$_2$ (40 mL) was added Dess-Martin periodinane (4.97 g, 11.71 mmol) at 25° C., and the mixture was allowed to stir at 25° C. for 1 hour. The mixture was poured into water (100 mL) and the aqueous was extracted with dichloromethane (50 mL×3). The combined organic layers were dried over sodium sulfate and then filtered. The filtrate was concentrated in vacuo to provide the crude product, which was purified using a silica gel column eluting with 2~10% MeOH/dichloromethane to provide compound Int-1M as an oil. $^1$H NMR (400 MHz, CHLOROFORM-d): δ 7.69 (s, 1H), 4.51 (d, J=13.2 Hz, 1H), 4.18-4.36 (m, 1H), 3.95-4.11 (m, 7H), 3.84-3.92 (m, 1H), 3.72-3.80 (m, 1H), 3.58-3.72 (m, 2H), 3.42-3.47 (m, 3H), 1.88-2.12 (m, 3H), 1.11-1.37 (m, 9H). MS: m/z=512.1 (M+1).

Step N—Synthesis of Compounds Int-1N, O, P and Q

A solution of diisopropylethylamine (1.027 mL, 5.88 mmol), Pd(Ph$_3$P)$_4$ (1.132 g, 0.980 mmol), compound Int-1M (1 g, 1.960 mmol) and (2,4-difluorophenyl)methanamine (0.365 g, 2.55 mmol) in DMSO (15 mL) was degassed and purged with CO for 3 times, and then the mixture was allowed to stir at 80° C. under CO for 2 hours. The mixture was poured into water (20 mL) and extracted with EtOAc (20 mL×3). The combined organic layers were dried over sodium sulfate and filtered, the filtrate was concentrated under reduced pressure and the residue was purified using a silica gel column eluting with 17~100% EtOAc/petroleum ether to provide a mixture of compounds Int-N, O, P and Q as an oil. $^1$H NMR (400 MHz, CHLOROFORM-d): δ 10.30-10.57 (m, 1H), 8.33-8.50 (m, 1H), 7.35 (d, J=11.9 Hz, 1H), 6.71-6.94 (m, 2H), 4.49-4.77 (m, 3H), 3.94-4.28 (m, 8H), 3.59-3.90 (m, 4H), 3.38-3.55 (m, 3H), 2.53-2.71 (m, 2H), 1.89-2.13 (m, 2H), 1.68-1.77 (m, 1H), 1.41-1.51 (m, 1H), 1.21-1.48 (m, 6H). MS: m/z=601.2 (M+1).

This material was further separated using an SFC (Column: AS (250 mm*50 mm, 10 um) Mobile phase: 25% Base-ETOH (contained 0.1% NH$_3$.H$_2$O) in CO$_2$ Flow rate: 200 mL/min Wavelength: 220 nm) to provide compound Int-N (the first eluting isomer) as an oil, compound Int-0 (the second eluting isomer) as an oil, compound Int-P (the third eluting isomer) as an oil and compound Int-Q (the fourth eluting isomer) as an oil.

Compound Int-N: $^1$H NMR (400 MHz, CHLOROFORM-d): δ 10.45 (t, J=5.5 Hz, 1H), 8.38 (s, 1H), 7.28-7.39 (m, 1H), 6.72-6.84 (m, 2H), 4.53-4.64 (m, 3H), 4.17 (dd, J=13.7, 5.1 Hz, 1H), 3.95-4.07 (m, 6H), 3.85 (d, J=3.1 Hz, 1H), 3.77 (d, J=9.0 Hz, 1H), 3.60 (dt, J=13.5, 6.9 Hz, 2H), 3.45 (t, J=4.5 Hz, 1H), 3.39 (s, 3H), 2.59 (s, 1H), 1.88-2.01 (m, 2H), 1.21-1.30 (m, 6H), 1.11-1.18 (m, 3H).

Compound Int-O: $^1$H NMR (400 MHz, CHLOROFORM-d): δ 10.45 (t, J=5.5 Hz, 1H), 8.38 (s, 1H), 7.34 (d, J=4.3 Hz, 1H), 6.73-6.83 (m, 2H), 4.52-4.63 (m, 3H), 4.17 (dd, J=13.3, 5.1 Hz, 1H), 3.95-4.07 (m, 6H), 3.86 (d, J=3.5 Hz, 1H), 3.77 (d, J=9.0 Hz, 1H), 3.60 (dt, J=13.7, 6.8 Hz, 2H), 3.45 (t, J=4.5 Hz, 1H), 3.39 (s, 3H), 2.59 (s, 1H), 1.88-2.00 (m, 2H), 1.21-1.29 (m, 6H), 1.10-1.17 (m, 3H).

Compound Int-P: $^1$H NMR (400 MHz, CHLOROFORM-d): δ 10.39 (t, J=5.3 Hz, 1H), 8.40 (s, 1H), 7.27-7.34 (m, 1H), 6.70-6.81 (m, 2H), 4.57 (d, J=5.5 Hz, 2H), 4.41 (dd, J=13.9, 3.3 Hz, 1H), 4.23 (d, J=12.9 Hz, 1H), 3.98-4.11 (m, 4H), 3.94 (s, 3H), 3.82 (br. s., 1H), 3.76 (d, J=9.0 Hz, 1H), 3.59-3.73 (m, 3H), 3.34-3.42 (m, 3H), 1.97-2.09 (m, 2H), 1.17-1.33 (m, 9H).

Compound Int-Q: $^1$H NMR (400 MHz, CHLOROFORM-d): δ 10.40 (t, J=5.3 Hz, 1H), 8.41 (s, 1H), 7.26-7.36 (m, 1H), 6.76 (q, J=8.3 Hz, 2H), 4.58 (d, J=5.1 Hz, 2H), 4.42 (dd, J=13.7, 3.5 Hz, 1H), 4.23 (d, J=12.9 Hz, 1H), 3.98-4.12 (m, 4H), 3.94 (s, 3H), 3.82 (br. s., 1H), 3.76 (d, J=9.0 Hz, 1H), 3.59-3.72 (m, 3H), 3.35-3.42 (m, 3H), 1.97-2.09 (m, 2H), 1.21-1.31 (m, 9H).

Step O—Synthesis of Compounds 32-35

A mixture of magnesium bromide (107 mg, 0.583 mmol) and compound Int-N (70 mg, 0.117 mmol) in acetonitrile (1 mL) was allowed to stir at 25° C. for 3 hours. The mixture was purified using preparative HPLC (Column: Boston Green ODS 150 mm*30 mm*5 um; Condition: water (0.1% TFA)-ACN; Gradient: 44% to 54%; B, 0~8 min. FlowRate: 30 mL/min) to provide compound 32 as a solid. $^1$H NMR (400 MHz, METHANOL-d$_4$): δ 8.51 (s, 1H), 7.37-7.47 (m, 1H), 6.86-7.02 (m, 2H), 4.78 (d, J=13.7 Hz, 1H), 4.63 (s, 2H), 4.55 (dd, J=13.6, 4.7 Hz, 1H), 3.92-4.07 (m, 5H), 3.77 (d, J=9.3 Hz, 1H), 3.57-3.68 (m, 3H), 3.47 (s, 3H), 2.03 (dt, J=18.0, 6.6 Hz, 2H), 1.16-1.34 (m, 9H). MS: m/z=587.2 (M+1).

A mixture of magnesium bromide (107 mg, 0.583 mmol) and compound Int-O (70 mg, 0.117 mmol) in acetonitrile (2 mL) was allowed to stir at 25° C. for 1 hour. The mixture was purified using preparative HPLC (Column: Boston Green ODS 150 mm*30 mm*5 um; Condition: water (0.1% TFA)-ACN; Gradient: 45% to 55%; B, 0~8 min. FlowRate: 30 mL/min) to provide compound 33 as a solid. $^1$H NMR (400 MHz, METHANOL-$d_4$): δ 8.51 (br. s., 1H), 7.41 (d, J=6.6 Hz, 1H), 6.84-7.03 (m, 2H), 4.77 (d, J=13.5 Hz, 1H), 4.62 (br. s., 2H), 4.55 (d, J=13.5 Hz, 1H), 3.87-4.10 (m, 5H), 3.76 (d, J=9.3 Hz, 1H), 3.54-3.70 (m, 3H), 3.40-3.51 (m, 3H), 1.95-2.10 (m, 2H), 1.08-1.42 (m, 9H). MS: m/z=587.1 (M+1).

A mixture of magnesium bromide (77 mg, 0.416 mmol) and compound Int-P (50 mg, 0.083 mmol) in acetonitrile (2 mL) was allowed to stir at 25° C. for 1 hour. The mixture was purified using preparative HPLC (Column: Boston Green ODS 150 mm*30 mm*5 um; Condition: water (0.1% TFA)-ACN; Gradient: 45% to 55%; B, 0~8 min. FlowRate: 30 mL/min) to provide compound 34 as a solid. $^1$H NMR (400 MHz, METHANOL-$d_4$): δ 8.50 (s, 1H), 7.38-7.49 (m, 1H), 6.87-7.02 (m, 2H), 4.69-4.77 (m, 1H), 4.62 (s, 2H), 4.53 (d, J=13.7 Hz, 1H), 4.09 (br. s., 4H), 3.95 (br. s., 1H), 3.68-3.85 (m, 4H), 3.46 (s, 3H), 2.15 (dt, J=18.0, 6.8 Hz, 2H), 1.23-1.44 (m, 9H). MS: m/z=587.2 (M+1).

A mixture of magnesium bromide (77 mg, 0.416 mmol) and compound Int-Q (50 mg, 0.083 mmol) in acetonitrile (1 mL) was allowed to stir at 25° C. for 3 hours. The mixture was purified using preparative HPLC (Column: Boston Green ODS 150 mm*30 mm*5 um; Condition: water (0.1% TFA)-ACN; Gradient: 45% to 55%; B, 0~8 min. FlowRate: 30 mL/min) to provide compound 35 as a solid. $^1$H NMR (400 MHz, METHANOL-$d_4$): δ 8.51 (br. s., 1H), 7.36-7.46 (m, 1H), 6.88-7.03 (m, 2H), 4.73 (br. s., 1H), 4.63 (br. s., 2H), 4.54 (br. s., 1H), 4.09 (br. s., 4H), 3.95 (br. s., 1H), 3.68-3.86 (m, 4H), 3.46 (s, 3H), 2.15 (dt, J=17.9, 6.7 Hz, 2H), 1.20-1.44 (m, 9H). MS: m/z=587.2 (M+1).

Example 2

Preparation of Compounds 36-39

A mixture of TMSBr (0.5 mL, 3.85 mmol) and compound 32 (15 mg, 0.026 mmol) in acetonitrile (0.5 mL) was allowed to stir at 25° C. for 10 hours. The mixture was quenched by addition of MeOH (3 mL) and concentrated under reduced pressure, the residue was purified using preparative HPLC (Column: Waters Xbridge Prep OBD C18 150 mm*30 mm*5 um; Condition: water (0.1% TFA)-ACN; Gradient: 15% to 35%; B, 0~10 min. FlowRate: 25 mL/min) to provide compound 36 as an oil. $^1$H NMR (400 MHz, METHANOL-$d_4$): δ 8.48 (s, 1H), 7.38-7.48 (m, 1H), 6.85-7.01 (m, 2H), 4.81 (br. s., 1H), 4.63 (s, 2H), 4.55 (dd, J=14.3, 4.2 Hz, 1H), 3.98 (d, J=2.9 Hz, 1H), 3.74 (d, J=9.3 Hz, 1H), 3.57-3.68 (m, 3H), 3.46 (s, 3H), 1.90 (dt, J=18.2, 6.8 Hz, 2H), 1.28 (s, 3H). MS: m/z=531.1 (M+1).

A mixture of TMSBr (0.5 mL, 3.85 mmol) and compound 33 (15 mg, 0.026 mmol) in acetonitrile (0.5 mL) was allowed to stir at 25° C. for 10 hours. LCMS showed the reaction was completed. The mixture was quenched by addition of MeOH (3 mL) and concentrated under reduced pressure, the residue was purified using preparative HPLC (Column: Waters Xbridge Prep OBD C18 150 mm*30 mm*5 um; Condition: water (0.1% TFA)-ACN; Gradient: 15% to 35%; B, 0~10 min. FlowRate: 25 mL/min) to provide compound 37 as an oil. $^1$H NMR (400 MHz, METHANOL-$d_4$): δ 8.48 (s, 1H), 7.39-7.46 (m, 1H), 6.90-7.00 (m, 2H), 4.81 (br. s., 1H), 4.63 (s, 2H), 4.55 (dd, J=13.8, 4.5 Hz, 1H), 3.99 (d, J=2.6 Hz, 1H), 3.74 (d, J=9.3 Hz, 1H), 3.57-3.68 (m, 3H), 3.46 (s, 3H), 1.90 (dt, J=18.2, 6.9 Hz, 2H), 1.28 (s, 3H). MS: m/z=531.1 (M+1).

A mixture of TMSBr (0.5 mL, 3.85 mmol) and compound 34 (30 mg, 0.051 mmol) in acetonitrile (0.5 mL) was allowed to stir at 25° C. for 10 hours. The mixture was quenched by addition of MeOH (3 mL) and concentrated under reduced pressure, the residue was purified using preparative HPLC (Column: Waters Xbridge Prep OBD C18 150 mm*30 mm*5 um; Condition: water (0.1% TFA)-ACN; Gradient: 5% to 95%; B, 0~10 min. FlowRate: 25 mL/min) to provide compound 38 as an oil. $^1$H NMR (400 MHz, METHANOL-$d_4$): δ 8.50 (s, 1H), 7.38-7.47 (m, 1H), 6.88-7.02 (m, 2H), 4.73 (dd, J=14.1, 4.2 Hz, 1H), 4.63 (s, 2H), 4.52 (d, J=13.5 Hz, 1H), 3.97 (br. s., 1H), 3.68-3.84 (m, 4H), 3.46 (s, 3H), 2.04 (dt, J=18.5, 7.3 Hz, 2H), 1.39 (s, 3H). MS: m/z=531.1 (M+1).

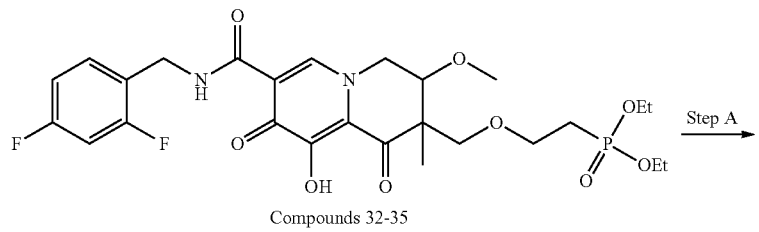

Compounds 32-35

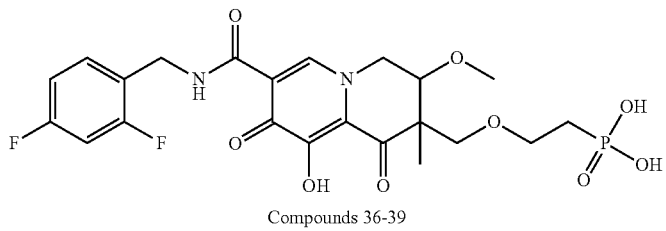

Compounds 36-39

A mixture of TMSBr (0.5 mL, 3.85 mmol) and compound 35 (30 mg, 0.051 mmol) in acetonitrile (0.5 mL) was allowed to stir at 25° C. for 10 hours. The mixture was quenched by addition of MeOH (3 mL) and concentrated under reduced pressure, the residue was purified using preparative HPLC (Column: Waters Xbridge Prep OBD C18 150 mm*30 mm*5 um; Condition: water (0.1% TFA)-ACN; Gradient: 5% to 95%; B, 0~10 min. FlowRate: 25 mL/min) to provide compound 39 as an oil. $^1$H NMR (400 MHz, METHANOL-$d_4$): δ 8.50 (s, 1H), 7.37-7.47 (m, 1H), 6.86-7.01 (m, 2H), 4.73 (dd, J=14.1, 3.7 Hz, 1H), 4.63 (s, 2H), 4.52 (d, J=13.7 Hz, 1H), 3.97 (br. s., 1H), 3.68-3.85 (m, 4H), 3.46 (s, 3H), 2.04 (dt, J=18.5, 7.3 Hz, 2H), 1.39 (s, 3H). MS: m/z=531.1 (M+1).

Example 3

Preparation of Compound 40

Step A—Synthesis of Compound Int-3a

A mixture of TMSBr (1 mL, 7.71 mmol) and compound Int-1N (80 mg, 0.133 mmol) in acetonitrile (0.5 mL) was allowed to stir at 25° C. for 10 hours. The mixture was quenched by addition of MeOH (3 mL) and concentrated under reduced pressure to provide crude compound Int-3A as an oil, which was used for next step without further purification. MS: m/z=545.1 (M+1).

Step B—Synthesis of Compound Int-3B

A mixture of tetrabutylammoniumbromide (41.4 mg, 0.129 mmol), disopropylethylamine (0.225 mL, 1.286 mmol), compound Int-3A (70 mg, 0.129 mmol) and chloromethyl isopropyl carbonate (196 mg, 1.286 mmol) in acetonitrile (2 mL) was allowed to stir at 60° C. for 4 hours. The mixture was purified using preparative TLC plate eluting with 0.02% MeOH in EtOAc to provide compound Int-3B as an oil. MS: m/z=777 0.3 (M+1).

Step C—Synthesis of Compound 40

A mixture of magnesium bromide (61.8 mg, 0.336 mmol) and compound Int-3B (50 mg, 0.067 mmol) in acetonitrile (1

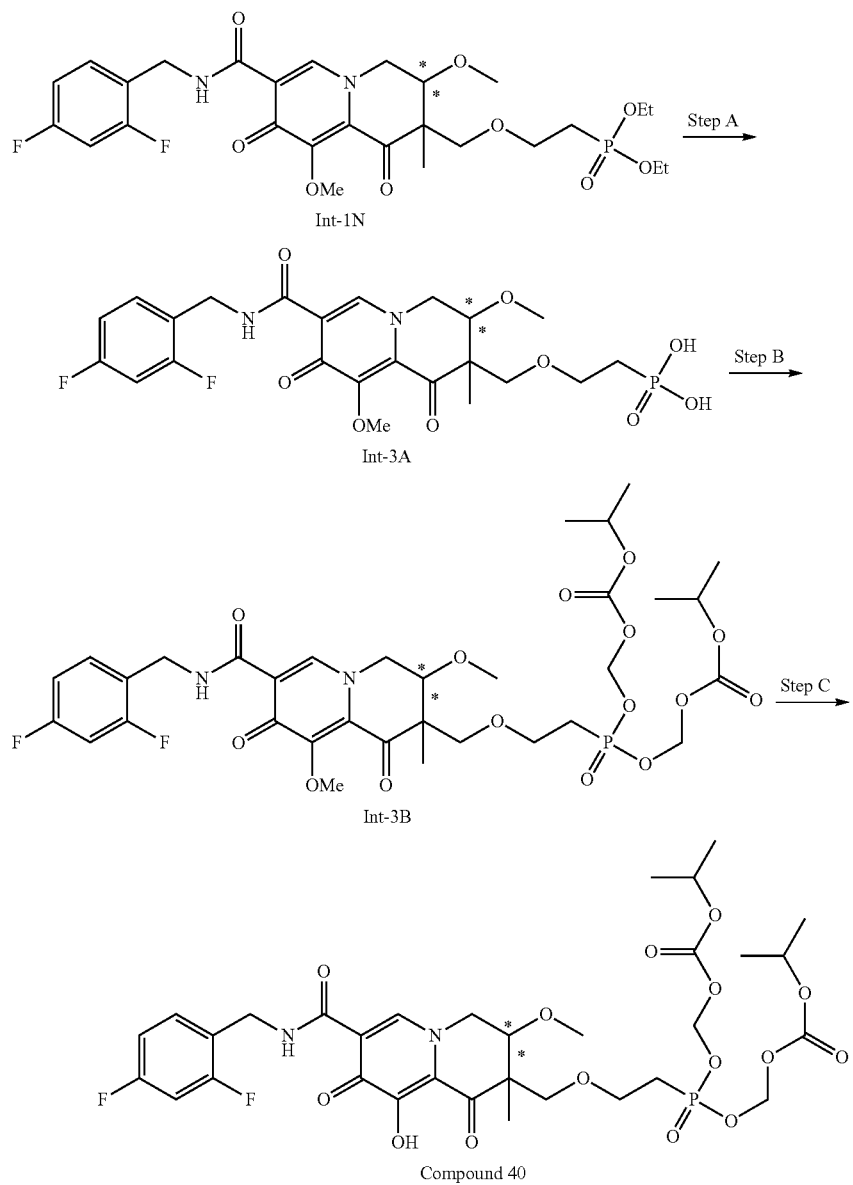

mL) was allowed to stir at 25° C. for 3 hours. The mixture was purified using preparative HPLC (Column: Boston Green ODS 150 mm*30 mm*5 um; Condition: water (0.1% TFA)-ACN; Gradient: 50% to 80%; B, 0~8 min. FlowRate: 30 mL/min) to provide compound 40 as an oil. $^1$H NMR (400 MHz, METHANOL-d$_4$): δ 8.52 (s, 1H), 7.37-7.48 (m, 1H), 6.88-7.01 (m, 2H), 5.46-5.65 (m, 4H), 4.77-4.86 (m, 3H), 4.62 (br. s., 2H), 4.53 (dd, J=13.9, 5.5 Hz, 1H), 4.05 (d, J=3.3 Hz, 1H), 3.77 (d, J=9.3 Hz, 1H), 3.57-3.71 (m, 3H), 3.48 (s, 3H), 2.09-2.25 (m, 2H), 1.20-1.33 (m, 15H). MS: m/z=763.1 (M+1).

Example 4

Preparation of Compounds 41-43

Compounds 41, 42 and 42 were prepared from compounds Int-1O, Int-1P and Int-1Q, respectively, using the method described in Example 3.

Compound 41: $^1$H NMR (400 MHz, METHANOL-d$_4$): δ 8.52 (s, 1H), 7.37-7.48 (m, 1H), 6.87-7.02 (m, 2H), 5.46-5.66 (m, 4H), 4.77-4.87 (m, 3H), 4.62 (br. s., 2H), 4.53 (dd, J=13.9, 5.5 Hz, 1H), 4.05 (d, J=3.3 Hz, 1H), 3.77 (d, J=9.3 Hz, 1H), 3.57-3.72 (m, 3H), 3.48 (s, 3H), 2.09-2.26 (m, 2H), 1.21-1.33 (m, 15H). MS: m/z=763.2 (M+1).

Compound 42: $^1$H NMR (400 MHz, METHANOL-d$_4$): δ 8.51 (br. s., 1H), 7.36-7.49 (m, 1H), 6.86-7.00 (m, 2H), 5.59-5.74 (m, 4H), 4.92 (br. s., 2H), 4.72 (br. s., 1H), 4.63 (br. s., 2H), 4.53 (d, J=12.8 Hz, 1H), 3.99 (br. s., 1H), 3.69-3.85 (m, 4H), 3.46 (s, 3H), 2.23-2.37 (m, 2H), 1.16-1.45 (m, 15H). MS: m/z=763.2 (M+1).

Compound 43: $^1$H NMR (400 MHz, METHANOL-d$_4$): δ 8.51 (s, 1H), 7.37-7.47 (m, 1H), 6.85-7.02 (m, 2H), 5.56-5.73 (m, 4H), 4.90-4.95 (m, 2H), 4.68-4.77 (m, 1H), 4.63 (s, 2H), 4.53 (d, J=13.9 Hz, 1H), 3.99 (br. s., 1H), 3.67-3.85 (m, 4H), 3.46 (s, 3H), 2.23-2.36 (m, 2H), 1.15-1.51 (m, 15H). MS: m/z=763.2 (M+1).

Example 5

Preparation of Compounds 44-47

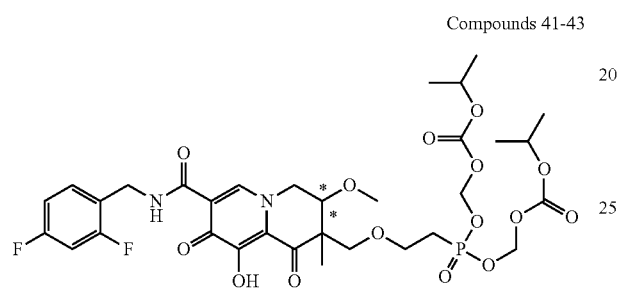

Compounds 41-43

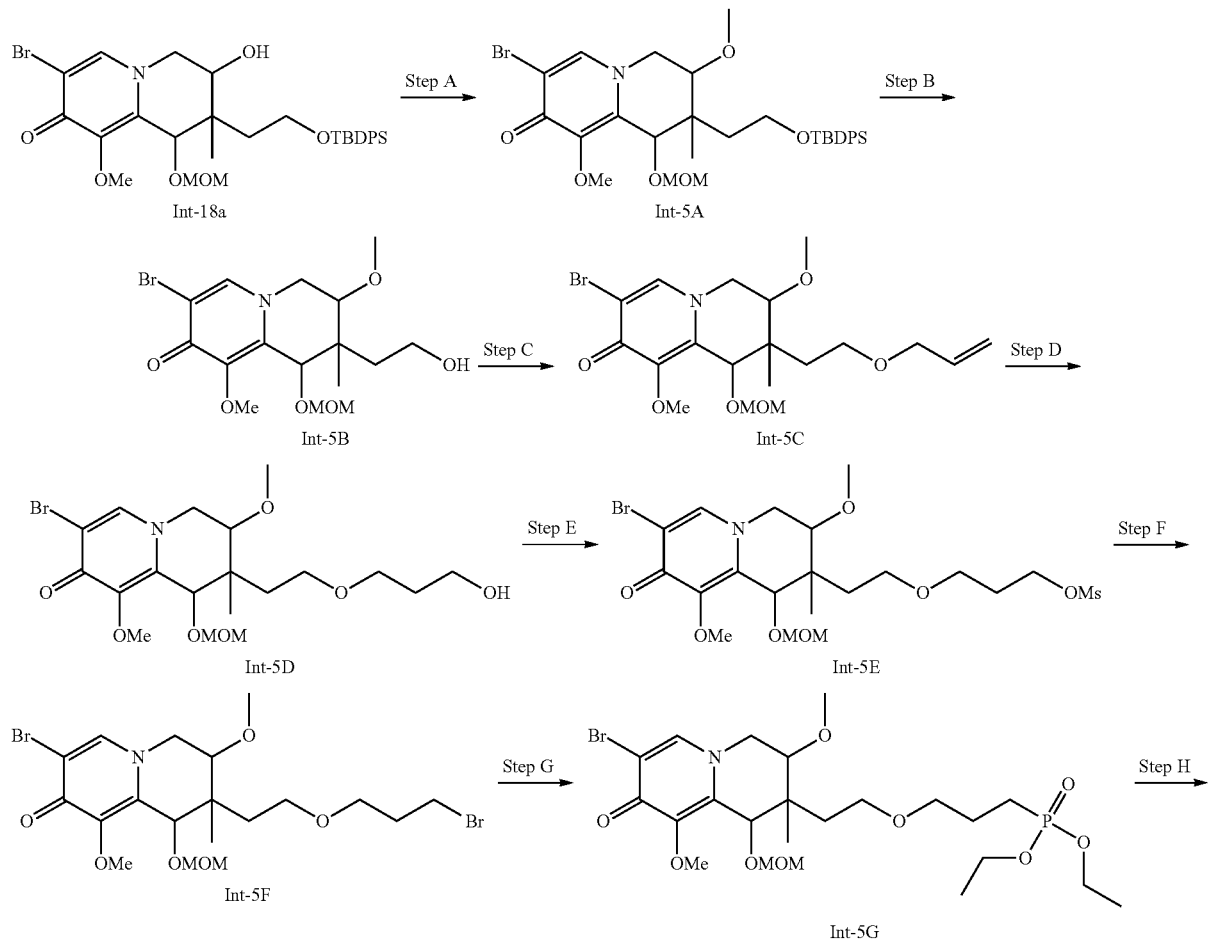

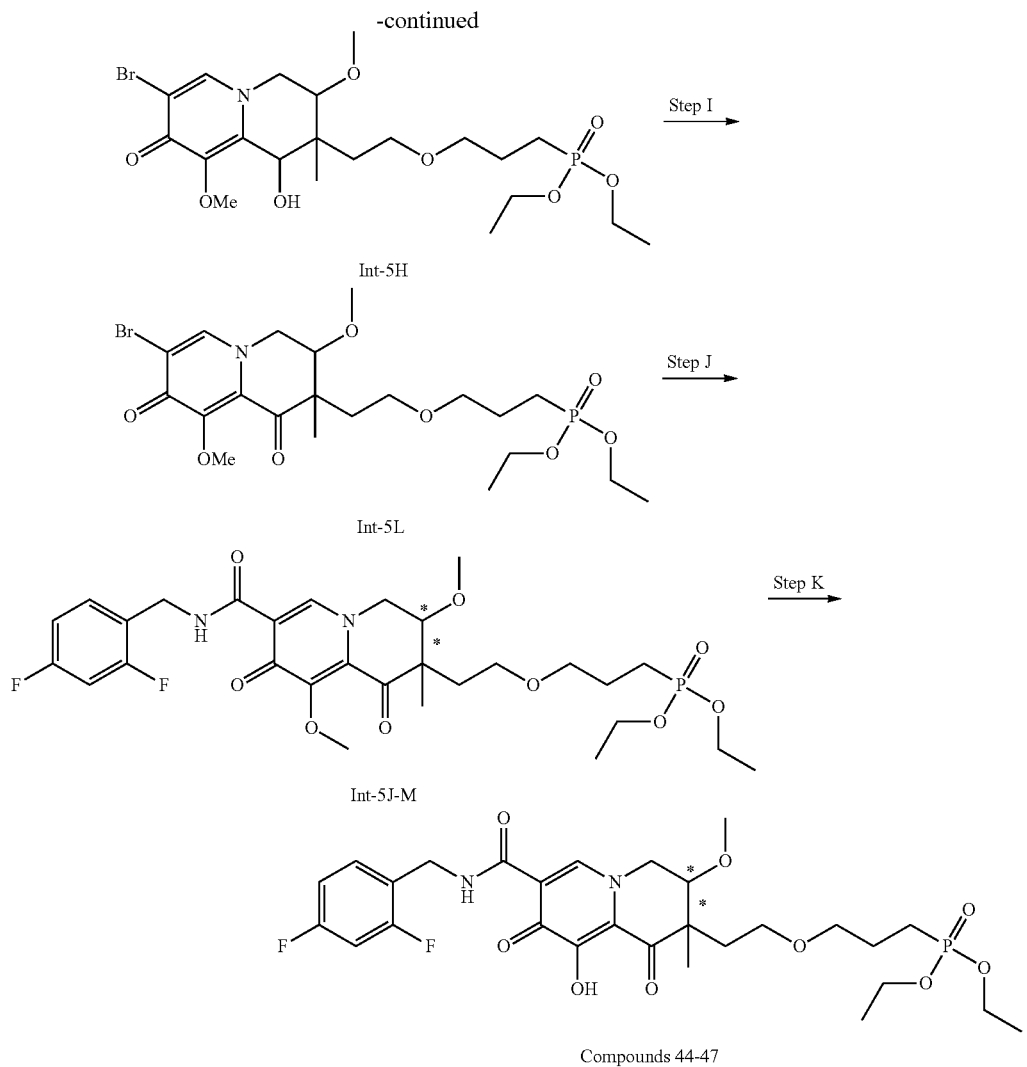

Compounds 44-47

Step A—Synthesis of Compound Int-5A

To a solution of compound Int-18a (9 g, 14.27 mmol) in DMF (100 mL) was added NaH (1.142 g, 28.5 mmol, 60% w/w) and MeI (4.46 mL, 71.4 mmol). The mixture was allowed to stir at 25° C. for 1 hour. The mixture was quenched with $H_2O$ (100 mL) and the aqueous was extracted with EtOAc (200 mL×3). The organic phase was dried over $Na_2SO_4$, filtered, concentrated and purified using a silica gel column eluting with 5% MeOH/dichloromethane to provide compound Int-5A as a solid. $^1$H NMR (400 MHz, CHLOROFORM-d): δ 7.61-7.74 (m, 1H), 7.41-7.44 (m, 3H), 7.37-7.39 (m, 6H), 4.90 (s, 1H), 4.54-4.61 (m, 2H), 4.07-4.25 (m, 1H), 3.94-4.07 (m, 3H), 3.76-3.78 (m, 4H), 3.28-3.35 (m, 6H), 1.87-1.89 (m, 1H), 1.45-1.47 (m, 1H), 0.78-1.15 (m, 12H). MS: m/z=500.1 (M+1)

Step B—Synthesis of Compound Int-5B

To a solution of compound Int-5A (10 g, 15.51 mmol) in THF (3 mL) was added TBAF (23.27 mL, 23.27 mmol). The mixture was allowed to stir at 20° C. for 2 hours. The mixture was concentrated and the residue was purified using a silica gel column eluting with 5% MeOH/dichloromethane to provide compound Int-5B as a solid. $^1$H NMR (400 MHz, CHLOROFORM-d): δ 7.61-7.74 (m, 1H), 4.90 (s, 1H), 4.45-4.71 (m, 2H), 4.07-4.25 (m, 1H), 3.94-4.03 (m, 3H), 3.79-3.90 (m, 1H), 3.73 (br. s., 1H), 3.32-3.40 (m, 6H), 1.94-2.20 (m, 2H), 1.34 (td, J=14.6, 7.2 Hz, 2H), 1.25 (s, 3H). MS: m/z=406.1 (M+1).

Step C—Synthesis of Compound Int-5C

To a solution of compound Int-5B (4.5 g, 11.08 mmol) in DMF (100 mL) was added NaH (1.329 g, 33.2 mmol, 60% w/w) and 3-bromoprop-1-ene (2.68 g, 22.15 mmol) at 0° C. The mixture was allowed to stir at 30° C. for 12 hours. The mixture was quenched with water (20 mL) and the aqueous was extracted with EtOAc (100 mL×3). The organic phase was dried over $Na_2SO_4$, filtered, concentrated and purified using a silica gel column eluting with 5% MeOH/dichloromethane to provide compound Int-5C as an oil. $^1$H NMR (400 MHz, CHLOROFORM-d): δ 7.62-7.69 (m, 1H), 5.82-5.88 (m., 2H), 5.15-5.21 (m, 1H), 4.50-4.66 (m, 1H), 4.10-4.21 (m, 1H), 3.85-4.04 (m, 5H), 3.57-3.78 (m, 2H), 3.41-3.53 (m, 5H), 3.34 (d, J=4.4 Hz, 3H), 2.06-2.10 (m, 1H), 1.31-1.41 (m, 1H), 1.24 (s, 3H). MS: m/z=445.1 (M+1).

Step D—Synthesis of Compound Int-5D

To an ice-cold solution of compound Int-5C (2.9 g, 6.50 mmol) in THF (300 mL) was added $BH_3$-$Me_2S$ (0.494 g, 6.50 mmol) under $N_2$. The mixture was then stirred at 20° C. for 2 hours. After successive addition of $H_2O$ (20 mL, 16.65 mmol) slowly, sodium perborate tetrahydrate (1.0 g, 6.50 mmol) was added. The resulting mixture was allowed to stir for another 10 hours. LCMS analysis showed the starting material was consumed. The reaction mixture was partitioned between water (100 mL) and dichloromethane (100 mL×3). The combined organic extracts were dried over anhydrous $Na_2SO_4$, filtered and concentrated in vacuo, the residue was purified using a silica gel column eluting with 5% MeOH/dichloromethane to provide compound Int-5D as a colorless oil. $^1$H NMR (400 MHz, CHLOROFORM-d): δ 7.68-7.73 (m, 1H), 4.94 (s, 1H), 4.50-4.70 (m, 2H), 4.08-4.27 (m, 1H), 3.93-4.06 (m, 4H), 3.71-3.85 (m, 2H), 3.61-3.69 (m, 1H), 3.46-3.54 (m, 5H), 3.28-3.44 (m, 5H), 2.02-2.14 (m, 1H), 1.79-1.88 (m, 2H), 1.34-1.44 (m, 1H), 1.14-1.30 (m, 3H). MS: m/z=466.0 (M+1).

Step E—Synthesis of Compound Int-5E

To a solution of compound Int-5D (900 mg, 1.938 mmol) in dichloromethane (20 mL) was added diisopropylethylamine (1.693 mL, 9.69 mmol) and methanesulfonyl chloride (0.469 mL, 5.81 mmol) at 0° C. The resulting mixture was allowed to stir at 0° C. for 2 hours. The mixture was quenched with $H_2O$ (20 mL) and the aqueous was extracted with dichloromethane (10 mL×2). The combined organic extracts were dried over anhydrous $Na_2SO_4$, filtered, and concentrated, and the residue was purified using a silica gel column eluting with 5% MeOH/dichloromethane to provide compound Int-5E as a colorless oil. $^1$H NMR (400 MHz, CHLOROFORM-d): δ 7.63-7.72 (m, 1H), 4.88-4.96 (m, 1H), 4.51-4.65 (m, 2H), 4.08-4.42 (m, 4H), 4.00 (d, J=7.5 Hz, 4H), 3.52-3.66 (m, 2H), 3.45 (s, 5H), 3.34 (br. s., 3H), 3.01 (br. s., 3H), 1.93-2.07 (m, 2H), 1.30-1.50 (m, 2H), 1.03-1.27 (m, 3H). MS: m/z=542 (M+1).

Step F—Synthesis of Compound Int-5F

To a solution of compound Int-5E (1.4 g, 2.58 mmol) in DMF (20 mL) was added sodium bromide (0.797 g, 7.74 mmol). The mixture was allowed to stir at 40° C. for 12 hours. The mixture was concentrated and purified using a silica gel column eluting with 5% MeOH/dichloromethane to provide compound Int-5F as an oil. $^1$H NMR (400 MHz, CHLOROFORM-d): δ 7.60-7.71 (m, 1H), 4.86-4.99 (m, 1H), 4.47-4.66 (m, 2H), 3.87-4.25 (m, 6H), 3.40-3.75 (m, 9H), 3.33 (s, 3H), 1.95-2.19 (m, 3H), 1.31-1.43 (m, 1H), 1.13-1.26 (m, 3H). MS: m/z=528.1 (M+1).

Step G—Synthesis of Compound Int-5G

To an ice-cold solution of compound Int-5F (0.5 g, 0.948 mmol) in ethyl dipropyl phosphite (9.21 g, 47.4 mmol) was allowed to stir at 140° C. for 12 hours. The mixture was concentrated and the residue was purified using a preparative TLC plate eluting with 5% MeOH/dichloromethane to provide compound Int-5G as a colorless oil. $^1$H NMR (400 MHz, CHLOROFORM-d): δ 7.62-7.72 (m, 1H), 4.88 (s, 1H), 4.43-4.70 (m, 3H), 4.04-4.23 (m, 5H), 3.86-4.03 (m, 4H), 3.59 (br. s., 1H), 3.25-3.52 (m, 9H), 1.99-2.11 (m, 1H), 1.66-1.95 (m, 5H), 1.28-1.41 (m, 6H), 1.09-1.27 (m, 3H). MS: m/z=585.9 (M+1).

Step H—Synthesis of Compound Int-5H

To a solution of compound Int-5G (800 mg, 1.369 mmol) in MeOH (30 mL) was added HCl/MeOH (0.684 mL, 2.74 mmol, 4M) and the mixture was allowed to stir at 20° C. for 13 hours. The mixture was concentrated to provide compound Int-5H as a solid. The crude product was used for next step without further purification. MS: m/z=542.1 (M+1).

Step I—Synthesis of Compound Int-5I

To a solution of compound Int-5H (700 mg, 1.295 mmol) in dichloromethane (5 mL) was added Dess-Martin periodinane (1099 mg, 2.59 mmol), and the mixture was allowed to stir at 20° C. for 13 hours. The mixture was concentrated and the residue was purified using a preparative TLC plate eluting with 5% MeOH/dichloromethane to provide compound Int-5I as a solid. $^1$H NMR (400 MHz, CHLOROFORM-d): δ 7.49-7.73 (m, 1H), 4.61-4.74 (m, 1H), 4.00-4.16 (m, 5H), 3.96 (s, 3H), 3.58-3.74 (m, 2H), 3.45 (s, 6H), 1.72 (br. s., 6H), 1.22-1.38 (m, 9H). MS: m/z=538.1 (M+1).

Step J—Synthesis of Compounds Int-5J, K, L, M

To a solution of compound Int-5I (300 mg, 0.557 mmol) in DMSO (3 mL) under CO balloon was added (2,4-difluorophenyl)methanamine (120 mg, 0.836 mmol), diisopropylethylamine (0.292 mL, 1.672 mmol) and $Pd(Ph_3P)_4$ (129 mg, 0.111 mmol). The mixture was allowed to stir at 90° C. for 12 hours. The mixture was quenched with water (30 mL), and extracted with EtOAc (50 mL×3). The organic phase was washed by brine (30 mL), dried over $Na_2SO_4$, filtered, concentrated, and the residue was purified using a silica gel column eluting with 5% MeOH/dichloromethane to provide a mixture of compounds Int-5J, K, L M as a solid. MS: m/z=629.3 (M+1). This material was further separated by a chiral preparative SFC (Column. AS (250 mm*30 mm, 10 um) Mobile phase: Supercritical $CO_2$/EtOH=20/20 at 50 mL/min Wavelength: 220 nm) to provide compound Int-5J (the first eluting isomer) as a solid, compound Int-5K (the second eluting isomer) as a solid, compound Int-5L (the third eluting isomer) as a solid and compound Int-5M (the fourth eluting isomer) as a solid.

Compound Int-5J: $^1$H NMR (400 MHz, CHLOROFORM-d): δ 10.42-10.51 (m, 1H), 8.40 (s, 1H), 7.32-7.40 (m, 1H), 6.76-6.84 (m, 2H), 4.63 (br. s., 2H), 4.44 (br. s., 1H), 4.19-4.29 (m, 2H), 4.07 (d, J=7.3 Hz, 4H), 3.99 (s, 3H), 3.77 (br. s., 1H), 3.51-3.55 (m, 1H), 3.36-3.44 (m, 5H), 1.89-1.99 (m, 2H), 1.73-1.82 (m, 4H), 1.28-1.34 (m, 9H).

Compound Int-5K: $^1$H NMR (400 MHz, CHLOROFORM-d): δ 10.38-10.54 (m, 1H), 8.39 (s, 1H), 7.33-7.41 (m, 1H), 6.81 (d, J=8.4 Hz, 2H), 4.63 (br. s., 2H), 4.44 (br. s., 1H), 4.22-4.27 (m, 1H), 4.04-4.15 (m, 4H), 3.99 (s, 3H), 3.76-3.79 (m, 1H), 3.51-3.60 (m, 2H), 3.36-3.45 (m, 5H), 1.89-1.99 (m, 2H), 1.72-1.81 (m, 4H), 1.27-1.38 (m, 9H).

Compound Int-5L: $^1$H NMR (400 MHz, CHLOROFORM-d): δ 10.32-10.52 (m, 1H), 8.39 (s, 1H), 7.36 (d, J=7.1 Hz, 1H), 6.80 (d, J=8.4 Hz, 2H), 4.62 (d, J=5.7 Hz, 2H), 4.29 (br. s., 2H), 4.03-4.17 (m, 4H), 3.98 (s, 3H), 3.82 (br. s., 1H), 3.57 (t, J=5.8 Hz, 2H), 3.43 (t, J=5.6 Hz, 2H), 3.39 (s, 3H), 2.12-2.19 (m, 1H), 2.02 (br. s., 1H), 1.79 (d, J=6.4 Hz, 4H), 1.31 (t, J=6.9 Hz, 6H), 1.26 (s, 3H).

Compound Int-5M: $^1$H NMR (400 MHz, CHLOROFORM-d): δ 10.39-10.49 (m, 1H), 8.39 (s, 1H), 7.31-7.41 (m, 1H), 6.72-6.88 (m, 2H), 4.63 (d, J=5.7 Hz, 2H), 4.29 (br. s., 2H), 4.08 (d, J=7.1 Hz, 4H), 3.99 (s, 3H), 3.83 (br. s., 1H), 3.57 (t, J=6.0 Hz, 2H), 3.43 (t, J=5.8 Hz, 2H), 3.39 (s, 3H), 2.11-2.19 (m, 1H), 1.97-2.04 (m, 1H), 1.78-1.89 (m, 4H), 1.27-1.45 (m, 9H). MS: m/z=447.1 (M+1).

Step J—Synthesis of Compounds 44-47

To a solution of compound Int-5J (40 mg, 0.064 mmol) in ACN (4 mL) was added magnesium bromide (35.1 mg, 0.191 mmol), and the mixture was allowed to stir at room temperature (26° C.) for 16 hours. LCMS showed the reaction was completed. The reaction mixture was filtered, and the filtrate was purified using a reverse phase-HPLC (Column: Boston Green ODS 150*25 mm*5 um, Condition: 0.1% TFA-ACN, 37% to 67%, Flow Rate, 30 mL/min) to provide Compound 44 as a solid. $^1$H NMR (400 MHz, CHLOROFORM-d): δ 10.29-10.52 (m, 1H), 8.41 (s, 1H), 7.32-7.43 (m, 1H), 6.81 (d, J=7.8 Hz, 2H), 4.65 (t, J=4.7 Hz, 2H), 4.51 (s, 1H), 4.29 (dd, J=13.7, 4.3 Hz, 1H), 4.09 (d, J=7.0 Hz, 4H), 3.81 (d, J=2.0 Hz, 1H), 3.55-3.61 (m, 1H), 3.47-3.52 (m, 1H), 3.42 (s, 3H), 3.38 (t, J=5.7 Hz, 2H), 2.03 (d, J=5.1 Hz, 1H), 1.65-1.83 (m, 5H), 1.37 (s, 3H), 1.27-1.35 (m, 6H). MS: m/z=615.1 (M+1).

Compound 45 was prepared from compound Int-5K using the procedure described above. $^1$H NMR (400 MHz, CHLOROFORM-d): δ 10.23-10.54 (m, 1H), 8.40 (s, 1H), 7.28-7.40 (m, 1H), 6.78 (d, J=8.2 Hz, 2H), 4.57-4.68 (m, 2H), 4.46-4.53 (m, 1H), 4.23-4.31 (m, 1H), 4.06 (dt, J=12.7, 6.6 Hz, 4H), 3.78 (d, J=2.0 Hz, 1H), 3.52-3.57 (m, 1H), 3.44-3.49 (m, 1H), 3.40 (s, 3H), 3.35 (br. s., 2H), 1.96-2.05 (m, 1H), 1.63-1.81 (m, 5H), 1.34 (s, 3H), 1.19-1.33 (m, 6H). MS: m/z=615.2 (M+1).

Compound 46 was prepared from compound Int-5L using the procedure described above. $^1$H NMR (400 MHz, CHLOROFORM-d): δ 10.32-10.52 (m, 1H), 8.41 (s, 1H), 7.36 (s, 1H), 6.81 (d, J=7.8 Hz, 2H), 4.65 (t, J=5.1 Hz, 2H), 4.29-4.39 (m, 2H), 4.05-4.17 (m, 4H), 3.87-3.91 (m, 1H), 3.62 (d, J=5.5 Hz, 2H), 3.43-3.48 (m, 2H), 3.40 (s, 3H), 2.13-2.24 (m, 2H), 1.76-1.89 (m, 4H), 1.29-1.38 (m, 9H). MS: m/z=615.2 (M+1).

Compound 47 was prepared from compound Int-5M using the procedure described above. $^1$H NMR (400 MHz, CHLOROFORM-d) δ 10.33-10.43 (m, 1H), 8.40 (s, 1H), 7.31-7.41 (m, 1H), 6.80 (s, 2H), 4.65 (t, J=5.1 Hz, 2H), 4.29-4.38 (m, 2H), 4.04-4.16 (m, 4H), 3.85-3.93 (m, 1H), 3.62 (d, J=5.5 Hz, 2H), 3.44-3.49 (m, 2H), 3.40 (s, 3H), 2.18 (d, J=9.0 Hz, 2H), 1.83 (br. s., 4H), 1.28-1.38 (m, 9H). MS: m/z=615.2 (M+1).

Example 6

Preparation of Compounds 48-50

Step A—Synthesis of Compound Int-6A

To a solution of compound Int-5J (90 mg, 0.143 mmol) in MeCN (2 mL) was added TMSBr (2 mL, 15.42 mmol) at 0° C. After stirred at 0° C. for 1 h, the mixture was stirred at 40° C. for another 1 hour. The reaction was quenched with MeOH (5 mL) and the mixture was concentrated in vacuo. The residue was purified using preparative HPLC (Column: Waters Xbridge Prep OBD C18 150*30 mm*5 um; Condition: 0.1% TFA-ACN; Gradient: 17% to 37%; B, 0~10 min. FlowRate: 25 mL/min) to provide compound Int-6A as a solid. $^1$H NMR (400 MHz, CHLOROFORM-d): δ 8.52 (s, 1H), 7.37-7.49 (m, 1H), 6.88-7.03 (m, 2H), 4.63 (s, 4H), 3.87 (s, 4H), 3.43 (s, 5H), 3.33-3.39 (m, 2H), 1.89-2.02 (m, 2H), 1.59-1.80 (m, 4H), 1.29 (s, 3H). MS: m/z=573.2 (M+1).

Step B—Synthesis of Compound 48

To a solution of compound Int-6A (20 mg, 0.035 mmol) in MeCN (1 mL) was added magnesium bromide (64.3 mg, 0.349 mmol) and the mixture was stirred 15° C. for 12 hours. The reaction mixture was filtered and the filtrate was purified using a reverse phase-HPLC (Column: Waters Xbridge Prep OBD C18 150 mm*25 mm*5 um, Condition: 0.1% TFA-ACN, 5% to 95%, Flow Rate, 25 mL/min) to provide compound 48 as a solid. $^1$H NMR (400 MHz, CHLOROFORM-d): δ 8.45-8.52 (m, 1H), 7.36-7.48 (m, 1H), 6.86-7.01 (m, 2H), 4.63 (s, 4H), 3.92 (br. s., 1H), 3.60 (br. s., 1H), 3.49-3.54 (m, 1H), 3.45 (s, 3H), 3.34-3.41 (m, 2H), 2.05-2.16 (m, 1H), 1.85-1.94 (m, 1H), 1.56-1.80 (m, 4H), 1.37 (s, 3H). MS: m/z=559.2 (M+1).

Compounds 49 and compound 50 were prepared from the corresponding compound Int-5L and compound Int-5M, respectively, using the method described in Step A and Step B of this example.

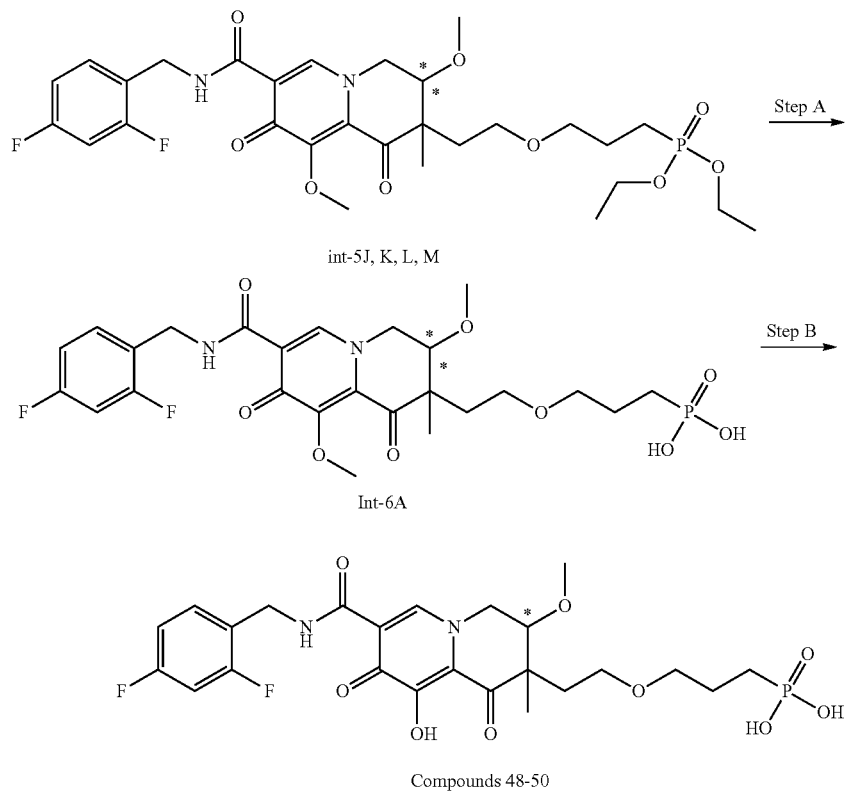

int-5J, K, L, M

Int-6A

Compounds 48-50

Compound 49: ¹H NMR (400 MHz, CHLOROFORM-d): δ 8.45-8.53 (m, 1H), 7.38-7.47 (m, 1H), 6.87-7.02 (m, 2H), 4.63 (s, 4H), 3.89-3.94 (m, 1H), 3.56-3.63 (m, 1H), 3.49-3.55 (m, 1H), 3.45 (s, 3H), 3.35-3.41 (m, 2H), 2.07-2.14 (m, 1H), 1.86-1.93 (m, 1H), 1.68 (br. s., 4H), 1.37 (s, 3H). MS: m/z=559.2 (M+1).

Compound 50: ¹H NMR (400 MHz, METHANOL-d4): δ 8.39-8.59 (m, 1H), 7.37-7.47 (m, 1H), 6.88-7.04 (m, 2H), 4.63 (s, 3H), 4.47-4.56 (m, 1H), 3.98 (br. s., 1H), 3.59-3.67 (m, 2H), 3.50 (br. s., 2H), 3.43 (s, 3H), 2.07-2.20 (m, 2H), 1.68-1.90 (m, 4H), 1.37 (s, 3H). MS: m/z=559.2 (M+1).

Example 7

Preparation of Compounds 51-53

Compounds 51-53

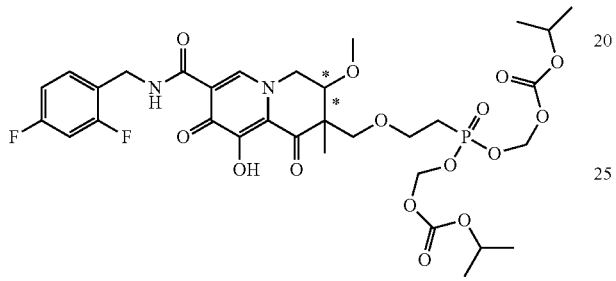

Using the method described in Example 3, and starting from compounds Int-5J, K and M, compounds 51-53 were each respectively prepared as a single stereoisomer.

Compound 51: ¹H NMR (400 MHz, METHANOL-d4): δ 8.47-8.53 (m, 1H), 7.40-7.48 (m, 1H), 6.90-6.99 (m, 2H), 5.56-5.66 (m, 4H), 4.89-4.94 (m, 2H), 4.60-4.73 (m, 4H), 3.91 (br. s., 1H), 3.56-3.61 (m, 1H), 3.49-3.53 (m, 1H), 3.45 (s, 3H), 3.34-3.38 (m, 2H), 2.07-2.14 (m, 1H), 1.81-1.93 (m, 3H), 1.65-1.75 (m, 2H), 1.36 (s, 3H), 1.28 (dd, J=6.0, 2.0 Hz, 12H). MS: m/z=791.3 (M+1).

Compound 52: ¹H NMR (400 MHz, METHANOL-d4): δ 8.47-8.56 (m, 1H), 7.38-7.50 (m, 1H), 6.72-7.07 (m, 2H), 5.54-5.69 (m, 4H), 4.89-4.93 (m, 2H), 4.57-4.73 (m, 4H), 3.89-3.93 (m, 1H), 3.58 (d, J=7.7 Hz, 1H), 3.49-3.54 (m, 1H), 3.45 (s, 3H), 3.36 (d, J=5.7 Hz, 2H), 2.09-2.17 (m, 1H), 1.79-1.91 (m, 3H), 1.63-1.73 (m, 2H), 1.36 (s, 3H), 1.28 (dd, J=6.0, 2.0 Hz, 12H). MS: m/z=791.3 (M+1).

Compound 53: ¹H NMR (400 MHz, METHANOL-d4): δ 8.47-8.51 (m, 1H), 7.39-7.46 (m, 1H), 6.90-6.99 (m, 2H), 5.64 (s, 4H), 4.92 (br. s., 2H), 4.63 (s, 3H), 4.50-4.56 (m, 1H), 3.95-3.99 (m, 1H), 3.60-3.66 (m, 2H), 3.47 (t, J=5.8 Hz, 2H), 3.43 (s, 3H), 2.13-2.17 (m, 2H), 1.93-2.02 (m, 2H), 1.79-1.85 (m, 2H), 1.36 (s, 3H), 1.30 (d, J=6.2 Hz, 12H). MS: m/z=791.3 (M+1).

Example 8

Preparation of Compound Int-8

Compound Int-8 was prepared using the method described from Step H to Step M in Example 1, except replacing compound Int-1g with compound Int-5c. ¹H NMR (400 MHz, CHLOROFORM-d): δ 7.62-7.73 (m, 1H), 4.41 (d, J=13.6 Hz, 1H), 4.02-4.24 (m, 4H), 3.99 (s, 3H), 3.80-3.91 (m, 1H), 3.52-3.72 (m, 4H), 3.37-3.49 (m, 4H), 1.78-2.18 (m, 4H), 1.26-1.34 (m, 9H). MS: m/z=524.2, 526.2 (M+1).

Example 9

Preparation of Compounds 54-57

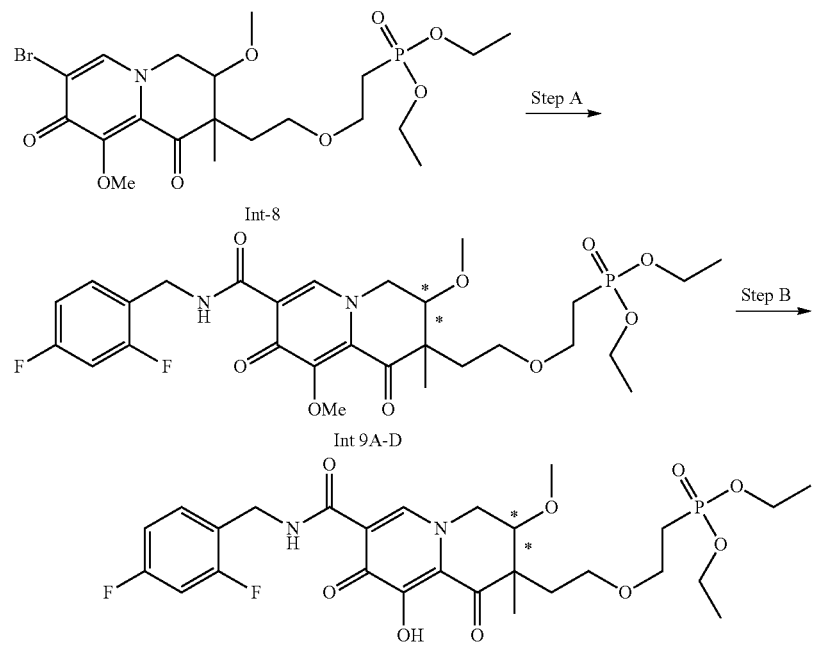

Step A—Synthesis of Compounds Int-9A, 9B, 9C, 9D

To a solution of compound Int-8 (200 mg, 0.381 mmol) in DMSO (3 mL) was added diisopropylethylamine (0.200 mL, 1.144 mmol), Pd(Ph$_3$P)$_4$ (88 mg, 0.076 mmol) and (2,4-difluorophenyl)methanamine (82 mg, 0.572 mmol). The mixture was allowed to stir at 90° C. under CO balloon for 3 hours. The reaction was filtered and the filtrate was purified using preparative HPLC (Column: YMC-Actus Pro C18 150*30*5 um; Condition: 0.1% TFA-ACN; Gradient: 28% to 58%; B, 0~11 min. FlowRate: 40 mL/min) to provide a mixture of compounds Int-9A, 9B, 9C and 9D as a solid. MS: m/z=615.1 (M+1). This material was further separated by a chiral preparative SFC (Column: AD 250 mm*30 mm, 10 um; Condition: Base-EtOH; Begin B 25% End B 25%; FlowRate: 70 mL/min) to provide compound Int-9A (the first eluting isomer) as an oil, compound Int-9B (the second eluting isomer) as an oil and a mixture of compound Int-9C and compound Int-9D. This mixture was further separated by a chiral preparative SFC (Column: OD 250 mm*30 mm, 10 um; Condition: Base-EtOH; Begin B 25% End B 25%; FlowRate: 80 mL/min) to provide compound Int-9C (the first eluting isomer) as an oil and compound Int-9D (the second eluting isomer) as an oil.

Compound Int-9A: $^1$H NMR (400 MHz, CHLOROFORM-d): δ 10.46 (s, 1H), 8.40 (s, 1H), 7.32-7.41 (m, 1H), 6.74-6.86 (m, 2H), 4.56-4.71 (m, 2H), 4.47 (d, J=12.1 Hz, 1H), 4.21-4.25 (m, 1H), 4.02-4.12 (m, 3H), 3.99 (s, 3H), 3.84-3.86 (m, 1H), 3.55-3.61 (m, 3H), 3.38-3.50 (m, 4H), 1.91-2.06 (m, 3H), 1.73-1.85 (m, 2H), 1.17-1.39 (m, 9H).

Compound Int-9B: $^1$H NMR (400 MHz, CHLOROFORM-d): δ 10.46 (s, 1H), 8.40 (s, 1H), 7.46 (s, 1H), 6.74-6.88 (m, 2H), 4.54-4.72 (m, 2H), 4.47 (d, J=12.3 Hz, 1H), 4.22-4.26 (m, 1H), 3.97-4.14 (m, 6H), 3.83-3.85 (m, 1H), 3.52-3.59 (m, 3H), 3.35-3.51 (m, 4H), 1.78-2.05 (m, 5H), 1.19-1.40 (m, 9H).

Compound Int-9C: $^1$H NMR (400 MHz, CHLOROFORM-d): δ 10.46 (s, 1H), 8.39 (s, 1H), 7.30-7.40 (s, 1H), 6.74-6.87 (m, 2H), 4.62-4.71 (m, 2H), 4.26-4.30 (m, 2H), 4.04-4.18 (m, 4H), 3.99 (s, 3H), 3.84-3.89 (m, 1H), 3.55-3.66 (m, 3H), 3.39 (s, 3H), 1.95-2.23 (m, 5H), 1.18-1.38 (m, 9H).

Compound Int-9D: $^1$H NMR (400 MHz, CHLOROFORM-d): δ 10.44 (s, 1H), 8.39 (s, 1H), 7.30-7.41 (m, 1H), 6.75-6.86 (m, 2H), 4.55-4.63 (m, 2H), 4.25-4.30 (m, 2H), 4.03-4.14 (m, 4H), 3.99 (s, 3H), 3.83-3.89 (m, 1H), 3.55-3.73 (m, 3H), 3.39 (s, 3H), 1.98-2.19 (m, 5H), 1.18-1.37 (m, 9H).

Step B—Synthesis of Compounds 54-57

To a solution of compound Int-9A (100 mg, 0.163 mmol) in acetonitrile (5 mL) was added magnesium bromide (300 mg, 1.627 mmol) and the mixture was allowed to stir at 25° C. for 12 hours. The mixture was filtered and the filtrate was purified using preparative HPLC (Column: Boston Green ODS 150 mm*30 mm*5 um; Condition: 0.1% TFA-ACN; Gradient: 35% to 65%; B, 0~8 min. FlowRate: 30 mL/min) to provide compound 54 as an oil. $^1$H NMR (400 MHz, CHLOROFORM-d): δ 10.40 (s, 1H), 8.40 (s, 1H), 7.31-7.40 (m, 1H), 6.76-6.86 (m, 2H), 4.60-4.71 (m, 2H), 4.51-4.54 (m, 1H), 4.28-4.30 (m, 1H), 4.00-4.14 (m, 4H), 3.87-3.88 (m, 1H), 3.49-3.66 (m, 4H), 3.42 (s, 3H), 1.95-2.06 (m, 3H), 1.76-1.81 (m, 1H) 1.23-1.42 (m, 9H). MS: m/z=601.2 (M+1).

To a solution of compound Int-9B (70 mg, 0.114 mmol) in acetonitrile (5 mL) was added magnesium bromide (210 mg, 1.139 mmol) and the mixture was allowed to stir at 25° C. for 12 hours. The mixture was filtered and the filtrate was purified using preparative HPLC (Column: Boston Green ODS 150 mm*30 mm*5 um; Condition: 0.1% TFA-ACN; Gradient: 35% to 65%; B, 0~8 min. FlowRate: 30 mL/min) to provide compound 55 as an oil. $^1$H NMR (400 MHz, CHLOROFORM-d): δ 10.41 (s, 1H), 8.40 (s, 1H), 7.31-7.42 (m, 1H), 6.73-6.86 (m, 2H), 4.60-4.65 (m, 2H), 4.51-4.53 (m, 1H), 4.28-4.30 (m, 1H), 3.98-4.14 (m, 4H), 3.87-3.88 (m, 1H), 3.46-3.65 (m, 4H), 3.42 (s, 3H), 1.92-2.08 (m, 3H), 1.76-1.80 (m, 1H), 1.27-1.37 (m, 9H). MS: m/z=601.2 (M+1).

To a solution of compound Int-9C (105 mg, 0.570 mmol) and the mixture was allowed to stir at 25° C. for 12 hours. LCMS showed the reaction was completed. The mixture was filtered and the filtrate was purified using preparative HPLC (Column: Boston Green ODS 150 mm*30 mm*5 um; Condition: 0.1% TFA-ACN; Gradient: 35% to 65%; B, 0~8 min. FlowRate: 30 mL/min) to provide compound 56 as an oil. $^1$H NMR (400 MHz, CHLOROFORM-d): δ 10.39 (s, 1H), 8.40 (s, 1H), 7.30-7.42 (m, 1H), 6.75-6.86 (m, 2H), 4.62-4.65 (m, 2H), 4.29-4.33 (m, 2H), 4.03-4.19 (m, 4H), 3.94-3.95 (m, 1H), 3.57-3.75 (m, 4H), 3.39 (s, 3H), 2.01-2.24 (m, 4H), 1.21-1.42 (m, 9H). MS: m/z=601.2 (M+1).

To a solution of compound Int-9D (35 mg, 0.057 mmol) in acetonitrile (5 mL) was added magnesium bromide (105 mg, 0.570 mmol) and the mixture was allowed to stir at 25° C. for 12 hours. LCMS showed the reaction was completed. The mixture was filtered and the filtrate was purified using preparative HPLC (Column: Boston Green ODS 150*30*5 um; Condition: 0.1% TFA-ACN; Gradient: 35% to 65%; B, 0~8 min. FlowRate: 30 mL/min) to provide compound 57 as an oil. $^1$H NMR (400 MHz, CHLOROFORM-d): δ 10.38 (s, 1H), 8.39 (s, 1H), 7.30-7.41 (m, 1H), 6.75-6.87 (m, 2H), 4.62-4.65 (m, 2H), 4.29-4.33 (m, 2H), 4.04-4.18 (m, 4H), 3.94-3.95 (m, 1H), 3.57-3.73 (m, 4H), 3.38 (s, 3H), 2.01-2.25 (m, 4H), 1.22-1.41 (m, 9H). MS: m/z=601.2 (M+1).

Example 10

Preparation of Compounds 58-61

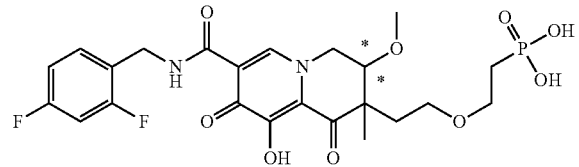

Compounds 58-61

Compounds 58, 59, 60 and 61 were prepared from compounds Int-9A, 9B, 9C, and 9D respectively using the method described in Example 6.

Compound 58: $^1$H NMR (400 MHz, METHANOL-d$_4$): δ 8.48 (s, 1H), 7.37-7.51 (m, 1H), 6.84-7.02 (m, 2H), 4.52-4.76 (m, 4H), 3.95-3.97 (m, 1H), 3.48-3.72 (m, 4H), 3.44 (s, 3H), 2.03-2.16 (m, 1H), 1.80-1.96 (m, 3H), 1.37 (s, 3H). MS: m/z=545.1 (M+1).

Compound 59: $^1$H NMR (400 MHz, METHANOL-d4): δ 8.48 (s, 1H), 7.38-7.47 (m, 1H), 6.89-7.01 (m, 2H), 4.53-4.76 (m, 4H), 3.95-3.97 (m, 1H), 3.49-3.71 (m, 4H), 3.44 (s, 3H), 2.03-2.18 (m, 1H), 1.82-1.97 (m, 3H), 1.37 (s, 3H). MS: m/z=545.1 (M+1).

Compound 60: $^1$H NMR (400 MHz, METHANOL-d4): δ 8.49 (s, 1H), 7.39-7.44 (m, 1H), 6.88-7.00 (m, 2H), 4.46-4.69 (m, 4H), 4.03-4.05 (m, 1H), 3.65-3.71 (m, 4H), 3.43 (s, 3H), 1.96-2.20 (m, 4H), 1.37 (s, 3H). MS: m/z=545.1 (M+1).

Compound 61: $^1$H NMR (400 MHz, METHANOL-d4): δ 8.49 (s, 1H), 7.39-7.46 (m, 1H), 6.93-7.00 (m, 2H), 4.63-4.68 (m, 3H), 4.48-4.54 (m, 1H), 4.02-4.05 (m, 1H), 3.62-3.68 (m, 4H), 3.43 (s, 3H), 1.95-2.15 (m, 4H), 1.37 (s, 3H). MS: m/z=545.1 (M+1).

Example 11

Preparation of Compounds 62-64

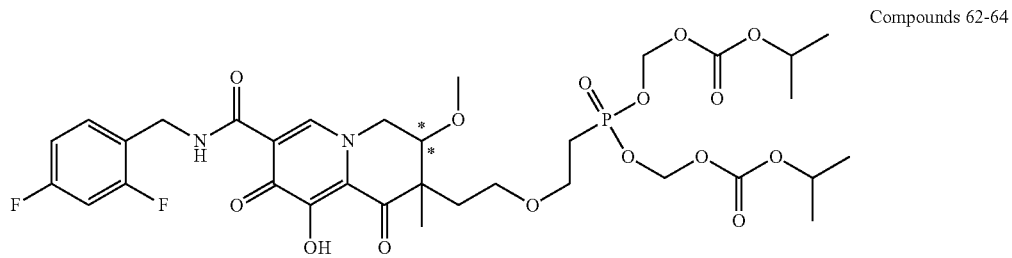 [SMILES: COC1Cn2cc(C(=O)NCc3ccc(F)cc3F)c(=O)c(O)c2C(=O)C1(C)CCOCCP(=O)(OCOC(=O)OC(C)C)OCOC(=O)OC(C)C]

Compounds 62, 63 and 64 were prepared from compounds Int-9A, 9C and 9D respectively using the method described in Example 3.

Compound 62: $^1$H NMR (400 MHz, METHANOL-d4): δ 8.50 (s, 1H), 7.37-7.47 (m, 1H), 6.87-7.03 (m, 2H), 5.54-5.65 (m, 4H), 4.91-4.98 (m, 2H), 4.53-4.78 (m, 4H), 3.97-3.98 (m, 1H), 3.48-3.69 (m, 4H), 3.45 (s, 3H), 2.03-2.23 (m, 3H), 1.82-1.92 (m, 1H), 1.37 (s, 3H), 1.25-1.31 (m, 12H). MS: m/z=777.3 (M+1).

Compound 63: $^1$H NMR (400 MHz, CHLOROFORM-d): δ 8.49 (s, 1H), 7.38-7.47 (m, 1H), 6.90-7.01 (m, 2H), 5.58-5.73 (m, 4H), 4.91-4.98 (m, 2H), 4.48-4.71 (m, 4H), 4.01-4.03 (m, 1H), 3.60-3.75 (m, 4H), 3.43 (s, 3H), 2.11-2.35 (m, 4H), 1.37 (s, 3H), 1.29-1.31 (m, 12H). MS: m/z=777.3 (M+1).

Compound 64: $^1$H NMR (400 MHz, CHLOROFORM-d): δ 8.49 (s, 1H), 7.37-7.47 (m, 1H), 6.88-7.01 (m, 2H), 5.58-5.72 (m, 4H), 4.90-4.95 (m, 2H), 4.48-4.72 (m, 4H), 4.01-4.03 (m, 1H), 3.60-3.76 (m, 4H), 3.43 (s, 3H), 2.10-2.35 (m, 4H), 1.37 (s, 3H), 1.29-1.31 (m, 12H). MS: m/z=777.3 (M+1).

Example 12

Preparation of Compound 65 and 66

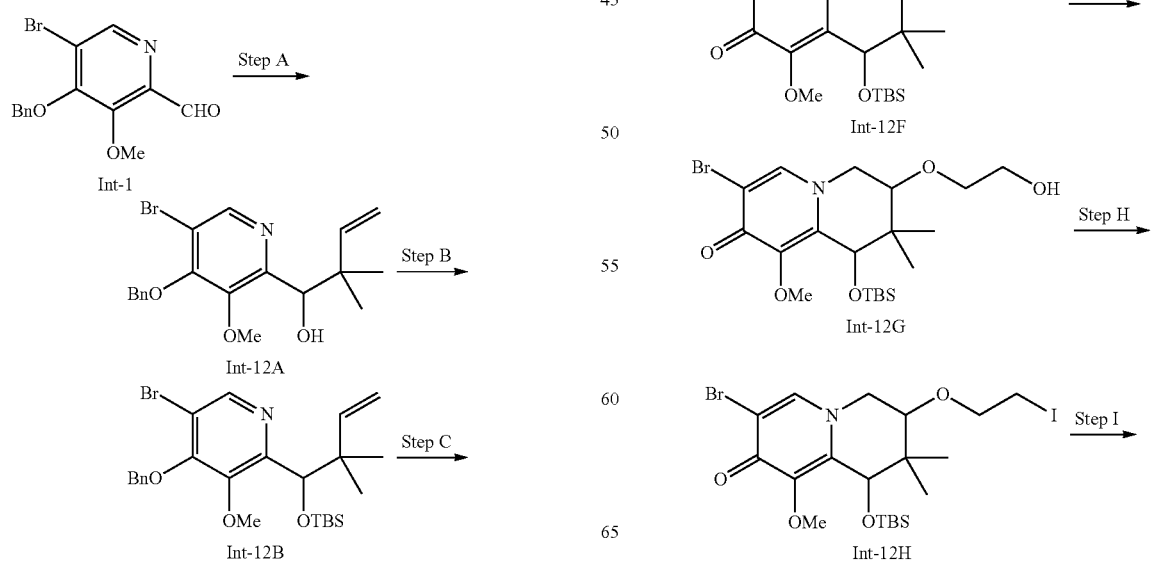

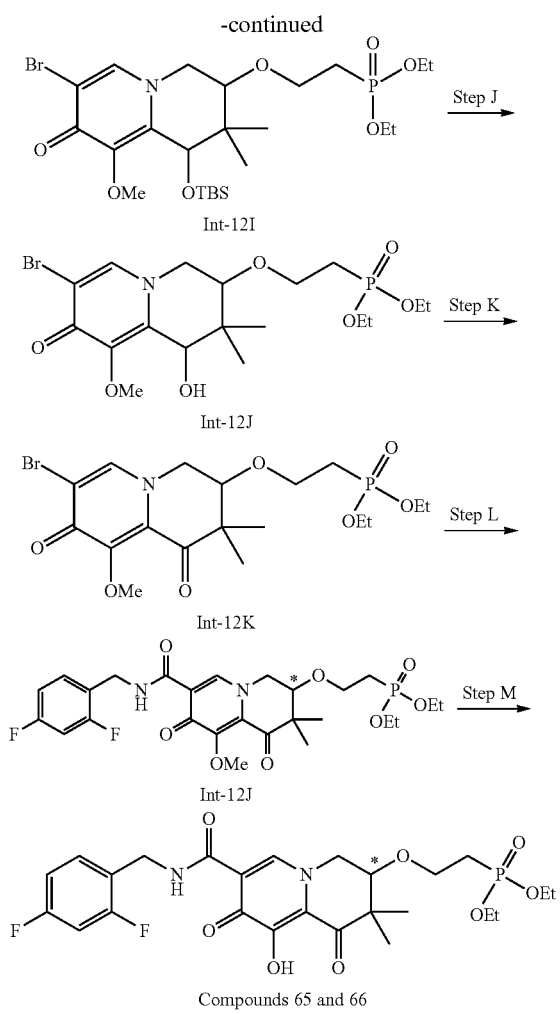

Step A—Synthesis of Compound Int-12A

To a solution of sodium iodide (6979 mg, 46.6 mmol), indium (13400 mg, 116 mmol) and 1-bromo-3-methylbut-2-ene (5204 mg, 34.9 mmol) in DMF (60 mL) was added compound Int-1 (7500 mg, 23.28 mmol). The mixture was allowed to stir at 25° C. for 2 hours. The reaction was diluted with 200 mL EtOAc. The organic phase was washed with water (200 mL), brine (200 mL) and then dried over anhydrous sodium sulfate. After filtration, the organic solvent was removed under vacuum and the residue was purified using a silica gel column eluting with 14% EtOAc/petroleum ether to provide compound Int-12A as an oil. $^1$H NMR (400 MHz, CHLOROFORM-d): δ 8.34 (s, 1H), 7.41-7.50 (m, 2H), 7.31-7.38 (m, 3H), 5.85 (t, J=10.8 Hz, 1H), 5.22 (d, J=11.2 Hz, 1H), 5.10 (d, J=11.2 Hz, 1H), 4.99 (d, J=10.8 Hz, 1H), 4.91 (d, J=10.8 Hz, 1H), 4.61-4.72 (m, 1H), 3.87 (s, 3H), 1.03 (s, 3H), 1.01 s, 3H). MS: m/z=394.1 (M+1).

Step B—Synthesis of Compound Int-12B

To a solution of compound Int-12A (7500 mg, 19.12 mmol) in CH$_2$Cl$_2$ (120 mL) were added 2,6-lutidine (4.45 mL, 38.2 mmol), tert-butyldimethylsilyl 2-methylpropane-2-sulfonate (7240 mg, 28.7 mmol) at 0° C. After addition, the mixture was allowed to stir at 25° C. for 6 hours. It was quenched by addition of saturated NaHCO$_3$ solution (40 mL). The aqueous was extracted with DCM (30 mL×2), dried over anhydrous sodium sulfate, filtered and concentrated to provide the crude product, which was purified using a silica gel column eluting with 6% EtOAc/petroleum ether to provide compound Int-12B as an oil. $^1$H NMR (400 MHz, CHLOROFORM-d): δ 8.67 (s, 1H), 7.52-7.73 (m, 5H), 6.22-6.29 (m, 1H), 5.27-5.38 (m, 2H), 5.11-5.21 (m, 3H), 4.14 (s, 3H), 1.29 (s, 6H), 1.12 (s, 9H), 0.32 (s, 3H), 0.25 (s, 3H). MS: m/z=508.2 (M+1).

Step C—Synthesis of Compound Int-12C

To a solution of compound Int-12B (7500 mg, 14.81 mmol) in THF (80 mL), water (40 mL) was added osmium tetroxide (0.465 mL, 1.481 mmol), NMO (3469 mg, 29.6 mmol) and the mixture was allowed to stir at 25° C. for 6 hours. The reaction was quenched by adding saturated aqueous Na$_2$SO$_3$ (30 mL) and then stirred for another 30 min. The reaction mixture was extracted with EtOAc (50 mL×3), dried over anhydrous sodium sulfate, filtered and concentrated to provide a crude residue, which was purified using a silica gel column eluting with 50% EtOAc/petroleum ether to provide compound Int-12C as an oil. $^1$H NMR (400 MHz, CHLOROFORM-d): δ 8.73-8.82 (m, 1H), 7.61-7.83 (m, 5H), 5.41-5.53 (m, 2H), 5.11-5.23 (m, 1H), 4.28 (d, J=4.0 Hz, 3H), 3.84-4.05 (m, 3H), 1.06-1.26 (m, 15H), 0.39-0.49 (m, 3H), 0.01-0.07 (m, 3H). MS: m/z=540.2 (M+1).

Step D—Synthesis of Compound Int-12D

To a solution of compound Int-12C (3800 mg, 7.03 mmol) in pyridine (55 mL) was added TsCl (2412 mg, 12.65 mmol). The mixture was allowed to stir at 30° C. for 16 hours. The reaction was quenched by addition of MeOH (25 mL) and the mixture was allowed to stir for another 1 hour. The mixture was diluted with EtOAc (500 mL), washed with aqueous HCl solution (1.0 M, 500 mL), brine (100 mL). The organic phase was dried over anhydrous sodium sulfate, filtered and the filtrate was concentrated in vacuo. The residue was purified using a silica gel column eluting 5% methanol/DCM to provide compound Int-12D as a solid. $^1$H NMR (400 MHz, CHLOROFORM-d): δ 7.81 (s, 1H), 4.48-4.59 (m, 1H), 4.22-4.35 (m, 2H), 3.98 (s, 3H), 3.66-3.76 (m, 1H), 1.25-1.35 (m, 3H), 0.76-0.95 (m, 12H), 0.01-0.26 (m, 6H). MS: m/z=434.2 (M+1).

Step E—Synthesis of Compound Int-12E

To a solution of compound Int-12D (1000 mg, 2.313 mmol) in DMF (9.5 mL) was added sodium hydride (185 mg, 4.63 mmol) and the mixture was allowed to stir at −5° C. for 10 min. This was followed by addition of a solution of 3-bromoprop-1-ene (420 mg, 3.47 mmol) in DMF (0.5 mL). The mixture was allowed to stir at −5° C. for 1 h, then quenched with aqueous saturated NH$_4$Cl (2 mL). The resulting mixture was diluted with EtOAc (150 mL), washed with water (150 mL), brine (35 mL), The organic was dried over anhydrous sodium sulfate, filtered. The filtrate was concentrated and the residue was purified using a silica gel column eluting with 25% EtOAc/petroleum ether to provide compound Int-12E as an oil. $^1$H NMR (400 MHz, CHLOROFORM-d): δ 7.76 (d, J=11.6 Hz, 1H), 5.91-6.03 (m, 1H), 5.28-5.42 (m, 2H), 4.26-4.48 (m, 3H), 4.05-4.21 (m, 4H), 3.76-3.94 (m, 2H), 1.26-1.38 (m, 3H), 0.91-1.12 (m, 12H), 0.03-0.26 (m, 6H). MS: m/z=474.2 (M+1).

Step F—Synthesis of Compound Int-12F

To a solution of compound Int-12E (1520 mg, 3.22 mmol) in THF (20 mL), water (10 mL) was added NMO (565 mg, 4.83 mmol), osmium tetroxide (0.101 mL, 0.322 mmol). The mixture was allowed to stir at 26° C. for 12 hours. It was diluted with EtOAc (150 mL), washed with aqueous $Na_2SO_3$ (50 mL×2). The organic phase was dried over anhydrous sodium sulfate, filtered and the filtrate was concentrated in vacuo. The residue was dissolved in THF (8 mL) and water (16 mL). To this solution was added sodium periodate (642 mg, 3.00 mmol) and the resulting mixture was allowed to stir at 26° C. for 3 hours. It was diluted with EtOAc (100 mL) and washed with brine (50 mL). The organic layer was dried over anhydrous sodium sulfate and filtered. The filtrate was concentrated to provide compound Int-12F. $^1$H NMR (400 MHz, CHLOROFORM-d): δ 9.70 (d, J=5.2 Hz, 1H), 7.68 (d, J=3.2 Hz, 1H), 3.61-4.73 (m, 9H), 1.28 (d, J=4.8 Hz, 3H), 0.78-0.97 (m, 12H), 0.02-0.28 (m, 6H). MS: m/z=476.2 (M+1). This compound was used for the next step without further purification.

Step G—Synthesis of Compound Int-12G

To a solution of compound Int-12F (1460 mg, 3.08 mmol)) in EtOH (15 mL) was added sodium tetrahydroborate (116 mg, 3.08 mmol)) and the mixture was allowed to stir at 26° C. for 3 hours. The solvent was removed and the residue was re-dissolved in DCM (150 mL). The solution was washed with brine (30 mL). The organic phase was dried over anhydrous sodium sulfate, filtered and the filtrate was concentrated in vacuo to provide compound Int-12G as an oil, which was used for the next step without further purification. $^1$H NMR (400 MHz, CHLOROFORM-d): δ 7.66 (d, J=4.8 Hz, 1H), 3.45-4.75 (m, 12H), 1.21-1.31 (m, 3H), 0.76-0.97 (m, 12H), 0.02-0.28 (m, 6H). MS: m/z=478.3 (M+1).

Step H—Synthesis of Compound Int-12H

To a solution of compound Int-12G (1440 mg, 3.02 mmol) in $CH_2Cl_2$ (15 mL) were added 1H-imidazole (823 mg, 12.09 mmol), triphenylphosphine (1585 mg, 6.04 mmol) and diiodine (2301 mg, 9.07 mmol) at 0° C. The mixture was allowed to stir at 26° C. for 3 hours. It was diluted with DCM (180 mL), and washed with saturated $Na_2SO_3$ solution (60 mL×2). The organic layer was dried over anhydrous sodium sulfate, filtered and concentrated to provide the crude product which was purified using a silica gel column eluting with 25% EtOAc/petroleum ether to provide compound Int-12G as an oil. $^1$H NMR (400 MHz, CHLOROFORM-d): δ 7.75 (s, 1H), 4.80 (s, 1H), 4.45-4.56 (m, 1H), 4.08 (s, 3H), 3.89-4.01 (m, 4H), 3.55-3.65 (m, 2H), 1.37 (d, J=7.2 Hz, 3H), 0.85-1.05 (m, 12H), 0.02-0.26 (m, 6H). MS: m/z=588.1 (M+1).

Step I—Synthesis of Compound Int-12I

A mixture of compound Int-12H (800 mg, 1.364 mmol) and triethyl phosphite (4534 mg, 27.3 mmol) was heated to 140° C. for 1 hour. The solvent was removed under vacuum to provide the crude compound Int-12I as an oil. MS: m/z=598.2 (M+1). This material was used in the next reaction without further purification Step J—Synthesis of Compound Int-12J To a solution of compound Int-12I (758 mg, 1.271 mmol) in THF (2 mL) was added TBAF (1.525 mL, 1.525 mmol), and the mixture was allowed to stir at 30° C. for 12 hours. The solvent was removed under vacuum. The residue was purified using a silica gel column eluting with 5% methanol/DCM to provide compound Int-12J as a foam. $^1$H NMR (400 MHz, CHLOROFORM-d): δ 7.65 (d, J=6.4 Hz, 1H), 3.68-4.67 (m, 13H), 1.87-2.01 (m, 2H), 0.75-1.28 (m, 12H). MS: m/z=484.1 (M+1).

Step K—Synthesis of Compound Int-12K

To a solution of compound Int-12J (520 mg, 1.078 mmol) in $CH_2Cl_2$ mL) was added Dess-Martin Periodinane (732 mg, 1.725 mmol), and the mixture was allowed to stir at 30° C. for 12 hours. The solvent was removed under vacuum. The residue was purified using a silica gel column eluting with 5% methanol/DCM to provide the compound Int-12K as an oil. $^1$H NMR (CHLOROFORM-d): δ 7.78 (s, 1H), 3.78-4.36 (m, 12H), 1.97-2.08 (m, 2H), 1.06-1.28 (m, 12H). MS: m/z=482.1 (M+1).

Step L—Synthesis of Compounds Int-12L and Int-12M

To a solution of compound Int-12K (150 mg, 0.312 mmol) in DMSO (3 mL) was added diisopropylethylamine (0.164 mL, 0.937 mmol), (2,4-difluorophenyl)methanamine (89 mg, 0.625 mmol), $Pd(Ph_3P)_4$ (180 mg, 0.156 mmol). The mixture was allowed to stir at 86° C. under carbon monoxide atmosphere for 8 hours. The mixture was diluted with EtOAc (50 mL), washed with water (40 mL×2), brine (20 mL). The organic layer was dried over anhydrous sodium sulfate, filtered. The filtrate was concentrated in vacuo. The residue was purified using a preparative TLC plate eluting with pure EtOAc to provide a mixture of compound Int-12L and compound Int-12M as an oil. This material was further separated by a chiral preparative SFC (Column: AD (250 mm*30 mm, 5 um) Mobile phase: 40% Base-IPA (contained 0.1% $NH_3H_2O$) in $CO_2$ Flow rate: 65 mL/min Wavelength: 220 nm) to provide compound Int-12L (the first eluting isomer) as an oil and compound Int-12M (the second eluting isomer) as an oil.

Compound Int-12L: $^1$H NMR (400 MHz, CHLOROFORM-d): δ 10.88 (d, J=5.2 Hz, 1H), 8.42 (s, 1H), 7.33-7.41 (m, 1H), 6.78-6.86 (m, 2H), 4.64 (d, J=5.6 Hz, 2H), 4.38 (d, J=2.0 Hz, 2H), 3.65-4.08 (m, 10H), 1.98-2.10 (m, 2H), 1.12-131 (m, 12H). MS: m/z=571.1 (M+1).

Compound Int-12M: $^1$H NMR (400 MHz, CHLOROFORM-d): δ 10.87 (d, J=5.2 Hz, 1H), 8.43 (s, 1H), 7.33-7.41 (m, 1H), 6.78-6.86 (m, 2H), 4.64 (d, J=5.6 Hz, 2H), 4.38 (d, J=2.0 Hz, 2H), 3.65-4.08 (m, 10H), 1.98-2.10 (m, 2H), 1.12-131 (m, 12H). MS: m/z=571.1 (M+1).

Step M—Synthesis of Compound 65 and Compound 66

To a mixture of compound Int-12L (20 mg, 0.035 mmol) in acetonitrile (1 mL) was added magnesium bromide (129 mg, 0.701 mmol). The reaction was allowed to stir at 28° C. for 12 hours. LC-MS showed the starting material was consumed. The mixture was purified using a preparative HPLC (Column: Phenomenex Synergi C18 150 mm*30 mm*4 um; Condition: 0.1% TFA-ACN; Gradient: 31% to 61%; B, 0~8 min. FlowRate: 30 mL/min) to provide compound 65 as a solid. $^1$H NMR (400 MHz, Methanol-d): δ 8.48 (s, 1H), 7.38-7.46 (m, 1H), 6.88-6.97 (m, 2H), 4.64 (m, 3H), 3.81-3.98 (m, 7H), 3.65-3.76 (m, 2H), 2.02-2.11 (m, 2H), 1.38 (s, 3H), 1.32 (s, 3H), 1.19 (t, J=7.6 Hz, 6H). MS: m/z=557.1 (M+1).

To a mixture of compound Int-12M (21 mg, 0.035 mmol) in acetonitrile (1 mL) was added magnesium bromide (129 mg, 0.701 mmol). The reaction was allowed to stir at 28° C. for 12 hours. The mixture was purified using a preparative HPLC (Column: Phenomenex Synergi C18 150 mm*30 mm*4 um; Condition: 0.1% TFA-ACN; Gradient: 31% to 61%; B, 0~8 min. FlowRate: 30 mL/min) to provide compound 66 as a solid. $^1$H NMR (400 MHz, Methanol-d): δ

8.47 (s, 1H), 7.38-7.46 (m, 1H), 6.88-6.97 (m, 2H), 4.64 (m, 3H), 3.81-3.98 (m, 7H), 3.65-3.76 (m, 2H), 2.02-2.11 (m, 2H), 1.38 (s, 3H), 1.32 (s, 3H), 1.19 (t, J=7.6 Hz, 6H). MS: m/z=557.1 (M+1).

Example 13

Preparation of Compounds 67 and 68

Compounds 67 and 68

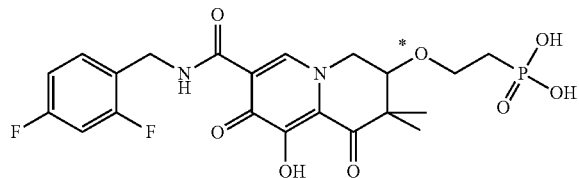

Compounds 67 and 68 were prepared from compounds Int-12L and 12K respectively using the method described in Example 6.

Compound 67: $^1$H NMR (400 MHz, MeOD): δ 8.47 (s, 1H), 7.39.-7.48 (m, 1H), 6.91-6.97 (m, 2H), 4.56-4.62 (m, 4H), 3.75-3.95 (m, 3H), 1.92-2.03 (m, 2H), 1.39 (s, 3H), 1.32 (s, 3H). MS: m/z=501.1 (M+1).

Compound 68: $^1$H NMR (400 MHz, MeOD): δ 8.47 (s, 1H), 7.39.-7.48 (m, 1H), 6.91-6.97 (m, 2H), 4.56-4.62 (m, 4H), 3.75-3.95 (m, 3H), 1.92-2.03 (m, 2H), 1.39 (s, 3H), 1.32 (s, 3H). MS: m/z=501.1 (M+1).

Example 14

Preparation of Compounds 69 and 70

Compounds 69 and 70

Compounds 69 and 70 were prepared from compounds Int-12L and 12M respectively using the method described in Example 3.

Compound 69: $^1$H NMR (400 MHz, MeOD): δ 8.51 (s., 1H), 7.39-7.46 (m, 1H), 6.91-6.98 (m, 2H), 5.47-5.59 (m, 4H), 4.69 (br, 5H), 3.37-3.96 (m, 4H), 2.26 (dd, J=6.0 Hz, 2H), 1.39 (s, 3H), 1.34 (s, 3H), 1.29 (s, 6H), 1.27 (s, 6H). MS: m/z=733.3 (M+1).

Compound 70: $^1$H NMR (400 MHz, MeOD): δ 8.51 (s., 1H), 7.39-7.46 (m, 1H), 6.91-6.98 (m, 2H), 5.47-5.59 (m, 4H), 4.69 (br, 5H), 3.37-3.96 (m, 4H), 2.26 (dd, J=6.0 Hz, 2H), 1.39 (s, 3H), 1.34 (s, 3H), 1.29 (s, 6H), 1.27 (s, 6H). MS: m/z=733.3 (M+1).

Example 15

Preparation of Compounds 71 and 72

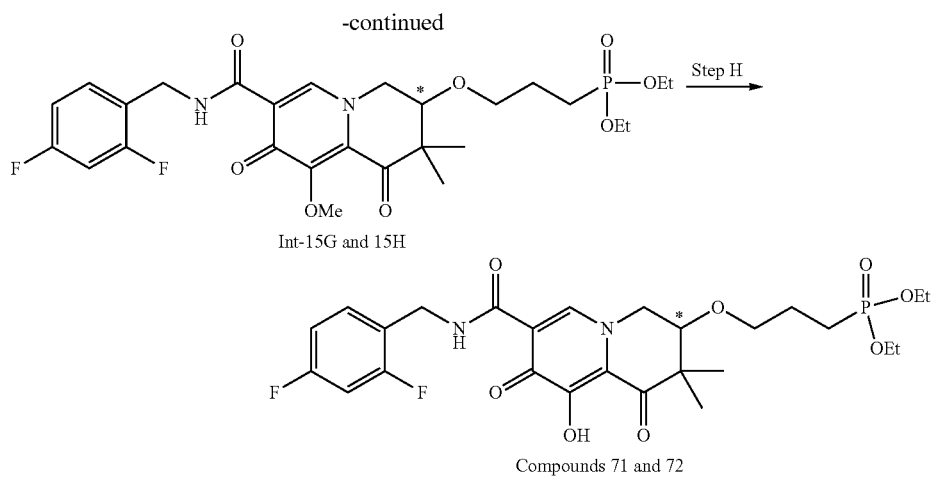

Int-15G and 15H

Compounds 71 and 72

Step A—Synthesis of Compound Int-15A

To a solution of compound Int-12D (1000 mg, 2.31 mmol) in DMF (10 mL) was added sodium hydride (185 mg, 4.63 mmol) at 0° C. The mixture was allowed to stir at 0° C. for 10 min followed by addition of 3-bromoprop-1-ene (420 mg, 3.47 mmol) at 0° C. The reaction mixture was allowed to stir at 0° C. for 1 hour. The mixture was quenched with 5 mL aqueous NH$_4$Cl, and the mixture was extracted with EtOAc (100 mL). The organic layer was washed with water (100 mL), brine (50 mL), dried over anhydrous sodium sulfate, filtered and concentrated. The residue was purified using a silica gel column eluting with 33% EtOAc/petroleum ether to provide compound Int-15A as an oil. $^1$H NMR (400 MHz, CDCl$_3$): δ 7.65 (s, 1H), 5.84-5.92 (m, 1H), 5.22-5.31 (m, 2H), 3.73-4.48 (m, 9H), 1.18 (s, 3H), 0.98 (s, 3H), 0.88 (s, 9H), 0.15 (s, 3H), 0.10 (s, 3H). MS: m/z=472.3 (M+1).

Step B—Synthesis of Compound Int-15B

To a solution of compound Int-15A (200 mg, 0.42 mmol) in THF (3 mL) was added BH$_3$.DMS (0.080 mL, 0.847 mmol) at 0° C. The mixture was allowed to stir at 20° C. for 6 hours. To the reaction mixture was added water (1.5 mL), sodium perborate tetrahydrate (130 mg, 0.847 mmol), and the mixture was allowed to stir at 20° C. for 16 hours. The mixture was diluted with EtOAc (100 mL), and washed with brine (25 mL). The organic phase was dried over sodium sulfate, filtered and concentrated to provide the crude product which was purified using a preparative TLC plate eluting with 5% MeOH/dichloromethane to provide compound Int-15B. MS: m/z=492.2 (M+1).

Step C—Synthesis of Compound Int-15C

To a solution of compound Int-15B (150 mg, 0.31 mmol) in THF (3 mL) were added imidazole (104 mg, 1.53 mmol), Ph$_3$P (241 mg, 0.92 mmol), and I$_2$ (155 mg, 0.61 mmol) sequentially. The mixture was allowed to stir at 20° C. for 16 hours. The solvent was removed and the residue was purified using a preparative TLC plate eluting with 67% petroleum ether/EtOAc to provide compound Int-15C as an oil. $^1$H NMR (400 MHz, CDCl$_3$): δ 7.67 (s, 1H), 4.70 (br, 1H), 4.39-4.48 (m, 1H), 4.09-4.17 (m, 1H), 3.97 (s, 3H), 3.62-3.69 (m, 2H), 3.41-3.55 (m, 1H), 3.21-3.32 (m, 2H), 1.65-1.88 (m, 2H), 1.27 (s, 3H), 0.84-0.91 (m, 12H), 0.07-0.16 (m, 6H). MS: m/z=601.1 (M+1).

Step D—Synthesis of Compound Int-15D

A mixture of compound Int-15C (100 mg, 0.17 mmol) and triethyl phosphate (277 mg, 1.67 mmol) was heated to 140° C. for 1 hour. The solvent was removed under vacuum to provide the crude compound Int-15D as an oil which was used for the next step without further purification. MS: m/z=610.1 (M+1).

Step E—Synthesis of Compound Int-15E

To the mixture of compound Int-15D (710 mg, 1.16 mmol) in THF (5 mL) was added TBAF (1.39 mL, 1.39 mmol). The reaction was allowed to stir at 23° C. for 6 hours. The solvent was removed under vacuum, the residue was purified using a preparative TLC plate eluting with 5% MeOH/dichloromethane to provide compound Int-15E as an oil. MS: m/z=496.1 (M+1).

Step F—Synthesis of Compound Int-15F

To a solution of compound Int-15E (140 mg, 0.28 mmol) in dichloromethane (2 mL) was added Dess-Martin Periodinane (239 mg, 0.56 mmol). The reaction was allowed to stir at 23° C. for 12 hours. The mixture was purified using a preparative TLC plate eluting with 5% MeOH/dichloromethane to provide compound Int-15F as an oil. MS: m/z=496.1 (M+1).

Step G—Synthesis of Compound Int-15G and Compound Int-15H

To a solution of compound Int-15F (130 mg, 0.263 mmol) in DMSO (3 mL) were added diisopropylethylamine (0.14 mL, 0.79 mmol), (2,4-difluorophenyl)methanamine (60.2 mg, 0.42 mmol) and Pd(Ph$_3$P)$_4$ (152 mg, 0.13 mmol). The mixture was stirred under carbon monoxide atmosphere at 86° C. for 6 hours. The mixture was diluted with EtOAc (50 mL), washed with water (50 mL) and brine (30 mL). The organic phase was dried over anhydrous sodium sulfate, filtered and concentrated in vacuo. The residue was purified using a preparative TLC plate eluting with 2.5% MeOH/dichloromethane to provide the desired racemic product as an oil. This was further separated by a chiral preparative SFC (Column: OD (250 mm*30 mm, 10 um), Mobile phase: Supercritical CO$_2$/IPA (base)=100/40 at 80 mL/min Wavelength: 220 nm) to provide compound Int-15G (the first eluting compound) as an oil and compound Int-15H (the second eluting compound) as an oil.

Compound Int-15G: $^1$H NMR (400 MHz, CDCl$_3$): δ 10.39 (s, 1H), 8.35 (s, 1H), 7.25-7.33 (m, 1H), 6.71-6.78 (m, 2H), 4.56 (d, J=6.0 Hz, 2H), 4.26 (d, J=5.2 Hz, 2H), 3.94-4.05 (m, 7H), 3.54-3.64 (m, 2H), 3.43-3.51 (m, 1H), 1.64-1.81 (m, 4H), 1.17-1.26 (m, 12H). MS: m/z=585.3 (M+1).

Compound Int-15H: $^1$H NMR (400 MHz, CDCl$_3$): δ 10.35 (s, 1H), 8.35 (s, 1H), 7.25-7.33 (m, 1H), 6.71-6.78 (m, 2H), 4.56 (d, J=6.0 Hz, 2H), 4.26 (d, J=5.2 Hz, 2H), 3.92-4.05 (m, 7H), 3.54-3.64 (m, 2H), 3.43-3.51 (m, 1H), 1.64-1.81 (m, 4H), 1.17-1.26 (m, 12H). MS: m/z=585.2 (M+1).

Step H—Synthesis of Compound 71 and Compound 72

To a solution of compound Int-15G (15 mg, 0.026 mmol) in acetonitrile (1 mL) was added magnesium bromide (97 mg, 0.53 mmol). The reaction was allowed to stir at 23° C. for 12 hours. The mixture was purified using a prep-HPLC (Column: Phenomenex Synergi C18 150 mm*30 mm*4 um; Condition: 0.1% TFA-ACN; Gradient: 16% to 46%; B, 2~8 min. FlowRate: 30 mL/min) to provide compound 71 as a solid. $^1$H NMR (400 MHz, CDCl$_3$): δ 10.36 (s, 1H), 8.38 (s, 1H), 7.25-7.35 (m, 1H), 6.74-6.81 (m, 2H), 4.62 (br, 2H), 4.35 (br, 2H), 4.05 (t, J=7.2 Hz, 4H), 3.54-3.71 (m, 2H), 3.31-3.49 (m, 1H), 1.72-1.82 (m, 2H), 1.63-1.71 (m, 2H), 1.23-1.38 (m, 12H). MS: m/z=571.0 (M+1).

To a solution of compound Int-15H (17 mg, 0.029 mmol) in acetonitrile (1 mL) was added magnesium bromide (97 mg, 0.53 mmol). The reaction was allowed to stir at 23° C. for 12 hours. The mixture was purified using a pre-HPLC (Column: Phenomenex Synergi C18 150 mm*30 mm*4 um; Condition: 0.1% TFA-ACN; Gradient: 16% to 46%; B, 2~8 min. FlowRate: 30 mL/min) to provide compound 72 as a solid. $^1$H NMR (400 MHz, CDCl$_3$): δ 10.36 (s, 1H), 8.36 (s, 1H), 7.29-7.35 (m, 1H), 6.74-6.81 (m, 2H), 4.62 (br, 2H), 4.35 (br, 2H), 4.05 (t, J=7.2 Hz, 4H), 3.54-3.71 (m, 2H), 3.31-3.49 (m, 1H), 1.63-1.82 (m, 4H), 1.23-1.38 (m, 12H). MS: m/z=571.2 (M+1).

Example 16

Preparation of Compound 73 and Compound 74

Compound 73: $^1$H NMR (400 MHz, MeOD): δ 8.49 (s, 1H), 7.41-7.47 (m, 1H), 6.92-6.99 (m, 2H), 4.62-4.80 (m, 4H), 3.54-3.79 (m, 2H), 3.51-3.57 (m, 1H), 1.62-1.83 (m, 4H), 1.34-1.39 (m, 6H). MS: m/z=515.1 (M+1).

Compound 74: $^1$H NMR (400 MHz, MeOD): δ 8.50 (s, 1H), 7.40-7.46 (m, 1H), 6.92-6.99 (m, 2H), 4.62-4.80 (m, 4H), 3.54-3.79 (m, 2H), 3.51-3.57 (m, 1H), 1.62-1.83 (m, 4H), 1.34-1.39 (m, 6H). MS: m/z=515.2 (M+1).

Example 17

Preparation of Compounds 75 and 76

Compound 75 and 76

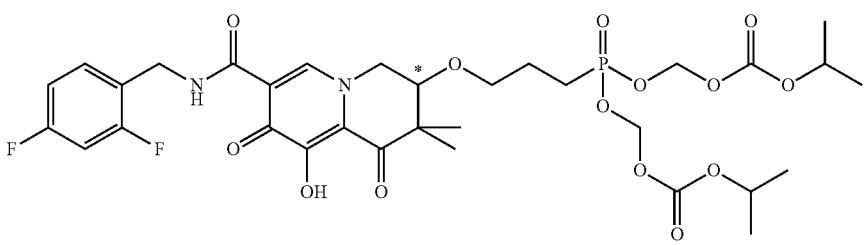

Compounds 75 and 76 were prepared from compound Int-15G and compound Int-15m respectively using the method described in Example 3.

Compound 75: $^1$H NMR (400 MHz, CDCl$_3$): δ 10.46 (s, 1H), 8.49 (s, 1H), 7.29-7.35 (m, 1H), 6.74-6.81 (m, 2H), 5.56-5.66 (m, 4H), 4.84-4.91 (m, 2H), 4.61-4.68 (m, 2H), 4.36-4.59 (m, 2H), 3.51-3.73 (m, 3H), 1.79-1.85 (m, 4H), 127-1.37 (m, 18H). MS: m/z=747.1 (M+1).

Compound 76: $^1$H NMR (400 MHz, CDCl$_3$): δ 10.46 (s, 1H), 8.50 (s, 1H), 7.29-7.36 (m, 1H), 6.75-6.82 (m, 2H), 5.56-5.66 (m, 4H), 4.84-4.91 (m, 2H), 4.61-4.68 (m, 2H), 4.36-4.59 (m, 2H), 3.51-3.73 (m, 3H), 1.79-1.85 (m, 4H), 127-1.37 (m, 18H). MS: m/z=747.2 (M+1).

Example 18

Preparation of Compounds 77-80

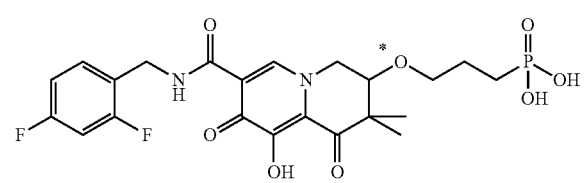

Compound 73 and 74

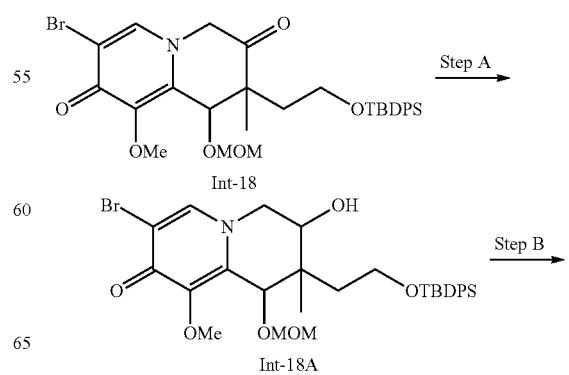

Compounds 73 and 74 were prepared from compound Int-15G and compound Int-15M respectively using the method described in Example 6.

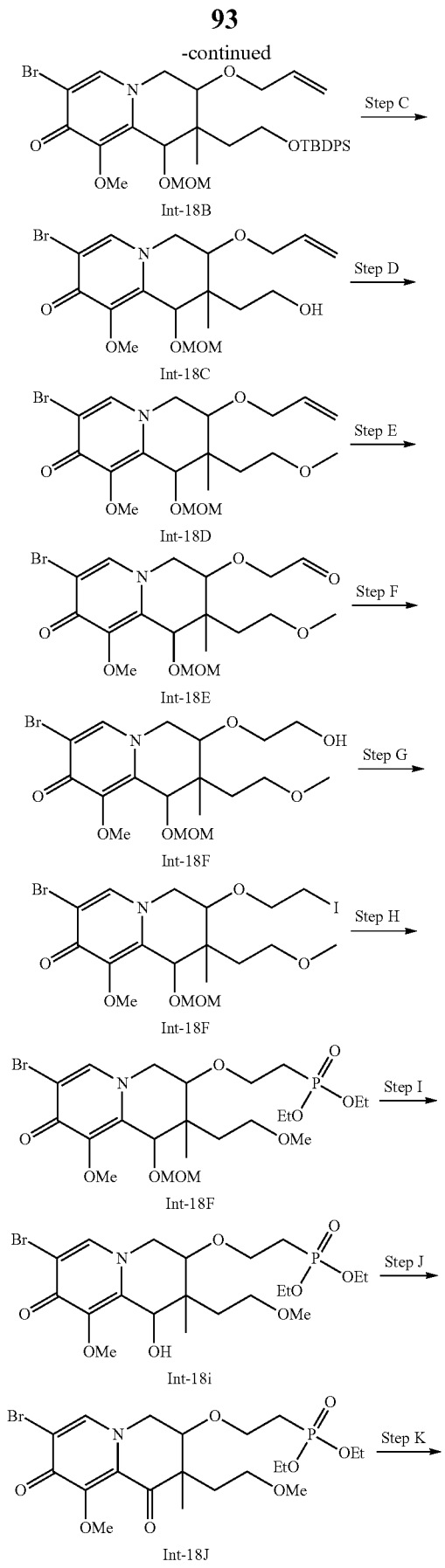

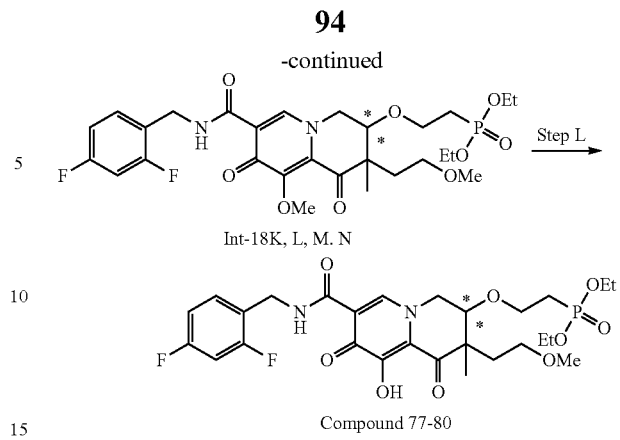

Compound 77-80

Step A—Synthesis of Compound Int-18A

To a solution of compound Int-18 (15 g, 23.86 mmol) in methanol (100 mL) was added NaBH$_4$ (1.354 g, 35.8 mmol) at 0° C. The mixture was allowed to stir at 25° C. for 10 min. The mixture was poured into water (150 mL) and the aqueous was extracted with ethyl acetate (100 mL×2). The combined organic layers were dried over anhydrous sodium sulfate, the mixture was filtered and the filtrate was concentrated under reduced pressure to provide compound Int-18A as a solid. $^1$H NMR (400 MHz, CHLOROFORM-d): δ 7.69 (d, J=13.2 Hz, 2H), 7.53-7.64 (m, 3H), 7.35-7.49 (m, 6H), 4.73-4.93 (m, 2H), 4.43-4.70 (m, 2H), 4.11-4.16 (m, 1H), 3.87-3.98 (m, 5H), 3.76 (t, J=6.1 Hz, 1H), 3.37 (d, J=9.3 Hz, 3H), 2.05 (s, 1H), 1.34 (s, 2H), 1.22-1.30 (m, 2H), 1.01-1.11 (m, 9H).

Step B—Synthesis of Compound Int-18B

To a solution of compound Int-18A (6 g, 9.51 mmol) in DMF (60 mL) was added sodium hydride (0.761 g, 19.03 mmol) and 3-bromoprop-1-ene (1.381 g, 11.42 mmol). The mixture was allowed to stir at 0° C. for 30 min. The mixture was poured into water (100 mL) and the aqueous was extracted with ethyl acetate (100 mL×2). The organic layer was dried by anhydrous sodium sulfate. The mixture was filtered and the filtrate was concentrated in vacuo. The residue was purified using a silica gel column eluting with 33% ethyl acetate/petroleum ether to provide compound Int-18B as a solid. $^1$H NMR (400 MHz, CHLOROFORM-d): δ 7.67-7.75 (m, 2H), 7.54-7.65 (m, 3H), 7.33-7.48 (m, 6H), 5.80 (ddd, J=16.9, 10.9, 6.0 Hz, 1H), 5.12-5.29 (m, 2H), 4.58 (d, J=6.8 Hz, 1H), 4.44-4.52 (m, 1H), 4.07-4.15 (m, 1H), 3.97 (s, 2H), 3.86-3.93 (m, 3H), 3.72-3.80 (m, 1H), 3.50 (s, 1H), 3.29-3.35 (m, 2H), 2.96 (s, 2H), 2.89 (s, 2H), 2.06-2.15 (m, 1H), 1.39-1.48 (m, 1H), 1.27 (t, J=6.9 Hz, 3H), 1.00-1.09 (m, 9H).

Step C—Synthesis of Compound Int-18C

To a solution of compound Int-18B (5 g, 7.45 mmol) in tetrahydrofuran (50 mL) was added TBAF (8.95 mL, 8.95 mmol) (1M) at 0° C. The mixture was allowed to stir at 26° C. for 2 hours. The mixture was concentrated to dryness and purified using a silica gel column eluting with 50% ethyl acetate/petroleum ether to provide compound Int-18C as a colorless oil. $^1$H NMR (400 MHz, CHLOROFORM-d): δ 7.62-7.75 (m, 2H), 7.29-7.48 (m, 2H), 5.90 (ddt, J=16.8, 11.0, 5.5 Hz, 1H), 5.19-5.38 (m, 2H), 4.88-4.98 (m, 1H), 4.50-4.67 (m, 2H), 4.17-4.25 (m, 1H), 4.09 (d, J=5.3 Hz, 1H), 3.94-4.03 (m, 3H), 3.84-3.92 (m, 1H), 3.58 (dd, J=9.9, 6.4 Hz, 1H), 3.24-3.42 (m, 3H), 1.28-1.40 (m, 2H), 0.99-1.14 (m, 3H).

Step D—Synthesis of Compound Int-18D

To a solution of compound Int-18C (2.9 g, 6.71 mmol) in DMF (30 mL) was added sodium hydride (0.537 g, 13.42 mmol) and iodomethane (1.904 g, 13.42 mmol). The mixture was allowed to stir at 0° C. for 2 hours. The mixture was poured into water (10 mL) and the aqueous was extracted with ethyl acetate (20 mL). The organic layer was dried by anhydrous sodium sulfate. The mixture was filtered and the filtrate was concentrated in vacuo. The residue was purified using a silica gel column eluting with 50% ethyl acetate/petroleum ether to provide compound Int-18D as a colorless oil. $^1$H NMR (400 MHz, CHLOROFORM-d): δ 8.02 (s, 1H), 7.66 (s, 1H), 5.86-5.97 (m, 1H), 5.22-5.36 (m, 2H), 4.51-4.66 (m, 2H), 4.09-4.23 (m, 3H), 3.99-4.03 (m, 3H), 3.39-3.50 (m, 2H), 3.36 (s, 3H), 3.26 (s, 2H), 2.96 (s, 3H), 2.06-2.21 (m, 1H), 1.35 (dd, J=14.1, 7.0 Hz, 1H), 1.27 (br. s., 3H). MS: m/z=446.1, 448.1 (M+1).

Step E—Synthesis of Compound Int-18E

To a solution of compound Int-18E (2.8 g, 6.27 mmol) in tetrahydrofuran (30 mL) and water (30 mL) were added sodium periodate (4.03 g, 18.82 mmol) and osmium(VIII) oxide (0.159 g, 0.627 mmol). The mixture was allowed to stir at 26° C. for 4 hours. The reaction was quenched with saturated sodium sulfite solution (10 mL) and aqueous was extracted with dichloromethane (20 mL×3). The organic layer was dried over anhydrous sodium sulfate and then filtered. The filtrate was concentrated and purified using a silica gel column eluting with 50% ethyl acetate/petroleum ether to provide compound Int-18E as a colorless oil. $^1$H NMR (400 MHz, CHLOROFORM-d): δ 9.68 (s, 1H), 8.01 (s, 1H), 4.51-4.65 (m, 3H), 4.13 (dd, J=15.4, 7.3 Hz, 2H), 3.98-4.01 (m, 3H), 3.58 (d, J=6.8 Hz, 1H), 3.35 (t, J=4.9 Hz, 5H), 3.25 (s, 2H), 2.88 (s, 3H), 1.26 (q, J=6.9 Hz, 5H). MS: m/z=447.9, 449.9 (M+1).

Step F—Synthesis of Compound Int-18F

To a solution of compound Int-18E (2.4 g, 5.35 mmol) in methanol (20 mL) was added NaBH$_4$ (0.304 g, 8.03 mmol) at 0° C. The mixture was allowed to stir at 26° C. for 30 min. The mixture was then poured into water (20 mL) and extracted with dichloromethane (20 mL×2). The combined organic layer was dried over sodium sulfate, filtered and the filtrate was concentrated under reduced pressure to provide compound Int-18F as an oil. $^1$H NMR (400 MHz, CHLOROFORM-d): δ 7.68 (s, 1H), 4.81-4.87 (m, 1H), 4.58-4.66 (m, 1H), 4.47-4.55 (m, 1H), 4.14-4.22 (m, 1H), 3.93-4.02 (m, 4H), 3.74-3.77 (m, 1H), 3.61-3.73 (m, 3H), 3.42-3.58 (m, 3H), 3.30-3.38 (m, 4H), 3.25 (s, 2H), 2.19-2.37 (m, 1H), 1.37 (t, J=6.3 Hz, 1H), 1.13-1.33 (m, 3H). MS: m/z=450.1, 452.1 (M+1).

Step G—Synthesis of Compound Int-18G

To a solution of compound Int-18F (1.8 g, 4.00 mmol) in tetrahydrofuran (30 mL) was added imidazole (0.816 g, 11.99 mmol), Ph$_3$P (3.15 g, 11.99 mmol) and iodine (2.029 g, 7.99 mmol) at 0° C. The mixture was allowed to stir at 26° C. for 6 hours. The mixture was then quenched by aqueous sodium sulfite (20 mL) and the mixture was extracted with ethyl acetate (20 mL×2). The combined organic layers were dried over sodium sulfate, filtered and the filtrate was concentrated under reduced pressure to provide a crude residue which was purified using a silica gel column eluting with 50% ethyl acetate/petroleum ether to provide compound Int-18G as an oil. $^1$H NMR (400 MHz, CHLOROFORM-d): δ 7.68 (s, 1H), 4.85 (m, 1H), 4.61-4.66 (m, 1H), 4.49-4.56 (m, 1H), 4.17-4.26 (m, 1H), 3.98-4.05 (m, 3H), 3.94 (dd, J=12.1, 6.4 Hz, 2H), 3.83 (t, J=6.3 Hz, 2H), 3.76 (dd, J=10.0, 6.5 Hz, 1H), 3.45-3.64 (m, 2H), 3.33-3.44 (m, 4H), 3.20-3.31 (m, 4H), 1.57-1.69 (m, 3H), 1.29-1.32 (m, 2H). MS: m/z=560.1, 562.1 (M+1).

Step H—Synthesis of Compound Int-18H

A solution of compound Int-18G (1.9 g, 3.39 mmol) in triethyl phosphite (10 g, 60.2 mmol) was allowed to stir at 140° C. for 1 hour. The reaction content was concentrated in vacuo to provide crude compound Int-18H as an oil MS: m/z=570.0, 572.0 (M+1). This material was used without further purification in the next step.

Step I—Synthesis of Compound Int-18I

A solution of compound Int-18H (1.7 g, 2.98 mmol) in HCl/MeOH (10 mL, 20.00 mmol, 2 M) was allowed to stir at 26° C. for 1 hour. The reaction content was concentrated in vacuo. The residue was purified using a silica gel column eluting with 5% methanol/dichloromethane to provide compound Int-18I as a solid. $^1$H NMR (400 MHz, CHLOROFORM-d): δ 7.59-7.67 (m, 1H), 4.66 (d, J=11.3 Hz, 1H), 4.25 (d, J=5.1 Hz, 1H), 3.89-4.12 (m, 10H), 3.76 (br. s., 1H), 3.49 (br. s., 3H), 3.27 (s, 2H), 1.98-2.16 (m, 2H), 1.28-1.38 (m, 8H), 1.18-1.26 (m, 3H). MS: m/z=526.1, 528.1 (M+1).

Step J—Synthesis of Compound Int-18J

To a solution of compound Int-18I (1.3 g, 2.470 mmol) in dichloromethane (10 mL) and tetrahydrofuran (10 mL) was added Dess-Martin periodinane (2.095 g, 4.94 mmol) at 0° C. The reaction mixture was allowed to stir at 26° C. for 1 hour. The mixture was poured into water (20 mL), and then treated with 20 mL of saturated sodium sulfite solution. The resulting mixture was extracted with dichloromethane (20 mL×2). The organic layer was dried by anhydrous sodium sulfate, filtered and the filtrate was concentrated in vacuo. The residue was purified using a silica gel column eluting with 5% methanol/dichloromethane to provide compound Int-18J as an oil. $^1$H NMR (400 MHz, METHANOL-d$_4$): δ 8.21-8.26 (m, 1H), 4.43-4.61 (m, 2H), 3.90-4.09 (m, 6H), 3.86 (s, 3H), 3.67-3.78 (m, 1H), 3.34-3.56 (m, 3H), 3.18 (s, 3H), 2.07-2.15 (m, 2H), 1.89-1.94 (m, 1H), 1.19-1.34 (m, 9H). MS: m/z=524.2, 526.2 (M+1).

Step K—Synthesis of Compounds Int-18K, L, M, N

To a solution of compound Int-18J (400 mg, 0.763 mmol) in DMSO (2 mL) was added (2,4-difluorophenyl)methanamine (164 mg, 1.144 mmol), diisopropylethylamine (0.533 mL, 3.05 mmol) and Pd(Ph$_3$P)$_4$ (441 mg, 0.381 mmol). The mixture was allowed to stir at 90° C. under CO atmosphere for 2 hours. The mixture was diluted with ethyl acetate (20 mL) and washed with 1M HCl (10 mL) and brine (10 mL). The organic layer was concentrated and purified using a prep-TLC (EtOAc:MeOH=20:1) to provide a mixture of compounds Int-18K, L, M, N as a solid. MS: m/z=615.2 (M+1). This material was further purified using a SFC (Column: AD (250 mm*30 mm, 5 um), Base-EtOH, Flow rate: 60 mL/min) to provide Int-18K (the first eluting isomer), compound Int-18L (the second eluting isomer), compound Int-18M (the third eluting isomer) and compound Int-18N (the fourth eluting isomer) individually as a colorless oil.

Compound Int-18K: $^1$H NMR (400 MHz, CHLOROFORM-d): δ 10.45 (t, J=5.5 Hz, 1H), 8.38 (s, 1H), 7.30-7.40 (m, 1H), 6.73-6.84 (m, 2H), 4.55-4.67 (m, 2H), 4.41-4.49 (m, 1H), 4.25 (dd, J=13.7, 4.3 Hz, 1H), 3.96-4.06 (m, 7H), 3.92 (br. s., 1H), 3.85 (dd, J=11.9, 8.8 Hz, 1H), 3.70-3.75 (m, 1H), 3.47 (td, J=9.1, 3.7 Hz, 1H), 3.37 (dt, J=9.9, 5.0 Hz, 1H), 3.18 (s, 3H), 1.97-2.06 (m, 3H), 1.83 (t, J=6.3 Hz, 1H), 1.23-1.30 (m, 9H).

Compound Int-18L: $^1$H NMR (400 MHz, CHLOROFORM-d): δ 10.45 (br. s., 1H), 8.38 (s, 1H), 7.30-7.39 (m, 1H), 6.68-6.89 (m, 2H), 4.57-4.66 (m, 2H), 4.45 (d, J=13.3 Hz, 1H), 4.25 (dd, J=13.7, 3.9 Hz, 1H), 3.96-4.09 (m, 7H), 3.92 (br. s., 1H), 3.81-3.88 (m, 1H), 3.66-3.75 (m, 1H), 3.48 (td, J=8.9, 3.7 Hz, 1H), 3.37 (dt, J=9.8, 4.9 Hz, 1H), 3.18 (s, 3H), 1.94-2.08 (m, 3H), 1.72-1.79 (m, 1H), 1.24-1.32 (m, 9H).

Compound Int-18M: $^1$H NMR (400 MHz, CHLOROFORM-d): δ 10.43 (t, J=5.5 Hz, 1H), 8.40 (s, 1H), 7.28-7.42 (m, 1H), 6.67-6.89 (m, 2H), 4.60 (d, J=5.5 Hz, 2H), 4.32-4.38 (m, 1H), 4.25-4.31 (m, 1H), 3.94-4.06 (m, 8H), 3.78-3.86 (m, 1H), 3.71 (dd, J=14.7, 6.5 Hz, 1H), 3.51 (t, J=5.5 Hz, 2H), 3.27 (s, 3H), 2.11-2.18 (m, 1H), 1.95-2.03 (m, 3H), 1.22-1.29 (m, 9H).

Compound Int-18N: $^1$H NMR (400 MHz, CHLOROFORM-d): δ 10.40 (t, J=5.5 Hz, 1H), 8.36 (s, 1H), 7.25-7.35 (m, 1H), 6.68-6.79 (m, 2H), 4.56 (d, J=5.1 Hz, 2H), 4.30-4.36 (m, 1H), 4.20-4.26 (m, 1H), 3.90-4.00 (m, 8H), 3.74-3.82 (m, 1H), 3.62-3.72 (m, 1H), 3.47 (t, J=5.7 Hz, 2H), 3.23 (s, 3H), 2.07-2.14 (m, 1H), 1.92-2.00 (m, 3H), 1.17-1.23 (m, 9H).

Step L—Synthesis of Compounds 77-80

A solution of compound Int-18K (20 mg, 0.033 mmol) in acetonitrile (0.5 mL) was added magnesium bromide (59.9 mg, 0.325 mmol), then the mixture was allowed to stir at room temperature (26° C.) for 16 hours. LCMS showed the reaction was completed. The mixture was filtered, the crude product was purified using a reverse phase-HPLC (Column: Boston Green ODS 150 mm*30 mm, 5 um, Condition: 0.1% TFA-ACN, 36% to 66%, Flow Rate, 30 mL/min) to provide compound 77 as a solid. $^1$H NMR (400 MHz, CHLOROFORM-d): δ 10.42 (br. s., 1H), 8.41 (br. s., 1H), 7.31-7.43 (m, 1H), 6.74-6.88 (m, 2H), 4.65 (d, J=4.3 Hz, 2H), 4.56 (d, J=13.7 Hz, 1H), 4.33 (d, J=13.3 Hz, 1H), 3.96-4.09 (m, 5H), 3.88 (dd, J=13.3, 7.4 Hz, 1H), 3.75 (dd, J=14.3, 7.2 Hz, 1H), 3.56 (d, J=8.2 Hz, 1H), 3.39-3.46 (m, 1H), 3.23 (s, 3H), 1.97-2.09 (m, 3H), 1.77 (d, J=14.9 Hz, 1H), 1.40 (s, 3H), 1.28 (q, J=6.8 Hz, 6H). MS: m/z=600.1 (M+1).

Compound 78 was prepared from compound Int-18L using the procedure described above. $^1$H NMR (400 MHz, CHLOROFORM-d): δ 10.42 (br. s., 1H), 8.41 (s, 1H), 7.32-7.41 (m, 1H), 6.73-6.88 (m, 2H), 4.65 (d, J=5.5 Hz, 2H), 4.55 (d, J=13.7 Hz, 1H), 4.32 (dd, J=14.1, 3.5 Hz, 1H), 3.98-4.08 (m, 5H), 3.87 (dd, J=14.1, 7.4 Hz, 1H), 3.75 (dt, J=15.1, 7.3 Hz, 1H), 3.53-3.60 (m, 1H), 3.42 (dt, J=9.9, 4.6 Hz, 1H), 3.22 (s, 3H), 1.98-2.08 (m, 3H), 1.73-1.80 (m, 1H), 1.39 (s, 3H), 1.28 (q, J=7.4 Hz, 6H). MS: m/z=601.2 (M+1).

Compound 79 was prepared from compound Int-18M using the procedure described above. $^1$H NMR (400 MHz, CHLOROFORM-d): δ 10.36 (br. s., 1H), 8.40 (s, 1H), 7.34-7.42 (m, 1H), 6.74-6.89 (m, 2H), 4.66 (br. s., 2H), 4.30-4.41 (m, 2H), 3.95-4.10 (m, 5H), 3.74-3.88 (m, 2H), 3.54-3.63 (m, 2H), 3.31 (s, 3H), 2.15-2.24 (m, 2H), 2.03 (dd, J=18.4, 7.0 Hz, 2H), 1.24-1.34 (m, 9H). MS: m/z=601.2 (M+1).

Compound 80 was prepared from compound Int-18N using the procedure described above. $^1$H NMR (400 MHz, CHLOROFORM-d): δ 10.30 (br. s., 1H), 8.33 (s, 1H), 7.25-7.35 (m, 1H), 6.67-6.81 (m, 2H), 4.58 (d, J=4.3 Hz, 2H), 4.22-4.37 (m, 2H), 3.89-4.04 (m, 5H), 3.67-3.82 (m, 2H), 3.48-3.57 (m, 2H), 3.24 (s, 3H), 2.06-2.17 (m, 2H), 1.91-2.01 (m, 2H), 1.14-1.28 (m, 9H). MS: m/z=600.1 (M+1).

Example 19

Preparation of Compounds 81-84

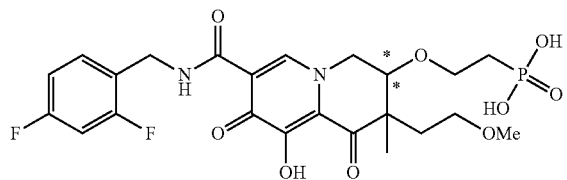

Compound 81-84

Compounds 81-84 were prepared from compounds 77-80 respectively using the method described in Example 2.

Compound 81: $^1$H NMR (400 MHz, METHANOL-d$_4$): δ 8.46 (s, 1H), 7.39-7.47 (m, 1H), 6.89-7.02 (m, 2H), 4.55-4.73 (m, 4H), 4.04 (br. s., 1H), 3.88-3.98 (m, 1H), 3.71-3.80 (m, 1H), 3.53-3.60 (m, 1H), 3.43 (dt, J=10.3, 5.2 Hz, 1H), 3.20 (s, 3H), 1.87-2.11 (m, 4H), 1.39 (s, 3H). MS: m/z=545.2 (M+1).

Compound 82: $^1$H NMR (400 MHz, METHANOL-d$_4$): δ 8.46 (s, 1H), 7.38-7.47 (m, 1H), 6.89-7.00 (m, 2H), 4.53-4.73 (m, 4H), 4.04 (br. s., 1H), 3.88-3.96 (m, 1H), 3.72-3.81 (m, 1H), 3.53-3.60 (m, 1H), 3.40-3.47 (m, 1H), 3.20 (s, 3H), 1.87-2.09 (m, 4H), 1.39 (s, 3H). MS: m/z=545.2 (M+1).

Compound 83: $^1$H NMR (400 MHz, METHANOL-d$_4$): δ 8.47 (br. s., 1H), 7.37-7.48 (m, 1H), 6.88-7.01 (m, 2H), 4.58-4.71 (m, 3H), 4.53 (d, J=14.3 Hz, 1H), 4.11 (br. s., 1H), 3.92 (br. s., 1H), 3.77 (br. s., 1H), 3.60 (br. s., 2H), 3.33 (s, 3H), 2.10-2.26 (m, 2H), 1.88-2.03 (m, 2H), 1.35 (s, 3H). MS: m/z=545.2 (M+1).

Compound 84: $^1$H NMR (400 MHz, METHANOL-d$_4$): δ 8.49 (s, 1H), 7.38-7.48 (m, 1H), 6.87-7.03 (m, 2H), 4.59-4.75 (m, 3H), 4.52 (d, J=14.1 Hz, 1H), 4.09 (br. s., 1H), 3.86-3.96 (m, 1H), 3.74 (dd, J=9.6, 5.6 Hz, 1H), 3.59 (d, J=5.3 Hz, 2H), 3.32-3.35 (m, 3H), 2.08-2.25 (m, 2H), 1.79-2.01 (m, 2H), 1.25-1.40 (m, 3H). MS: m/z=545.1 (M+1).

Example 20

Preparation of Compounds 85-88

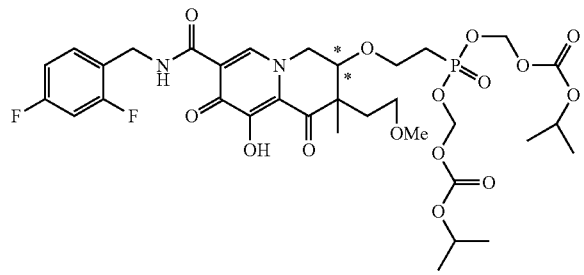

Compounds 85-88

Compounds 85-88 were prepared from compounds Int-18K, L, M and N respectively using the method described in Example 3.

Compound 85: ¹H NMR (400 MHz, METHANOL-$d_4$): δ 8.47 (s, 1H), 7.37-7.46 (m, 1H), 6.87-7.00 (m, 2H), 5.46-5.59 (m, 4H), 4.79-4.84 (m, 2H), 4.53-4.71 (m, 4H), 4.04 (br. s., 1H), 3.87-3.97 (m, 1H), 3.69-3.82 (m, 1H), 3.51-3.59 (m, 1H), 3.38-3.44 (m, 1H), 3.18 (s, 3H), 2.22 (dt, J=18.6, 6.4 Hz, 2H), 2.03-2.10 (m, 1H), 1.83-1.92 (m, 1H), 1.37 (s, 3H), 1.26 (d, J=6.3 Hz, 12H). MS: m/z=777.2 (M+1).

Compound 86: ¹H NMR (400 MHz, METHANOL-$d_4$): δ 8.47 (s, 1H), 7.36-7.47 (m, 1H), 6.86-7.00 (m, 2H), 5.45-5.59 (m, 4H), 4.83 (br. s., 2H), 4.54-4.72 (m, 4H), 4.04 (br. s., 1H), 3.88-3.99 (m, 1H), 3.71-3.82 (m, 1H), 3.51-3.58 (m, 1H), 3.39-3.46 (m, 1H), 3.18 (s, 3H), 2.22 (dt, J=18.6, 6.4 Hz, 1H), 2.02-2.10 (m, 1H), 1.87 (dt, J=14.7, 5.2 Hz, 1H), 1.37 (s, 3H), 1.26 (d, J=6.3 Hz, 12H). MS: m/z=777.2 (M+1).

Compound 87: ¹H NMR (400 MHz, METHANOL-$d_4$): δ 8.50 (s, 1H), 7.37-7.47 (m, 1H), 6.89-7.02 (m, 2H), 5.41-5.63 (m, 4H), 4.84 (br. s., 2H), 4.49-4.69 (m, 4H), 4.12 (br. s., 1H), 3.92 (dd, J=16.6, 9.4 Hz, 1H), 3.73-3.83 (m, 1H), 3.54-3.66 (m, 2H), 3.33 (s, 3H), 2.08-2.29 (m, 4H), 1.35 (s, 3H), 1.27 (d, J=6.2 Hz, 12H). MS: m/z=777.3 (M+1).

Compound 88: ¹H NMR (400 MHz, METHANOL-$d_4$): δ 8.50 (s, 1H), 7.37-7.48 (m, 1H), 6.88-7.02 (m, 2H), 5.43-5.64 (m, 4H), 4.84 (br. s., 2H), 4.48-4.71 (m, 4H), 4.12 (br. s., 1H), 3.88-3.98 (m, 1H), 3.72-3.84 (m, 1H), 3.54-3.66 (m, 2H), 3.33 (s, 3H), 2.10-2.32 (m, 4H), 1.35 (s, 3H), 1.27 (d, J=6.2 Hz, 12H). MS: m/z=777.3 (M+1).

Example 21

Preparation of Compounds 89-92

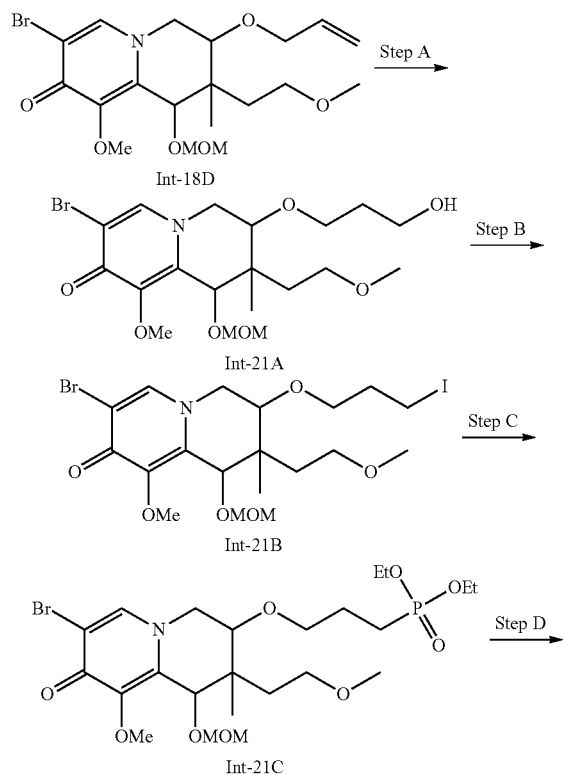

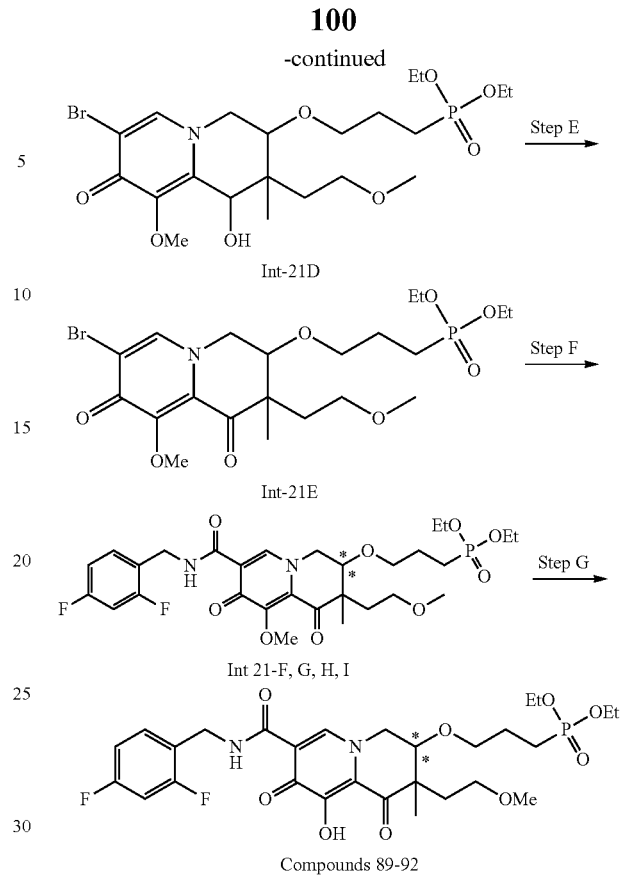

Compounds 89-92

Step A—Synthesis of Compound Int-21A

To an ice-cold solution of compound Int-18D (5.5 g, 12.32 mmol) in THF (60 mL) was added borane dimethyl sulfide complex (1.404 g, 18.48 mmol)) under nitrogen. The mixture was allowed to stir at 26° C. for 2 hours. After slow addition of 20 mL of water, sodium perborate tetrahydrate (2.84 g, 18.48 mmol) was added to the mixture. The resulting mixture was allowed to stir for additional 10 hours. The reaction was quenched by addition of 50 mL of water, followed by dichloromethane (50 mL). The aqueous layer was extracted with dichloromethane (2×50 mL). The combined organic extracts were dried over anhydrous sodium sulfate and filtered. The filtrate was concentrated in vacuo and the residue was purified using a silica gel column eluting with 5% methanol in dichloromethane to provide compound Int-21A as a colorless oil. MS: m/z=464.1, 466.1 (M+1).

Step B—Synthesis of Compound Int-21B

To a solution of compound Int-21A (3.8 g, 8.18 mmol) in THF (50 mL) was added imidazole (2.228 g, 32.7 mmol), Ph₃P (6.44 g, 24.55 mmol) and iodine (4.15 g, 16.37 mmol). After stirred at 26° C. for 15 h, the reaction mixture was concentrated in vacuo and the residue was purified using a silica gel column eluting with 50% ethyl acetate in petroleum ether to provide compound Int-21B as a solid. ¹H NMR (400 MHz, METHANOL-$d_4$): δ 8.20-8.27 (m, 1H), 4.98 (br. s., 1H), 4.61-4.66 (m, 2H), 4.55 (dd, J=13.9, 5.1 Hz, 1H), 4.12 (q, J=7.0 Hz, 2H), 3.91-3.97 (m, 3H), 3.48-3.76 (m, 5H), 3.38 (dd, J=12.7, 2.9 Hz, 7H), 2.03-2.05 (m, 2H), 1.87 (d, J=6.8 Hz, 1H), 1.26 (t, J=7.2 Hz, 2H), 0.76-0.86 (m, 2H). MS: m/z=574.0, 576.0 (M+1).

Step C—Synthesis of Compound Int-21C

A solution of compound Int-21B (3.2 g, 5.57 mmol) in triethyl phosphite (15 mL, 5.57 mmol) was allowed to stir at 140° C. for 2 hours. The mixture was concentrated under reduced pressure and the residue was purified using a silica gel column eluting with EtOAc to provide compound Int-21C as an oil. $^1$H NMR (400 MHz, METHANOL-d$_4$): δ 8.16-8.27 (m, 1H), 4.89-5.13 (m, 3H), 4.48-4.70 (m, 3H), 4.04-4.14 (m, 7H), 3.79-3.95 (m, 3H), 3.69 (br. s., 3H), 3.32-3.41 (m, 3H), 3.22-3.30 (m, 3H), 1.91-2.10 (m, 2H), 1.72-1.81 (m, 2H), 1.32 (t, J=7.1 Hz, 9H). MS: m/z=584.2, 586.2 (M+1).

Step D—Synthesis of Compound Int-21D

A solution of diethyl compound Int-21C (3.0 g, 5.13 mmol) in methanol (20 mL) was added HCl/MeOH (10 mL, 40.0 mmol, 4 M). The mixture was allowed to stir at room temperature (20° C.) for 1 hour. The reaction mixture was concentrated in vacuo. The residue was purified using a silica gel column eluting with 5% methanol in dichloromethane to provide compound Int-21D as an oil. $^1$H NMR (400 MHz, METHANOL-d$_4$): δ 8.15 (d, J=13.5 Hz, 1H), 4.29-4.83 (m, 3H), 3.99-4.22 (m, 4H), 3.82-3.98 (m, 3H), 3.49-3.74 (m, 3H), 3.31-3.42 (m, 3H), 3.14-3.29 (m, 4H), 1.97 (t, J=6.7 Hz, 2H), 1.66-1.85 (m, 2H), 1.27-1.39 (m, 9H). MS: m/z=540.1, 542.1 (M+1).

Step E—Synthesis of Compound Int-21E

A solution of diethyl compound Int-21D (2.4 g, 4.44 mmol) in dichloromethane (30 mL) was added Dess-Martin periodinane (3.77 g, 8.88 mmol). The reaction was allowed to stir at 40° C. for 3 hours. The reaction mixture was poured into 30 mL of water. The resulting mixture was extracted with dichloromethane (2×30 mL), the organic layer was dried over anhydrous sodium sulfate. After filtration, the filtrate was concentrated in vacuo and the residue was purified using a silica gel column eluting with 5% methanol in dichloromethane to provide compound Int-21E as an oil. $^1$H NMR (400 MHz, METHANOL-d$_4$): δ 8.20-8.29 (m, 1H), 4.31-4.67 (m, 3H), 3.94-4.13 (m, 5H), 3.86 (s, 2H), 3.73 (d, J=4.6 Hz, 1H), 3.48-3.57 (m, 2H), 3.36-3.45 (m, 1H), 3.34 (s, 1H), 3.10-3.24 (m, 2H), 1.97-2.13 (m, 2H), 1.74-1.96 (m, 4H), 1.13-1.41 (m, 9H). MS: m/z=538.1, 540.1 (M+1).

Step F—Synthesis of Compounds Int-21F, G, H and I

To a solution of diisopropylethylamine (0.779 mL, 4.46 mmol), compound Int-21E (0.8 g, 1.486 mmol) and (2,4-difluorophenyl)methanamine (0.234 g, 1.635 mmol) in DMSO (10 mL) was added Pd(Ph$_3$P)$_4$ (0.859 g, 0.743 mmol). The mixture was allowed to stir at 85° C. under carbonic oxide for 3 hours. The reaction content was poured into water (20 mL) and the resulting mixture was extracted with dichloromethane (20 mL×2). The organic layer was dried over anhydrous sodium sulfate. After filtration, the filtrate was concentrated in vacuo and the residue was purified using a silica gel column eluting with 5% methanol in dichloromethane to remove most of the impurity. The product containing fraction was further purified using a reverse phase HPLC (Column: Waters Xbridge Prep OBD C18 150 mm*30 mm, 5 um, Condition: water (0.05% ammonia hydroxide v/v)-ACN, 40% to 70%, Flow Rate, 25 mL/min) to provide a mixture of compounds Int-21F, G, H and I as a colorless oil. The isomeric mixture was further separated by SFC (Column: AD (250 mm*30 mm, 5 um); Base-ETOH; Flow rate: 60 mL/min) to provide compound Int-21F (the first eluting isomer), compound Int-21G (the second eluting isomer), compound Int-21H (the third eluting isomer), compound Int-21I (the fourth eluting isomer) individually as a solid.

Compound Int-21F: $^1$H NMR (400 MHz, METHANOL-d$_4$): δ 8.51 (s, 1H), 7.39-7.48 (m, 1H), 6.90-7.01 (m, 2H), 4.61-4.68 (m, 3H), 4.51-4.57 (m, 1H), 3.95-4.09 (m, 5H), 3.87 (s, 3H), 3.71-3.79 (m, 1H), 3.47-3.55 (m, 2H), 3.38-3.44 (m, 1H), 3.18 (s, 3H), 1.94 (dt, J=11.7, 5.8 Hz, 2H), 1.69-1.82 (m, 4H), 1.20-1.34 (m, 9H). MS: m/z=629.3 (M+1).

Compound Int-21H: $^1$H NMR (400 MHz, METHANOL-d$_4$): δ 8.52 (s, 1H), 7.40-7.47 (m, 1H), 6.91-7.01 (m, 2H), 4.58-4.66 (m, 3H), 4.49 (d, J=13.7 Hz, 1H), 3.93-4.10 (m, 5H), 3.86 (s, 3H), 3.69-3.74 (m, 1H), 3.54 (t, J=6.5 Hz, 3H), 3.34 (br. s., 3H), 2.06-2.13 (m, 1H), 1.95-2.02 (m, 1H), 1.64-1.81 (m, 4H), 1.10-1.45 (m, 9H). MS: m/z=629.3 (M+1).

Compound Int-21H: $^1$H NMR (400 MHz, METHANOL-d$_4$): δ 8.49 (s, 1H), 7.37-7.46 (m, 1H), 6.88-6.99 (m, 2H), 4.59-4.65 (m, 3H), 4.49-4.56 (m, 1H), 3.94-4.06 (m, 5H), 3.85 (s, 3H), 3.71-3.77 (m, 1H), 3.46-3.54 (m, 2H), 3.36-3.42 (m, 1H), 3.16 (s, 3H), 1.87-1.99 (m, 2H), 1.67-1.79 (m, 4H), 1.20-1.31 (m, 9H). MS: m/z=629.3 (M+1).

Compound Int-21I: $^1$H NMR (400 MHz, METHANOL-d$_4$): δ 8.50 (s, 1H), 7.37-7.46 (m, 1H), 6.88-7.01 (m, 2H), 4.58-4.64 (m, 3H), 4.45-4.51 (m, 1H), 3.92-4.07 (m, 5H), 3.84 (s, 3H), 3.67-3.74 (m, 1H), 3.47-3.55 (m, 3H), 3.26-3.29 (m, 3H), 2.09 (dt, J=14.2, 7.0 Hz, 1H), 1.92-2.00 (m, 1H), 1.62-1.79 (m, 4H), 1.17-1.33 (m, 9H). MS: m/z=629.3 (M+1).

Step G—Synthesis of Compounds 89-92

To a solution of compound Int-21F (20 mg, 0.032 mmol) in acetonitrile (0.5 mL) was added magnesium bromide (29.3 mg, 0.159 mmol) at room temperature (15° C.). The mixture was allowed to stir at 15° C. for 16 hours. The mixture was filtered and the filter cake was washed with 5 mL of acetonitrile, the crude product solution was purified using a prep-HPLC (Column Boston Green ODS 150 mm*30 mm, 5 um, Condition: water (0.1% TFA)-ACN, 37% to 67%, FlowRate: 30 mL/min) to provide compound 89 as a solid. $^1$H NMR (400 MHz, METHANOL-d$_4$): δ 8.48 (s, 1H), 7.37-7.48 (m, 1H), 6.89-7.01 (m, 2H), 4.56-4.74 (m, 4H), 3.89-4.10 (m, 5H), 3.70-3.80 (m, 1H), 3.52-3.62 (m, 2H), 3.41-3.49 (m, 1H), 3.20 (s, 3H), 2.03-2.11 (m, 1H), 1.85-1.92 (m, 1H), 1.60-1.81 (m, 4H), 1.39 (s, 3H), 1.25 (td, J=7.0, 3.0 Hz, 6H). MS: m/z=615.2 (M+1).

Compound 90 was prepared from compound Int-21G using the procedure described above.

Compound 90: $^1$H NMR (400 MHz, METHANOL-d$_4$): δ 8.49 (br. s., 1H), 7.39-7.47 (m, 1H), 6.90-6.99 (m, 2H), 4.49-4.68 (m, 4H), 3.95-4.12 (m, 5H), 3.72 (br. s., 1H), 3.54-3.63 (m, 3H), 3.33 (s, 3H), 2.15 (t, J=6.0 Hz, 2H), 1.62-1.79 (m, 4H), 1.36 (s, 3H), 1.24 (td, J=6.9, 3.1 Hz, 6H). MS: m/z=615.2 (M+1).

Compound 91 was prepared from compound Int-21H using the procedure described above.

Compound 91: $^1$H NMR (400 MHz, METHANOL-d$_4$): δ 8.48 (s, 1H), 7.37-7.49 (m, 1H), 6.88-7.02 (m, 2H), 4.56-4.73 (m, 4H), 3.87-4.14 (m, 5H), 3.70-3.80 (m, 1H), 3.51-3.62 (m, 2H), 3.39-3.49 (m, 1H), 3.20 (s, 3H), 2.02-2.13 (m, 1H), 1.88 (dt, J=14.5, 5.2 Hz, 1H), 1.62-1.82 (m, 4H), 1.39 (s, 3H), 1.25 (td, J=6.9, 2.9 Hz, 6H). MS: m/z=615.2 (M+1).

Compound 92 was prepared from compound Int-21I using the procedure described above.

Compound 92: $^1$H NMR (400 MHz, METHANOL-d$_4$): δ 8.48 (br. s., 1H), 7.37-7.49 (m, 1H), 6.89-6.99 (m, 2H), 4.49-4.70 (m, 4H), 3.91-4.13 (m, 5H), 3.73 (d, J=8.6 Hz, 1H), 3.52-3.63 (m, 3H), 3.33 (s, 3H), 2.15 (t, J=5.8 Hz, 2H), 1.60-1.80 (m, 4H), 1.36 (s, 3H), 1.24 (td, J=6.9, 3.1 Hz, 6H). MS: m/z=615.2 (M+1).

Example 22

Preparation of Compounds 93-96

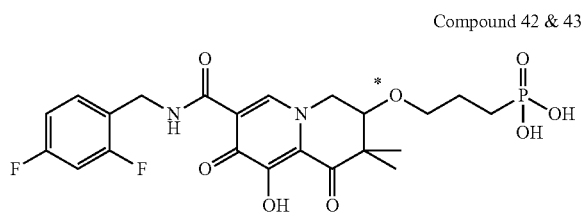 [SMILES: CC1(C)C(=O)c2c(O)c(=O)c(C(=O)NCc3ccc(F)cc3F)cn2CC1OCCCP(=O)(O)O]

Compound 42 & 43

Compounds 93-96 were prepared from compounds Int-21F, G, H and I, respectively using the method described in Example 6.

Compound 93: $^1$H NMR (400 MHz, METHANOL-d$_4$): δ 8.46 (br. s., 1H), 7.34-7.49 (m, 1H), 6.86-7.00 (m, 2H), 4.52-4.72 (m, 4H), 4.01 (br. s., 1H), 3.70-3.80 (m, 1H), 3.50-3.62 (m, 2H), 3.38-3.47 (m, 1H), 3.19 (s, 3H), 2.02-2.12 (m, 1H), 1.73-1.92 (m, 3H), 1.56-1.71 (m, 2H), 1.38 (s, 3H). MS: m/z=559.2 (M+1).

Compound 94: $^1$H NMR (400 MHz, METHANOL-d$_4$): δ 8.47 (br. s., 1H), 7.41 (d, J=7.4 Hz, 1H), 6.84-7.01 (m, 2H), 4.61 (br. s., 4H), 4.05 (br. s., 1H), 3.74 (br. s., 1H), 3.51-3.59 (m, 3H), 3.33-3.38 (m, 3H), 2.13 (br. s., 2H), 1.76 (br. s., 2H), 1.60 (d, J=7.8 Hz, 2H), 1.34 (br. s., 3H). MS: m/z=559.1 (M+1)

Compound 95: $^1$H NMR (400 MHz, METHANOL-d$_4$): δ 8.47 (s, 1H), 7.36-7.47 (m, 1H), 6.87-7.02 (m, 2H), 4.54-4.74 (m, 4H), 4.01 (br. s., 1H), 3.72-3.84 (m, 1H), 3.52-3.61 (m, 2H), 3.38-3.48 (m, 1H), 3.19 (s, 3H), 2.03-2.14 (m, 1H), 1.76-1.93 (m, 3H), 1.57-1.72 (m, 2H), 1.39 (s, 3H). MS: m/z=559.2 (M+1)

Compound 96: $^1$H NMR (400 MHz, METHANOL-d$_4$): δ 8.49 (br. s., 1H), 7.37-7.50 (m, 1H), 6.86-7.03 (m, 2H), 4.50-4.73 (m, 4H), 4.08 (br. s., 1H), 3.78 (d, J=8.4 Hz, 1H), 3.49-3.67 (m, 3H), 3.34 (br. s., 3H), 2.17 (br. s., 2H), 1.79 (br. s., 2H), 1.64 (dd, J=17.6, 8.4 Hz, 2H), 1.37 (s, 3H). MS: m/z=559.2 (M+1).

Example 23

Preparation of Compounds 97-100

Compounds 97-100 were prepared from compounds Int-21F, G, H and I, respectively using the method described in Example 3.

Compound 97: $^1$H NMR (400 MHz, METHANOL-d$_4$): δ 8.49 (s, 1H), 7.37-7.47 (m, 1H), 6.88-7.01 (m, 2H), 5.53-5.67 (m, 4H), 4.83-4.88 (m, 2H), 4.57-4.71 (m, 4H), 4.02 (br. s., 1H), 3.74-3.83 (m, 1H), 3.52-3.61 (m, 2H), 3.40-3.48 (m, 1H), 3.20 (s, 3H), 2.03-2.11 (m, 1H), 1.75-1.93 (m, 5H), 1.39 (s, 3H), 1.27 (t, J=4.7 Hz, 12H). MS: m/z=791.2 (M+1).

Compound 98: $^1$H NMR (400 MHz, METHANOL-d$_4$): δ 8.50 (s, 1H), 7.37-7.49 (m, 1H), 6.87-7.02 (m, 2H), 5.52-5.66 (m, 4H), 4.82-4.87 (m, 2H), 4.60-4.71 (m, 3H), 4.52 (d, J=14.1 Hz, 1H), 4.08 (br. s., 1H), 3.76 (br. s., 1H), 3.53-3.64 (m, 3H), 3.33 (s, 3H), 2.10-2.20 (m, 2H), 1.73-1.90 (m, 4H), 1.36 (s, 3H), 1.18-1.33 (m, 12H). MS: m/z=791.2 (M+1)

Compound 99: $^1$H NMR (400 MHz, METHANOL-d$_4$): δ 8.47 (s, 1H), 7.36-7.47 (m, 1H), 6.87-7.01 (m, 2H), 5.49-5.64 (m, 4H), 4.81-4.86 (m, 2H), 4.55-4.70 (m, 4H), 4.00 (br. s., 1H), 3.73-3.81 (m, 1H), 3.51-3.59 (m, 2H), 3.39-3.46 (m, 1H), 3.18 (s, 3H), 2.01-2.10 (m, 1H), 1.74-1.91 (m, 5H), 1.37 (s, 3H), 1.25 (t, J=4.6 Hz, 12H). MS: m/z=791.2 (M+1).

Compound 100: $^1$H NMR (400 MHz, METHANOL-d$_4$): δ 8.50 (s, 1H), 7.38-7.48 (m, 1H), 6.89-7.01 (m, 2H), 5.50-5.66 (m, 4H), 4.82-4.88 (m, 2H), 4.60-4.72 (m, 3H), 4.52 (d, J=14.3 Hz, 1H), 4.08 (br. s., 1H), 3.74-3.82 (m, 1H), 3.52-3.62 (m, 3H), 3.33 (s, 3H), 2.11-2.20 (m, 2H), 1.73-1.90 (m, 4H), 1.36 (s, 3H), 1.19-1.32 (m, 12H). MS: m/z=791.2 (M+1).

Example 24

Preparation of Compounds 101 and 102

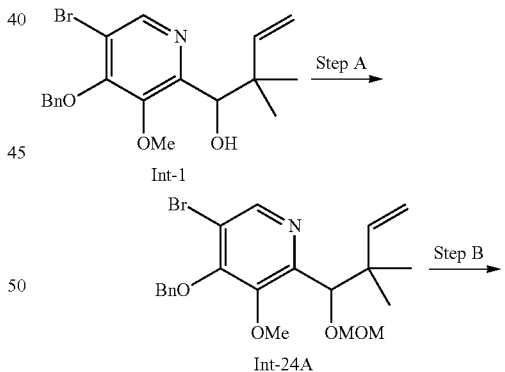

Int-1

Int-24A

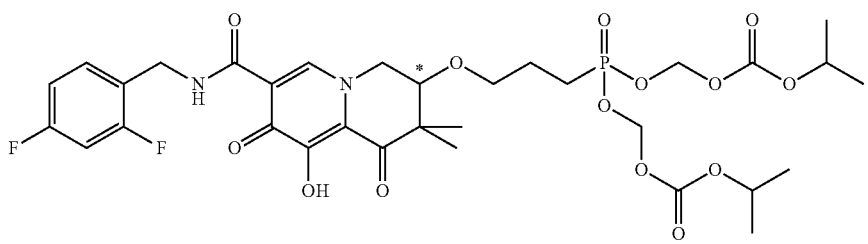

Compounds 97-100

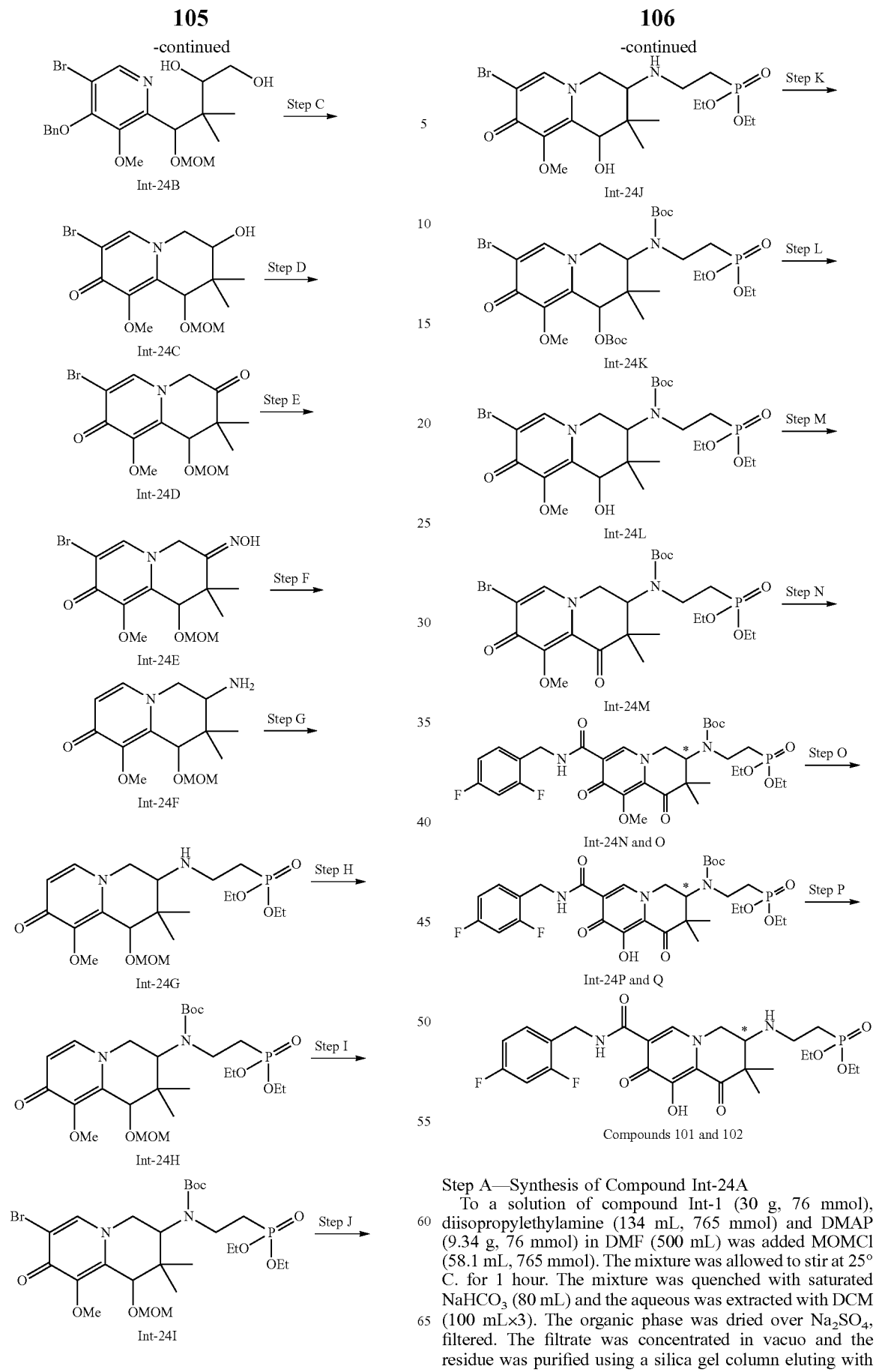

Step A—Synthesis of Compound Int-24A

To a solution of compound Int-1 (30 g, 76 mmol), diisopropylethylamine (134 mL, 765 mmol) and DMAP (9.34 g, 76 mmol) in DMF (500 mL) was added MOMCl (58.1 mL, 765 mmol). The mixture was allowed to stir at 25° C. for 1 hour. The mixture was quenched with saturated NaHCO$_3$ (80 mL) and the aqueous was extracted with DCM (100 mL×3). The organic phase was dried over Na$_2$SO$_4$, filtered. The filtrate was concentrated in vacuo and the residue was purified using a silica gel column eluting with 5% petroleum ether/EtOAc to provide compound Int-24A as an oil. $^1$H NMR (400 MHz, CHLOROFORM-d): δ 8.32 (brs, 1H), 7.23-7.47 (m, 5H), 5.92 (br dd, J=10.9, 17.44 Hz, 1H), 5.02-5.28 (m, 2H), 4.73-4.93 (m, 3H), 4.11-4.64 (m, 2H), 3.77-3.92 (m, 3H), 3.12-3.29 (m, 3H), 0.97 (brs, 6H) MS: m/z=438.0 (M+1).

Step B—Synthesis of Compound Int-24B

To a solution of compound Int-24A (26 g, 59.6 mmol) in 440 mL of a co-solvent THF/t-BuOH/water (5:5:1), was added NMO (13.96 g, 119 mmol), followed by osmium (VIII) oxide (1.515 g, 5.96 mmol). The reaction was allowed to stir at 25° C. for 16 hours. The reaction was quenched by solid $Na_2S_2O_5$ (40 g). The mixture was allowed to stir at 25° C. for 1 h, and then diluted with 70 mL of 10% DCM/MeOH. The brown solid was filtered off. The filtrate was washed with water and concentrated. The residue was purified using a silica gel column eluting with 10% MeOH/DCM to provide compound Int-24B as a colorless oil. $^1$H NMR (400 MHz, CHLOROFORM-d): δ 8.44 (br d, J=9.5 Hz, 1H), 7.45 (br s, 2H), 7.35 (br s, 3H), 5.23-5.29 (m, 1H), 5.13-5.22 (m, 1H), 4.87-4.98 (m, 2H), 4.54-4.63 (m, 1H), 4.37-4.46 (m, 2H), 3.91 (br d, J=10.6 Hz, 3H), 3.53-3.70 (m, 1H), 3.25 (br d, J=9.3 Hz, 3H), 1.58 (s, 6H). MS: m/z=470.1 (M+1).

Step C—Synthesis of Compound Int-24C

To a mixture of compound Int-24B (26.2 g, 55.7 mmol) in 30 mL of pyridine was added TsCl (19.12 g, 100 mmol). The reaction solution was allowed to stir at 25° C. overnight. The reaction was quenched by 5 mL of MeOH, and stirred at 25° C. for 1 hour. The resulting solution was diluted with 400 mL of EtOAc, and then washed with 1 N HCl (aq.) (2×20 mL). The organic was concentrated, and the residue was purified using a silica gel column eluting with 5% MeOH/DCM to provide compound Int-24C as a colorless film. $^1$H NMR (400 MHz, CHLOROFORM-d): δ 7.65 (s, 1H), 4.78-4.83 (m, 1H), 4.70 (d, J=6.6 Hz, 1H), 4.46 (d, J=6.6 Hz, 1H), 4.26-4.39 (m, 2H), 3.97 (s, 3H), 3.69 (br dd, J=6.0, 12.8 Hz, 1H), 3.32-3.43 (m, 3H), 1.60 (s, 3H), 1.31 (s, 3H). MS: m/z=362.2 (M+1).

Step D—Synthesis of Compound Int-24D

To a mixture of compound Int-24C (17 g, 46.9 mmol) in DCM (300 mL) was added DMP (39.8 g, 94 mmol). The reaction was allowed to stir at 25° C. overnight. The mixture was filtered and the filtrate was concentrated. The residue was purified using a silica gel column eluting with 5% MeOH/DCM to provide compound Int-24D (12.3 g, 30.7 mmol, 65.5% yield) as a colorless film. $^1$H NMR (400 MHz, METHANOL-d4): δ 8.18 (s, 1H), 5.11 (s, 1H), 4.73 (br d, J=7.8 Hz, 2H), 4.63-4.67 (m, 1H), 4.57-4.62 (m, 1H), 3.91-3.96 (m, 3H), 3.31 (s, 3H), 1.35 (s, 3H), 0.92 (s, 3H).

Step E—Synthesis of Compound Int-24E

To a solution of compound Int-24D (4 g, 11.10 mmol) in EtOH (60 mL) were added hydroxylamine hydrochloride (15.43 g, 222 mmol) and $Et_3N$ (31.0 mL, 222 mmol). The mixture was allowed to stir at 80° C. for 16 hours. The mixture was concentrated and treated with $H_2O$ (100 mL), the resulting mixture was extracted with DCM (100 mL×3). The combined organic was concentrated and the residue was purified using a silica gel column chromatography eluting with 50% EtOAc/DCM to provide compound Int-24E as an oil. $^1$H NMR (400 MHz, $CDCl_3$): δ 9.95 (br s, 1H), 7.75 (s, 1H), 5.03 (br d, J=18.1 Hz, 1H), 4.87-4.93 (m, 1H), 4.71-4.80 (m, 1H), 4.58-4.65 (m, 1H), 4.47 (br d, J=6.8 Hz, 1H), 3.91-4.01 (m, 3H), 3.27-3.37 (m, 3H), 1.42 (s, 3H), 0.91 (s, 3H). MS: m/z=377.1 (M+2).

Step F—Synthesis of Compound Int-24F

To a solution of compound Int-24E (3.3 g, 8.79 mmol) in MeOH (30 mL) and ammonium hydroxide (30 mL) was added Raney Ni (2 g, 8.79 mmol). The mixture was allowed to stir at 25° C. under $H_2$ balloon for 16 hours. The mixture was filtered and the filtrate was concentrated to dryness to provide compound Int-24F as an oil. $^1$H NMR (400 MHz, $CDCl_3$): δ 7.10-7.24 (m, 1H), 6.41 (br s, 1H), 4.73-5.02 (m, 2H), 4.62-4.71 (m, 1H), 4.39-4.53 (m, 1H), 4.15 (br s, 1H), 3.87-3.98 (m, 3H), 3.37 (br s, 3H), 2.94 (br s, 1H), 1.28 (br d, J=11.7 Hz, 3H), 0.77 (br s, 3H). MS: m/z=283.1 (M+1). This material was used for the next step without further purification.

Step G—Synthesis of Compound Int-24G

To a solution of the crude compound Int-24F (1.6 g, 5.67 mmol) in MeOH (20 mL) were added diethyl (2-oxoethyl) phosphonate (1.531 g, 8.50 mmol) and $NaBH_3CN$ (0.712 g, 11.33 mmol). The mixture was allowed to stir at 25° C. for 0.5 hours. The solvent was removed under vacuum. The residue was purified using a silica gel column chromatography eluting with 10% DCM/MeOH to provide compound Int-24G as a colorless oil. $^1$H NMR (400 MHz, $CDCl_3$): δ 7.17-7.26 (m, 1H), 6.41 (br d, J=7.0 Hz, 1H), 4.66-4.76 (m, 1H), 4.60 (br d, J=6.7 Hz, 1H), 4.46 (br d, J=5.9 Hz, 1H), 4.24 (br dd, J=12.5, 6.7 Hz, 1H), 4.07 (br dd, J=12.1, 6.7 Hz, 4H), 3.81-3.98 (m, 4H), 3.56 (br dd, J=12.9, 7.4 Hz, 1H), 3.24-3.44 (m, 3H), 2.77-3.06 (m, 2H), 2.65 (br t, J=7.4 Hz, 1H), 1.80-1.99 (m, 2H), 1.12-1.36 (m, 9H), 0.66-0.89 (m, 3H). MS: m/z=447.2 (M+1).

Step H—Synthesis of Compound Int-24H

A mixture of compound Int-24G (1.55 g, 3.47 mmol) in $(BOC)_2O$ (15 mL, 64.6 mmol) was allowed to stir at 100° C. under $N_2$ balloon for 16 hours. The mixture was purified using a silica gel column eluting with 100% petroleum ether to removed excess $(BOC)_2O$, and then with 5% DCM/MeOH to provide compound Int-24H as an oil. $^1$H NMR (400 MHz, $CDCl_3$): δ 7.14-7.23 (m, 1H), 6.36-6.46 (m, 1H), 4.66-4.84 (m, 2H), 4.46-4.59 (m, 2H), 4.22-4.42 (m, 2H), 4.00-4.14 (m, 4H), 3.94 (br s, 3H), 3.68-3.80 (m, 1H), 3.51-3.65 (m, 1H), 3.31-3.40 (m, 3H), 2.02 (br d, J=6.7 Hz, 2H), 1.40-1.62 (m, 9H), 1.04-1.36 (m, 9H), 0.73-0.96 (m, 3H). MS: m/z=547.3 (M+1).

Step I—Synthesis of Compound Int-24I

To a solution compound Int-24H (300 mg, 0.549 mmol) in DCM (5 mL) was added NBS (195 mg, 1.098 mmol) at 0° C. The mixture was allowed to stir at 25° C. for 1.5 hours. The solution was quenched with $Na_2SO_3$ (aq) (5 mL) and the aqueous was extracted with DCM (10 mL×3). The organic layer was dried over $Na_2SO_4$, filtered and the filtrate was concentrated in vacuo. The residue was purified using a preparative TLC plate eluting with 5% DCM/MeOH to provide compound Int-24I as an oil. $^1$H NMR (400 MHz, $CDCl_3$): δ 7.60-7.74 (m, 1H), 4.65-4.81 (m, 2H), 4.28-4.59 (m, 3H), 4.04-4.19 (m, 4H), 3.98 (br d, J=3.5 Hz, 3H), 3.51-3.86 (m, 3H), 3.31-3.42 (m, 3H), 2.22-2.52 (m, 2H), 1.41-1.58 (m, 9H), 1.22-1.37 (m, 6H), 0.73-1.17 (m, 6H).

Step J—Synthesis of Compound Int-24J

To a solution of compound Int-24I (640 mg, 1.023 mmol) in EtOAc (4 mL) was added 4M HCl\EtOAc (12 mL) at 0° C. The mixture was allowed to stir at 25° C. for 2 hours. The reaction mixture was concentrated in vacuo. The residue was purified using a prep-HPLC (Column: Waters XSELECT C18 150 mm*30 mm*5 um: water (0.1% TFA)-ACN; Gradient: 0% to 30%; B, 0~10 min. Flow Rate: 25 mL/min) to provide compound Int-24J as an oil. $^1$H NMR (400 MHz, $CDCl_3$): δ 8.08-8.25 (m, 1H), 4.72-4.81 (m, 1H), 4.50-4.63 (m, 2H), 4.09-4.25 (m, 4H), 3.85-3.94 (m, 3H), 3.69 (br s, 1H), 3.32-3.56 (m, 2H), 2.26-2.52 (m, 2H), 1.26-1.54 (m, 9H), 0.86-1.09 (m, 3H). MS: m/z=483.1 (M+2).

Step K—Synthesis of Compound Int-24K

A mixture of the compound Int-24J (220 mg, 0.457 mmol) in (BOC)$_2$O (2 mL, 8.61 mmol) was allowed to stir at 100° C. for 16 h under N$_2$ balloon. The mixture was concentrated in vacuo to provide compound Int-24K as an oil. It was used for the next step without further purification. MS: m/z=483.2 (M+1).

Step L—Synthesis of Compound Int-24L

A mixture of the compound Int-24K (200 mg, 0.293 mmol) and K$_2$CO$_3$ (203 mg, 1.467 mmol) in EtOH (5 mL) was allowed to stir at 40° C. for 22 h under N$_2$ balloon. The mixture was filtered, and pH was adjusted to 5-6 using AcOH. The residue was concentrated in vacuo and the residue was purified using a preparative TLC plate eluting with 5% DCM/MeOH to provide compound Int-24L as an oil. $^1$H NMR (400 MHz, CDCl$_3$): δ 7.60-7.70 (m, 1H), 4.49-4.82 (m, 4H), 4.05-4.16 (m, 6H), 3.71-3.86 (m, 5H), 1.47 (br s, 6H), 1.33 (br t, J=6.5 Hz, 9H), 1.10 (br s, 3H), 0.83-0.89 (m, 3H). MS: m/z=581.1 (M+1).

Step M—Synthesis of Compound Int-24M

To a stirred solution of compound Int-24L (130 mg, 0.224 mmol) in DCM (1 mL) was added Dess-Martin periodinane (190 mg, 0.447 mmol). The reaction mixture was allowed to stir at 25° C. for 2 hours. It was diluted with 0.1 mL of H$_2$O. The solid was filtered off. The solvent was concentrated and the residue was purified using a silica gel column chomatography eluting with 5% DCM/MeOH to provide compound Int-24M as an oil. $^1$H NMR (400 MHz, CDCl$_3$): δ 7.69-7.80 (m, 1H), 4.36-4.57 (m, 2H), 4.26 (s, 1H), 3.90-4.12 (m, 7H), 3.44 (br s, 1H), 3.25 (br s, 1H), 2.06-2.24 (m, 1H), 1.94 (br d, J=16.0 Hz, 1H), 1.40 (br s, 9H), 1.13-1.32 (m, 12H). MS: m/z=581.2 (M+2).

Step N—Synthesis of Compounds Int-24N and O

To a solution of compound Int-24M (132 mg, 0.228 mmol) in DMSO (1 mL) were added (2,4-difluorophenyl)methanamine (65.2 mg, 0.456 mmol), diisopropylethylamine (0.159 mL, 0.911 mmol) and Pd(Ph$_3$P)$_4$ (132 mg, 0.114 mmol). The mixture was allowed to stir at 80° C. under CO balloon for 9 hours. The mixture was filtered and the filtrate was diluted with water (10 mL) and extracted with EtOAc (20 mL×3). The organic layer was washed with NaHCO$_3$ (20 mL)(aq) and brine (20 mL), dried over anhydrous Na$_2$SO$_4$ and then filtered. The filtrate was concentrated and purified using a prep-HPLC (Column: Phenomenex Synergi C18 150 mm*30 mm*4 um; Condition: water (0.1% TFA)-ACN; Gradient: 44% to 64%; B, 0-12 min. Flow Rate: 25 mL/min) to provide racemic mixture of compound Int-24N and compound Int-24O as yellow oil. This material was further separated by a chiral preparative SFC (Column: AD (250 mm*30 mm, 5 um) Mobile phase: 45% Base-IPA (contained 0.1% NH$_3$H$_2$O) in CO$_2$ Flow rate: 60 mL/min Wavelength: 220 nm) to provide compound Int-24N (the first eluting compound) as a colorless oil and compound Int-24O (the second eluting compound) as a colorless oil.

Compound Int-24N: $^1$H NMR (400 MHz, CDCl$_3$): δ 10.50 (br s, 1H), 8.39 (br s, 1H), 7.32-7.40 (m, 1H), 6.74-6.85 (m, 2H), 4.54-4.69 (m, 3H), 4.45 (br s, 1H), 4.07 (br s, 3H), 3.99 (s, 3H), 3.25 (br s, 1H), 1.84-2.21 (m, 5H), 1.40 (br s, 9H), 1.21-1.34 (m, 12H).

Compound Int-24O: $^1$H NMR (400 MHz, CDCl$_3$): δ 10.50 (br s, 1H), 8.40 (br s, 1H), 7.32-7.41 (m, 1H), 6.74-6.86 (m, 2H), 4.52-4.69 (m, 3H), 4.45 (br s, 1H), 4.07 (br s, 3H), 3.99 (s, 3H), 3.25 (br s, 1H), 1.81-2.35 (m, 5H), 1.40 (br s, 9H), 1.23-1.34 (m, 12H).

Step N—Synthesis of Compound Int-24P and Q

To a solution of compound Int-24N (20 mg, 0.030 mmol) in Acetonitrile (2 mL) was added magnesium bromide (110 mg, 0.597 mmol) at 0° C. The mixture was allowed to stir at 25° C. for 16 hours. To the mixture was diluted with H$_2$O and extracted with DCM. The DCM layer was dried over Na$_2$SO$_4$, filtered and the filtrate was concentrated in vacuo to provide compound Int-24P as an oil. It was used for the next step without further purification. MS: m/z=656.2 (M+1).

Compound Int-24Q was prepared from compound Int-24O using the above method. MS: m/z=656.2 (M+1).

Step P—Synthesis of Compound 101 and Compound 102

To a solution of compound Int-24P (20 mg, 0.031 mmol) in DCM (2 mL) was added TFA (0.5 mL) at 0° C. The mixture was allowed to stir at 25° C. for 2 hours. The mixture was concentrated. The residue was purified using prep-HPLC (Column: Phenomenex Synergi C18 150 mm*30 mm*4 um; Condition: water (0.1% TFA)-ACN; Gradient: 21% to 51%; B, 0-11 min. Flow Rate: 25 mL/min) to provide compound 101 as an oil. $^1$H NMR: (400 MHz, MeOH-d$_4$): δ 8.52 (br s, 1H), 7.39-7.45 (m, 1H), 6.90-7.00 (m, 2H), 4.72 (br d, J=14.1 Hz, 1H), 4.62 (s, 2H), 4.52 (br d, J=9.7 Hz, 1H), 4.03-4.16 (m, 4H), 3.55 (br s, 1H), 3.12 (br s, 2H), 2.01-2.24 (m, 3H), 1.22-1.49 (m, 12H). MS: m/z=556.1 (M+1).

Compound 102 was prepared from compound Int-24Q using the above method. $^1$H NMR: (400 MHz, MeOH-d$_4$): δ 8.53 (s, 1H), 7.40-7.47 (m, 1H), 6.90-7.00 (m, 2H), 4.76 (br d, J=13.7 Hz, 1H), 4.53-4.65 (m, 3H), 4.10 (quin, J=7.2 Hz, 4H), 3.64 (br s, 1H), 3.10-3.29 (m, 2H), 2.02-2.35 (m, 3H), 1.28-1.50 (m, 12H). MS: m/z=556.2 (M+1).

Example 25

Preparation of Compound 103 and 104

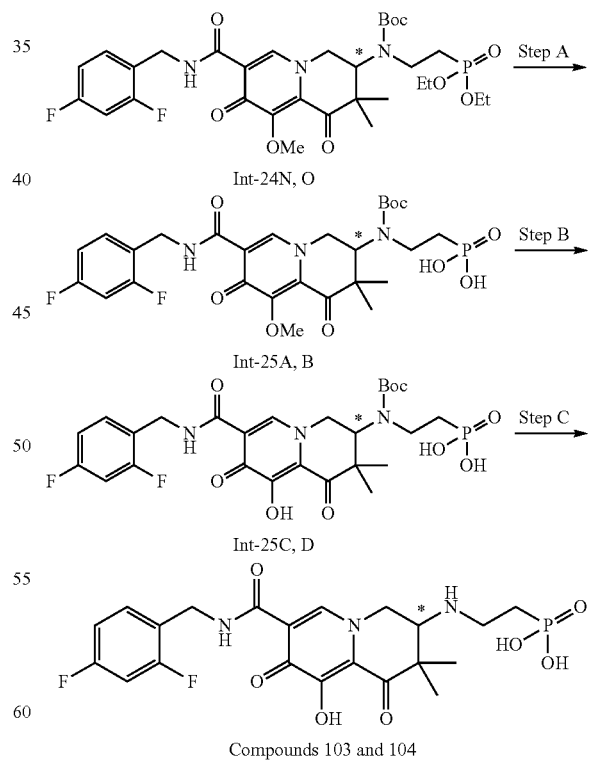

Compounds 103 and 104

Step A—Synthesis of Compound Int-25A and Int-25B

To a solution of compound Int-24N (5 mg, 7.47 μmol) in acetonitrile (2 mL) was added 2,6-dimethylpyridine (9.60 mg, 0.090 mmol), TMSBr (9.69 μL, 0.075 mmol) and the mixture was allowed to stir at 50° C. for 4 hours. The solvent was removed to provide crude compound Int-25A as a solid which was used for the next step without further purification. MS: m/z=614.2 (M+1).

Compound Int-25B was prepared using the above method, except substituting compound Int-24N with compound Int-24O. MS: m/z=614.2 (M+1).

Step B—Synthesis of Compound Int-25C and Int-25D

To a solution of compound Int-25A (10 mg, 0.016 mmol) in acetonitrile (2 mL) was added magnesium bromide (60.0 mg, 0.326 mmol) at 0° C. The mixture was allowed to stir at 25° C. for 16 hours. The solution was concentrated in vacuo to provide to provide compound Int-25C as an oil. This material was used for the next step without further purification. MS: m/z=600.2 (M+1).

Compound Int-25D was prepared using the above method, except substituting compound Int-25A with compound Int-25B. MS: m/z=600.2 (M+1).

Step C—Synthesis of Compound 103 and Compound 104

To a solution of compound Int-25C (10 mg, 0.017 mmol) in DCM (2 mL) was added TFA (0.5 mL) at 0° C. The mixture was allowed to stir at 25° C. for 2 hours. The mixture was concentrated in vacuo. The residue was purified using prep-HPLC (Column: Phenomenex Synergi C18 150 mm*30 mm*4 um; Condition: water (0.1% TFA)-ACN; Gradient: 21% to 51%; B, 0-11 min. Flow Rate: 25 mL/min) to provide compound 103 as an oil. $^1$H NMR: (400 MHz, MeOH-$d_4$): δ 8.57 (br s, 1H), 7.43 (br s, 1H), 6.95 (br d, J=13.9 Hz, 2H), 4.62 (br s, 4H), 3.91 (br s, 1H), 3.56 (br s, 2H), 1.93 (br s, 2H), 1.52 (br s, 3H), 1.45 (br s, 3H). MS: m/z=500.2 (M+1).

Compound 104 was prepared using the above method, except substituting compound Int-25c with compound Int-25d. $^1$H NMR: (400 MHz, MeOH-$d_4$): δ 8.57 (br s, 1H), 7.42 (br d, J=8.4 Hz, 1H), 6.95 (br d, J=13.9 Hz, 2H), 4.62 (br s, 4H), 3.93 (br s, 1H), 3.57 (br s, 2H), 1.96 (br s, 2H), 1.52 (br s, 3H), 1.45 (br s, 3H). MS: m/z=500.1 (M+1).

Example 26

Preparation of Compounds 105 and 106

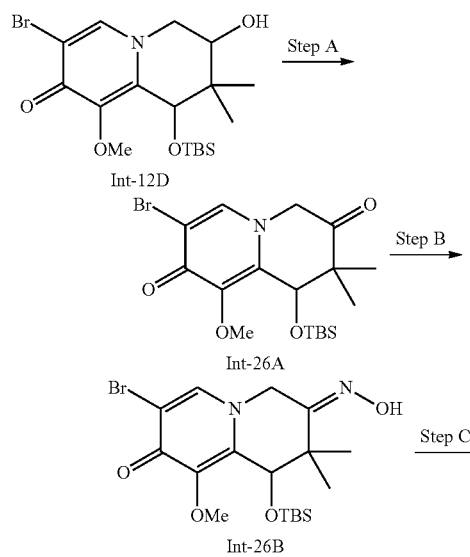

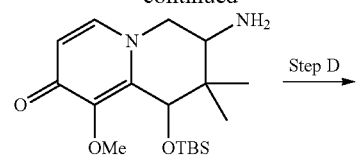

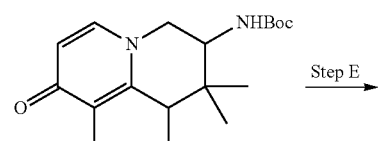

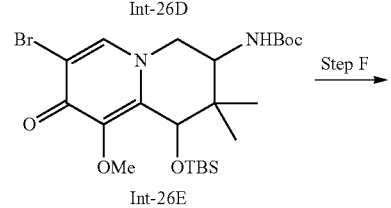

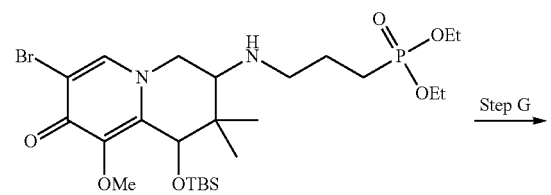

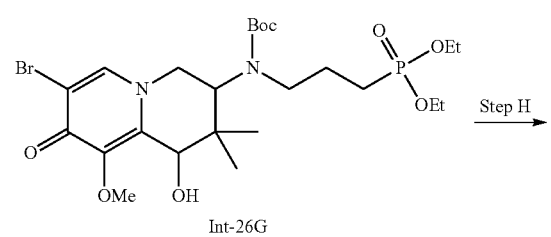

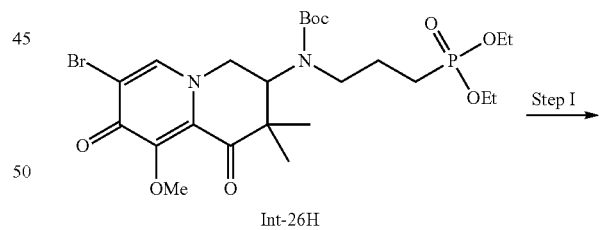

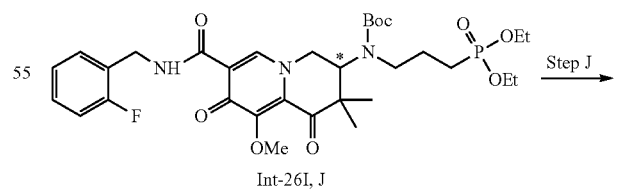

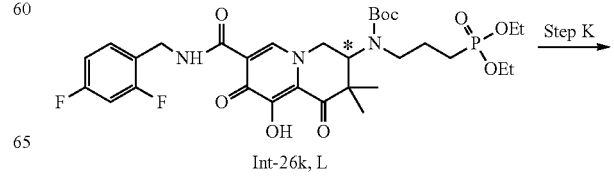

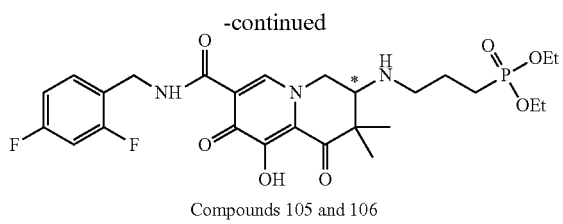

Compounds 105 and 106

Step A—Synthesis of Compound Int-26A

To a stirred solution of compound Int-12D (1 g, 3.313 mmol) in DCM (10 mL) was added Dess-Martin periodinane (1.471 g, 3.47 mmol). The reaction mixture was allowed to stir at 20° C. for 2 hours. The reaction mixture was diluted with 5 drops water and the solid was filtered off. The filtrate was concentrated and the residue was purified using a silica gel column eluting with 33% EtOAc/DCM to provide compound Int-26A as a solid. $^1$H NMR (400 MHz, CDCl$_3$): δ 7.65 (s, 1H), 5.01 (s, 1H), 4.68 (d, J=17.6 Hz, 1H), 4.30 (d, J=18.1 Hz, 1H), 4.05 (s, 3H), 1.33 (s, 3H), 0.89 (s, 3H), 0.80 (s, 9H), 0.15 (s, 3H), −0.07 (s, 3H). MS: m/z=430.2 (M+1).

Step B—Synthesis of Compound Int-26B

To a solution of compound Int-26A (1 g, 3.32 mmol)) in ethanol (15 mL) was added hydroxylamine hydrochloride (3.23 g, 46.5 mmol) and Et$_3$N (6.48 mL, 46.5 mmol) under N$_2$. The reaction was allowed to stir at 80° C. for 16 hours. The mixture was concentrated and treated with H$_2$O (20 mL). The aqueous was extracted with DCM (10 mL×3), and the organic was concentrated in vacuo to provide compound Int-26B as a solid. This material was used in the next step without further purification. $^1$H NMR (400 MHz, CDCl$_3$): δ 7.70 (s, 1H), 5.00 (d, J=17.9 Hz, 1H), 4.65-4.84 (m, 2H), 4.00 (s, 3H), 1.37 (s, 3H), 0.89 (s, 3H), 0.79 (s, 9H), 0.13 (s, 3H), −0.10 (s, 3H). MS: m/z=445.1 (M+1).

Step C—Synthesis of Compound Int-26C

To a solution of compound Int-26B (0.8 g, 1.796 mmol)) in MeOH (15 mL) and ammonium hydroxide (15 mL) was added Raney Ni (80 mg, 1.796 mmol). The mixture was allowed to stir at 20° C. under H$_2$ balloon for 16 hours. The mixture was filtered and the filtrate was concentrated to dryness to provide compound Int-26C as an oil. $^1$H NMR (400 MHz, CDCl$_3$): δ 7.62 (br. s, 1H), 6.82 (br. s., 1H), 5.19 (s, 1H), 3.23-4.55 (m, 6H), 1.64 (br. s., 3H), 1.19 (br. s., 12H), −0.04-0.68 (m, 6H). MS: m/z=353.2 (M+1).

Step D—Synthesis of Compound Int-26D

To a solution of compound Int-26C (600 mg, 1.702 mmol) in DCM (10 mL) was added Et$_3$N (0.712 mL, 5.11 mmol) and BOC anhydride (0.474 mL, 3.042 mmol) at 0° C. The mixture was allowed to stir at 20° C. for 16 hours. It was diluted with H$_2$O (20 mL), and extracted with DCM (10 mL×3). The organic phase was concentrated in vacuo and the residue was purified using a preparative TLC plate eluting with 5% MeOH/dichloromethane to provide compound Int-26D as a solid. $^1$H NMR (400 MHz, CDCl$_3$): δ 7.16 (d, J=7.3 Hz, 1H), 6.44 (d, J=7.5 Hz, 1H), 5.98 (d, J=9.5 Hz, 1H), 4.63-4.79 (m, 1H), 3.83-4.15 (m, 5H), 1.52 (s, 3H), 1.43 (s, 9H), 1.15 (s, 3H), 0.88 (s, 9H), 0.20 (s, 3H), −0.10 (s, 3H). MS: m/z=453.2 (M+1).

Step E—Synthesis of Compound Int-26E

To a solution of compound Int-26D (0.6 g, 1.325 mmol) in DCM (10 mL) was added NBS (0.472 g, 3.65 mmol) at 0° C. The mixture was allowed to stir at 20° C. for 2 hours. It was quenched by adding Na$_2$SO$_3$ (aq.) (3 mL). The resulting mixture was extracted with DCM (10 mL×3), dried over anhydrous sodium sulfate and filtered. The filtrate was concentrated in vacuo and the residue was purified using a preparative TLC plate eluting with 50% EtOAc/dichloromethane to provide compound Int-26E as a solid. $^1$H NMR (400 MHz, CDCl$_3$): δ 7.57-7.67 (m, 1H), 5.99 (d, J=9.5 Hz, 1H), 4.68 (s, 1H), 3.84-4.18 (m, 5H), 1.35-1.66 (m, 12H), 1.23 (s, 3H), 0.88 (s, 9H), 0.19 (s, 3H), −0.10 (s, 3H). MS: m/z=531.1 (M+1).

Step F—Synthesis of Compound Int-26F

To a stirred solution of compound Int-26E (1000 mg, 1.881 mmol) in DMF (15 mL) was added NaH (226 mg, 5.64 mmol). The mixture was allowed to stir at 0° C. for 15 min. Diethyl (3-bromopropyl)phosphonate (1462 mg, 5.64 mmol) and sodium iodide (846 mg, 5.64 mmol) were then added successively. The mixture was allowed to stir at 0° C. for 3 hours. The reaction was quenched with NH$_4$Cl (1 mL), and the mixture was extracted with DCM (3×20 mL). The organic was concentrated in vacuo and the residue was purified using by a preparative TLC plate eluting with 6% MeOH/dichloromethane. The product containing fraction was further purified using a preparative HPLC (Column: YMC-Actus Pro C18 150 mm*30 mm, 5 um; Condition: 0.1% TFA-ACN; Gradient: 48% to 79%; B, 0~11 min. FlowRate: 40 mL/min) to provide compound Int-26F as an oil. $^1$H NMR (400 MHz, CHLOROFORM-d): δ 7.55-7.81 (m, 1H), 3.85-4.79 (m, 10H), 3.05-3.77 (m, 3H), 1.43-1.54 (m, 13H), 1.24-1.37 (m, 12H), 0.81-0.95 (m, 9H), 0.16 (s, 3H), 0.00 (s, 3H). MS: m/z=709.2 (M+1).

Step G—Synthesis of Compound Int-26G

To a solution of compound Int-26F (250 mg, 0.352 mmol) in THF (5 mL) was added TBAF (0.352 mL, 0.352 mmol). The mixture was allowed to stir at 25° C. for 2 hours. The mixture was concentrated to dryness. The residue was dissolved in DCM (20 mL) and washed with H$_2$O (10 mL). The organic phase was concentrated in vacuo and the residue was purified using a preparative TLC plate eluting with 6% MeOH/dichloromethane to provide compound Int-26G as an oil. $^1$H NMR (400 MHz, CHLOROFORM-d): δ 7.56-7.70 (m, 1H), 5.04 (br. s., 1H), 4.49-4.63 (m, 1H), 4.27 (d, J=12.6 Hz, 1H), 4.08 (br. s., 4H), 3.69-3.87 (m, 3H), 3.24-3.43 (m, 1H), 1.07-1.95 (m, 27H). MS: m/z=595.6 (M+1).

Step H—Synthesis of Compound Int-26H

To a solution of compound Int-26G (150 mg, 0.252 mmol) in DCM (5 mL) was added Dess-Martin periodinane (214 mg, 0.504 mmol). The mixture was allowed to stir at 25° C. for 2 hours. The mixture was concentrated to dryness. The residue was dissolved in DCM (20 mL) and washed with H$_2$O (10 mL). The organic phase was concentrated in vacuo and the residue was purified using a preparative TLC plate eluting with 6% MeOH/dichloromethane to provide compound Int-26H as an oil. $^1$H NMR (400 MHz, CHLOROFORM-d): δ 7.52-7.87 (m, 1H), 4.22-4.67 (m, 2H), 3.78-4.13 (m, 7H), 3.34 (br. s., 1H), 1.50-1.91 (m, 6H), 1.07-1.44 (m, 21H). MS: m/z=595.6 (M+1).

Step I—Synthesis of Compounds Int-26I and J

To a mixture of compound Int-26H (100 mg, 0.169 mmol), diisopropylethylamine (0.147 mL, 0.843 mmol) and (2,4-difluorophenyl)methanamine (48.2 mg, 0.337 mmol) in DMSO (3 mL) was added Pd(Ph$_3$P)$_4$ (97 mg, 0.084 mmol) under N$_2$. The mixture was allowed to stir at 80° C. for 6 h under a CO balloon. The reaction mixture was diluted with EtOAc (10 mL) and washed with H$_2$O (20 mL). The organic layer was concentrated to under vacuum and the residue was purified using a preparative TLC plate eluting with 50% EA/dichloromethane to provide a racemic mixture of the desired product. MS: m/z=684.3 (M+1). This material was further purified using a chiral preparative SFC (Column: AD (250 mm*30 mm, 5 um). Mobile phase: 20% Base-IPA (contained 0.1% NH₃H₂O) in CO₂. Flow rate: 60 mL/min, Wavelength: 220 nm) to provide compound Int-26I (the first eluting isomer) as an oil and compound Int-26J (the second eluting isomer) as an oil.

Compound Int-26I: ¹H NMR (400 MHz, CHLOROFORM-d): δ 10.49 (br. s., 1H), 8.40 (br. s., 1H), 7.29-7.43 (m, 1H), 6.72-6.88 (m, 2H), 4.56-4.72 (m, 2H), 4.22-4.55 (m, 2H), 3.94-4.17 (m, 7H), 3.12 (br. s., 1H), 1.75 (br. s., 9H), 1.15-1.49 (m, 18H). MS: m/z=684.3 (M+1).

Compound Int-26J: ¹H NMR (400 MHz, CHLOROFORM-d): δ 10.49 (br. s., 1H), 8.40 (br. s., 1H), 7.29-7.43 (m, 1H), 6.72-6.88 (m, 2H), 4.56-4.72 (m, 2H), 4.22-4.55 (m, 2H), 3.94-4.17 (m, 7H), 3.12 (br. s., 1H), 1.75 (br. s., 9H), 1.15-1.49 (m, 18H). MS: m/z=684.3 (M+1).

Step J—Synthesis of Compounds Int-26K and L

A solution of compound Int-26I (20 mg, 0.029 mmol) and magnesium bromide (53.9 mg, 0.293 mmol) in 2 mL of CH₃CN was allowed to stir at 25° C. for 16 hours. The reaction was quenched with H₂O (5 mL) and the resulting mixture was extracted with DCM (5 mL×2). The organic phase was concentrated in vacuo to provide compound Int-26K as an oil. MS: m/z=670.3 (M+1). This material was used in the next step without purification.

Compound Int-26L was prepared using the above method, except substituting compound Int-26I with compound Int-26J.

Step K—Synthesis of Compounds 105 and 106

To a solution of compound Int-26K (15 mg, 0.022 mmol) in DCM (1 mL) was added TFA (0.3 mL) at 0° C. The mixture was allowed to stir at 25° C. for 1 hour. The mixture was concentrated in vacuo and the residue was purified using a preparative HPLC (Column: Boston Green ODS 150 mm*30 mm, 5 um using TFA water and acetonitrile as the eluents; Condition: 0.1% TFA-ACN; Gradient: 27% to 47%; B, 0~12 min. FlowRate: 25 mL/min) to provide compound 105 as an oil. ¹H NMR (400 MHz, METHANOL-d₄): δ 8.55 (br. s., 1H), 7.43 (d, J=7.1 Hz, 1H), 6.90-7.00 (m, 2H), 4.77-4.83 (m, 1H), 4.59-4.72 (m, 3H), 4.09 (d, J=5.7 Hz, 4H), 3.91 (br. s., 1H), 3.32-3.39 (m, 1H), 3.23 (br. s., 1H), 1.93 (d, J=11.7 Hz, 4H), 1.48 (d, J=19.4 Hz, 6H), 1.22-1.37 (m, 6H). MS: m/z=570.0 (M+1).

Compound 106 was prepared using the above method, except substituting compound Int-26K with compound Int-26L. ¹H NMR (400 MHz, METHANOL-d₄): δ 8.56 (br. s., 1H), 7.42 (d, J=7.1 Hz, 1H), 6.90-7.00 (m, 2H), 4.77-4.83 (m, 1H), 4.59-4.72 (m, 3H), 4.09 (d, J=5.7 Hz, 4H), 3.91 (br. s., 1H), 3.32-3.39 (m, 1H), 3.23 (br. s., 1H), 1.93 (d, J=11.7 Hz, 4H), 1.48 (d, J=19.4 Hz, 6H), 1.22-1.37 (m, 6H). MS: m/z=570.0 (M+1).

Example 27

Preparation of Compound 107

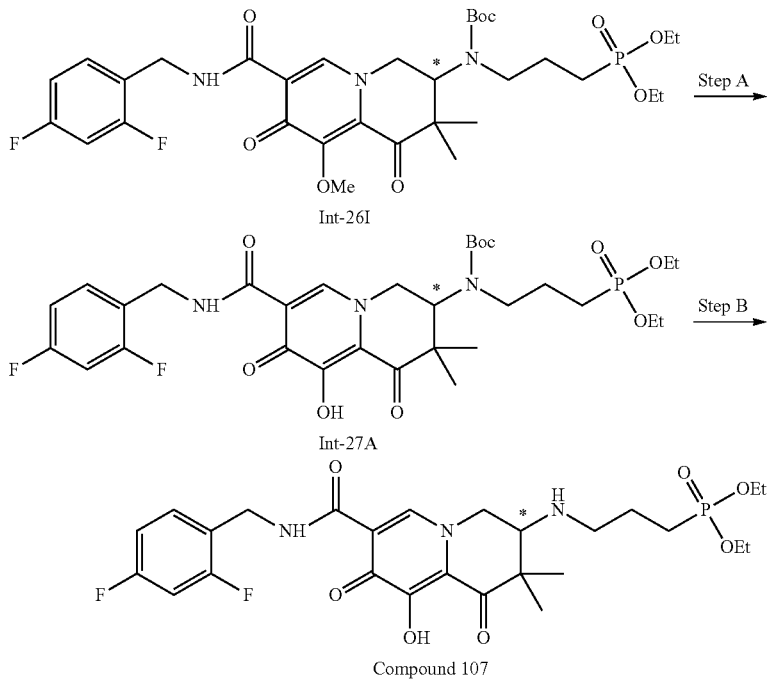

Step A—Synthesis of Compound Int-27A

To a solution of compound Int-26I (10 mg, 0.015 mmol) in acetonitrile (0.2 mL) was added magnesium bromide (53.9 mg, 0.293 mmol) and the mixture was allowed to stir at 23° C. for 2 hours. The reaction mixture was diluted with DCM (50 mL) and washed with water (10 mL), brine (25 mL) sequentially. The organic layer was dried over anhydrous sodium sulfate. It was then filtered and the filtrate was concentrated in vacuo to provide compound Int-27A as a solid. MS: m/z=670.1 (M+1). This material was used for the next step without further purification.

Step B—Synthesis of Compound 107

To a solution of compound Int-27A (5 mg, 7.47 μmol) in acetonitrile (0.2 mL) was added TMSBr (9.69 μL, 0.075 mmol) and the mixture was allowed to stir at 23° C. for 72 hours. The mixture was concentrated and purified using Pre-HPLC (TFA) to provide compound 107 as a solid. ¹H NMR (400 MHz, MeOD): δ 8.56 (s, 1H), 7.35-7.43 (m, 1H), 6.91-6.99 (m, 2H), 4.62-4.88 (m, 4H), 3.90 (br, 1H), 3.25-3.37 (m, 2H), 1.79-2.04 (m, 4H), 1.52 (s, 3H), 1.46 (s, 3H).

Example 28

Preparation of Compound 108

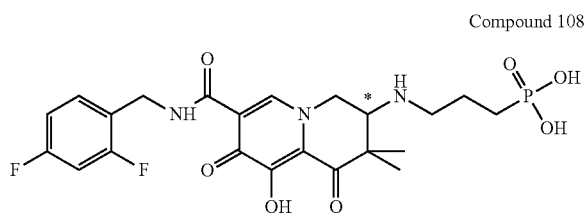 [SMILES: CC1(C)C(=O)c2c(O)c(=O)c(C(=O)NCc3ccc(F)cc3F)cn2CC1NCCCP(=O)(O)O]

Compound 108

Compound 108 was prepared using the method described in Example 27, except replacing compound Int-26I with compound Int-26J.

Compound 108: $^1$H NMR (400 MHz, MeOD): δ 8.57 (s, 1H), 7.38-7.46 (m, 1H), 6.91-6.99 (m, 2H), 4.62-4.88 (m, 4H), 3.90 (br, 1H), 3.25-3.37 (m, 2H), 1.79-2.04 (m, 4H), 1.52 (s, 3H), 1.46 (s, 3H). MS: m/z=514.1 (M+1).

Example 29

Preparation of Compound 109

Step A—Synthesis of Compound Int-29A

To a mixture of compound Int-26I (20 mg, 0.029 mmol) and 2,6-lutidine (0.037 mL, 0.322 mmol) in acetonitrile (0.2 mL), was added a solution of bromotrimethylsilane (44.8 mg, 0.293 mmol) in acetonitrile (0.2 mL). The mixture was allowed to stir at 50° C. for 45 minutes. The solvent was removed under vacuum to provide crude compound Int-29A as a solid. MS: m/z=628.2 (M+1). This material was used in the next step without further purification.

Step B—Synthesis of Compound Int-29B

To a solution of compound Int-29A (15 mg, 0.024 mmol) in ACN (0.4 mL) was added N-ethyl-N-isopropylpropan-2-amine (61.8 mg, 0.478 mmol) and the mixture was allowed to stir at 23° C. for 10 min. Tetrabutylammonium bromide (7.71 mg, 0.024 mmol) was then added and the mixture was allowed to stir at the same temperature for additional 5 min. To the mixture was added dropwise chloromethyl isopropyl carbonate (36.5 mg, 0.239 mmol). The reaction mixture was allowed to stir at 60° C. for 24 hours. The resulting mixture was purified using a preparative TLC plate eluting with EtOAc to provide compound Int-29B as a solid. MS: m/z=860.1 (M+1).

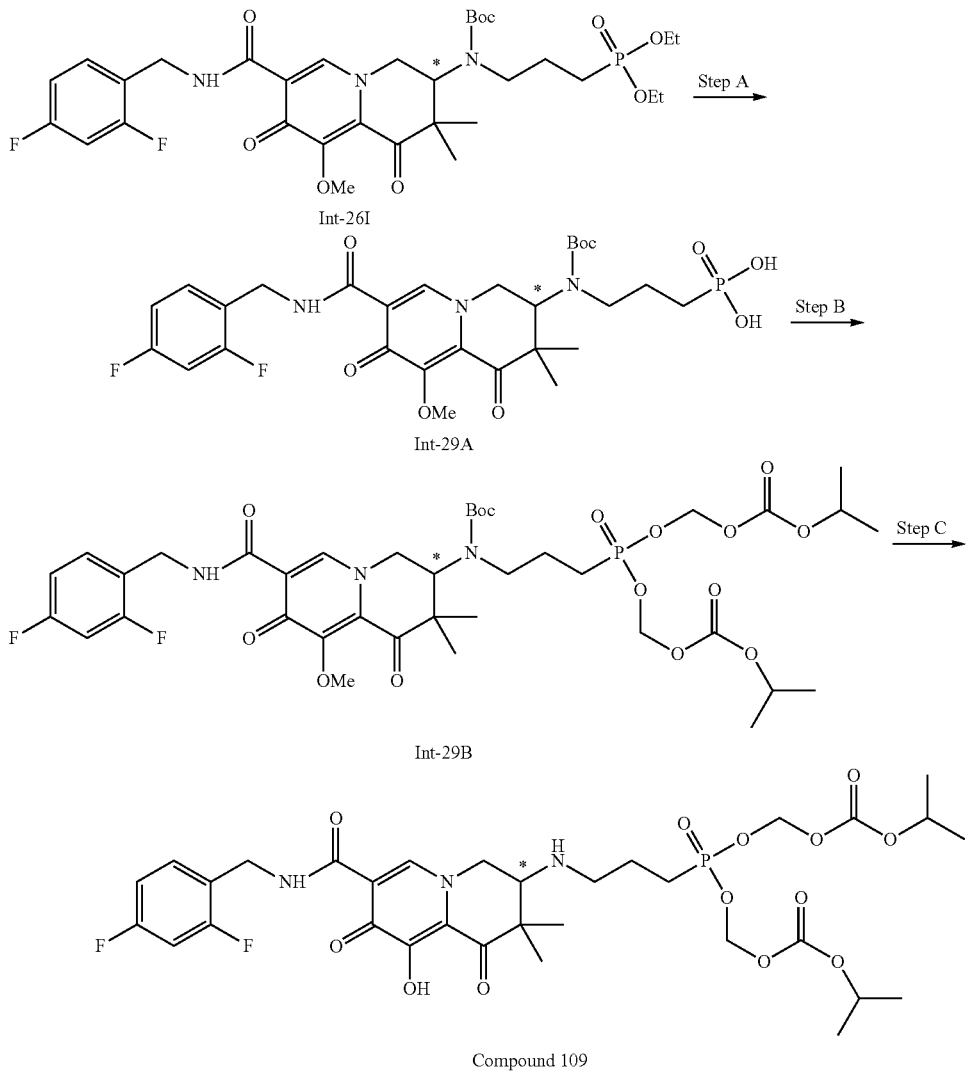

Step C—Synthesis of Compound 109

To a solution of compound Int-29B (11 mg, 0.013 mmol) in acetonitrile (0.2 mL) was added magnesium bromide (47.1 mg, 0.256 mmol) and the mixture was allowed to stir at 23° C. for 12 hours. The mixture was diluted with DCM (5 mL) and filtered, the filtrate was concentrated in vacuo. The residue was then dissolved in DCM (0.3 mL), and TFA (0.1 mL, 1.298 mmol) was then added. The mixture was allowed to stir at 23° C. for 4 hours. The solvent was removed under vacuum and the residue was purified using a prep-HPLC (Column: Phenomenex Synergi C18 150*30 mm*4 um; Condition: 0.1% TFA-ACN; Gradient: 15% to 45%; B, 2~8 min. FlowRate: 30 mL/min) to provide compound 109 as a red solid. $^1$H NMR (400 MHz, MeOD): δ 8.55 (s, 1H), 7.35-7.43 (m, 1H), 6.91-6.99 (m, 2H), 5.60-5.68 (m, 4H), 4.62-4.88 (m, 6H), 3.71 (br, 1H), 3.12-3.30 (m, 2H), 2.01-2.08 (m, 4H), 1.48 (s, 3H), 1.41 (s, 3H), 1.29 (s, 6H), 1.28 (s, 6H). MS: m/z=746.2 (M+1).

Example 30

Preparation of Compound 110

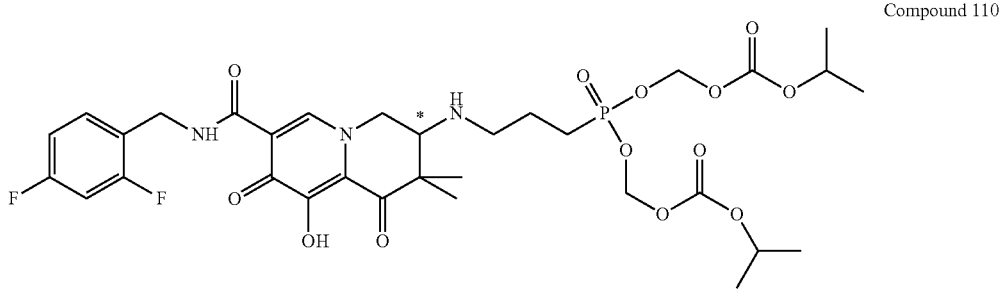 [SMILES: CC(C)OC(=O)OCOP(=O)(CCCNC1Cn2cc(C(=O)NCc3ccc(F)cc3F)c(=O)c(O)c2C(=O)C1(C)C)OCOC(=O)OC(C)C]

Compound 110

Compound 110 was prepared using the method described in Example 29, except replacing compound Int-26I with compound Int-26J.

Compound 110: $^1$H NMR (400 MHz, MeOD): δ 8.54 (s, 1H), 7.35-7.43 (m, 1H), 6.91-6.99 (m, 2H), 5.60-5.69 (m, 4H), 4.62-4.88 (m, 6H), 3.71 (br, 1H), 3.12-3.30 (m, 2H), 2.01-2.08 (m, 4H), 1.48 (s, 3H), 1.41 (s, 3H), 1.29 (s, 6H), 1.28 (s, 6H). MS: m/z=746.1 (M+1).

Assay for Inhibition of HIV Replication

This assay is useful for assessing the ability of a compound of the present inventiongin to inhibit HIV replication. The assay is a kinetic assay that employs a reporter cell line (MT4-gag-GFP) to quantify the number of new cells infected in each round of replication.

MT4-GFP cells (250,000 cells/ml) are bulk-infected with HIV-1 (NL4-3 strain) at low multiplicity of infection (MOI) in RPMI+10% FBS for 24 hours. Cells are then washed once in RPMI+10% FBS and resuspended in RPMI+0% or 10% or 100% normal human serum (NHS). Test compounds are serial-diluted in DMSO using an ECHO liquid handler. The infected MT4-GFP cells are added to a 384-well poly-D-lysine coated black plate with clear bottom in which the diluted test compounds are placed. The cells are seeded at 8,000 cells per well and the final DMSO concentration is adjusted to 0.4%. The infected cells (Green GFP cells) are then quantified at both 24 and 48 hours post incubation using Acumen eX3. Viral reproductive ratio ($R_0$) is determined using the number of infected cells at 48 hours divided by the number of infected cells at 24 hours. Percent viral growth inhibition is calculated by $[1-(R-R_{tripledrug})/(R_{DMSO}-R_{tripledrug})]*100$. Compound potency IP or $IC_{50}$ can be determined using a 4-parameter dose response curve analysis.

The table below provides data for illustrative compounds of the present invention that were tested using this assay protocol.

| Compound No. | WILD TYPE CELL ASSAY Viking IP (0% NHS) (nM) | WILD TYPE CELL ASSAY Viking IP (100% NHS) (nM) |
|---|---|---|
| 32 | 7.5 | 425 |
| 33 | 13 | 188 |
| 34 | 8.2 | 238 |
| 35 | 3.5 | 86 |
| 36 | 629 | 3600 |
| 37 | >1000 | >8000 |
| 38 | 738 | 6050 |
| 39 | 337 | 6929 |

-continued

| Compound No. | WILD TYPE CELL ASSAY Viking IP (0% NHS) (nM) | WILD TYPE CELL ASSAY Viking IP (100% NHS) (nM) |
|---|---|---|
| 40 | 0.50 | 118 |
| 41 | 0.97 | >8000 |
| 42 | 1.2 | 407 |
| 43 | 1.4 | 1477 |
| 44 | 7.2 | 159 |
| 45 | 8.2 | 300 |
| 46 | 4.2 | 102 |
| 47 | 298 | 4597 |
| 48 | 626 | 6945 |
| 49 | >1050 | >8400 |
| 50 | >1050 | >8400 |
| 51 | 14 | 461 |
| 52 | 43 | >8400 |
| 53 | 13 | 242 |
| 54 | 11 | 223 |
| 55 | 6.7 | 128 |
| 56 | 4.6 | 86 |
| 57 | 7.0 | 84 |
| 58 | >1050 | >8400 |
| 59 | >1050 | 4259 |
| 60 | 765 | 5180 |
| 61 | 970 | 2495 |
| 62 | 14 | 4701 |
| 63 | 4.6 | 566 |
| 64 | 2.9 | 289 |
| 65 | 5.4 | 131 |

-continued

| Compound No. | WILD TYPE CELL ASSAY Viking IP (0% NHS) (nM) | WILD TYPE CELL ASSAY Viking IP (100% NHS) (nM) |
|---|---|---|
| 66 | 19 | 1284 |
| 67 | 669 | 4259 |
| 68 | >1000 | >8000 |
| 69 | 1.1 | 25 |
| 70 | 13 | 2015 |
| 71 | 9.5 | 173 |
| 72 | 26 | 923 |
| 73 | 836 | >8400 |
| 74 | >1050 | >8400 |
| 75 | 6.3 | 191 |
| 76 | 45 | 2768 |
| 77 | 5.5 | 128 |
| 78 | 17 | 580 |
| 79 | 15 | 177 |
| 80 | 378 | 2747 |
| 81 | 665 | 2120 |
| 82 | 729 | >8000 |
| 83 | >1000 | 5384 |
| 84 | 492 | 2929 |
| 85 | 0.2912 | 7.7 |
| 86 | 3.5 | 980 |
| 87 | 0.8 | 21 |
| 88 | 0.9 | 29 |
| 89 | 15 | 211 |
| 90 | 15 | 123 |
| 91 | 31 | 600 |
| 92 | 143 | 2319 |
| 93 | >1050 | 2473 |
| 94 | >1050 | >8400 |
| 95 | >1050 | 3260 |
| 96 | >1050 | 6175 |
| 97 | 3.9 | 194 |
| 98 | 3.0 | 115 |
| 99 | 29 | 5674 |
| 100 | 22 | 434 |
| 101 | 50 | 891 |
| 102 | 25 | 150 |
| 103 | ND | ND |
| 104 | ND | ND |
| 105 | 15 | 628 |
| 106 | 3.6 | 95 |
| 107 | >1050 | 1935 |
| 108 | 95 | 1255 |
| 109 | 38 | 3516 |
| 110 | 8.8 | 154 |

Treatment or Prevention of HIV Infection

The Phosphate-Substituted Quinolizine Derivatives may be useful in the inhibition of HIV, the inhibition of HIV integrase, the treatment of HIV infection and/or reduction of the likelihood or severity of symptoms of HIV infection and the inhibition of HIV viral replication and/or HIV viral production in a cell-based system. For example, the Phosphate-Substituted Quinolizine Derivatives may be useful in treating infection by HIV after suspected past exposure to HIV by such means as blood transfusion, exchange of body fluids, bites, accidental needle stick, or exposure to subject blood during surgery or other medical procedures.

Accordingly, in one embodiment, the invention provides methods for treating HIV infection in a subject, the methods comprising administering to the subject an effective amount of at least one Phosphate-Substituted Quinolizine Derivative or a pharmaceutically acceptable salt or prodrug thereof. In a specific embodiment, the amount administered is effective to treat or prevent infection by HIV in the subject.

In another embodiment, the amount administered is effective to inhibit HIV viral replication and/or viral production in the subject.

In one embodiment, the HIV infection has progressed to AIDS.

The Phosphate-Substituted Quinolizine Derivatives are also useful in the preparation and execution of screening assays for antiviral compounds. For example the Phosphate-Substituted Quinolizine Derivatives may be useful for identifying resistant HIV cell lines harboring mutations, which are excellent screening tools for more powerful antiviral compounds. Furthermore, the Phosphate-Substituted Quinolizine Derivatives may be useful in establishing or determining the binding site of other antivirals to the HIV Integrase.

The compositions and combinations of the present invention can be useful for treating a subject suffering from infection related to any HIV genotype.

Combination Therapy

In another embodiment, the present methods for treating or preventing HIV infection can further comprise the administration of one or more additional therapeutic agents which are not Phosphate-Substituted Quinolizine Derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: (i) at least one Phosphate-Substituted Quinolizine Derivative (which may include two or more different Phosphate-Substituted Quinolizine Derivatives), or a pharmaceutically acceptable salt or prodrug thereof, and (ii) at least one additional therapeutic agent that is other than a Phosphate-Substituted Quinolizine Derivative, wherein the amounts administered are together effective to treat or prevent a viral infection.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Phosphate-Substituted Quinolizine Derivative and an additional therapeutic agent may be present in fixed amounts (dosage amounts) in a single dosage unit (e.g., a capsule, a tablet and the like).

In one embodiment, at least one Phosphate-Substituted Quinolizine Derivative is administered during a time when the additional therapeutic agent(s) exert their prophylactic or therapeutic effect, or vice versa.

In another embodiment, at least one Phosphate-Substituted Quinolizine Derivative and the additional therapeutic agent(s) are administered in doses commonly employed when such agents are used as monotherapy for treating a viral infection.

In another embodiment, at least one Phosphate-Substituted Quinolizine Derivative and the additional therapeutic agent(s) are administered in doses lower than the doses commonly employed when such agents are used as monotherapy for treating a viral infection.

In still another embodiment, at least one Phosphate-Substituted Quinolizine Derivative and the additional therapeutic agent(s) act synergistically and are administered in doses lower than the doses commonly employed when such agents are used as monotherapy for treating a viral infection.

In one embodiment, at least one Phosphate-Substituted Quinolizine Derivative and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HIV infection.

In another embodiment, the HIV infection has progressed to AIDS.

The at least one Phosphate-Substituted Quinolizine Derivative and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Phosphate-Substituted Quinolizine Derivative and the additional therapeutic agent(s) may inhibit the resistance of a viral infection to these agents.

As noted above, the present invention is also directed to use of a compound of Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS. Suitable HIV antivirals for use in combination with the compounds of the present invention include, for example, those listed in Table A as follows:

TABLE A

| Name | Type |
| --- | --- |
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| darunavir, Prezista ® | PI |
| ddC, zalcitabine, dideoxycytidine, Hivid ® | nRTI |

TABLE A-continued

| Name | Type |
| --- | --- |
| ddI, didanosine, dideoxyinosine, Videx ® | nRTI |
| ddI (enteric coated), Videx EC ® | nRTI |
| delavirdine, DLV, Rescriptor ® | nnRTI |
| dolutegravir, Tivicay ® | II |
| efavirenz, EFV, Sustiva ®, Stocrin ® | nnRTI |
| efavirenz + emtricitabine + tenofovir DF, Atripla ® | nnRTI + nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| rilpivirine, TMC-278 | nnRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor;
FI = fusion inhibitor;
PI = protease inhibitor;
nRTI = nucleoside reverse transcriptase inhibitor;
II = integrase inhibitor;
nnRTI = non-nucleoside reverse transcriptase inhibitor.
Some of the drugs listed in the table are used in a salt form; e.g., abacavir sulfate, indinavir sulfate, atazanavir sulfate, nelfinavir mesylate.

In one embodiment, one or more anti-HIV drugs are selected from, lamivudine, abacavir, ritonavir, darunavir, atazanavir, emtricitabine, tenofovir, rilpivirine and lopinavir.

In another embodiment, the compound of formula (I) is used in combination with lamivudine.

In another embodiment, the compound of formula (I) is used in combination with abacavir.

In still another embodiment, the compound of formula (I) is used in combination atazanavir.

In another embodiment, the compound of formula (I) is used in combination with darunavir.

In another embodiment, the compound of formula (I) is used in combination with rilpivirine.

In yet another embodiment, the compound of formula (I) is used in combination with lamivudine and abacavir.

In another embodiment, the compound of formula (I) is used in combination with emtricitabine and tenofovir.

In another embodiment, the compound of formula (I) is used in combination with ritonavir and lopinavir.

In one embodiment, the present invention provides pharmaceutical compositions comprising (i) a compound of formula (I) or a pharmaceutically acceptable salt or prodrug thereof; (ii) a pharmaceutically acceptable carrier; and (iii) one or more additional anti-HIV agents selected from lamivudine, abacavir, ritonavir and lopinavir, or a pharmaceutically acceptable salt or prodrug thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula (I) or a pharmaceutically acceptable salt or prodrug thereof and (ii) one or more additional anti-HIV agents selected from lamivudine, abacavir, ritonavir and lopinavir, or a pharmaceutically acceptable salt or prodrug thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, 57$^{th}$ edition (2003), the 58$^{th}$ edition (2004), the 59$^{th}$ edition (2005), and the like. The dosage ranges for a compound of the invention in these combinations are the same as those set forth above.

The doses and dosage regimen of the other agents used in the combination therapies of the present invention for the treatment or prevention of HIV infection can be determined by the attending clinician, taking into consideration the approved doses and dosage regimen in the package insert; the age, sex and general health of the subject; and the type and severity of the viral infection or related disease or disorder. When administered in combination, the Phosphate-Substituted Quinolizine Derivative(s) and the other agent(s) can be administered simultaneously (i.e., in the same composition or in separate compositions one right after the other) or sequentially. This is particularly useful when the components of the combination are given on different dosing schedules, e.g., one component is administered once daily and another component is administered every six hours, or when the pharmaceutical compositions are different, e.g., one is a tablet and one is a capsule. A kit comprising the separate dosage forms is therefore advantageous.

Compositions and Administration

When administered to a subject, the Phosphate-Substituted Quinolizine Derivatives can be administered as a component of a composition that comprises a pharmaceutically acceptable carrier or vehicle. The present invention provides pharmaceutical compositions comprising an effective amount of at least one Phosphate-Substituted Quinolizine Derivative and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like.

Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Phosphate-Substituted Quinolizine Derivatives are administered orally.

In another embodiment, the one or more Phosphate-Substituted Quinolizine Derivatives are administered intravenously.

In one embodiment, a pharmaceutical preparation comprising at least one Phosphate-Substituted Quinolizine Derivative is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Phosphate-Substituted Quinolizine Derivative(s) by weight or volume. In various embodiments, the present compositions can contain, in one embodiment, from about 1% to about 70% or from about 5% to about 60% of the Phosphate-Substituted Quinolizine Derivative(s) by weight or volume.

The compounds of Formula I can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The unit dosages of the Phosphate-Substituted Quinolizine Derivatives may be administered at varying frequencies. In one embodiment, a unit dosage of a Phosphate-Substituted Quinolizine Derivative can be administered once daily. In another embodiment, a unit dosage of a Phosphate-Substituted Quinolizine Derivative can be administered twice weekly. In another embodiment, a unit dosage of a Phosphate-Substituted Quinolizine Derivative can be administered once weekly. In still another embodiment, a unit dosage of a Phosphate-Substituted Quinolizine Derivative can be administered once biweekly. In another embodiment, a unit dosage of a Phosphate-Substituted Quinolizine Derivative can be administered once monthly. In yet another embodiment, a unit dosage of a Phosphate-Substituted Quinolizine Derivative can be administered once bimonthly. In another embodiment, a unit dosage of a Phosphate-Substituted Quinolizine Derivative can be administered once every 3 months. In a further embodiment, a unit dosage of a Phosphate-Substituted Quinolizine Derivative can be administered once every 6 months. In another embodiment, a unit dosage of a Phosphate-Substituted Quinolizine Derivative can be administered once yearly.

The amount and frequency of administration of the Phosphate-Substituted Quinolizine Derivatives will be regulated according to the judgment of the attending clinician considering such factors as age, condition and size of the subject as well as severity of the symptoms being treated. The compositions of the invention can further comprise one or more additional therapeutic agents, selected from those listed above herein.

Kits

In one aspect, the present invention provides a kit comprising a therapeutically effective amount of at least one Phosphate-Substituted Quinolizine Derivative, or a pharmaceutically acceptable salt or prodrug of said compound and a pharmaceutically acceptable carrier, vehicle or diluent.

In another aspect the present invention provides a kit comprising an amount of at least one Phosphate-Substituted Quinolizine Derivative, or a pharmaceutically acceptable salt or prodrug of said compound and an amount of at least one additional therapeutic agent listed above, wherein the amounts of the two or more active ingredients result in a desired therapeutic effect. In one embodiment, the one or more Phosphate-Substituted Quinolizine Derivatives and the one or more additional therapeutic agents are provided in the same container. In one embodiment, the one or more Phosphate-Substituted Quinolizine Derivatives and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:
1. A compound having the formula:

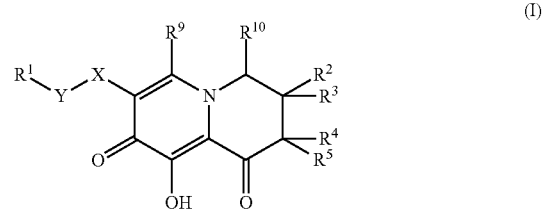

(I)

or a pharmaceutically acceptable salt thereof,
wherein:
$R^1$ is selected from $C_6$-$C_{10}$ aryl, 5 or 6-membered monocyclic heteroaryl and 9 or 10-membered bicyclic heteroaryl, wherein said $C_6$-$C_{10}$ aryl group, said 5 or 6-membered monocyclic heteroaryl group and said 9 or 10-membered bicyclic heteroaryl group can each be optionally substituted with up to three $R^8$ groups;
$R^2$ is selected from H, $C_1$-$C_6$ alkyl, —N($R^1$)$_2$, —($C_1$-$C_6$ alkylene)$_m$-Z—($C_1$-$C_6$ alkylene)$_m$-$R^{13}$, —($C_1$-$C_6$ alkylene)$_m$-Z—($C_1$-$C_6$ alkylene)$_m$-N($R^{22}$)$_2$ and —O$R^7$, or $R^2$ and $R^4$, together with the carbon atoms to which they are attached, can join to form a 5 to 8-membered monocyclic cycloalkyl group, 5 to 8-membered monocyclic heterocycloalkyl group, 5 to 8-membered monocyclic heterocycloalkenyl group or a 8 to 11-membered bicyclic heterocycloalkyl, wherein said 5 to 8-membered monocyclic cycloalkyl group, said 5 to 8-membered monocyclic heterocycloalkyl group, said 5 to 8-membered monocyclic heterocycloalkenyl group and said 8 to 11-membered bicyclic heterocycloalkyl group can be optionally substituted with up to three $R^8$ groups, which can be the same or different;
$R^3$ is H, $C_1$-$C_6$ alkyl, —N($R^{11}$)$_2$ or —O$R^7$;
$R^4$ is selected from H, $C_1$-$C_6$ alkyl, —($C_1$-$C_6$ alkylene)-O—($C_1$-$C_6$ alkyl), —($C_1$-$C_6$ alkylene)$_m$-Z—($C_1$-$C_6$ alkylene)$_m$-$R^{13}$, —($C_1$-$C_6$ alkylene)$_m$-Z—($C_1$-$C_6$ alkylene)$_m$-N($R^{22}$)$_2$, —N($R^{11}$)$_2$ and —O$R^7$, such that when $R^2$ and/or $R^3$ are —N($R^{11}$)$_2$, then $R^4$ is other than H;

$R^5$ is selected from H, $C_1$-$C_6$ alkyl, —($C_1$-$C_6$ alkylene)-O—($C_1$-$C_6$ alkyl), —$N(R^{11})_2$ and —$OR^7$, such that when $R^2$ and/or $R^3$ are —$N(R^{11})_2$, then $R^5$ is other than H;

each occurrence of $R^6$ is independently H or $C_1$-$C_6$ alkyl;

each occurrence of $R^7$ is independently selected from H, $C_1$-$C_6$ alkyl, —($C_1$-$C_6$ alkylene)-O—($C_1$-$C_6$ alkyl) and $C_3$-$C_7$ cycloalkyl;

each occurrence of $R^8$ is independently selected from $C_1$-$C_6$ alkyl, halo, —$OR^6$, —$SR^6$, $C_1$-$C_6$ haloalkyl, $C_1$-$C_6$ hydroxyalkyl, —($C_1$-$C_6$ alkylene)$_m$-Z—$R^{13}$, —$N(R^{22})_2$, —O—($C_1$-$C_6$ haloalkyl), —CN, —$NO_2$, —$N(R^6)_2$, —$C(O)OR^7$, —$C(O)N(R^7)_2$ and —$NHC(O)R^7$;

$R^9$ is selected from H, $C_1$-$C_6$ alkyl, —$C_1$-$C_6$ alkyl-O—$C_1$-$C_6$ alkyl, —$C_1$-$C_6$ alkyl-$NR^6$—$C_1$-$C_6$ alkyl, —$C_1$-$C_6$ haloalkyl and —$C_1$-$C_6$ hydroxyalkyl;

$R^{10}$ is selected from H, $C_1$-$C_6$ alkyl, —($C_1$-$C_6$ alkylene)$_m$-Z—($C_1$-$C_6$ alkylene)$_m$-$R^{13}$, —($C_1$-$C_6$ alkylene)$_m$-Z—($C_1$-$C_6$ alkylene)$_m$-$N(R^{22})_2$, —($C_1$-$C_6$ alkylene)-O—$C_1$-$C_6$ alkyl, —($C_1$-$C_6$ alkylene)-N($R^6$)—$C_1$-$C_6$ alkyl, —$C_1$-$C_6$ haloalkyl and —$C_1$-$C_6$ hydroxyalkyl;

each occurrence of $R^{11}$ is independently selected from H, $C_1$-$C_6$ alkyl, —$S(O)_2R^{12}$ and —$C(O)R^{12}$; and each occurrence of $R^{12}$ is independently selected from $C_1$-$C_6$ alkyl, $C_3$-$C_7$ cycloalkyl, $C_6$-$C_{10}$ aryl, 4 to 7-membered monocyclic heterocycloalkyl, 8 to 11-membered bicyclic heterocycloalkyl, 5 or 6-membered monocyclic heteroaryl and 9 or 10-membered bicyclic heteroaryl, wherein said $C_3$-$C_7$ cycloalkyl group, said $C_6$-$C_{10}$ aryl group, said 4 to 7-membered monocyclic heterocycloalkyl, said 8 to 11-membered bicyclic heterocycloalkyl group, said 5 or 6-membered monocyclic heteroaryl group and said 9 or 10-membered bicyclic heteroaryl group can each be optionally substituted with up to three $R^8$ groups;

each occurrence of $R^{13}$ is independently selected from —$P(O)(—OR^{21})_2$,

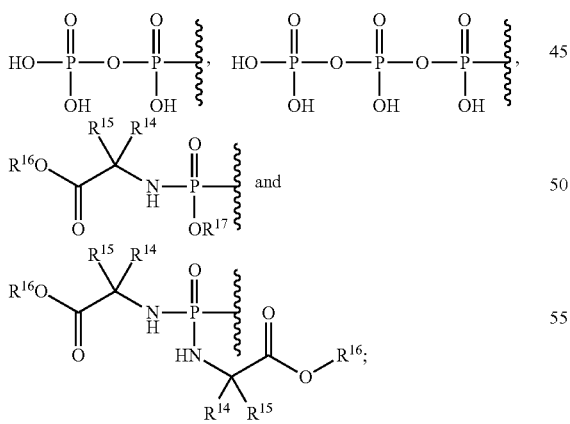

and each occurrence of $R^{14}$ is independently selected from H, $C_1$-$C_6$ alkyl, $C_3$-$C_7$ cycloalkyl, phenyl and benzyl, wherein said $C_1$-$C_6$ alkyl can be optionally substituted with a group selected from halo, —$OR^{18}$, —$SR^{18}$, guanidino, —$N(R^{18})_2$, —$C(O)OR^{18}$, —$C(O)N(R^{18})_2$, —$NHC(O)R^{18}$, 5- or 6-membered monocyclic heteroaryl and 9- or 10-membered bicyclic heteroaryl, and wherein said phenyl group and said benzyl group can be optionally substituted with up to 2 groups, each independently selected from $C_1$-$C_6$ alkyl, halo and —$OR^6$;

each occurrence of $R^{15}$ is independently selected from H, $C_1$-$C_6$ alkyl, $C_3$-$C_7$ cycloalkyl, phenyl and benzyl, wherein said $C_1$-$C_6$ alkyl can be optionally substituted with a group selected from halo, —$OR^{18}$, —$SR^{18}$, guanidino, —$N(R^{18})_2$, —$C(O)OR$, —$C(O)N(R^{18})_2$, —$NHC(O)R^{18}$, 5- or 6-membered monocyclic heteroaryl and 9- or 10-membered bicyclic heteroaryl, and wherein said phenyl group and said benzyl group can be optionally substituted with up to 2 groups, each independently selected from $C_1$-$C_6$ alkyl, halo and —$OR^{18}$;

each occurrence of $R^{16}$ is independently selected from H, $C_1$-$C_{20}$ alkyl, $C_2$-$C_{20}$ alkenyl, —($C_1$-$C_3$ alkylene)$_m$-($C_3$-$C_7$ cycloalkyl), —($C_1$-$C_3$ alkylene)$_m$-($C_6$-$C_{10}$ aryl) and —($C_1$-$C_3$ alkylene)$_m$-adamantyl, wherein said $C_1$-$C_{20}$ alkyl group, said $C_2$-$C_{20}$ alkenyl group, said $C_6$-$C_{10}$ aryl group and said adamantyl group can be optionally substituted with up to three groups, each independently selected from halo, —$OR^{18}$, —$C(O)OR^{18}$, —CN, —$NO_2$, $C_1$-$C_6$ haloalkyl, $C_1$-$C_6$ hydroxyalkyl, $C_3$-$C_7$ cycloalkyl, $C_6$-$C_{10}$ aryl, 5- or 6-membered monocyclic heteroaryl, 9- or 10-membered bicyclic heteroaryl, —$N(R^{18})_2$, —$C(O)N(R^{18})_2$, —$SR^{18}$, —$S(O)R^{18}$, —$S(O)_2R^{18}$, —$S(O)_2N(R^{18})_2$, —$NHC(O)R^{18}$, —$NHC(O)OR^{18}$ and —$NHC(O)N(R^{18})_2$;

each occurrence of $R^{17}$ is independently selected from H, $C_6$-$C_{10}$ aryl, 5- or 6-membered monocyclic heteroaryl and 9- or 10-membered bicyclic heteroaryl, wherein said $C_6$-$C_{10}$ aryl group, said 5- or 6-membered monocyclic heteroaryl group and said 9- or 10-membered bicyclic heteroaryl group can be optionally substituted with up to five $R^{19}$ groups;

each occurrence of $R^{18}$ is independently H, $C_1$-$C_{10}$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl), wherein said $C_3$-$C_7$ cycloalkyl group, said $C_6$-$C_{10}$ aryl group, said 4 to 7-membered heterocycloalkyl group, said -5- or 6-membered monocyclic heteroaryl group or said 9- or 10-membered bicyclic heteroaryl group can be optionally substituted with up to five $R^{19}$ groups;

each occurrence of $R^{19}$ is independently selected from $C_1$-$C_6$ alkyl, halo, —$OR^{23}$, —$SR^{23}$, $C_1$-$C_6$ haloalkyl, $C_1$-$C_6$ hydroxyalkyl, —O—($C_1$-$C_6$ haloalkyl), —CN, —$NO_2$, —$N(R^{18})_2$, —$C(O)OR^{23}$, —$C(O)N(R^{23})_2$ and —$NHC(O)R^{23}$, or any two $R^{19}$ groups on adjacent ring carbon atoms can combine to form —O—$R^{20}$—O—;

$R^{20}$ is —$[C(R^6)_2]_n$—;

each occurrence of $R^{21}$ is independently selected from H, $C_1$-$C_6$ alkyl, $C_6$-$C_{10}$ aryl, —($C_1$-$C_6$ alkylene)-O—($C_1$-$C_{20}$ alkyl), —($C_1$-$C_6$ alkylene)-O—C(O)—$R^{18}$, and —($C_1$-$C_6$ alkylene)-O—C(O)—O—$R^{18}$;

each occurrence of $R^{22}$ is independently selected from H, $C_1$-$C_6$ alkyl and —($C_1$-$C_6$ alkylene)-Z—$R^{13}$;

each occurrence of $R^{23}$ is independently selected from H, $C_1$-$C_{10}$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —(C$_1$-C$_3$ alkylene)$_m$-(C$_6$-C$_{10}$ aryl), —(C$_1$-C$_3$ alkylene)$_m$-(4 to 7-membered heterocycloalkyl), —(C$_1$-C$_3$ alkylene)$_m$-(5- or 6-membered monocyclic heteroaryl) and —(C$_1$-C$_3$ alkylene)$_m$-(9- or 10-membered bicyclic heteroaryl);

X is selected from a single bond, 5 or 6-membered monocyclic heteroaryl and —N(R$^6$)C(O)—;

Y is a single bond or C$_1$-C$_3$ alkylene;

each occurrence of Z is independently O or a bond;

each occurrence of m is independently 0 or 1; and n is 1 or 2, such that at least one —(C$_1$-C$_6$ alkylene)$_m$-Z—(C$_1$-C$_6$ alkylene)$_m$-R$^{13}$ group or at least one —(C$_1$-C$_6$ alkylene)$_m$-Z—(C$_1$-C$_6$ alkylene)$_m$-N(R$^{22}$)$_2$ group is present in the compound of formula (I).

2. The compound of claim 1, wherein R$^2$ is —(C$_1$-C$_6$ alkylene)$_m$-Z—(C$_1$-C$_6$ alkylene)$_m$-R$^{13}$ or —N(R$^{22}$)$_2$, or a pharmaceutically acceptable salt thereof.

3. The compound of claim 1, wherein R$^4$ is —(C$_1$-C$_6$ alkylene)$_m$-Z—(C$_1$-C$_6$ alkylene)$_m$-R$^{13}$ or —N(R$^{22}$)$_2$, or a pharmaceutically acceptable salt thereof.

4. The compound of claim 1, wherein R$^{10}$ is —(C$_1$-C$_6$ alkylene)$_m$-Z—(C$_1$-C$_6$ alkylene)$_m$-R$^{13}$ or —N(R$^{22}$)$_2$, or a pharmaceutically acceptable salt thereof.

5. The compound of claim 1, wherein R$^2$ and R$^4$, together with the carbon atoms to which they are attached, join to form a 5 to 8-membered monocyclic heterocycloalkyl group, which is substituted with at least one —(C$_1$-C$_6$ alkylene)$_m$-Z—(C$_1$-C$_6$ alkylene)$_m$-R$^{13}$ group or at least one —N(R$^{22}$)$_2$ group, or a pharmaceutically acceptable salt thereof.

6. The compound of claim 1, wherein R$^2$ and R$^4$, together with the carbon atoms to which they are attached, join to form:

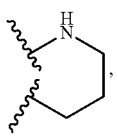

which is substituted on any ring atom with —(C$_1$-C$_6$ alkylene)$_m$-Z—R$^{13}$, or a pharmaceutically acceptable salt thereof.

7. The compound of claim 1, wherein the R$^{13}$ moiety of the —(C$_1$-C$_6$ alkylene)$_m$-Z—R$^{13}$ group or the —N(R$^{22}$)$_2$ group is selected from: —P(O)(—OH)$_2$, —P(O)(—OCH$_3$)$_2$, —P(O)(—OCH$_2$CH$_3$)$_2$, —P(O)(—CH$_2$OC(O)O—CH(CH$_3$)$_2$)$_2$, —P(O)(—CH$_2$OC(O)O—CH$_2$CH$_3$)$_2$ and

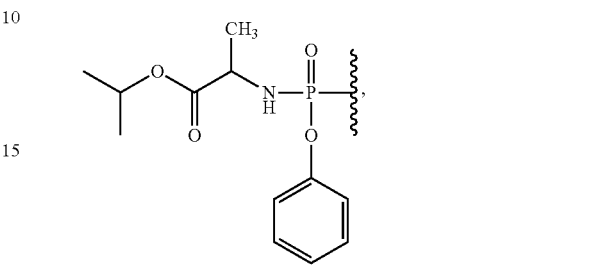

or a pharmaceutically acceptable salt thereof.

8. The compound of claim 1, wherein X is —NHC(O)—, or a pharmaceutically acceptable salt thereof.

9. The compound of claim 1, wherein X is 5 or 6-membered monocyclic heteroaryl, or a pharmaceutically acceptable salt thereof.

10. The compound of claim 1, wherein Y is CH$_2$, or a pharmaceutically acceptable salt thereof.

11. The compound of claim 10, wherein R$^1$ is phenyl, which is substituted by 1 to 3 halo groups, which can be the same or different, or a pharmaceutically acceptable salt thereof.

12. The compound of claim 1, wherein R$^2$ and R$^3$ are each independently selected from H, —OH and —O—(C$_1$-C$_6$ alkyl), or a pharmaceutically acceptable salt thereof.

13. The compound of claim 1, wherein R$^4$ and R$^5$ are each independently selected from H, C$_1$-C$_6$ alkyl and —(C$_1$-C$_6$ alkylene)-O—(C$_1$-C$_6$ alkyl), or a pharmaceutically acceptable salt thereof.

14. The compound of claim 1, wherein R$^5$ is methyl, or a pharmaceutically acceptable salt thereof.

15. The compound of claim 1, wherein R$^9$ is H, or a pharmaceutically acceptable salt thereof.

16. A compound selected from:

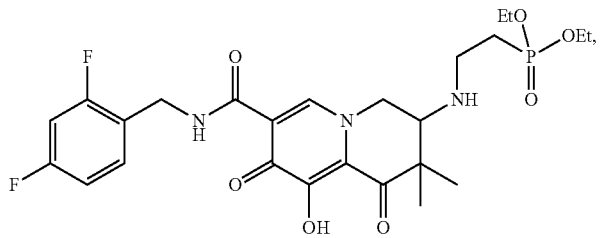

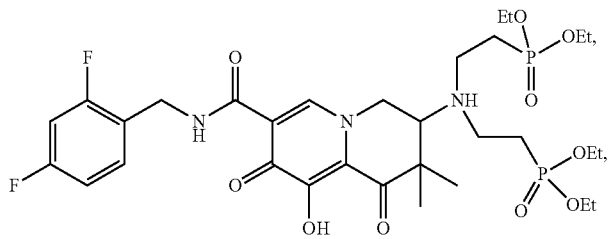

-continued
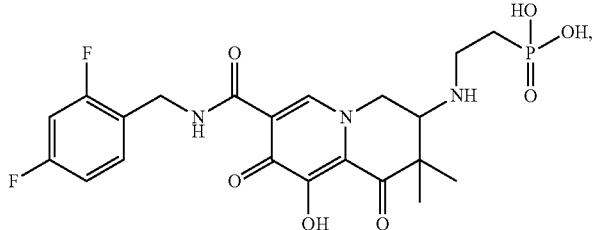
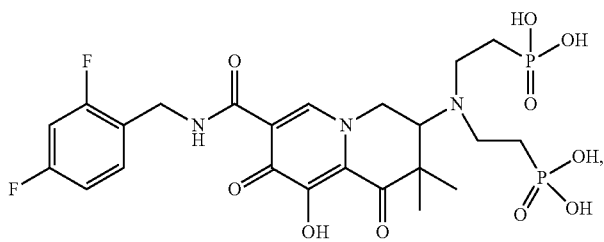
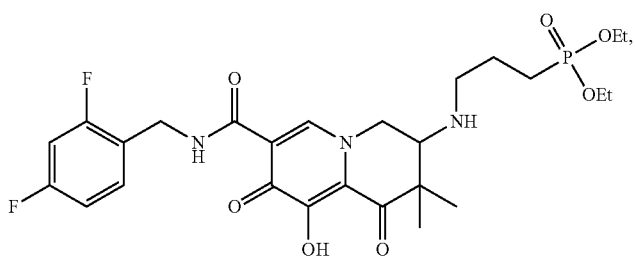
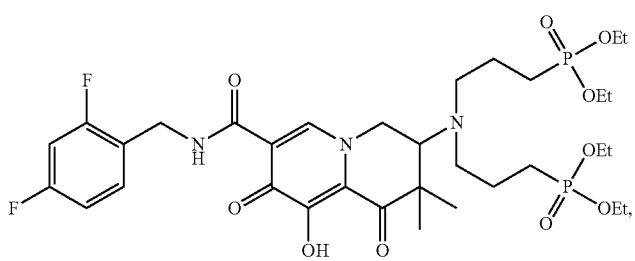
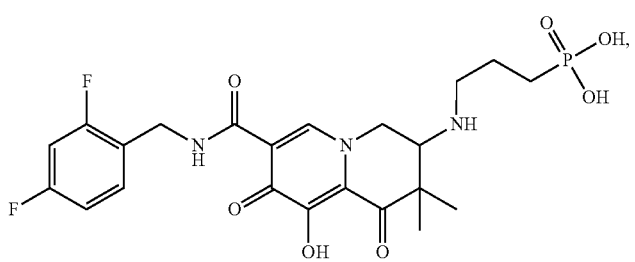
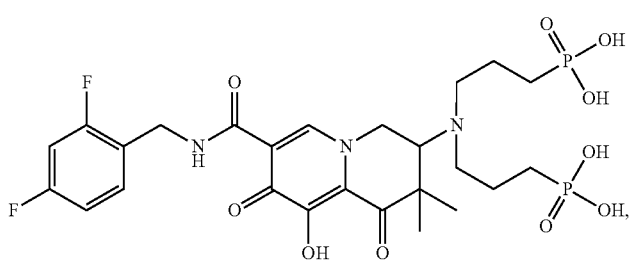

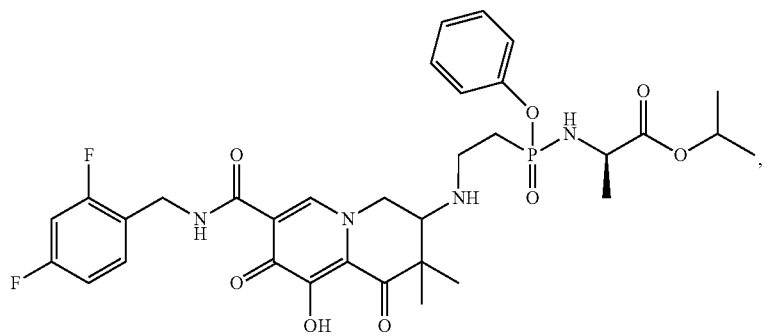
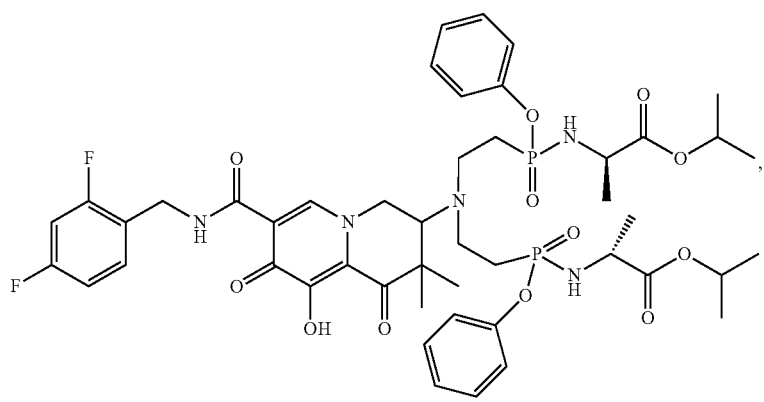
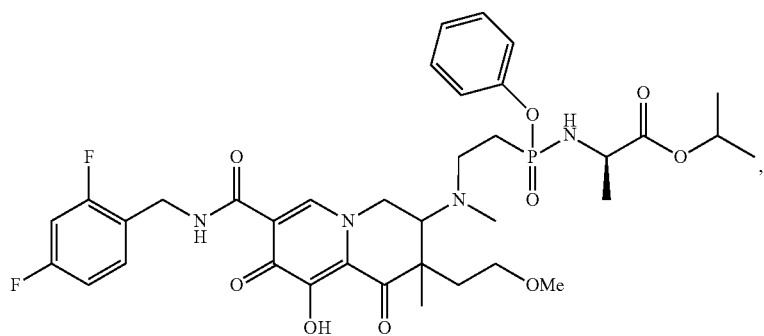
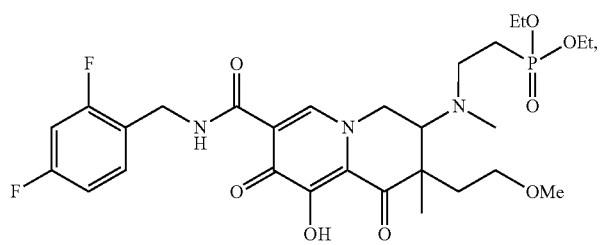
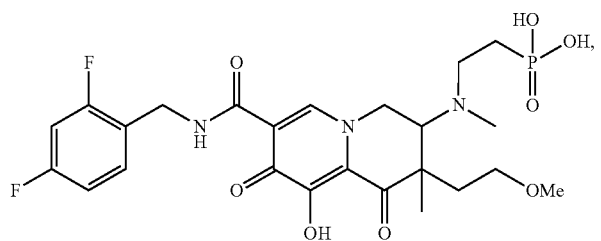

-continued
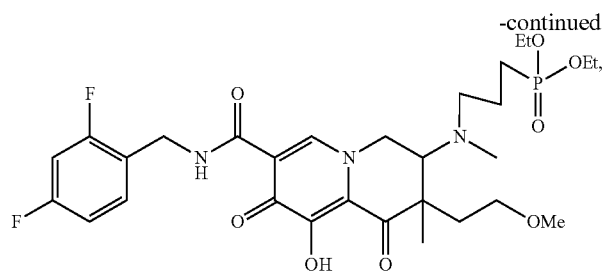
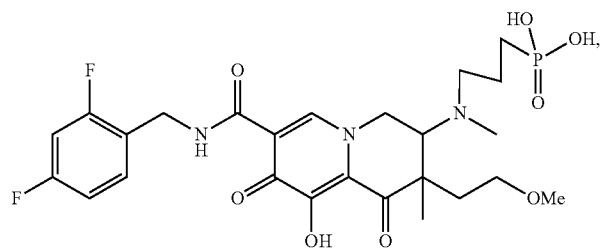
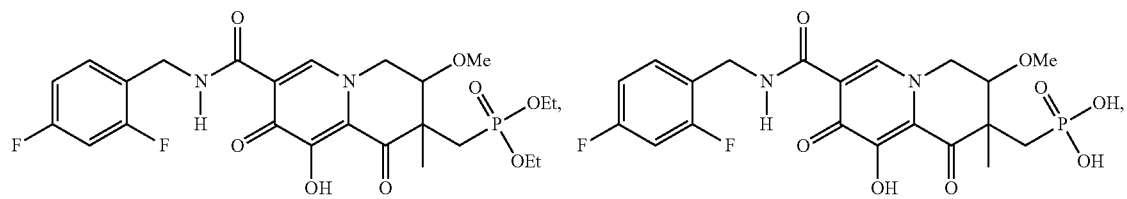
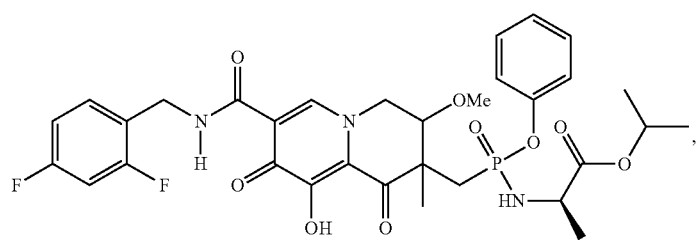
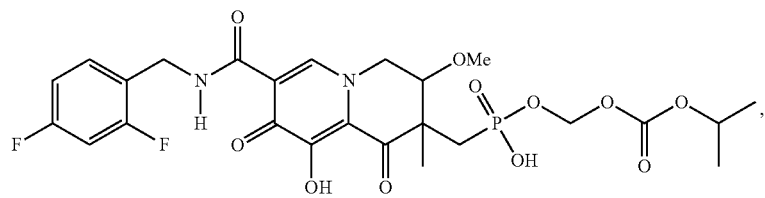
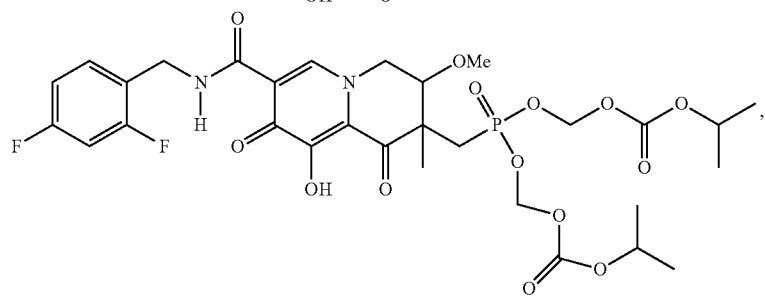
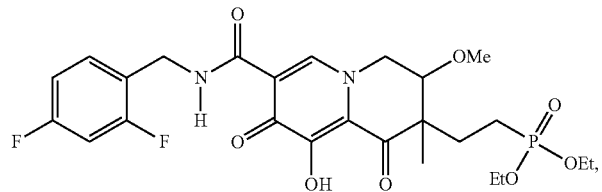

-continued
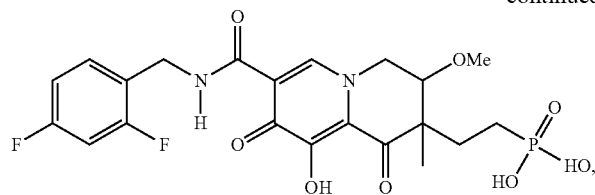
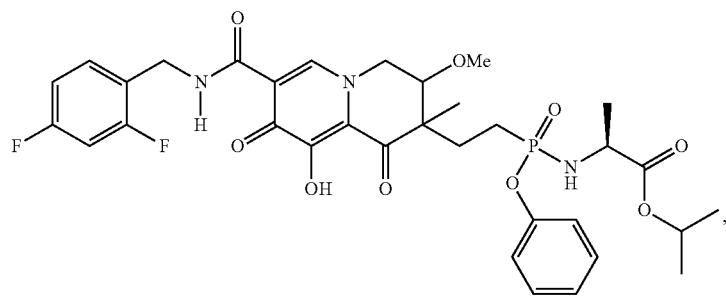
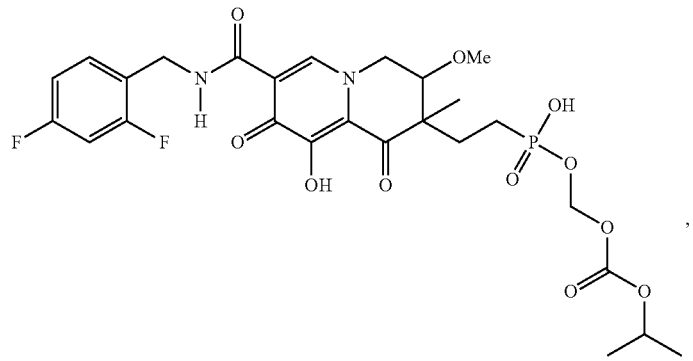
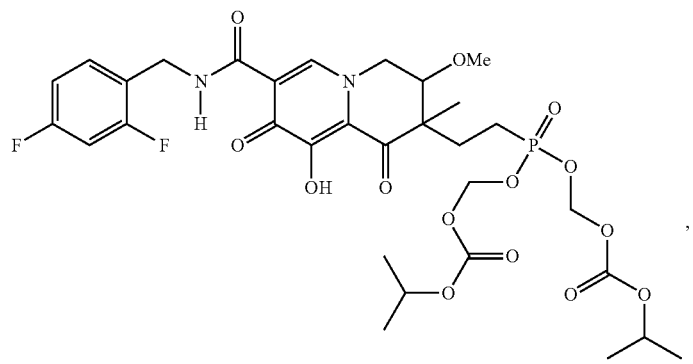
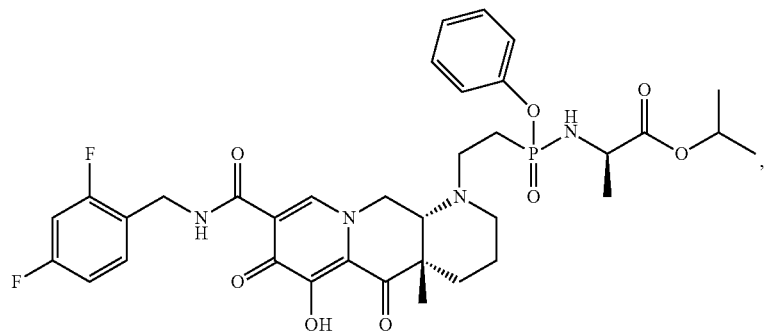

-continued
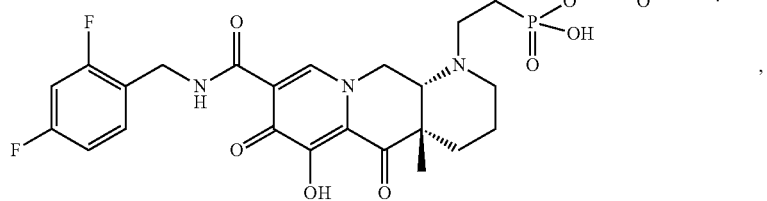
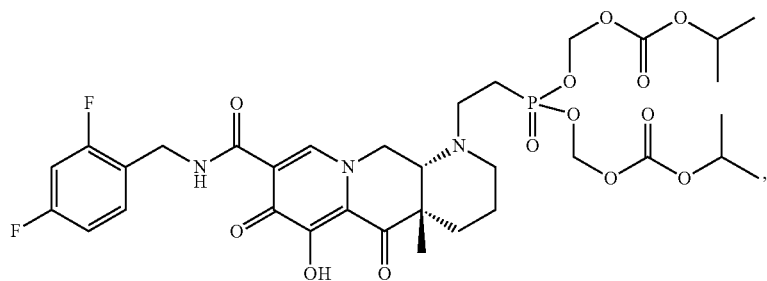
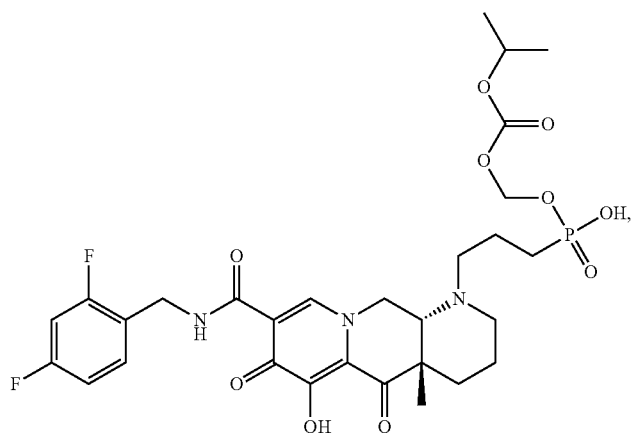
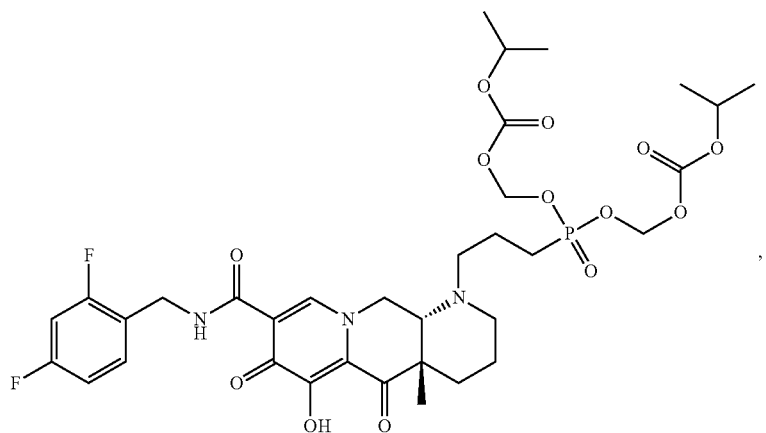

-continued
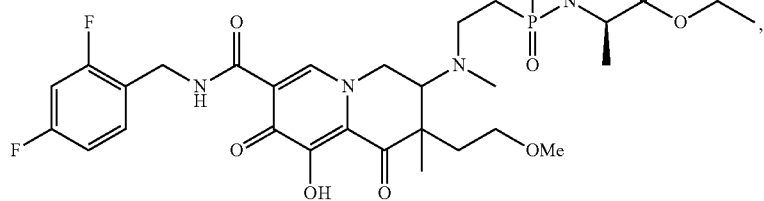
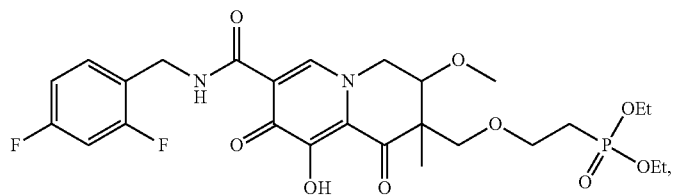
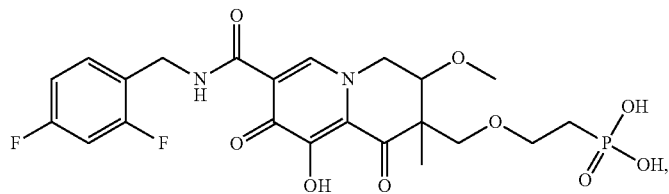
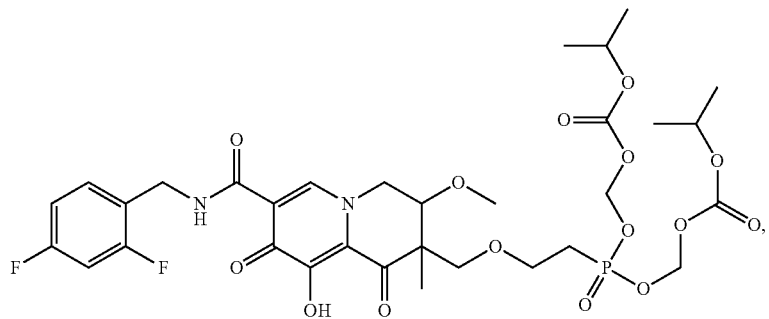
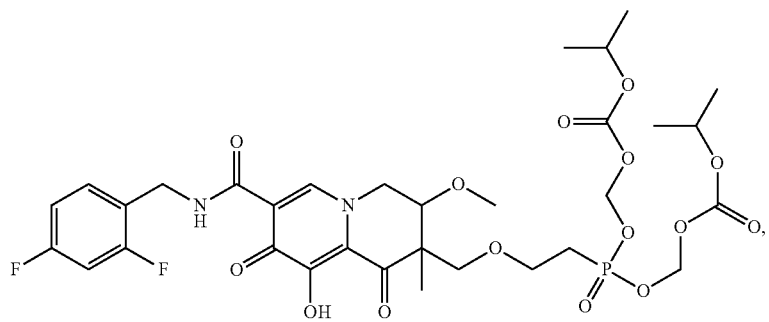
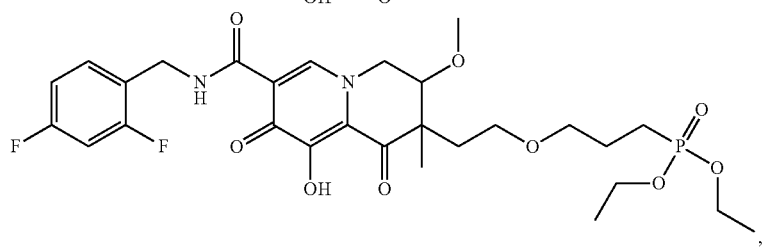

-continued
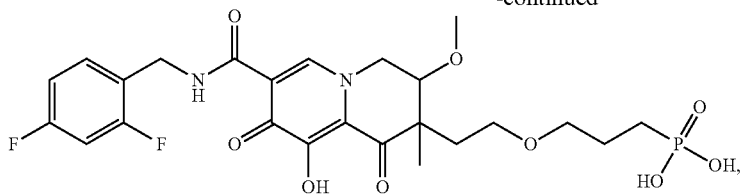
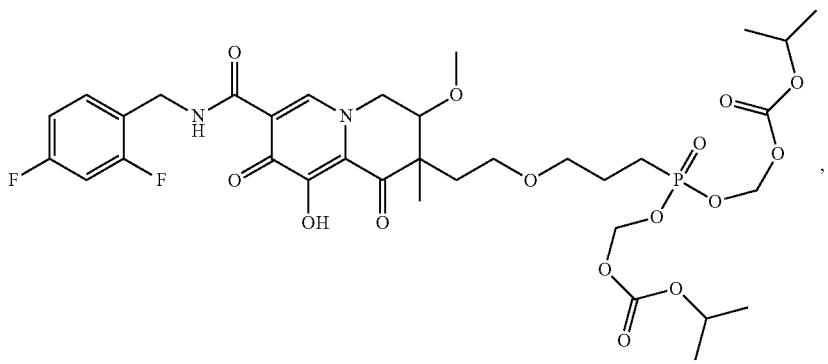
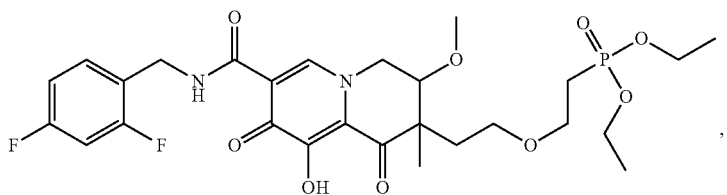
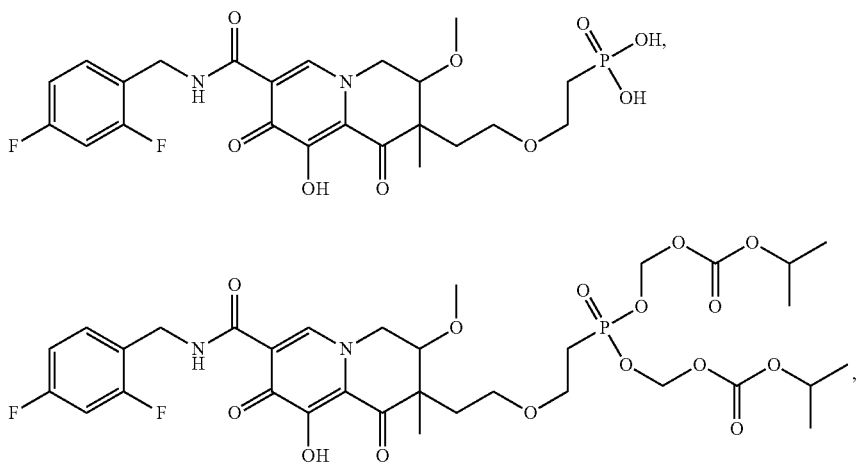
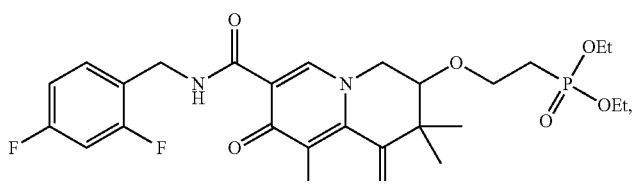
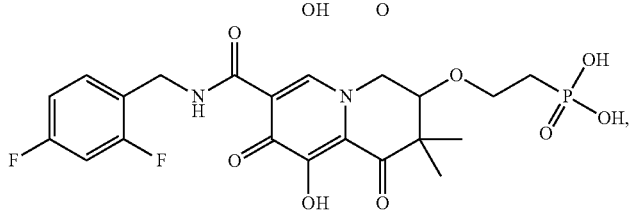

-continued
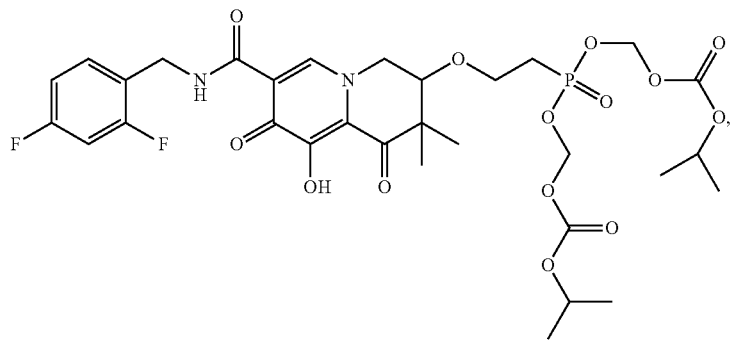
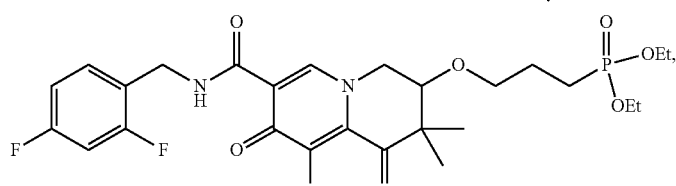
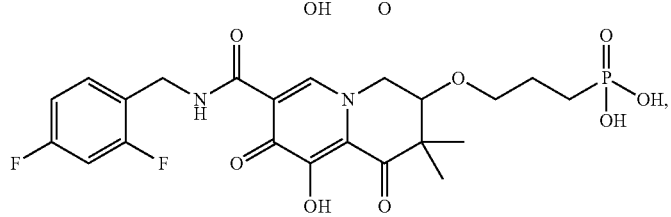
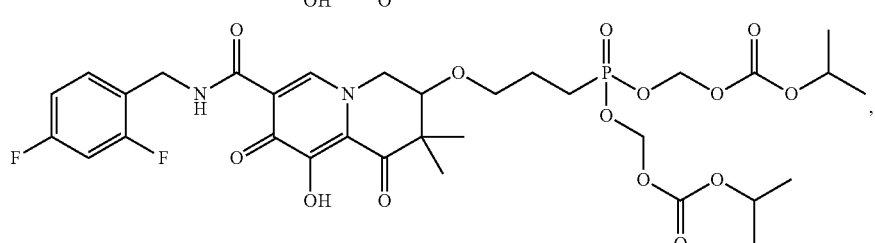
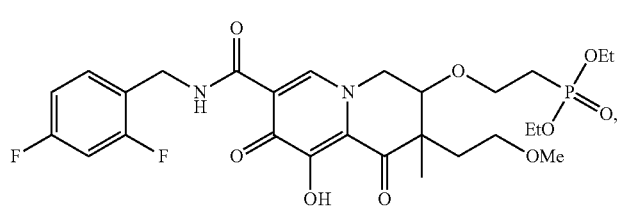
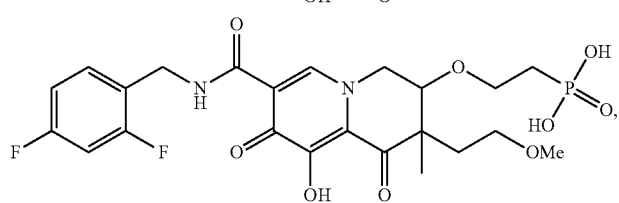
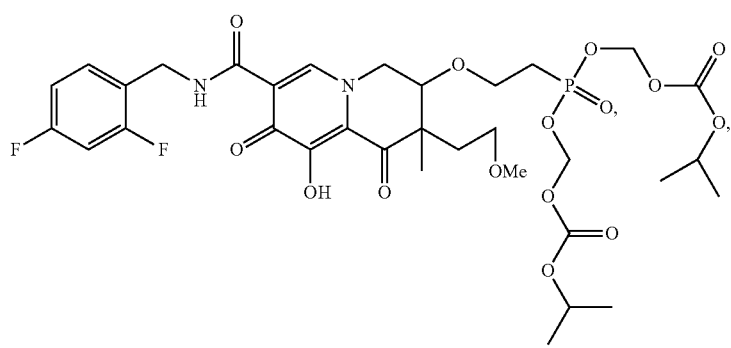

-continued
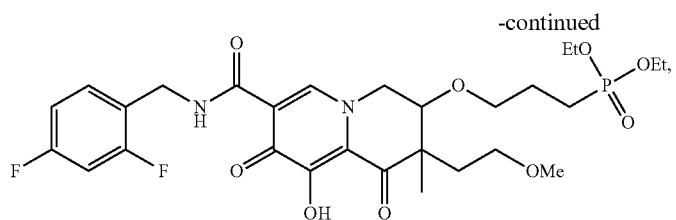
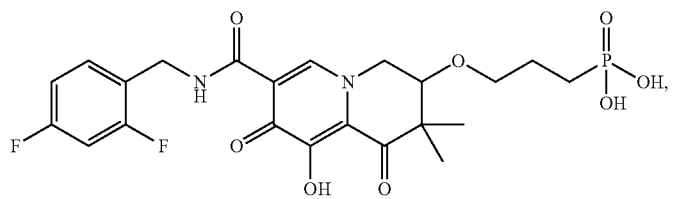
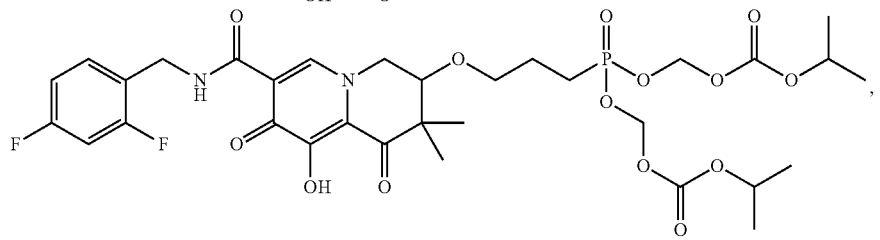
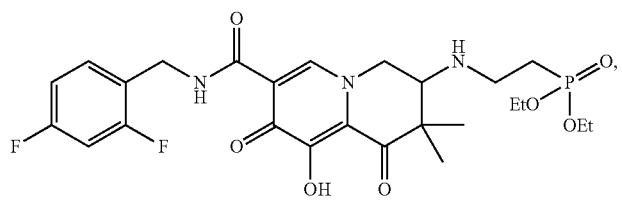
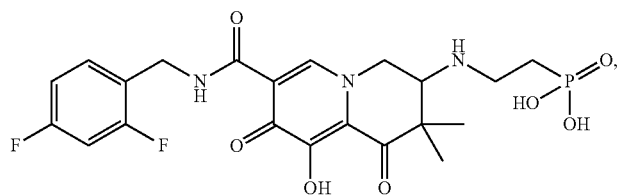
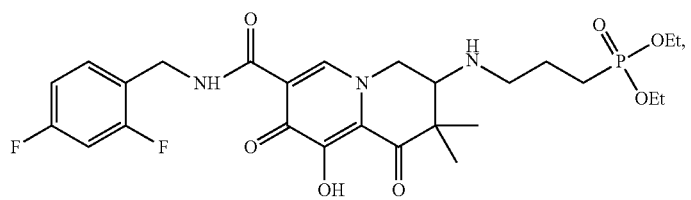
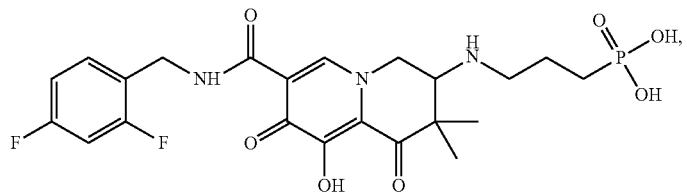
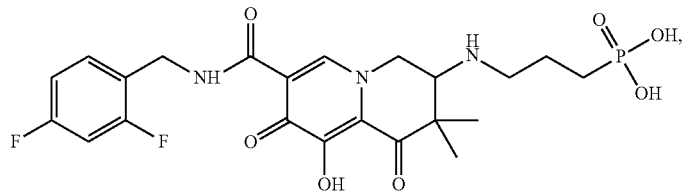

-continued

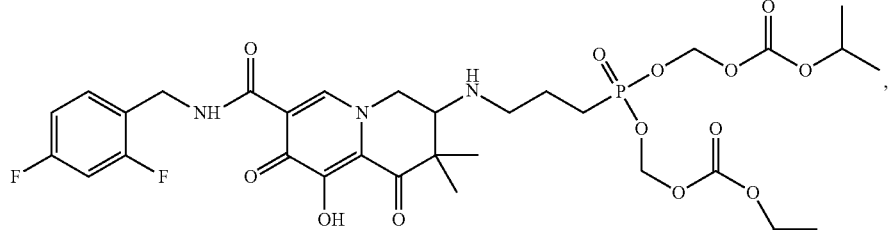

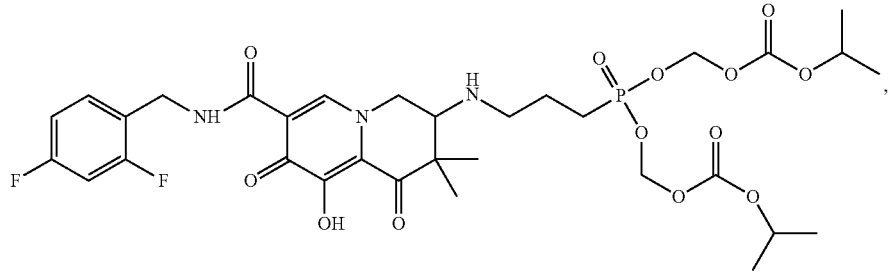

or a pharmaceutically acceptable salt thereof.

17. A pharmaceutical composition comprising an effective amount of a compound according to claim 1, or a pharmaceutically acceptable salt thereof, and a pharmaceutically acceptable carrier.

18. A method for the inhibition of HIV integrase in a subject in need thereof which comprises administering to the subject an effective amount of the compound according to claim 1, or a pharmaceutically acceptable salt thereof.

19. A method for the treatment of infection by HIV or for the treatment, prophylaxis, or delay in the onset or progression of AIDS in a subject in need thereof, which comprises administering to the subject an effective amount of the compound according to claim 1, or a pharmaceutically acceptable salt thereof.

20. The pharmaceutical composition of claim 17, further comprising one or more additional therapeutic agents selected from, lamivudine, abacavir, ritonavir, darunavir, atazanavir, emtricitabine, tenofovir, rilpivirine and lopinavir.

21. The method of claim 19, further comprising administering to the subject one or more additional therapeutic agents selected from, abacavir, lamivudine, ritonavir and lopinavir, wherein the amounts administered of the compound of claim 1 and the one or more additional therapeutic agents, are together effective to treat infection by HIV or to treat, prevent or delay the onset or progression of AIDS.

* * * * *